(12) United States Patent
Miller et al.

(10) Patent No.: US 10,968,232 B2
(45) Date of Patent: Apr. 6, 2021

(54) ANTIDIABETIC SPIROCHROMAN COMPOUNDS

(71) Applicant: Merck Sharp & Dohme Corp., Rahway, NJ (US)

(72) Inventors: Michael Miller, Scotch Plains, NJ (US); Harry R. Chobanian, Aberdeen, NJ (US); Shuwen He, Fanwood, NJ (US); Jinsong Hao, Belle Mead, NJ (US); Barbara Pio, West Orange, NJ (US); Yan Guo, Westfield, NJ (US); Dong Xiao, Warren, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/465,156

(22) PCT Filed: Dec. 15, 2017

(86) PCT No.: PCT/US2017/066568
§ 371 (c)(1),
(2) Date: May 30, 2019

(87) PCT Pub. No.: WO2018/118670
PCT Pub. Date: Jun. 28, 2018

(65) Prior Publication Data
US 2019/0337961 A1    Nov. 7, 2019

Related U.S. Application Data

(60) Provisional application No. 62/436,815, filed on Dec. 20, 2016.

(51) Int. Cl.
| | |
|---|---|
| C07D 491/107 | (2006.01) |
| A61P 3/10 | (2006.01) |
| C07D 311/96 | (2006.01) |
| C07D 405/12 | (2006.01) |

(52) U.S. Cl.
CPC ............ C07D 491/107 (2013.01); A61P 3/10 (2018.01); C07D 311/96 (2013.01); C07D 405/12 (2013.01)

(58) Field of Classification Search
CPC .......................... C07D 311/96; C07D 491/107
See application file for complete search history.

(56) References Cited

FOREIGN PATENT DOCUMENTS

| | | |
|---|---|---|
| EP | 1805141 B1 | 1/2010 |
| GB | 2498976 A | 7/2013 |
| WO | WO1993025527 A1 | 12/1993 |
| WO | WO2004022551 A1 | 3/2004 |
| WO | WO2004041266 A1 | 5/2004 |
| WO | WO2005051373 A1 | 6/2005 |
| WO | WO2005051890 A1 | 6/2005 |
| WO | WO2005063729 A1 | 7/2005 |
| WO | WO2005086661 A2 | 9/2005 |
| WO | WO2005087710 A1 | 9/2005 |
| WO | WO2006038738 A1 | 4/2006 |
| WO | WO2006083612 A1 | 8/2006 |
| WO | WO2006083781 A1 | 8/2006 |
| WO | WO2006127503 A2 | 11/2006 |
| WO | WO2007013689 A1 | 2/2007 |
| WO | WO2007033002 A1 | 3/2007 |
| WO | WO2007106469 A2 | 9/2007 |
| WO | WO2007123225 A1 | 11/2007 |
| WO | WO2007136572 A2 | 11/2007 |
| WO | WO2007136573 A2 | 11/2007 |
| WO | WO2008001931 A2 | 1/2008 |
| WO | WO2008030520 A1 | 3/2008 |
| WO | WO2008030618 A1 | 3/2008 |
| WO | WO2008054674 A2 | 5/2008 |
| WO | WO2008054675 A2 | 5/2008 |
| WO | WO2008066097 A1 | 6/2008 |
| WO | WO2008130514 A1 | 10/2008 |
| WO | WO2009048527 A1 | 4/2009 |
| WO | WO2009058237 A1 | 5/2009 |
| WO | 2009084034 A2 | 7/2009 |

(Continued)

OTHER PUBLICATIONS

Poitput. Drug Discovery Today, 2013, 18 (23/24), 1301-1308 (Year: 2013).*
"NDEP | Information and tips on diabetes prevention", http://ndep.nih.gov/diabetes/prev/prevention.htm, accessed May 26, 2009 (Year: 2009).*
Soukri. Tetrahedron, 2003, 59, 3665-3772 (Year: 2003).*
Dandu. Bioorganic and Medicinal Chemistry Letters, 2012, 22, 2151-53 (Year: 2012).*
Parenti. Journal of Medicinal Chemistry, 2014, 57, 479-4804 (Year: 2014).*

(Continued)

*Primary Examiner* — Noble E Jarrell
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

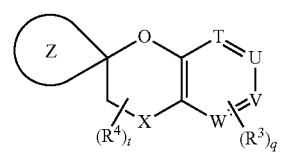

(I)

19 Claims, No Drawings

(56) References Cited

FOREIGN PATENT DOCUMENTS

| | | |
|---|---|---|
| WO | WO2009111056 A1 | 9/2009 |
| WO | 2010002010 A1 | 1/2010 |
| WO | WO2010004347 A1 | 1/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2010143733 A1 | 12/2010 |
| WO | WO2012072691 A1 | 6/2012 |
| WO | WO2013122028 A1 | 8/2013 |
| WO | WO2013122029 A1 | 8/2013 |
| WO | WO2016022448 A1 | 2/2016 |
| WO | WO2016022742 A1 | 2/2016 |

OTHER PUBLICATIONS

Briscoe, C. P. et al., The Orphan G Protein-coupled Receptor GPR40 Is Activated by Medium and Long Chain Fatty Acids, The Journal of Biological Chemistry, 2003, 11303-11311, No. 13, 278.

Brown, S. P. et al., Discovery of AM-1638: A Potent and Orally Bioavailable GPR40/FFA1 Full Agonist, American Chemical Society, 2012, p. 726-730, vol. 3.

Executive Summary, Detection, Evaluation, and Treatment of High Blood Cholesterol in Adults (Adult Treatment Panel III), National Institutes of Health, 2001, pp. 1-40, NIH Publication No. 01-3670.

Houze, J. B. et al., 265-AMG 837: A potent, orally bioavailable, partial allosteric agonist of GPR40, MEDI, 2012, p. 1, Abstracts of Papers, 243rd ACS National Meeting & Exposition, San Diego, CA, Mar. 25-29, 2012.

Houze, J. B. et al., AMG 837: A potent, orally bioavailable GPR40 agonist, Bioorganic & Medicinal Chemistry Letters, 2012, p. 1267-1270, vol. 22.

Itoh, Y. et al., Free fatty acids regulate insulin secretion from pancreatic B cells through GPR40, Nature, 2003, 173-176, 422.

Kotarsky, K. et al., A human cell surface receptor activated by free fatty acids and thiazolidinedione drugs, Biochemical and Biophysical Research Communications, 2003, 406-410, 301.

Lin, D. C. H. et al., Identification and Pharmacological Characterization of Multiple Allosteric Binding Sites on the Free Fatty Acid 1 Receptor, Molecular Pharmacology, 2012, p. 843-859, vol. 82, No. 5.

Lin, D. D. H. et al., AMG 837: A Novel GPR40/FFA1 Agonist that Enhances Insulin Secretion and Lowers Glucose Levels in Rodents, PLoS ONE, 2011, p. 1-10, vol. 6, No. 11.

Lou, J. et al., A Potent Class of GPR40 Full Agonist Engages the EnteroInsular Axis to Promote Glucose Control in Rodents, PLOS ONE, 2012, p. 6-12, vol. 7, Issue 10.

Pubchem, Compound-WQLZATQJGJRBEJ-UHFFFAOYSA-N, Create Date Jan. 31, 2011.

Tan, C. P. et al., Selective Small-Molecule Agonists of G Protein-Coupled Receptor 40 Promote Glucose-Dependen Insulin Secretion and Reduce Blood Glucose in Mice, Diabetes, 2008, p. 2211-2219, vol. 57.

Walsh, S. P. et al., 3-Substituted 3-(4-aryloxyaryl)-propanoic acids as GPR40 agonists, Bioorganic & Medicinal Chemistry Letters, 2011, p. 3390-3394, vol. 21.

Yang, L., 313—Discovery of selective small molecule GPR40 agonists as antidiabetic compounds, MEDI, 2010, p. 1, Abstracts of Papers, 239th ACS Meeting, San Francisco, CA, Mar. 21-25.

Zhou, C. et al., Discovery of 5-aryloxy-2,4-thiazolidinediones as potent GPR40 agonists, Bioorganic & Medicinal Chemistry Letters, 2010, p. 1298-1301, vol. 20.

Yamato, M. et al., Synthesis and structure-activity relationship of spiro[isochroman-piperidine] analogs for inhibition of histamine release, Chem. Pharm. Bull., 1981, 3494-3498, 29(12).

* cited by examiner

ANTIDIABETIC SPIROCHROMAN COMPOUNDS

CROSS-REFERENCE TO RELATED APPLICATIONS

This application is a U.S. National Phase application under 35 U.S.C. § 371 of PCT Application No. PCT/US2017/066568, filed on Dec. 15, 2017, which claims priority from and the benefit of U.S. Provisional Application Ser. No. 62/436,815, filed Dec. 20, 2016.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body. Patients having Type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results induction and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide, liraglutide, dulaglutide, semaglutide, lixisenatide, albiglutide and taspoglutide); (5) inhibitors of incretin hormone degradation (DPP-4 inhibitors, such as sitagliptin, alogliptin, vildagliptin, linagliptin, denagliptin and saxagliptin); and SGLT2 inhibitors (canagliflozin, dapagliflozin and empagliflozin).

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature*, 422: 173 (2003); Briscoe, C. P. et al., *J. Biol. Chem.*, 278: 11303 (2003); Kotarsky, K. et al., *Biochem. Biophys. Res. Comm.*, 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a potential target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent GPR40 agonists that have pharmacokinetic and pharmacodynamic properties suitable for use as human pharmaceuticals.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030520, WO 2008/030618, WO 2008/054674, WO 2008/054675, WO 2008/066097, WO 2008/130514, WO 2009/048527, WO 2009/058237, WO 2009/111056, WO 2010/004347, WO 2010/045258, WO 2010/085522, WO 2010/085525, WO 2010/085528, WO 2010/091176, WO 2010/143733, WO 2012/0004187, WO 2012/072691, WO 2013/122028, WO2013/122029, WO 2015/024448, and GB 2498976.

GPR40 agonists are also disclosed in Walsh et al., Bioorganic & Medicinal Chemistry Letters (2011), 21(11), 3390-3394; Zhou et al., Bioorganic & Medicinal Chemistry Letters (2010), 20(3), 1298-1301; Tan et al., Diabetes (2008), 57(8), 2211-2219; Houze et al., Bioorganic & Medicinal Chemistry Letters (2012), 22(2), 1267-1270; Brown et al., ACS Medicinal Chemistry Letters (2012), 3(9), 726-730; Lin et al., PloS One (2011), 6(11), e27270; Lou et al., PloS One (2012), 7(10), e46300; Lin et al., Molecular Pharmacology (2012), 82(5), 843-859; Yang, Lihu, Abstracts of Papers, 239th ACS Meeting, San Francisco, Calif., USA Mar. 21-25, 2010 MEDI-313; and Houze et al., Abstracts of Papers, 243rd ACS National Meeting & Exposition, San Diego, Calif., USA Mar. 25-29, 2012, MEDI-265.

SUMMARY OF THE INVENTION

The present invention relates to novel substituted compounds of structural formula I:

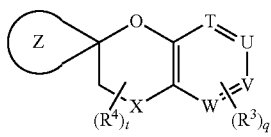

and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

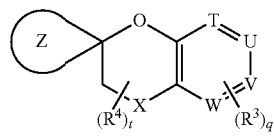

or a pharmaceutically acceptable salt thereof; wherein
T is selected from the group consisting of:
  (1) CH,
  (2) N, and
  (3) N-oxide;
U is selected from the group consisting of:
  (1) $CR^1$,
  (2) N, and
  (3) N-oxide;
V is selected from the group consisting of:
  (1) $CR^2$,
  (2) N, and
  (3) N-oxide;
W is selected from the group consisting of:
  (1) CH,
  (2) N, and
  (3) N-oxide,
provided that no more than two of T, U, V and W are selected from N and N-oxide, further provided that if both T and W are N or N-oxide, then $R^3$ is absent, and further provided that both U and V are not N or N-oxide;
X is selected from the group consisting of:
  (1) oxygen,
  (2) sulfur,
  (3) —$CR^bR^b$,
  (4) —C=O, and
  (5) —$C(R^b)OR^b$, and
  (6) $N(R^b)$;

Z is selected from:

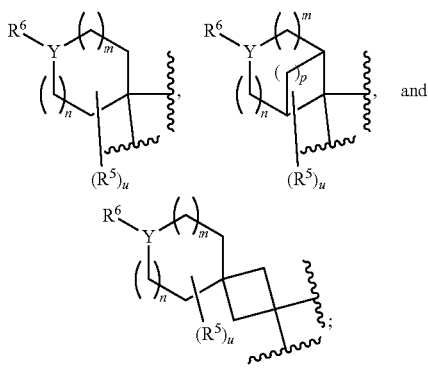

Y is selected from the group consisting of:
(1) —C(R$^g$)—,
(2) —C(F)—, and
(3) —N—;

R$^1$ and R$^2$ are each independently selected from:
(1) a bond,
(2) hydrogen,
(3) halogen,
(4) —OR$^k$,
(5) —CN,
(6) —C$_{1-6}$alkyl,
(7) C$_{3-6}$cycloalkyl,
(8) C$_{3-6}$cycloalkyl-C$_{1-3}$alkyl-,
(9) C$_{2-6}$cycloheteroalkyl, and
(10) C$_{2-6}$cycloheteroalkyl-C$_{1-3}$alkyl-, wherein each alkyl, cycloalkyl and cycloheteroalkyl is unsubstituted or substituted with one to three R$^L$ substituents, and wherein one of R$^1$ and R$^2$ is substituted with R$^7$, or R$^1$ and R$^2$ together with the atom(s) to which they are attached form a C$_{3-6}$cycloalkyl ring or a C$_{2-5}$cycloheteroalkyl ring, wherein each R$^1$ and R$^2$ is unsubstituted or substituted with one to three substituents selected from R$^L$, and wherein one of R$^1$ and R$^2$ is substituted with R$^7$;

each R$^3$ is independently selected from the group consisting of:
(1) hydrogen,
(2) halogen,
(3) —CN,
(4) —CF$_3$, and
(5) —C$_{1-6}$alkyl;

R$^4$ is independently selected from the group consisting of:
(1) hydrogen,
(2) halogen,
(3) —CF$_3$, and
(4) —C$_{1-6}$alkyl;

R$^5$ is independently selected from the group consisting of:
(1) hydrogen,
(2) halogen,
(3) —CN,
(4) —CF$_3$,
(5) —C$_{1-6}$alkyl, and
(6) —C$_{1-5}$spirocycloalkyl, or two R$^5$ groups, and the carbons they are attached to, form a —C$_{3-6}$cycloalkyl ring or a —C$_{2-5}$cycloheteroalkyl ring;

R$^6$ is selected from the group consisting of:
(1) aryl,
(2) aryl-SO$_2$—,
(3) aryl-C$_{1-10}$ alkyl-,
(4) aryl-N(R$^i$)—,
(5) aryl-C$_{1-10}$ alkyl-N(R$^i$)—,
(6) heteroaryl,
(7) heteroaryl-SO$_2$—,
(8) heteroaryl-C$_{1-10}$ alkyl-,
(9) heteroaryl-N(R$^i$)—, and
(10) heteroaryl-C$_{1-10}$ alkyl-N(R$^i$)—, wherein each CH$_2$ is unsubstituted or substituted with 1-2 substituents selected from R$^a$, and wherein each alkyl, aryl, and heteroaryl is unsubstituted or substituted with 1-5 substituents selected from R$^a$;

R$^7$ is selected from the group consisting of:
(1) —CO$_2$R$^8$,
(2) —C$_{1-6}$alkyl-CO$_2$R$^8$,
(3) —C$_{1-6}$alkyl-CONHSO$_2$R$^m$,
(4) —C$_{1-6}$alkyl-SO$_2$NHCOR$^m$,
(5) —C$_{1-6}$alkyl-tetrazolyl, and
(6) a cycloheteroalkyl selected from the group consisting of:

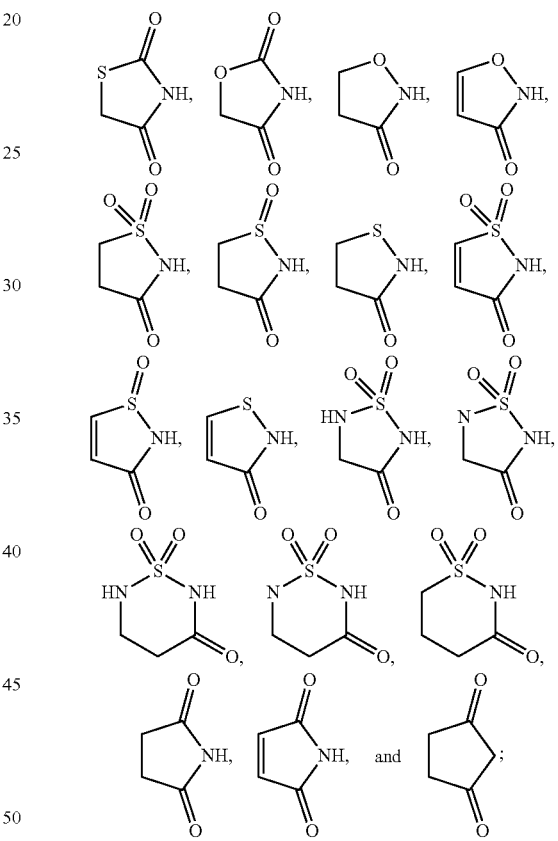

R$^8$ is selected from the group consisting of:
(1) hydrogen,
(2) —C$_{1-6}$alkyl,
(3) —C$_{3-6}$cycloalkyl, and
(4) aryl-C$_{1-6}$alkyl, wherein each alkyl, cycloalkyl and aryl is unsubstituted or substituted with one to three substituents selected from R$^j$;

R$^a$ is selected from the group consisting of:
(1) —C$_{1-6}$alkyl,
(2) —OC$_{1-6}$alkyl,
(3) halogen,
(4) —S(O)$_n$R$^e$,
(5) —S(O)$_n$NR$^c$R$^d$,
(6) —NR$^c$R$^d$,
(7) —C(O)R$^e$, (8) —OC(O)$R^e$,
(9) —$CO_2R^e$,
(10) —CN,
(11) —C(O)$NR^cR^d$,
(12) —$CF_3$,
(13) —$OCF_3$,
(14) —$OCHF_2$,
(15) —$OCH_2CF_3$,
(16) aryl,
(17) heteroaryl,
(18) —$C_{3-6}$cycloalkyl, and
(19) —$C_{2-5}$cycloheteroalkyl, wherein each alkyl, cycloalkyl, cycloheteroalkyl, aryl and heteroaryl is unsubstituted or substituted with 1-3 substituents selected from: halogen, —$C_{1-6}$alkyl, —O—$C_{1-6}$alkyl, —$CF_3$, $CO_2H$, and —$CO_2C_{1-6}$alkyl;

each $R^b$ is independently selected from the group consisting of:
(1) hydrogen,
(2) —C(O)$R^d$, and
(3) —$C_{1-10}$alkyl, wherein each alkyl is unsubstituted or substituted with one to five halogens;

$R^c$ and $R^d$ are each independently selected from the group consisting of:
(1) hydrogen,
(2) $C_{1-10}$alkyl,
(3) $C_{2-10}$alkenyl,
(4) $C_{3-6}$cycloalkyl,
(5) $C_{3-6}$ cycloalkyl-$C_{1-10}$alkyl-,
(6) $C_{2-5}$cycloheteroalkyl,
(7) $C_{2-5}$cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-, wherein each alkyl, alkenyl, cycloalkyl, cycloheteroalkyl, aryl and heteroaryl is unsubstituted or substituted with one to three $R^f$ substituents;

each $R^e$ is independently selected from the group consisting of:
(1) hydrogen,
(2) —$C_{1-10}$alkyl,
(3) —$C_{2-10}$ alkenyl,
(4) —$C_{3-6}$ cycloalkyl,
(5) —$C_{3-6}$ cycloalkyl-$C_{1-10}$alkyl-,
(6) —$C_{2-5}$cycloheteroalkyl,
(7) —$C_{2-5}$cycloheteroalkyl-$C_{1-10}$alkyl-,
(8) aryl,
(9) aryl-$C_{1-10}$alkyl-,
(10) heteroaryl, and
(11) heteroaryl-$C_{1-10}$alkyl-, wherein each alkyl, alkenyl, cycloalkyl, cycloheteroalkyl, aryl and heteroaryl is unsubstituted or substituted with one to three substituents selected from $R^h$;

each $R^f$ is selected from the group consisting of:
(1) halogen,
(2) $C_{1-10}$alkyl,
(3) —OH,
(4) —O—$C_{1-4}$alkyl,
(5) —S(O)$_m$—$C_{1-4}$alkyl,
(6) —CN,
(7) —$CF_3$,
(8) —$OCHF_2$, and
(9) —$OCF_3$, wherein each alkyl is unsubstituted or substituted with one to three substituents independently selected from: —OH, halogen, $C_{1-6}$alkyl, cyano and $S(O)_2C_{1-6}$alkyl;

$R^g$ is selected from the group consisting of:
(1) hydrogen, and
(2) —$C_{1-10}$alkyl, wherein each alkyl is unsubstituted or substituted with one to five halogens;

each $R^h$ is selected from the group consisting of:
(1) halogen,
(2) $C_{1-10}$alkyl,
(3) —OH,
(4) —O—$C_{1-4}$alkyl,
(5) —S(O)$_m$—$C_{1-4}$alkyl,
(6) —CN,
(7) —$CF_3$,
(8) —$OCHF_2$, and
(9) —$OCF_3$, wherein each alkyl is unsubstituted or substituted with one to three substituents independently selected from: —OH, halogen, $C_{1-6}$alkyl, cyano and $S(O)_2C_{1-6}$alkyl;

$R^i$ is independently selected from the group consisting of:
(1) hydrogen, and
(2) —$C_{1-6}$alkyl;

$R^j$ is independently selected from the group consisting of:
(1) —$C_{1-6}$alkyl,
(2) —$OR^e$,
(3) —$NR^cS(O)_mR^e$,
(4) halogen,
(5) —$S(O)_mR^e$,
(6) —$S(O)_mNR^cR^d$,
(7) —$NR^cR^d$,
(8) —C(O)$R^e$,
(9) —OC(O)$R^e$,
(10) —$CO_2R^e$,
(11) —CN,
(12) —C(O)$NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;

each $R^k$ is independently selected from the group consisting of:
(1) —$C_{1-10}$alkyl,
(2) —$C_{2-10}$ alkenyl,
(3) —$C_{3-6}$ cycloalkyl,
(4) —$C_{3-6}$ cycloalkyl-$C_{1-10}$alkyl-,
(5) —$C_{2-5}$cycloheteroalkyl,
(6) —$C_{2-5}$cycloheteroalkyl-$C_{1-10}$alkyl-,
(7) aryl,
(8) heteroaryl,
(9) aryl-$C_{1-10}$alkyl-, and
(10) heteroaryl-$C_{1-10}$alkyl-;

each $R^L$ is independently selected from the group consisting of:
(1) —$CO_2C_{1-6}$alkyl,
(2) —$C_{1-10}$alkyl,
(3) —$C_{2-10}$ alkenyl,
(4) —$C_{2-10}$alkynyl,
(5) —$C_{3-6}$cycloalkyl,
(6) —$C_{2-6}$cycloheteroalkyl,
(7) aryl, and
(8) heteroaryl, wherein each alkyl, alkenyl, alkynyl, cycloalkyl, cycloheteroalkyl, aryl and heteroaryl is unsubstituted or substituted with 1-4 substituents selected from $C_{1-6}$alkyl, halogen, and —$OC_{1-6}$alkyl;

each n is independently selected from: 0, 1 or 2;
each m is independently selected from: 0, 1 or 2;
each p is independently selected from: 0, 1, or 2;
each q is independently selected from: 0, 1 or 2;
each t is independently selected from: 0, 1 or 2; and
each u is independently selected from: 0, 1, 2, or 3.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, T is selected from the group consisting of: CH, N and N-oxide. In a class of this embodiment, T is selected from the group consisting of: CH and N. In another class of this embodiment, T is CH. In another class of this embodiment, T is N or N-oxide. In another class of this embodiment, T is N. In another class of this embodiment, T is N-oxide.

In another embodiment of the present invention, U is selected from the group consisting of: $CR^1$, N and N-oxide. In a class of this embodiment, U is selected from the group consisting of: $CR^1$ and N. In another class of this embodiment, U is $CR^1$. In another class of this embodiment, U is N or N-oxide. In another class of this embodiment, U is N. In another class of this embodiment, U is N-oxide.

In another embodiment of the present invention, V is selected from the group consisting of: $CR^2$, N and N-oxide. In a class of this embodiment, V is selected from the group consisting of: $CR^2$ and N.

In another class of this embodiment, V is $CR^2$. In another class of this embodiment, V is N or N-oxide. In another class of this embodiment, V is N. In another class of this embodiment, V is N-oxide.

In another embodiment of the present invention, W is selected from the group consisting of: CH, N and N-oxide, provided that no more than two of T, U, V and W are selected from N and N-oxide, further provided that if both T and W are N or N-oxide, then $R^3$ is absent, and further provided that both U and V are not N or N-oxide. In a class of this embodiment, W is selected from the group consisting of: CH and N, provided that no more than two of T, U, V and W are selected from N and N-oxide, further provided that if both T and W are N or N-oxide, then $R^3$ is absent, and further provided that both U and V are not N or N-oxide. In another class of this embodiment, W is CH, provided that no more than two of T, U, V and W are selected from N and N-oxide, further provided that if both T and W are N or N-oxide, then $R^3$ is absent, and further provided that both U and V are not N or N-oxide. In another class of this embodiment, W is N or N-oxide, provided that no more than two of T, U, V and W are selected from N and N-oxide, further provided that if both T and W are N or N-oxide, then $R^3$ is absent, and further provided that both U and V are not N or N-oxide. In another class of this embodiment, W is N, provided that no more than two of T, U, V and W are selected from N and N-oxide, further provided that if both T and W are N or N-oxide, then $R^3$ is absent, and further provided that both U and V are not N or N-oxide.

In another embodiment of the present invention, W is selected from the group consisting of: CH, N and N-oxide. In a class of this embodiment, W is selected from the group consisting of: CH and N. In another class of this embodiment, W is CH. In another class of this embodiment, W is N or N-oxide. In another class of this embodiment, W is N. In another class of this embodiment, W is N-oxide.

In another embodiment of the present invention, T is CH, U is $CR^1$, V is $CR^2$, and W is CH. In a class of this embodiment, T is CH, U is $CR^1$, V is CH, and W is CH. In another class of this embodiment, T is CH, U is CH, V is $CR^2$, and W is CH.

In another embodiment of the present invention, T is N or N-oxide, U is $CR^1$, V is $CR^2$, and W is CH. In a class of this embodiment, T is N, U is $CR^1$, V is $CR^2$, and W is CH.

In another embodiment of the present invention, T is CH, U is N or N-oxide, and V is $CR^2$, and W is CH. In a class of this embodiment, T is CH, U is N, V is $CR^2$, and W is CH.

In another embodiment of the present invention, T is CH, U is $CR^1$, V is N or N-oxide, and W is CH. In a class of this embodiment, T is CH, U is $CR^1$, and V is N or N-oxide, and W is CH.

In another embodiment of the present invention, T is CH, U is $CR^1$, V is $CR^2$, and W is CH, N or N-oxide.

In another embodiment of the present invention, T is CH, U is $CR^1$, V is $CR^2$, and W is N or N-oxide. In a class of this embodiment, T is CH, U is $CR^1$, V is $CR^2$, and W is N.

In another embodiment of the present invention, T is N or N-oxide, U is N or N-oxide, V is $CR^2$, and W is CH. In a class of this embodiment, T is N, U is N, V is $CR^2$, and W is CH.

In another embodiment of the present invention, T is N or N-oxide, U is $CR^1$, V is N or N-oxide, and W is CH. In a class of this embodiment, T is N, U is $CR^1$, V is N, and W is CH.

In another embodiment of the present invention, T is N or N-oxide, U is $CR^1$, V is $CR^2$, and W is N or N-oxide. In a class of this embodiment, T is N, U is $CR^1$, V is $CR^2$, and W is N.

In another embodiment of the present invention, T is N or N-oxide, U is $CR^1$, V is $CR^2$, and W is N or N-oxide; and $R^3$ is absent. In a class of this embodiment, T is N, U is $CR^1$, V is $CR^2$, and W is N; and $R^3$ is absent.

In another embodiment of the present invention, T is CH, U is N or N-oxide, V is $CR^2$, and W is N or N-oxide. In a class of this embodiment, T is CH, U is N, V is $CR^2$, and W is N.

In another embodiment of the present invention, T is CH, U is $CR^1$, V is N or N-oxide, and W is N or N-oxide. In a class of this embodiment, T is CH, U is $CR^1$, V is N, and W is N.

In another embodiment of the present invention, T is CH; U is $CR^1$; V is $CR^2$; and W is CH, N or N-oxide.

In another embodiment of the present invention, X is selected from the group consisting of: —$C(R^b)(R^b)$, C=O, and —$C(R^b)OR^b$. In a class of this embodiment, X is selected from the group consisting of: $CH_2$, C=O, and —CH(OH).

In another embodiment of the present invention, X is C=O.

In another embodiment of the present invention, X is —$C(R^b)OR^b$. In a class of this embodiment, X is —CH(OH).

In another embodiment of the present invention, X is —$C(R^b)(R^b)$. In a class of this embodiment, X is $CH_2$.

In another embodiment of the present invention, Y is selected from the group consisting of: —$C(R^g)$—, and —N—. In a class of this embodiment, Y is selected from the group consisting of: —C(H)—, and —N—.

In another embodiment of the present invention, Y is —$C(R^g)$—. In a class of this embodiment, Y is —C(H)—.

In another embodiment of the present invention, Y is —N—.

In another embodiment of the present invention, Z is selected from:

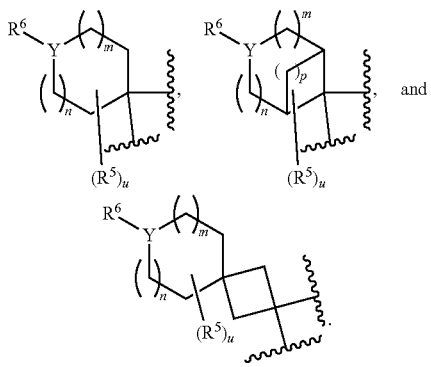

In a class of this embodiment, Z is selected from:

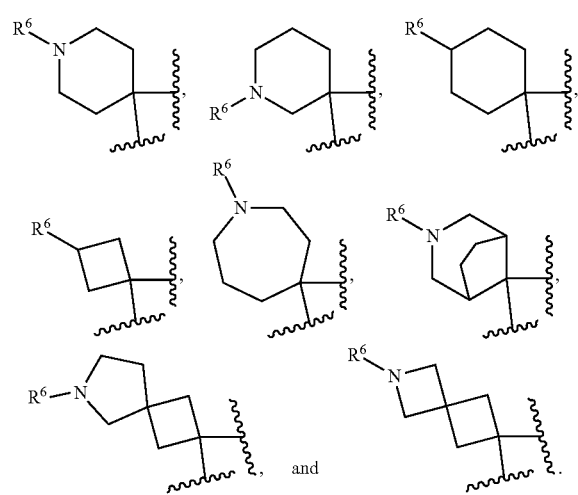

In another embodiment of the present invention, Z is selected from:

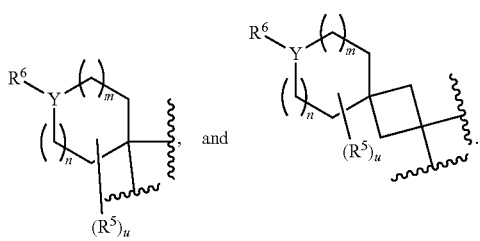

In a class of this embodiment, Z is selected from:

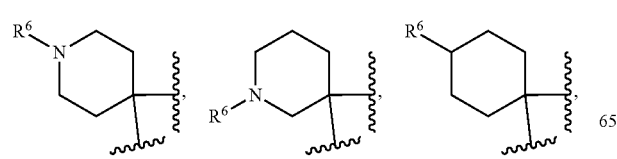

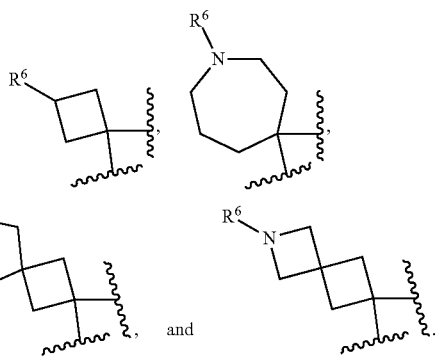

In another embodiment of the present invention, Z is

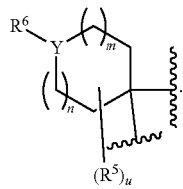

In a class of this embodiment, Z is selected from:

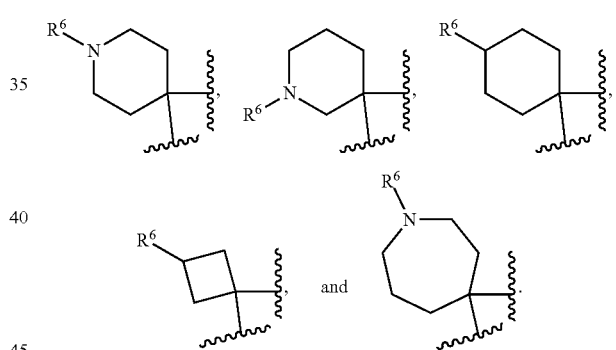

In another class of this embodiment, Z is

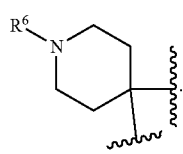

In another class of this embodiment, Z is

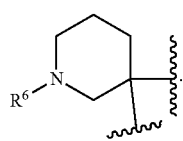

In another class of this embodiment, Z is

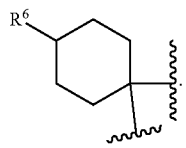

In another class of this embodiment, Z is

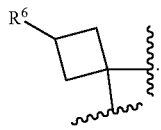

In another class of this embodiment, Z is

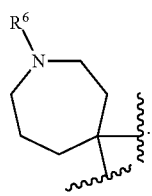

In another embodiment of the present invention, Z is:

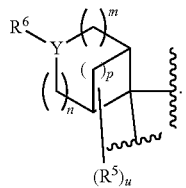

In a class of this embodiment, Z is

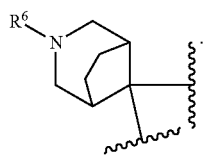

In another embodiment of the present invention, Z is:

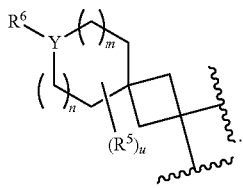

In a class of this embodiment, Z is selected from:

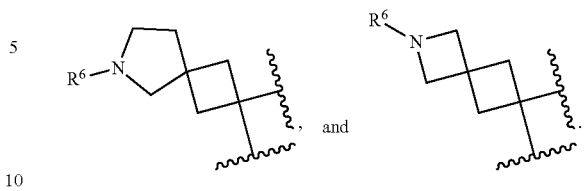

In another class of this embodiment of the present invention, Z is:

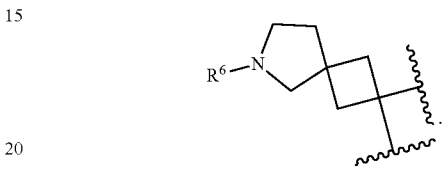

In another class of this embodiment, Z is:

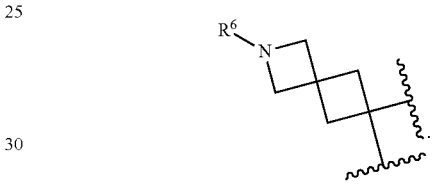

In another embodiment of the present invention, $R^1$ and $R^2$ are each independently selected from: a bond, hydrogen, —$OR^k$ and —$C_{1-6}$alkyl, wherein each alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with $R^7$. In a class of this embodiment, $R^1$ and $R^2$ are each independently selected from: a bond, hydrogen, —$OR^k$ and —$C_{1-6}$alkyl, wherein each alkyl is unsubstituted or substituted with one to three substituents selected from $R^L$, and wherein one of $R^1$ and $R^2$ is substituted with $R^7$.

In another embodiment of the present invention, $R^1$ and $R^2$ are each independently selected from: a bond, hydrogen, —OH, —$OC_{1-6}$alkyl and $C_{1-6}$alkyl, wherein each alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ and $R^2$ are each independently selected from: a bond, hydrogen, —OH, —$OC_{1-6}$alkyl, and $C_{1-6}$alkyl, wherein each alkyl is unsubstituted or substituted with one to three substituents selected from $R^L$, and wherein one of $R^1$ and $R^2$ is substituted with $R^7$.

In another embodiment of the present invention, $R^1$ and $R^2$ are each independently selected from: a bond, hydrogen, and —$C_{1-6}$alkyl, wherein each alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ and $R^2$ are each independently selected from: a bond, hydrogen and —$C_2$alkyl, wherein each alkyl is unsubstituted or substituted with one to three substituents selected from $R^L$, and wherein one of $R^1$ and $R^2$ is substituted with $R^7$.

In another embodiment of the present invention, $R^1$ and $R^2$ are each independently selected from: hydrogen and —$C_{1-6}$alkyl, wherein each alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^1$ and $R^2$ are each independently selected from: hydrogen and —$C_{1-6}$alkyl, wherein each alkyl is unsubstituted or substituted with one to three substituents selected from $R^L$, and wherein one of $R^1$ and $R^2$ is substituted with $R^7$. In another class of this embodiment, $R^1$ and $R^2$ are each independently selected from: hydrogen and $C_2$alkyl-, wherein each alkyl is unsubstituted or substituted with one to three substituents selected from $R^L$, and wherein one of $R^1$ and $R^2$ is substituted with $R^7$.

In another embodiment, $R^1$ is independently selected from: a bond, hydrogen, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^1$ is independently selected from: a bond, hydrogen, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is substituted with $R^7$.

In another embodiment of the present invention, $R^1$ is independently selected from: a bond, hydrogen, —$OR^k$ and —$C_{1-6}$alkyl, wherein each alkyl is unsubstituted or substituted with one to three substituents selected from $R^L$, and wherein $R^1$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^1$ is independently selected from: a bond, hydrogen, —$OR^k$ and —$C_{1-6}$alkyl, wherein each alkyl is unsubstituted or substituted with one to three substituents selected from $R^L$, and wherein $R^1$ is substituted with $R^7$.

In another embodiment of the present invention, $R^1$ is selected from: a bond, hydrogen, —OH, —$OC_{1-6}$alkyl and —$C_{1-6}$alkyl, wherein each alkyl is unsubstituted or substituted with one to three substituents selected from $R^L$, and wherein $R^1$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ is selected from: a bond, hydrogen, —OH, —$OC_{1-6}$alkyl, and —$C_{1-6}$alkyl-, wherein each alkyl is unsubstituted or substituted with one to three substituents selected from $R^L$, and wherein $R^1$ is substituted with $R^7$.

In another embodiment of the present invention, $R^1$ is selected from: a bond, hydrogen, and —$C_{1-6}$alkyl, wherein each alkyl is unsubstituted or substituted with one to three substituents selected from $R^L$, and wherein $R^1$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^1$ is selected from: a bond, hydrogen, and —$C_{1-6}$alkyl, wherein each alkyl is unsubstituted or substituted with one to three substituents selected from $R^L$, and wherein $R^1$ is substituted with $R^7$. In another class of this embodiment, $R^1$ is selected from: a bond, hydrogen and $C_2$alkyl-, wherein each alkyl is unsubstituted or substituted with one to three substituents selected from $R^L$, and wherein $R^1$ is substituted with $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ is selected from: a bond, hydrogen and $C_2$alkyl-, wherein each alkyl is unsubstituted or substituted with one to three substituents selected from $R^L$, and wherein $R^1$ is substituted with $R^7$.

In another embodiment of the present invention, $R^1$ is selected from: hydrogen and —$C_{1-6}$alkyl, wherein each alkyl is unsubstituted or substituted with one to three substituents selected from $R^L$, and wherein $R^1$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^1$ is selected from: hydrogen and —$C_{1-6}$alkyl-, wherein each alkyl is unsubstituted or substituted with one to three substituents selected from $R^L$, and wherein $R^1$ is substituted with $R^7$. In another class of this embodiment, $R^1$ is selected from: hydrogen and $C_2$alkyl-, wherein each alkyl is unsubstituted or substituted with one to three substituents selected from $R^L$, and wherein $R^1$ is substituted with $R^7$.

In another embodiment of the present invention, $R^1$ is selected from: —$C_{1-6}$alkyl-, wherein each alkyl is unsubstituted or substituted with one to three substituents selected from $R^L$, and wherein $R^1$ is substituted with $R^7$. In a class of this embodiment, $R^1$ is $C_2$alkyl-, wherein each alkyl is unsubstituted or substituted with one to three substituents selected from $R^L$, and wherein $R^1$ is substituted with $R^7$.

In another embodiment of the present invention, $R^1$ is hydrogen.

In another embodiment, $R^1$ is independently selected from: a bond, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is substituted with $R^7$; and $R^2$ is hydrogen.

In another embodiment of the present invention, $R^1$ is selected from: a bond, —$OR^k$ and —$C_{1-6}$alkyl, wherein each alkyl is unsubstituted or substituted with one to three substituents selected from $R^L$, and wherein $R^1$ is substituted with $R^7$; and $R^2$ is hydrogen. In a class of this embodiment, $R^1$ is selected from: a bond, —OH, —$OC_{1-6}$alkyl, and —$C_{1-6}$alkyl-, wherein each alkyl is unsubstituted or substituted with one to three substituents selected from $R^L$, and wherein $R^1$ is substituted with $R^7$; and $R^2$ is hydrogen.

In another embodiment of the present invention, $R^1$ is selected from: —$C_{1-6}$alkyl, wherein each alkyl is unsubstituted or substituted with one to three substituents selected from $R^L$, and wherein $R^1$ is substituted with $R^7$; and $R^2$ is hydrogen. In a class of this embodiment, $R^1$ is selected from: $C_2$alkyl-, wherein each alkyl is unsubstituted or substituted with one to three substituents selected from $R^L$, and wherein $R^1$ is substituted with $R^7$; and $R^2$ is hydrogen.

In another embodiment, $R^2$ is independently selected from: a bond, hydrogen, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$ cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^2$ is independently selected from: a bond, hydrogen, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$.

In another embodiment of the present invention, $R^2$ is independently selected from: a bond, hydrogen, —$OR^k$ and —$C_{1-6}$alkyl, wherein each alkyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^2$ is selected from: a bond, hydrogen, —$OR^k$ and —$C_{1-6}$alkyl, wherein each alkyl is unsubstituted or substituted with one to three substituents selected from $R^L$, and wherein $R^2$ is substituted with $R^7$. In another class of this embodiment, $R^2$ is selected from: a bond, hydrogen, —OH, —$OC_{1-6}$alkyl, and —$C_{1-6}$alkyl-, wherein each alkyl is unsubstituted or substituted with one to three substituents selected from $R^L$, and wherein $R^2$ is substituted with $R^7$.

In another embodiment of the present invention, $R^2$ is selected from: a bond, hydrogen, and —$C_{1-6}$alkyl, wherein each alkyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^2$ is selected from: a bond, hydrogen, and —$C_{1-6}$alkyl, wherein each alkyl is unsubstituted or substituted with one to three substituents selected from $R^L$, and wherein $R^2$ is substituted with $R^7$. In another class of this embodiment, $R^2$ is selected from: a bond, hydrogen and $C_2$alkyl-, wherein each alkyl is unsubstituted or substituted with one to three substituents selected from $R^L$, and wherein $R^2$ is substituted with $R^7$.

In another embodiment of the present invention, $R^2$ is selected from: hydrogen and —$C_{1-6}$alkyl-, wherein each alkyl is unsubstituted or substituted with one to three substituents selected from $R^L$, and wherein $R^2$ is substituted with $R^7$. In another class of this embodiment, $R^2$ is selected from: hydrogen and $C_2$alkyl-, wherein each alkyl is unsubstituted or substituted with one to three substituents selected from $R^L$, and wherein $R^2$ is substituted with $R^7$.

In another embodiment of the present invention, $R^2$ is selected from: —$C_{1-6}$alkyl-, wherein each alkyl is unsubstituted or substituted with one to three substituents selected from $R^L$, and wherein $R^2$ is substituted with $R^7$. In another class of this embodiment, $R^2$ is $C_2$alkyl-, wherein each alkyl is unsubstituted or substituted with one to three substituents selected from $R^L$, and wherein $R^2$ is substituted with $R^7$.

In another embodiment of the present invention, $R^2$ is hydrogen.

In another embodiment, $R^2$ is independently selected from: a bond, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$; and $R^1$ is hydrogen.

In another embodiment of the present invention, $R^2$ is selected from: a bond, —$OR^k$ and —$C_{1-6}$alkyl, wherein each alkyl is unsubstituted or substituted with one to three substituents selected from $R^L$, and wherein $R^2$ is substituted with $R^7$; and $R^1$ is hydrogen. In a class of this embodiment, $R^2$ is selected from: a bond, —OH, —$OC_{1-6}$alkyl, and —$C_{1-6}$alkyl-, wherein each alkyl is unsubstituted or substituted with one to three substituents selected from $R^L$, and wherein $R^2$ is substituted with $R^7$; and $R^1$ is hydrogen.

In another embodiment of the present invention, $R^2$ is selected from: a bond and $C_2$alkyl-, wherein each alkyl is unsubstituted or substituted with one to three substituents selected from $R^L$, and wherein $R^2$ is substituted with $R^7$; and $R^1$ is hydrogen.

In another embodiment of the present invention, $R^2$ is selected from: —$C_{1-6}$alkyl, wherein each alkyl is unsubstituted or substituted with one to three substituents selected from $R^L$, and wherein $R^2$ is substituted with $R^7$; and $R^1$ is hydrogen. In a class of this embodiment, $R^2$ is selected from: $C_2$alkyl-, wherein each alkyl is unsubstituted or substituted with one to three substituents selected from $R^L$, and wherein $R^2$ is substituted with $R^7$; and $R^1$ is hydrogen.

In another embodiment of the present invention, when present, $R^3$ is selected from the group consisting of: hydrogen, halogen, CN and —$C_{1-6}$alkyl.

In another embodiment of the present invention, when present, $R^3$ is selected from the group consisting of: hydrogen, halogen and —$C_{1-6}$alkyl.

In another embodiment of the present invention, when present, $R^3$ is selected from the group consisting of: hydrogen and halogen. In a class of this embodiment, $R^3$ is selected from the group consisting of: hydrogen and fluorine.

In another embodiment of the present invention, when present, $R^3$ is hydrogen.

In another embodiment of the present invention, when present, $R^3$ is halogen. In a class of this embodiment, $R^3$ is F.

In another embodiment, when present, $R^3$ is selected from the group consisting of: hydrogen and —$C_{1-6}$alkyl. In another embodiment of the present invention, $R^3$ is —$C_{1-6}$alkyl.

In another embodiment of the present invention, $R^4$ is independently selected from the group consisting of: hydrogen, halogen, and —$C_{1-6}$alkyl.

In another embodiment of the present invention, $R^4$ is independently selected from the group consisting of: hydrogen, and —$C_{1-6}$alkyl.

In another embodiment of the present invention, $R^4$ is —$C_{1-6}$alkyl.

In another embodiment of the present invention, $R^4$ is hydrogen.

In another embodiment of the present invention, $R^4$ is independently selected from the group consisting of: hydrogen, and halogen.

In another embodiment of the present invention, $R^4$ is halogen.

In another embodiment of the present invention, $R^5$ is independently selected from the group consisting of: hydrogen, halogen, —CN, —$CF_3$, —$C_{1-6}$alkyl, and —$C_{1-5}$spirocycloalkyl. In a class of this embodiment, the spirocycloalkyl is spirocyclopropyl.

In another embodiment of the present invention, $R^5$ is independently selected from the group consisting of: hydrogen, halogen, —CN, —$CF_3$, and —$C_{1-6}$alkyl.

In another embodiment of the present invention, $R^5$ is independently selected from the group consisting of: hydrogen, halogen, —$CF_3$, and —$C_{1-6}$alkyl.

In another embodiment of the present invention, $R^5$ is independently selected from the group consisting of: hydrogen, halogen, —CN, and —$C_{1-6}$alkyl.

In another embodiment of the present invention, $R^5$ is independently selected from the group consisting of: hydrogen, halogen, and —$C_{1-6}$alkyl.

In another embodiment of the present invention, $R^5$ is independently selected from the group consisting of: hydrogen, and —$C_{1-6}$alkyl.

In another embodiment of the present invention, $R^5$ is —$C_{1-6}$alkyl.

In another embodiment of the present invention, $R^5$ is hydrogen.

In another embodiment of the present invention, $R^6$ is selected from the group consisting of: aryl, aryl-$SO_2$—, aryl-$C_{1-10}$ alkyl-, aryl-N($R^i$)—, aryl-$C_{1-10}$ alkyl-N($R^i$)—, heteroaryl, heteroaryl-$SO_2$—, heteroaryl-$C_{1-10}$ alkyl-, heteroaryl-N($R^i$)—, and heteroaryl-$C_{1-10}$ alkyl-N($R^i$)—, wherein each $CH_2$ is unsubstituted or substituted with 1-2 substituents selected from $R^a$, and wherein each alkyl, aryl, and heteroaryl is unsubstituted or substituted with 1-4 substituents selected from $R^a$.

In another embodiment of the present invention, $R^6$ is selected from the group consisting of: aryl, aryl-$SO_2$—, aryl-$C_{1-10}$ alkyl-, aryl-N($R^i$)—, aryl-$C_{1-10}$ alkyl-N($R^i$)—, heteroaryl, heteroaryl-$C_{1-10}$ alkyl-, and heteroaryl-N($R^i$)—, wherein each $CH_2$ is unsubstituted or substituted with 1-2 substituents selected from $R^a$, and wherein each alkyl, aryl, cycloheteroalkyl, and heteroaryl is unsubstituted or substituted with 1-5 substituents selected from $R^a$.

In a class of this embodiment, $R^6$ is selected from the group consisting of: phenyl, phenyl-$SO_2$—, phenyl-$CH_2$—, phenyl-NH, phenyl-N($CH_3$)—, phenyl-$CH_2$—N(H)—, phenyl-$CH_2$—N($CH_3$)—, pyridine, pyrimidine, pyrazine, dihydrobenzofuran, indazole, imidazo[1,2-b]pyridazine, pyridine-$CH_2$—, pyrazole-$CH_2$—, thiazole-$CH_2$—, and pyridine-N($R^i$)—, wherein each $CH_2$ is unsubstituted or substituted with 1-2 substituents selected from $R^a$, and wherein each alkyl, aryl, and heteroaryl is unsubstituted or substituted with 1-5 substituents selected from $R^a$.

In another class of this embodiment, $R^6$ is selected from the group consisting of: phenyl, phenyl-$SO_2$—, phenyl-$CH_2$—, phenyl-NH, phenyl-$CH_2$—N(H)—, pyridine, pyrimidine, pyrazine, dihydrobenzofuran, indazole, imidazo[1,2-b]pyridazine, pyridine-$CH_2$—, pyrazole-$CH_2$—, thiazole-$CH_2$—, and pyridine-N($R^i$)—, wherein each $CH_2$ is unsubstituted or substituted with 1-2 substituents selected from $R^a$, and wherein each alkyl, aryl, and heteroaryl is unsubstituted or substituted with 1-5 substituents selected from $R^a$.

In another embodiment of the present invention, $R^6$ is aryl-$C_{1-10}$ alkyl-, wherein each alkyl and aryl is unsubstituted or substituted with 1-5 substituents selected from $R^a$.

In a class of this embodiment, $R^6$ is phenyl-$CH_2$—, wherein each $CH_2$ is unsubstituted or substituted with 1-2 substituents selected from $R^a$, and wherein each phenyl is unsubstituted or substituted with 1-4 substituents selected from $R^a$.

In another embodiment of the present invention, $R^7$ is selected from the group consisting of: —$CO_2R^8$, —$C_{1-6}$ alkyl-$CO_2R^8$, and a cycloheteroalkyl selected from the group consisting of:

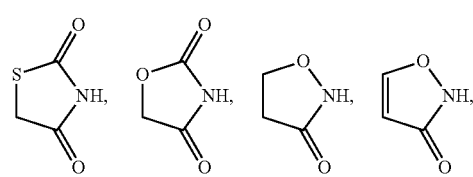

-continued

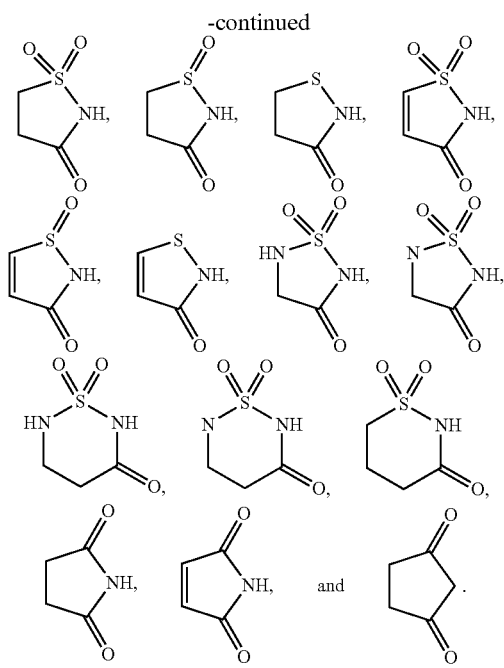

In another class of this embodiment, $R^7$ is selected from the group consisting of: —CO$_2$R$^8$, —C$_{1-6}$alkyl-CO$_2$R$^8$, and a cycloheteroalkyl selected from:

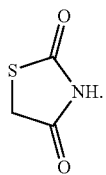

In another class of this embodiment, $R^7$ is selected from the group consisting of: —CO$_2$H, —CH$_2$CO$_2$H, —(CH$_2$)$_2$CO$_2$H, and a cycloheteroalkyl selected from:

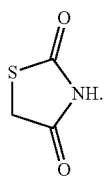

In another class of this embodiment, $R^7$ is selected from the group consisting of: —CO$_2$H, —CH$_2$CO$_2$H, and a cycloheteroalkyl selected from:

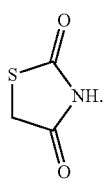

In another embodiment of the present invention, $R^7$ is —CO$_2$R$^8$. In a class of this embodiment, $R^7$ is —CO$_2$H.

In another embodiment of the present invention, $R^8$ is selected from the group consisting of: hydrogen, —C$_{1-6}$alkyl and —C$_{3-6}$cycloalkyl, wherein each alkyl and cycloalkyl is unsubstituted or substituted with one to three substituents selected from R$^j$. In a class of this embodiment, $R^8$ is selected from the group consisting of: hydrogen and —C$_{1-6}$alkyl, wherein each alkyl is unsubstituted or substituted with one to three substituents selected from R$^j$. In another class of this embodiment, $R^8$ is —C$_{1-6}$alkyl, wherein each alkyl is unsubstituted or substituted with one to three substituents selected from R$^j$. In another class of this embodiment, $R^8$ is hydrogen.

In another embodiment of the present invention, $R^a$ is selected from the group consisting of: —C$_{1-6}$alkyl, —OC$_{1-6}$alkyl, halogen, —S(O)$_n$R$^e$, —S(O)$_n$NR$^c$R$^d$, —NR$^c$R$^d$, —C(O)R$^e$, —OC(O)R$^e$, —CO$_2$R$^e$, —CN, —C(O)NR$^c$R$^d$, —CF$_3$, —OCF$_3$, —OCHF$_2$, —OCH$_2$CF$_3$, heteroaryl, and —C$_{3-6}$cycloalkyl, wherein each alkyl, cycloalkyl, and heteroaryl is unsubstituted or substituted with 1-3 substituents selected from: halogen, —C$_{1-6}$alkyl, —O—C$_{1-6}$alkyl, —CF$_3$, CO$_2$H, and —CO$_2$C$_{1-6}$alkyl.

In another embodiment of the present invention, $R^a$ is selected from the group consisting of: —C$_{1-6}$alkyl, —OC$_{1-6}$alkyl, halogen, —CN, —CF$_3$, —OCF$_3$, —OCHF$_2$, —OCH$_2$CF$_3$, aryl, heteroaryl, and —C$_{2-5}$cycloheteroalkyl, wherein each alkyl, cycloalkyl, cycloheteroalkyl, aryl and heteroaryl is unsubstituted or substituted with 1-3 substituents selected from: halogen, —C$_{1-6}$alkyl, —O—C$_{1-6}$alkyl, —CF$_3$, CO$_2$H, and —CO$_2$C$_{1-6}$alkyl.

In another class of this embodiment, $R^a$ is selected from the group consisting of: —C$_{1-6}$alkyl, —OC$_{1-6}$alkyl, halogen, —CN, —CF$_3$, —OCF$_3$, —OCHF$_2$, —OCH$_2$CF$_3$, heteroaryl, and —C$_{3-6}$cycloalkyl, wherein each alkyl, cycloalkyl and heteroaryl is unsubstituted or substituted with 1-3 substituents selected from: —C$_{1-6}$alkyl and CO$_2$H.

In another embodiment of the present invention, $R^a$ is selected from the group consisting of: —C$_{1-6}$alkyl, —OC$_{1-6}$alkyl, halogen, —CN, —CF$_3$, —OCF$_3$, —OCHF$_2$, —OCH$_2$CF$_3$, heteroaryl, and —C$_{3-6}$cycloalkyl, wherein each alkyl, cycloalkyl and heteroaryl is unsubstituted or substituted with 1-3 substituents selected from: halogen, —C$_{1-6}$alkyl, —O—C$_{1-6}$alkyl, —CF$_3$, CO$_2$H, and —CO$_2$C$_{1-6}$ alkyl.

In a class of this embodiment, $R^a$ is selected from the group consisting of: —CH$_3$, —CH$_2$CH$_3$, —C(CH$_3$)$_3$, —OCH$_3$, F, Cl, —CN, —CF$_3$, —OCF$_3$, —OCHF$_2$, —OCH$_2$CF$_3$, pyrazole, furan, isoxazole, thiophene, pyrrole, and cyclopropyl, wherein each alkyl, cycloalkyl and heteroaryl is unsubstituted or substituted with 1-3 substituents selected from: halogen, —C$_{1-6}$alkyl, —O—C$_{1-6}$alkyl, —CF$_3$, CO$_2$H, and —CO$_2$C$_{1-6}$alkyl.

In another embodiment of the present invention, $R^a$ is selected from the group consisting of: —C$_{1-6}$alkyl, halogen, —CF$_3$, and —OCF$_3$.

In a class of this embodiment, $R^a$ is selected from the group consisting of: —CH$_3$, F, Cl, —CF$_3$, and —OCF$_3$.

In another embodiment of the present invention, each $R^b$ is independently selected from the group consisting of: hydrogen, and —C$_{1-10}$alkyl, wherein each alkyl is unsubstituted or substituted with one to five halogens.

In another embodiment of the present invention, each $R^b$ is —C$_{1-10}$alkyl, wherein each alkyl is unsubstituted or substituted with one to five halogens.

In another embodiment of the present invention, each $R^b$ is hydrogen.

In another embodiment of the present invention, $R^c$ and $R^d$ are each independently selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three $R^f$ substituents, or $R^c$ and $R^d$ together with the atom(s) to which they are attached form a $C_{2-5}$cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^c$ and $R^d$ are each independently selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three $R^f$ substituents.

In another embodiment of the present invention, $R^c$ and $R^d$ are each independently selected from the group consisting of: hydrogen, $C_{1-10}$alkyl and $C_{2-10}$alkenyl, wherein each alkyl and alkenyl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^c$ and $R^d$ are each independently selected from the group consisting of: hydrogen, $C_{1-10}$alkyl and $C_{2-10}$alkenyl, wherein each alkyl and alkenyl is unsubstituted or substituted with one to three $R^f$ substituents.

In another embodiment of the present invention, $R^c$ and $R^d$ are each independently selected from the group consisting of: hydrogen and $C_{1-10}$alkyl, wherein each alkyl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents.

In a class of this embodiment, $R^c$ and $R^d$ are each independently selected from the group consisting of: hydrogen and $C_{1-10}$alkyl, wherein each alkyl is unsubstituted or substituted with one to three $R^f$ substituents.

In another embodiment of the present invention, $R^c$ and $R^d$ are each independently selected from the group consisting of: $C_{1-10}$alkyl, wherein each alkyl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^c$ and $R^d$ are each independently selected from the group consisting of: $C_{1-10}$alkyl, wherein each alkyl is unsubstituted or substituted with one to three $R^f$ substituents.

In another embodiment of the present invention, $R^c$ and $R^d$ are each hydrogen.

In another embodiment of the present invention, $R^c$ is independently selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl-, and heteroaryl-$C_{1-10}$alkyl-, wherein each alkyl, alkenyl, cycloalkyl, cycloheteroalkyl, aryl and heteroaryl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^c$ is independently selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl- and heteroaryl-$C_{1-10}$ alkyl-, wherein each alkyl, alkenyl, cycloalkyl, cycloheteroalkyl, aryl and heteroaryl is unsubstituted or substituted with one to three $R^f$ substituents.

In another embodiment of the present invention, $R^c$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^c$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three $R^f$ substituents.

In another embodiment of the present invention, $R^c$ is selected from the group consisting of: hydrogen, $C_{1-10}$alkyl and $C_{2-10}$alkenyl, wherein each alkyl and alkenyl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^c$ is selected from the group consisting of: hydrogen, $C_{1-10}$alkyl and $C_{2-10}$ alkenyl, wherein each alkyl and alkenyl is unsubstituted or substituted with one to three $R^f$ substituents.

In another embodiment of the present invention, $R^c$ is selected from the group consisting of: hydrogen and $C_{1-10}$alkyl, wherein each alkyl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^c$ is selected from the group consisting of: hydrogen and $C_{1-10}$alkyl, wherein each alkyl is unsubstituted or substituted with one to three $R^f$ substituents.

In another embodiment of the present invention, $R^c$ is selected from the group consisting of: $C_{1-10}$alkyl, wherein each alkyl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^c$ is selected from the group consisting of: $C_{1-10}$alkyl, wherein each alkyl is unsubstituted or substituted with one to three $R^f$ substituents.

In another embodiment of the present invention, $R^c$ is hydrogen.

In another embodiment of the present invention, $R^d$ is independently selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl- and heteroaryl-$C_{1-10}$ alkyl-, wherein each alkyl, alkenyl, cycloalkyl, cycloheteroalkyl, aryl and heteroaryl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents.

In another embodiment of the present invention, $R^d$ is independently selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl- and heteroaryl-$C_{1-10}$ alkyl-, wherein each alkyl, alkenyl, cycloalkyl, cycloheteroalkyl, aryl and heteroaryl is unsubstituted or substituted with one to three $R^f$ substituents.

In another embodiment of the present invention, $R^d$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^d$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three $R^f$ substituents.

In another embodiment of the present invention, $R^d$ is selected from the group consisting of: hydrogen, $C_{1-10}$alkyl and $C_{2-10}$alkenyl, wherein each alkyl and alkenyl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^d$ is selected from the group consisting of: hydrogen, $C_{1-10}$alkyl and $C_{2-10}$alkenyl, wherein each alkyl and alkenyl is unsubstituted or substituted with one to three $R^f$ substituents.

In another embodiment of the present invention, $R^d$ is selected from the group consisting of: hydrogen and $C_{1-10}$alkyl, wherein each alkyl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^d$ is selected from the group consisting of: hydrogen and $C_{1-10}$alkyl, wherein each alkyl is unsubstituted or substituted with one to three $R^f$ substituents.

In another class of this embodiment, $R^d$ is selected from the group consisting of: $C_{1-10}$alkyl, wherein each alkyl is unsubstituted or substituted with one to three $R^f$ substituents, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three $R^f$ substituents. In a class of this embodiment, $R^d$ is selected from the group consisting of: $C_{1-10}$alkyl, wherein each alkyl is unsubstituted or substituted with one to three $R^f$ substituents.

In another embodiment of the present invention, $R^d$ is hydrogen.

In another embodiment of the present invention, each $R^e$ is independently selected from the group consisting of: hydrogen, —$C_{1-10}$alkyl, —$C_{2-10}$ alkenyl, aryl, aryl-$C_{1-10}$alkyl-, heteroaryl and heteroaryl-$C_{1-10}$alkyl-, wherein each alkyl, alkenyl, aryl and heteroaryl is unsubstituted or substituted with one to three $R^h$ substituents.

In another embodiment of the present invention, each $R^e$ is independently selected from the group consisting of: hydrogen, —$C_{1-10}$alkyl and aryl-$C_{1-10}$alkyl-, wherein each alkyl and aryl is unsubstituted or substituted with one to three $R^h$ substituents. In a class of this embodiment, each $R^e$ is independently selected from the group consisting of: hydrogen, —$C_{1-10}$alkyl and phenyl-$C_{1-10}$alkyl-, wherein each alkyl and phenyl is unsubstituted or substituted with one to three $R^h$ substituents. In another class of this embodiment, each $R^e$ is independently selected from the group consisting of: hydrogen, —$CH_3$ and —$CH_2$-phenyl wherein each alkyl and phenyl is unsubstituted or substituted with one to three $R^h$ substituents.

In another embodiment, each $R^e$ is —$C_{1-10}$alkyl-, wherein each alkyl is unsubstituted or substituted with one to three $R^h$ substituents. In a class of this embodiment, each $R^e$ is —$CH_3$.

In another embodiment of the present invention, each $R^e$ is independently selected from the group consisting of: aryl-$C_{1-10}$alkyl-, wherein each alkyl and aryl is unsubstituted or substituted with one to three $R^h$ substituents. In a class of this embodiment, each $R^e$ is —$CH_2$-phenyl, wherein each $CH_2$ and phenyl is unsubstituted or substituted with one to three $R^h$ substituents.

In another embodiment of the present invention, each $R^e$ is hydrogen.

In another embodiment of the present invention, each $R^f$ is selected from the group consisting of: halogen, $C_{1-10}$alkyl, —OH, —O—$C_{1-4}$alkyl, —CN, —$CF_3$, —$OCHF_2$ and —$OCF_3$, wherein each alkyl is unsubstituted or substituted with one to three substituents independently selected from: —OH, halogen, $C_{1-6}$alkyl, cyano and $S(O)_2C_{1-6}$alkyl.

In another embodiment of the present invention, each $R^f$ is selected from the group consisting of: halogen, $C_{1-10}$alkyl and —OH, wherein each alkyl is unsubstituted or substituted with one to three substituents independently selected from: —OH, halogen, $C_{1-6}$alkyl, cyano and $S(O)_2C_{1-6}$alkyl.

In another embodiment of the present invention, each $R^f$ is selected from the group consisting of: halogen and $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In a class of this embodiment, each $R^f$ is selected from the group consisting of: $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In a subclass of this class, each $R^f$ is selected from the group consisting of: $C_{1-10}$alkyl. In another class of this embodiment, each $R^f$ is halogen.

In another embodiment of the present invention, $R^g$ is selected from the group consisting of: hydrogen and —$C_{1-10}$ alkyl. In another embodiment of the present invention, $R^g$ is —$C_{1-10}$alkyl unsubstituted or substituted with one to five halogens. In another embodiment of the present invention, $R^g$ is —$C_{1-10}$alkyl. In another embodiment of the present invention, $R^g$ is hydrogen.

In another embodiment of the present invention, each $R^h$ is selected from the group consisting of: halogen, $C_{1-10}$alkyl, —OH, —O—$C_{1-4}$alkyl, —CN, —CF$_3$, —OCHF$_2$ and —OCF$_3$, wherein each alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^h$ is selected from the group consisting of: halogen, $C_{1-10}$alkyl and —OH, wherein each alkyl is unsubstituted or substituted with one to three substituents independently selected from: —OH, halogen, $C_{1-6}$alkyl, cyano and $S(O)_2C_{1-6}$alkyl.

In another embodiment of the present invention, each $R^h$ is selected from the group consisting of: halogen and $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In a class of this embodiment, each $R^h$ is selected from the group consisting of: $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In another class of this embodiment, each $R^h$ is selected from the group consisting of: $C_{1-10}$alkyl. In another class of this embodiment, each $R^h$ is halogen.

In another embodiment of the present invention, $R^1$ is hydrogen.

In another embodiment of the present invention, $R^1$ is —$C_{1-6}$alkyl.

In another embodiment of the present invention, $R^j$ is independently selected from the group consisting of: —$C_{1-6}$alkyl, —OR$^e$, —NR$^c$S(O)$_m$R$^e$, halogen, —S(O)$_m$R$^e$, —S(O)$_m$ NR$^c$R$^d$, —NR$^c$R$^d$, —C(O)R$^e$, —OC(O)R$^e$, —CO$_2$R$^e$, —CN, —C(O)NR$^c$R$^d$, —NR$^c$C(O)R$^e$, —NR$^c$C(O)OR$^e$, —NR$^c$C(O)NR$^c$R$^d$, —CF$_3$, —OCF$_3$ and —OCHF$_2$. In another embodiment of the present invention, $R^j$ is independently selected from the group consisting of: —$C_{1-6}$alkyl, —OR$^e$, halogen, —NR$^c$R$^d$, —C(O)R$^e$, —OC(O)R$^e$, —CO$_2$R$^e$, —CN, —CF$_3$, —OCF$_3$, and —OCHF$_2$. In another embodiment of the present invention, $R^j$ is independently selected from the group consisting of: —$C_{1-6}$alkyl, —OR$^e$, and halogen. In another embodiment of the present invention, $R^j$ is independently selected from the group consisting of: —$C_{1-6}$alkyl and halogen. In another embodiment of the present invention, $R^j$ is independently selected from the group consisting of: —$C_{1-6}$alkyl.

In another embodiment of the present invention, each $R^k$ is independently selected from the group consisting of: —$C_{1-10}$alkyl, —$C_{2-10}$ alkenyl, —$C_{3-6}$ cycloalkyl, —$C_{2-5}$cycloheteroalkyl, aryl and heteroaryl.

In another embodiment of the present invention, each $R^k$ is independently selected from the group consisting of: —$C_{1-10}$alkyl and —$C_{2-10}$ alkenyl.

In another embodiment of the present invention, each $R^k$ is independently selected from the group consisting of: —$C_{1-10}$alkyl.

In another embodiment of the present invention, each $R^L$ is independently selected from the group consisting of: —$C_{1-10}$alkyl, —$C_{2-10}$ alkenyl, —$C_{2-10}$alkynyl, —$C_{3-6}$cycloalkyl, aryl, and heteroaryl, wherein alkyl, alkenyl, alkynyl, cycloalkyl, aryl and heteroaryl are unsubstituted or substituted with 1-4 substituents selected from $C_{1-6}$alkyl, halogen, and —OC$_{1-6}$alkyl. In a class of this embodiment, each $R^L$ is independently selected from the group consisting of: —$C_{1-10}$alkyl, —$C_{2-10}$ alkenyl, —$C_{2-10}$alkynyl, —$C_{3-6}$ cycloalkyl, phenyl and heteroaryl, wherein alkyl, alkenyl, alkynyl, cycloalkyl, cycloheteroalkyl, phenyl and heteroaryl are unsubstituted or substituted with 1-4 substituents selected from $C_{1-6}$alkyl, halogen, and —OC$_{1-6}$alkyl. In another class of this embodiment, each $R^L$ is independently selected from the group consisting of: —$C_{1-10}$alkyl, —$C_{2-10}$ alkenyl, —$C_{2-10}$alkynyl, —$C_{3-6}$cycloalkyl, phenyl, and pyridine, wherein alkyl, alkenyl, alkynyl, cycloalkyl, phenyl and pyridine are unsubstituted or substituted with 1-4 substituents selected from $C_{1-6}$alkyl, halogen, and —OC$_{1-6}$alkyl. In another class of this embodiment, each $R^L$ is independently selected from the group consisting of: —CH$_3$, —CH=C(CH$_3$)$_2$, —$C_2$alkynyl-CH$_3$, cyclopropyl, phenyl —OCH$_3$ and pyridine, wherein alkyl, alkenyl, alkynyl, cyclopropyl, phenyl and pyridine are unsubstituted or substituted with 1-4 substituents selected from $C_{1-6}$alkyl, halogen and —OC$_{1-6}$alkyl. In another class of this embodiment, each $R^L$ is independently selected from the group consisting of: —CH$_3$, —CH=C(CH$_3$)$_2$, —$C_2$alkynyl-CH$_3$, cyclopropyl, phenyl —OCH$_3$ and pyridine.

In another class of this embodiment, each $R^L$ is independently selected from the group consisting of: —$C_{1-10}$alkyl, —$C_{2-10}$ alkenyl, —$C_{2-10}$alkynyl, and —$C_{3-6}$cycloalkyl, wherein alkyl, alkenyl, alkynyl, and cycloalkyl are unsubstituted or substituted with 1-4 substituents selected from $C_{1-6}$alkyl, halogen, and —OC$_{1-6}$alkyl.

In another class of this embodiment, each $R^L$ is independently selected from the group consisting of: —CH$_3$, and cyclopropyl.

In another embodiment of the present invention, each $R^L$ is independently selected from the group consisting of: —$C_{2-10}$alkynyl, wherein alkynyl is unsubstituted or substituted with 1-4 substituents selected from $C_{1-6}$alkyl, halogen, and —OC$_{1-6}$alkyl. In a class of this embodiment, each $R^L$ is independently selected from the group consisting of: —$C_{2-6}$ alkynyl, wherein alkynyl is unsubstituted or substituted with 1-4 substituents selected from $C_{1-6}$alkyl, halogen, and —OC$_{1-6}$alkyl. In another class of this embodiment, each $R^L$ is independently selected from the group consisting of: —$C_{2-10}$alkynyl, wherein alkynyl is unsubstituted or substituted with 1-4 substituents selected from —CH$_3$. In another class of this embodiment, each $R^L$ is —$C_2$alkynyl-CH$_3$.

In another embodiment of the present invention, n is 0, 1 or 2. In a class of this embodiment, n is 0 or 1. In a class of this embodiment, n is 0 or 2. In another class of this embodiment, n is 1 or 2. In another class of this embodiment, n is 0. In another class of this embodiment, n is 1. In another class of this embodiment, n is 2.

In another embodiment of the present invention, m is 0, 1 or 2. In a class of this embodiment, m is 0 or 1. In a class of this embodiment, m is 0 or 2. In another class of this embodiment, m is 1 or 2. In another class of this embodiment, m is 0. In another class of this embodiment, m is 1. In another class of this embodiment, m is 2.

In another embodiment of the present invention, p is 0, 1 or 2. In a class of this embodiment, p is 0 or 1. In a class of this embodiment, p is 0 or 2. In another class of this embodiment, p is 1 or 2. In another class of this embodiment, p is 0. In another class of this embodiment, p is 1. In another class of this embodiment, p is 2.

In another embodiment of the present invention, q is 0, 1 or 2. In a class of this embodiment, q is 0 or 1. In a class of this embodiment, q is 0 or 2. In another class of this embodiment, q is 1 or 2. In another class of this embodiment, q is 0. In another class of this embodiment, q is 1. In another class of this embodiment, q is 2.

In another embodiment of the present invention, t is 0, 1 or 2. In a class of this embodiment, t is 0 or 1. In a class of this embodiment, t is 0 or 2. In another class of this embodiment, t is 1 or 2. In another class of this embodiment, t is 0. In another class of this embodiment, t is 1. In another class of this embodiment, t is 2.

In another embodiment of the present invention, u is 0, 1, 2 or 3. In a class of this embodiment, u is 0, 1 or 2. In a class of this embodiment, u is 0 or 1. In a class of this embodiment, u is 0 or 2. In another class of this embodiment, u is 1 or 2. In another class of this embodiment, u is 0. In another class of this embodiment, u is 1. In another class of this embodiment, u is 2. In another class of this embodiment, u is 3.

In another embodiment of the present invention, the invention relates to compounds of structural formula Ia:

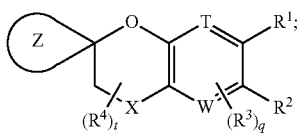

Ia or a pharmaceutically acceptable salt thereof.

In another embodiment of the present invention, the invention relates to compounds of structural formula Ib:

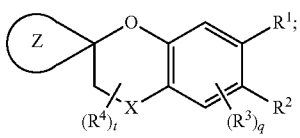

Ib or a pharmaceutically acceptable salt thereof.

In another embodiment of the present invention, the invention relates to compounds of structural formula Ic:

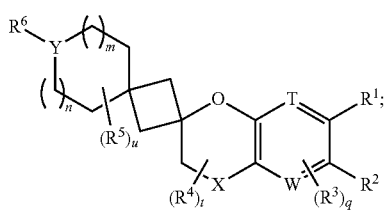

Ic or a pharmaceutically acceptable salt thereof.

In another embodiment of the present invention, the invention relates to compounds of structural formula Id:

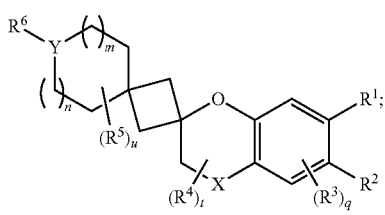

Id or a pharmaceutically acceptable salt thereof.

In another embodiment of the present invention, the invention relates to compounds of structural formula Ie:

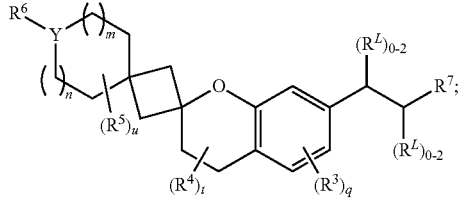

Ie or a pharmaceutically acceptable salt thereof.

In another embodiment of the present invention, the invention relates to compounds of structural formula If:

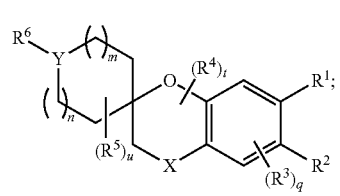

If or a pharmaceutically acceptable salt thereof.

In another embodiment of the present invention, the invention relates to compounds of structural formula Ig:

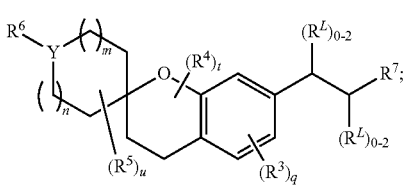

Ig or a pharmaceutically acceptable salt thereof.

In another embodiment of the present invention, the invention relates to compounds of structural formula Ih:

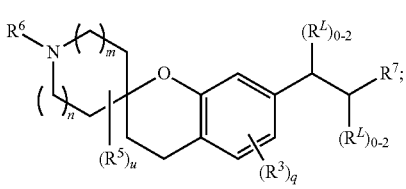

Ih or a pharmaceutically acceptable salt thereof.

In another embodiment of the present invention, the invention relates to compounds of structural formula Ii:

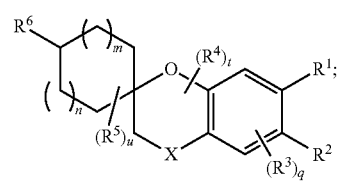

Ii or a pharmaceutically acceptable salt thereof.

In another embodiment of the present invention, the invention relates to compounds of structural formula Ij:

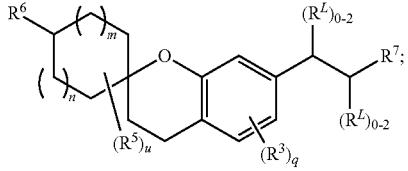

Ij or a pharmaceutically acceptable salt thereof.

In another embodiment of the present invention, the invention relates to compounds of structural formula Ik:

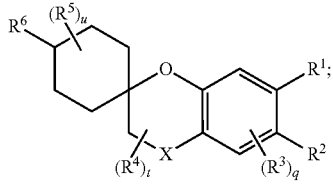

Ik or a pharmaceutically acceptable salt thereof.

In another embodiment of the present invention, the invention relates to compounds of structural formula Il:

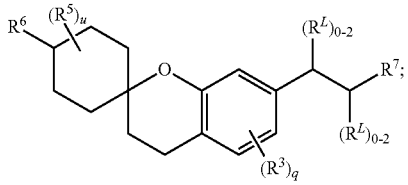

Il or a pharmaceutically acceptable salt thereof.

In another embodiment of the present invention, the invention relates to compounds of structural formula Im:

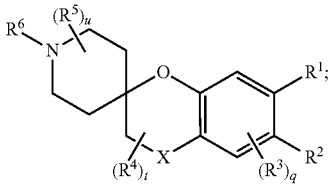

Im or a pharmaceutically acceptable salt thereof.

In another embodiment of the present invention, the invention relates to compounds of structural formula In:

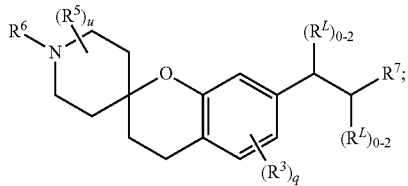

In or a pharmaceutically acceptable salt thereof.

In another embodiment of the present invention, the invention relates to compounds of structural formula Io:

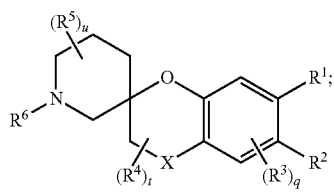

Io or a pharmaceutically acceptable salt thereof.

In another embodiment of the present invention, the invention relates to compounds of structural formula Ip:

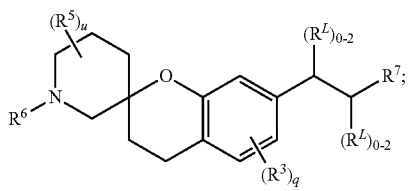

Ip or a pharmaceutically acceptable salt thereof.

In another embodiment of the present invention, the invention relates to compounds of structural formula Iq:

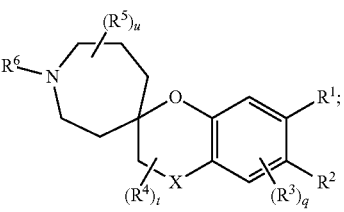

Iq or a pharmaceutically acceptable salt thereof.

In another embodiment of the present invention, the invention relates to compounds of structural formula Ir:

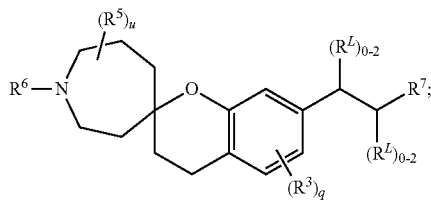

or a pharmaceutically acceptable salt thereof.

In another embodiment of the present invention, the invention relates to compounds of structural formula Is:

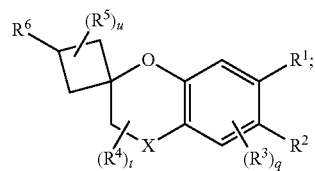

or a pharmaceutically acceptable salt thereof.

In another embodiment of the present invention, the invention relates to compounds of structural formula It:

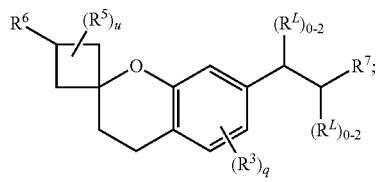

or a pharmaceutically acceptable salt thereof.

In another embodiment of the present invention, the invention relates to compounds of structural formula Iu:

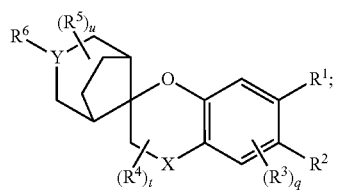

or a pharmaceutically acceptable salt thereof.

In another embodiment of the present invention, the invention relates to compounds of structural formula Iv:

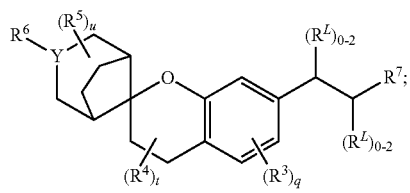

or a pharmaceutically acceptable salt thereof.

In another embodiment of the present invention, the invention relates to compounds of structural formula Iw:

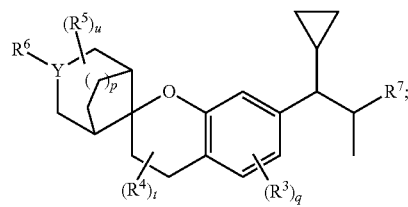

or a pharmaceutically acceptable salt thereof.

In another embodiment of the present invention, the invention relates to compounds of structural formula Ix:

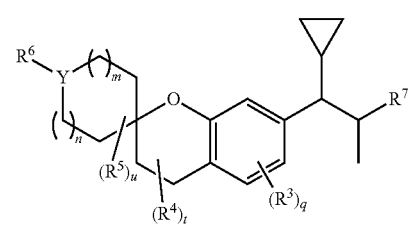

or a pharmaceutically acceptable salt thereof.

In another embodiment of the present invention, the invention relates to compounds of structural formula Iy:

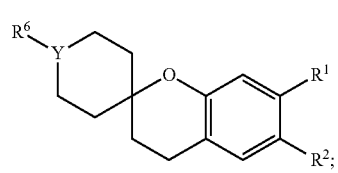

or a pharmaceutically acceptable salt thereof.

In another embodiment of the present invention, the invention relates to compounds of structural formula Iz:

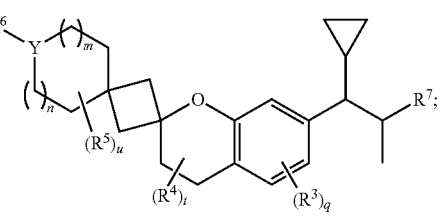

or a pharmaceutically acceptable salt thereof.

The compound of structural formula I includes the compounds of structural formulas Ia, Ib, Ic, Id, Ie, If, Ig, Ih, Ii, Ij, Ik, Il, Im, In, Io, Ip, Iq, Ir, Is, It, Iu, Iv, Iw, Ix, Iy, and Iz, and pharmaceutically acceptable salts, hydrates and solvates thereof.

Another embodiment of the present invention relates to compounds of structural formula Ib:

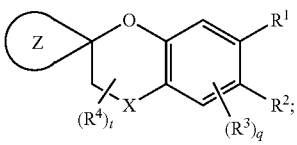

wherein
X is selected from the group consisting of:
(1) —C(R$^b$)(R$^b$),
(2) —C=O, and
(3) —C(R$^b$)OR$^b$;
Y is selected from the group consisting of:
(1) —C(R$^g$)—, and
(2) —N—;
Z is selected from:

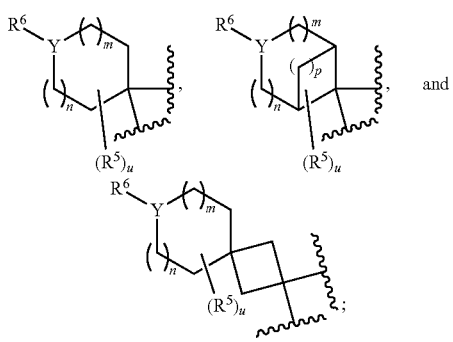

R$^1$ and R$^2$ are each independently selected from:
(1) hydrogen, and
(2) —C$_{1-6}$alkyl,
wherein alkyl is unsubstituted or substituted with one to three R$^L$ substituents, and wherein one of R$^1$ and R$^2$ is C$_{1-6}$alkyl substituted with R$^7$;
each R$^3$ is independently selected from the group consisting of:
(1) hydrogen, and
(2) halogen;
R$^4$ is hydrogen;
R$^5$ is hydrogen;
R$^6$ is selected from the group consisting of:
(1) aryl,
(2) aryl-SO$_2$—,
(3) aryl-C$_{1-10}$ alkyl-,
(4) aryl-N(R$^i$)—,
(5) aryl-C$_{1-10}$ alkyl-N(R$^i$)—,
(6) heteroaryl,
(7) heteroaryl-C$_{1-10}$ alkyl-, and
(8) heteroaryl-N(R$^i$)—,
wherein each CH$_2$ is unsubstituted or substituted with 1-2 R$^a$ substituents, and wherein each aryl, and heteroaryl is unsubstituted or substituted with 1-5 R$^a$ substituents;
R$^7$ is —CO$_2$R$^8$;
R$^8$ is hydrogen;
each R$^L$ is independently selected from the group consisting of: —C$_{1-10}$alkyl, —C$_{2-10}$ alkenyl, —C$_{2-10}$alkynyl, and —C$_{3-6}$cycloalkyl, wherein alkyl, alkenyl, alkynyl, and cycloalkyl are unsubstituted or substituted with 1-4 substituents selected from C$_{1-6}$alkyl, halogen, and —OC$_{1-6}$alkyl;
n is 0 or 1;
m is 0, 1 or 2;
p is 0 or 2;
q is 0 or 1;
t is 0 or 1;
u is 0 or 1;
and R$^a$, R$^b$, R$^c$, R$^d$, R$^e$, R$^f$, R$^g$, R$^h$, R$^i$, R$^j$ and R$^k$ are as defined above; or a pharmaceutically acceptable salt thereof.

In a class of this embodiment, R$^a$ is selected from the group consisting of:
(1) —C$_{1-6}$alkyl,
(2) —OC$_{1-6}$alkyl,
(3) halogen,
(4) —CN,
(5) —CF$_3$,
(6) —OCF$_3$,
(7) —OCHF$_2$,
(8) —OCH$_2$CF$_3$,
(9) heteroaryl, and
(10) —C$_{3-6}$cycloalkyl,
wherein each alkyl, cycloalkyl and heteroaryl is unsubstituted or substituted with 1-3 substituents selected from: halogen, —C$_{1-6}$alkyl, —O—C$_{1-6}$alkyl, —CF$_3$, CO$_2$H, and —CO$_2$C$_{1-6}$alkyl.

In another class of this embodiment, R$^b$ is hydrogen.
In another class of this embodiment, R$^g$ is hydrogen.
In another class of this embodiment, each R$^L$ is independently selected from the group consisting of: —C$_{1-10}$alkyl, and —C$_{3-6}$cycloalkyl, wherein each alkyl and cycloalkyl is unsubstituted or substituted with 1-4 substituents selected from C$_{1-6}$alkyl, halogen, and —OC$_{1-6}$alkyl.

Another embodiment of the present invention relates to compounds of structural Formula Iy:

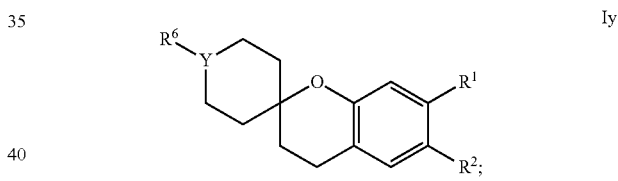

wherein
Y is —N—;
R$^1$ is —C$_{1-6}$alkyl, wherein alkyl is unsubstituted or substituted with one to three R$^L$ substituents, and wherein R$^1$ is substituted with R$^7$;
R$^2$ is hydrogen;
R$^6$ is phenyl-CH$_2$—, wherein each CH$_2$ is unsubstituted or substituted with 1-2 substituents selected from R$^a$, and wherein each phenyl is unsubstituted or substituted with 1-3 substituents selected from R$^a$;
R$^7$ is —CO$_2$R$^8$;
R$^8$ is hydrogen;
each R$^L$ is independently selected from the group consisting of: —CH$_3$, and cyclopropyl; and R$^a$, R$^b$, R$^c$, R$^d$, R$^e$, R$^f$, R$^h$, R$^i$, R$^j$ and R$^k$ are as defined above;
or a pharmaceutically acceptable salt thereof.

In a class of this embodiment, R$^a$ is selected from the group consisting of:
(1) —C$_{1-6}$alkyl,
(2) halogen,
(3) —CF$_3$, and
(4) —OCF$_3$.

In another class of this embodiment, R$^b$ is hydrogen.
In another class of this embodiment, each R$^L$ is independently selected from the group consisting of: —C$_{1-10}$alkyl, and —C$_{3-6}$cycloalkyl, wherein each alkyl and cycloalkyl is unsubstituted or substituted with 1-4 substituents selected from C$_{1-6}$alkyl, halogen, and —OC$_{1-6}$alkyl.

Illustrative, but non-limiting, examples of the compounds of the present invention that are useful as agonists of G-protein-coupled receptor 40 (GPR40) are the following compounds:

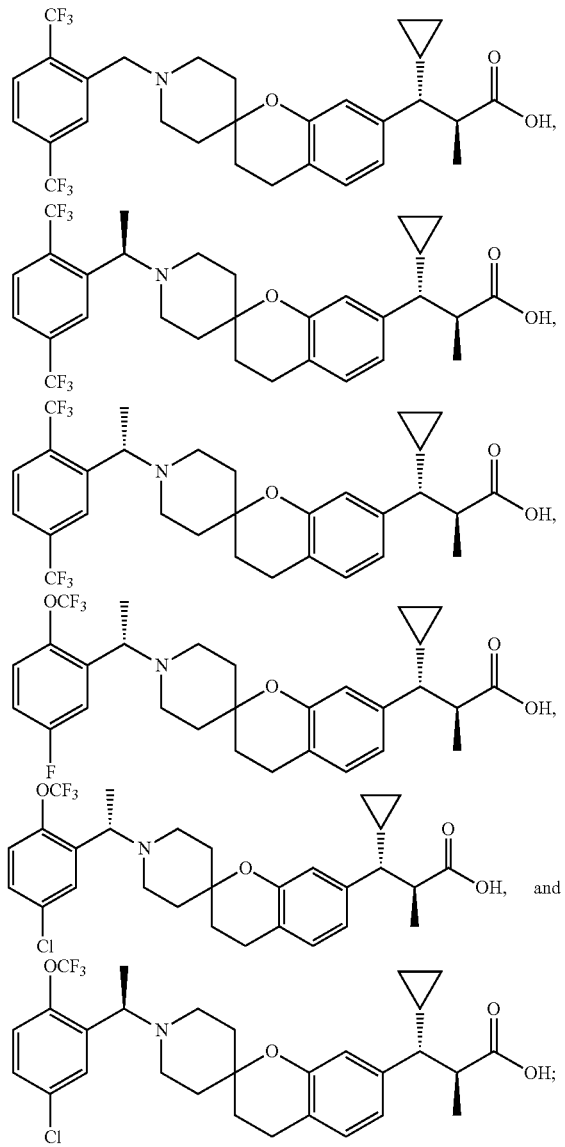

and pharmaceutically acceptable salts thereof.

Although the specific stereochemistries described herein are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

DEFINITIONS

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. In one embodiment of the present invention, alkyl is methyl.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is 2-methyl-1-propenyl.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like. In one embodiment, alkynyl is —C$_2$alkyne-CH$_3$.

"Cycloalkyl" means a saturated monocyclic, bicyclic or bridged carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. In one embodiment of the present invention, cycloalkyl is selected from: cyclopropane, cyclobutane and cyclohexane. In another embodiment of the present invention, cycloalkyl is selected from: cyclopropane.

"Spirocycloalkyl" means the cycloalkyl ring is attached to the atom it is substituted on via two bonds.

"Cycloalkenyl" means a nonaromatic monocyclic or bicyclic carbocylic ring containing at least one double bond. Examples of cycloalkenyl include cyclopropenyl, cyclobutenyl, cyclopentenyl, cyclohexenyl, cycloheptenyl, cyclooxtenyl and the like. In one embodiment of the present invention, cycloalkenyl is cyclopentenyl.

"Cycloheteroalkyl" means a saturated or partly unsaturated non-aromatic monocyclic, bicyclic or bridged carbocyclic ring or ring system containing at least one ring heteroatom selected from N, NH, S (including SO and SO$_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran, hexose, pentose, isosorbide and isomannide, dianhydromannitol, 1,4:3,6-dianhydromannitol, 1,4:3,6-dianhydro[D]mannitol, hexahydrofuro[3,2-b]furan, and 2,3,3a,5,6,6a-hexahydrofuro[3,2-b]furan. In one embodiment of the present invention, cycloheteroalkyl is selected from: hexose, pentose, isosorbide and isomannide. In another embodiment of the present invention, cycloheteroalkyl is selected from: isosorbide and isomannide. In another embodiment of the present invention, cycloheteroalkyl is selected from: oxetane, tetrahydropyran, azetidine, tetrahydrothiopyran and pyrrolidine. In another embodiment of the present invention cycloheteroalkyl is selected from: oxetane, -piperazine, azetidine, pyrrolidine, morpholine and spiro(indene-1,4-piperidine).

"Cycloheteroalkenyl" means a nonaromatic monocyclic, bicyclic or bridged carbocyclic ring or ring system containing at least one double bond and containing at least one heteroatom selected from N, NH, S and O.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl. In another embodiment of the present invention, aryl-O— is phenyl-O—. In another embodiment of the present invention, aryl-$C_{1-10}$alkyl-O— is phenyl-$CH_2$—O—.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzopyrazole (or indazole), benzothiophenyl (including S-oxide and dioxide), furo(2,3-b)pyridyl, quinolyl, indolyl, isoquinolyl, quinazolinyl, dibenzofuranyl, and the like. In one embodiment of the present invention, heteroaryl is selected from: pyridine, isoxazole, pyrimidine, thiazole, benzimidazole, benzthiazole, benzoxazole, and benzisoxazole. In another embodiment of the present invention, heteroaryl is selected from: pyridine, isoxazole and benzopyrazole. In another embodiment of the present invention, heteroaryl is pyridine or thiazole. In another embodiment of the present invention, heteroaryl is pyridine.

"Halogen" includes fluorine, chlorine, bromine and iodine. In one embodiment of the present invention, halogen is bromine, chlorine or fluorine. In another embodiment of the present invention, halogen is chlorine or fluorine. In another embodiment of the present invention, halogen is bromine. In another embodiment of the present invention, halogen is chlorine. In another embodiment of the present invention, halogen is fluorine.

"Me" represents methyl.

"Oxo" is =O.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to:

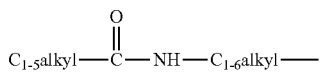

For example, —$NR^cC(O)R^e$ is equivalent to —$N(R^c)C(O)R^e$.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1H$), deuterium ($^2H$), and tritium ($^3H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

The present invention includes the pharmaceutically acceptable salts of the compounds of formula I, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases:

(1) non-insulin dependent diabetes mellitus (Type 2 diabetes);
(2) hyperglycemia;
(3) insulin resistance;
(4) Metabolic Syndrome;
(5) obesity;
(6) hypercholesterolemia;
(7) hypertriglyceridemia (elevated levels of triglyceride-rich-lipoproteins);
(8) mixed or diabetic dyslipidemia;
(9) low HDL cholesterol;
(10) high LDL cholesterol;
(11) hyperapo-B liproteinemia; and
(12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases:
(1) Type 2 diabetes, and specifically hyperglycemia associated with Type 2 diabetes;
(2) Metabolic Syndrome;
(3) obesity; and
(4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hyperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described herein.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated ($\geq 140$ mmHg/$\geq 90$ mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e., cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combination Therapy:

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPARγ agonists, when the patient's glycemic levels are not adequately responding to treatment.

When a compound of the present invention is used contemporaneously with one or more other drugs, a pharmaceutical composition in unit dosage form containing such other drugs and the compound of the present invention is preferred. However, the combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients/pharmaceutical agents that may be administered in combination with a compound of the present invention, and either administered separately or in the same pharmaceutical composition, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, inulin degludec, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, THO318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), aleglitazar, farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, ATI-802, E3080, and the like; (26) camitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)-methoxy)phenyl)iso, 5-(4-((3-(2-methyl-6-(3-hydroxypropoxy)pyridine-3-yl)-2-methylphenyl)methoxy)phenyl)-isothiazole-3-ol 1-oxide, and 5-[4-[[3-[4-(3-aminopropoxy)-2,6-dimethylphenyl]phenyl]-methoxy]phenyl]isothiazole-3-ol 1-oxide), and those disclosed in WO 11/078371; 42) SGLT-2 inhibitors such as canagliflozin, dapagliflozin, tofogliflozin, empagliflozin, ipragliflozin, luseogliflozin (TS-071), ertugliflozin (PF-04971729), and remogliflozin; and 43) SGLT-1/SGLT-2 inhibitors, such as LX4211.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532, 632, BAY63-2149 (Bayer), SC 591, SC 795, and the like; (7) squalene synthetase inhibitors; (8) anti-oxidants such as probucol, and the like; (9) PPARt agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche), ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTC0179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, and the like; (29) IBAT inhibitors such as BARI143/HMR145A/HMR1453 (Sanofi-Aventis, PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, bamidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) au/3 adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001, 836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A,S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (GlaxoSmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vemalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) 03 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. Nos. 5,705,515, 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899, (33) thyroid hormone 3 agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as LY-2523199, BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), omarigliptin, saxagliptin, alogliptin, linagliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune)Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) McSr (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55)C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, rosuvastatin, sitagliptin, omarigliptin, metformin, sibutramine, orlistat, topiramate, naltrexone, bupriopion, phentermine, losartan, losartan with hydrochlorothiazide, canagliflozin, dapagliflozin, ipragliflozin and ertugliflozin.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-diabetic compounds, anti-obesity compounds and anti-hypertensive agents.

The present invention also provides a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention: The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

LIST OF ABBREVIATIONS

Ac is acetyl; ACN and AcCN is acetonitrile; AcO is acetoxy; Alk is alkyl; anh. is anhydrous; APCI is atmospheric pressure chemical ionization; aq or aq. is aqueous; Ar is aryl; atm is atmosphere; Boc is tert-butoxycarbonyl; Bn—O is phenyl-$CH_2$—O or benzyloxy; Br is broad; Brett-Phos palladacycle precatalyst is Brettphos Pd GI precatalyst (Aldrich); bu is butyl; n-BuLi is n-butyl lithium; $Bu_3P$ is tributylphosphine; t-BuOK is potassium tert butoxide; t-BuOH is tert butanol, C—C refers to a carbon-carbon bond cross coupling reaction; C—N refers to a carbon-nitrogen bond cross coupling reaction; ° C. is degrees celsius; Cataxium precatalyst or Cataxium Pd precat or precatalyst is cataCXium A Pd G3 (Aldrich); Cbz is benzyloxycarbonyl; $CH_2Cl_2$ is dichloromethane; conc or conc. is concentrated; CV is column volumes; d is doublet; DAST is (diethylamino)sulfur trifluoride; DIAD is diisopropyl azodicarboxylate; DCM is dichloro=methane; DEA is diethyl amine; DIEA and DIPEA is N,N-diisopropylethylamine; DIPA is diisopropyl amine; DMP is Des Martin Periodinane; DMAP is 4-dimethylaminopyridine; DMF is N,N-dimethylformamide; DMS is dimethyl sulfide; DMSO is dimethylsulfoxide; dppf is 1,1'-Bis (diphenyl-phosphino)ferrocene; ESI is electrospray ionization; EA or EtOAc is ethyl acetate; Et is ethyl; $Et_2O$ is diethyl ether; EtMgBr is ethyl magnesium bromide; EtOH is ethanol; g is gram(s); h or hr or hrs is hour(s); HATU is (1-[Bis(dimethylamino)-methylene]-1H-1,2,3-triazolo[4,5-b]pyridinium 3-oxide hexafluorophosphate); hex is hexanes; HPLC is high pressure liquid chromatography; HOAc or AcOH is acetic acid; kg is kilogram(s); IPA is isopropanol; KOH ispotassium hydroxide; KOAc is potassium acetate; KOtBu is potassium tert-butoxide; kPa is kilopascal; L is liter; LAH is lithium aluminum hydride; M is molar; MS is mass spectroscopy; LC-MS is liquid chromatography-mass spectroscopy; LDA is lithium diisopropyl amide; m is multiplet; Me is methyl; MeO is methoxy; m-CPBA, MCPBA, or mCPBA is meta chloroperbenzoic acid; ml or mL is milliliter; min or mins is minute(s); mol is mole(s); mmol is mmole(s); mg is milligram(s); MeMgBr is methyl magnesium bromide; MeOH is methyl alcohol or methanol; $MgSO_4$ is magnesium sulfate; MPLC is medium pressure liquid chromatography; MsCl or Ms-Cl is methane sulfonyl chloride; MeCN is acetonitrile; MeI is methyl iodide; MsCl is methane sulfonyl chloride; MTBE is methyl tert-butyl ether; N is normal; $Na(AcO)_3BH$ is sodium triacetoxy borohydride; NaHMDS is sodium hexamethyl disilazide; NaOH is sodium hydroxide; $Na_2SO_4$ is sodium sulfate; $NH_4OAc$ is ammonium acetate; NBS is N-bromo succinamide; $NEt_3$ is triethyl amine; NIS is N-iodo succinamide; NMO is 4-methyl morpholine N-oxide; NMP is 1-methyl-2-pyrrolidinone; NMR is nuclear magnetic resonance spectroscopy; o.n. or ON is overnight; paraform is paraformaldehyde; PE is petroleum ether; PG is protecting group; i-PrOH is isopropanol; $P(Cy)_3$ is tricyclohexyl phosphine; $Pd_2(dba)_3$ is tris(dibenzylidene-acetone)-dipalladium(0); $Pd(OAc)_2$ is palladium acetate; $Pd[P(t-Bu)_3]_2$ is bis(tri-tert-butylphosphine)palladium (0); $Pd(dppf)Cl_2$ is [1,1'-bis(diphenylphosphino)-ferrocene]dichloro-palladium (II); $PdCl_2(dppf)_2CH_2Cl_2$ is [1,1'-Bis(diphenylphosphino)-ferrocene]dichloropalladium(II), complex with dichloromethane (Aldrich); $Pd(PPh_3)_4$ is tetrakis or tetrakis(triphenylphosphine) palladium (0); $PPh_3$ is triphenyl phosphine; $Pd(t-Bu_2P)_2FerrCl_2$ is bis-tri-tert-butylphosphino ferrocene dichloro palladium (II); PMB is para-methoxybenzyl; PMBCl is para-methoxybenzyl chloride; precat is precatalyst; prep is preparative; prep-HPLC is preparatory HPLC; prep. TLC or prep-TLC, or prep TCL is preparative thin layer chromatography; rbf or RBF is round bottom flask; RCM is ring closing metathesis reaction; rt or r.t. or RT is room temperature; Rt is retention time; RuCl[(R,R)-TSDPEN]-(mesitylene) is [N-[(1R,2R)-2-(Amino-N)-1,2-diphenylethyl]-4-methylbenzene-sulfonamidato-κN]chloro[(1,2,3,4,5,6-η)-1,3,5-trimethylbenzene]-ruthenium; Ru-Josiphos is generated using (Me-allyl)2Ru(COD) (Aldrich) and Josiphos SL-J502-2 (Aldrich); $R_f$ is retention factor; s is singlet; sat or sat. is saturated; SEM is trimethylsilyl ethoxy methyl, SEMCl is trimethylsilyl ethoxy methyl chloride; SFC is supercritical fluid chromatography; S-Phos is 2-dicyclohexylphosphino-2',6'-dimethoxy-biphenyl; S-Phos(Pd) is chloro (2-dicyclohexylphosphino-2',6'-dimethoxy-1,1'-biphenyl) [2-(2-aminoethylphenyl)]-palladium(II) [CAS-No. 1028206-58-7]; S-Phos precatalyst is S-Phos Pd G2 precatalyst—Aldrich; S-Phos second generation precatalyst is Chloro(2-dicyclohexyl-phosphino-2',6'-dimethoxy-1,1'-biphenyl)[2-(2'-amino-1,1'-biphenyl)]palladium-(II), SPhos-Pd-G2) [CAS-No. 1375325-64-6]; t is triplet; TBAF is tetrabutylammonium fluoride; TBSCl is tert-butyl dimethylsilyl chloride; TBTU is N,N,N',N'-Tetramethyl-O-(benzotriazol-1-yl)uronium tetrafluoroborate; TEA is triethyl amine; Tf is trifluoromethane sulfonyl; THF is tetrahydrofuran; $Ti(OiPr)_4$ is titanium isopropoxide; TFA is trifluoroacetic acid; TLC is thin-layer chromatography; Trixiephos is racemic-2-di-I-butylphosphino-1,1'-binaphtyl; TosCl and TsCl is p-toluene sulfonyl chloride; pTSA, pTsOH and TsOH is p-toluenesulfonic acid, $Ts_2O$ is tosic anhydride or p-toluene sulfonic anhydride; and xphos is 2-dicyclohexylphosphino-2',4',6'-triisopropylbiphenyl.

Several methods for preparing the compounds of this invention are illustrated in the following Schemes, Intermediates and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following Schemes and Examples are provided for the purpose of illustration only and are not to be construed as limitations on the disclosed invention. All temperatures are degrees Celsius unless otherwise noted.

Intermediate 1

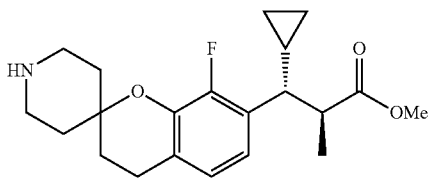 [SMILES: COC(=O)[C@@H](C)[C@H](c1ccc2c(c1F)OC1(CCNCC1)CC2)C1CC1]

Step A: tert-Butyl 7-((1R,2S)-1-cyclopropyl-3-methoxy-2-methyl-3-oxopropyl)-8-fluoro-4-oxospiro[chroman-2,4'-piperidine]-1'-carboxylate To a solution of (2S,3R)-methyl 3-(4-acetyl-2-fluoro-3-hydroxyphenyl)-3-cyclopropyl-2-methyl-propanoate (3.0 g, 10.2 mmol) and tert-butyl 4-oxopiperidine-1-carboxylate (2.23 g, 11.2 mmol) in MeOH (30 mL) was added pyrrolidine (0.870 g, 12.2 mmol). The reaction mixture was stirred at 60° C. for 3 h, then the solvent was removed under reduced pressure to give the crude product, which was purified by column chromatography (SiO$_2$, PE:EA=20:1 to PE:EA=10:1, v/v) to give the title compound. MS (ESI) m/z: 498.2 [M+Na]$^+$

Step B: tert-Butyl 7-((1R,2S)-1-cyclopropyl-3-methoxy-2-methyl-3-oxopropyl)-8-fluoro-4-hydroxyspiro[chroman-2,4'-piperidine]-1'-carboxylate To a solution of tert-butyl 7-((1R,2S)-1-cyclopropyl-3-methoxy-2-methyl-3-oxopropyl)-8-fluoro-4-oxospiro[chroman-2,4'-piperidine]-1'-carboxylate (4.50 g, 9.46 mmol) in MeOH (40 mL) was added NaBH$_4$ (0.72 g, 18.9 mmol) in three portions at 0° C. The reaction mixture was stirred at 0° C. under N$_2$ for 30 min. Then the reaction was quenched with saturated NH$_4$Cl aqueous (40 mL), and most of the MeOH solvent was removed under reduced pressure. The resulting mixture was extracted with EtOAc (60 mL×3), and the combined organic layers were washed with brine (30 mL), dried (MgSO$_4$) and filtered. The filtrate was concentrated in vacuo to give the title compound, which was used directly in the next step without purification. MS (ESI) m/z: 500.2 [M+Na]$^+$ $^1$H NMR (400 MHz, CDCl$_3$) δ=7.21-7.11 (m, 1H), 6.81-6.72 (m, 1H), 4.94-4.83 (m, 1H), 3.97-3.80 (m, 2H), 3.73 (s, 3H), 3.38-3.15 (m, 2H), 2.95-2.84 (m, 1H), 2.33-2.24 (m, 1H), 2.21-2.12 (m, 2H), 2.02-1.90 (m, 2H), 1.87-1.80 (m, 1H), 1.66-1.54 (m, 2H), 1.47 (s, 9H), 1.18-1.06 (m, 1H), 0.96 (d, J=7.0 Hz, 3H), 0.62-0.51 (m, 1H), 0.35-0.24 (m, 2H), 0.05--0.04 (m, 1H)

Step C: (2S,3R)-Methyl 3-cyclopropyl-3-(8-fluorospiro[chroman-2,4'-piperidin]-7-yl)-2-methylpropanoate To a solution of tert-butyl-7-((1R,2S)-1-cyclopropyl-3-methoxy-2-methyl-3-oxopropyl)-8-fluoro-4-hydroxyspiro[chroman-2,4'-piperidine]-1'-carboxylate (200 mg, 0.419 mmol) in DCM (3 mL) were added triethylsilane (1.0 mL, 6.26 mmol) and TFA (1.0 mL, 13.0 mmol). The reaction mixture was stirred at 25° C. for 24 h. Then the solvent was removed under reduced pressure to give a residue. Saturated aqueous NaHCO$_3$ (5 mL) was added to the residue, and the mixture was extracted with EtOAc (10 mL×3). The combined organic layers were washed with brine (10 mL), dried (MgSO$_4$) and filtered. The filtrate was concentrated in vacuo to give the title compound, which was used in next step directly without further purification. MS (ESI) m/z: 362.2 [M+H]$^+$

Example 1

Sodium (2S,3R)-3-cyclopropyl-3-(1'-(2-cyclopropyl-5-(trifluoromethyl)benzyl)spiro-[chroman-2,4'-piperidin]-7-yl)-2-methylpropanoate

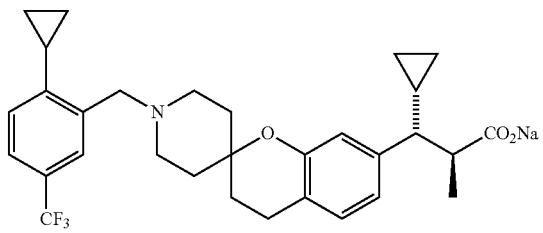

Step A: 2-Cyclopropyl-5-(trifluoromethyl)benzaldehyde

To a solution of 2-bromo-1-cyclopropyl-4-(trifluoromethyl)benzene (500 mg, 1.89 mmol) in THF (4 mL) was added butyllithium (1.13 ml, 2.83 mmol) at –78° C. The mixture was stirred at –78° C. for 30 min under nitrogen. Then DMF (0.37 ml, 4.72 mmol) was added dropwise at –78° C. The reaction mixture was stirred at –78° C. for 1 h under nitrogen. Then the reaction mixture was quenched with saturated NH$_4$Cl (2 mL) and water (2 mL). The mixture was extracted with EtOAc (20 mL×3). The combined organic layers were washed with brine (20 ml), dried over anhydrous Na$_2$SO$_4$ and filtered. The filtrate were evaporated under reduced pressure to give the residue, which was purified by silica gel chromatography (SiO$_2$, petroleum ether:ethyl acetate=20:1~10:1, v/v) to give the title compound. MS (ESI) m/z: 215.0 [M+H]$^+$ $^1$H NMR (400 MHz, CD$_3$OD): δ=10.59 (s, 1H), 8.06 (s, 1H), 7.79 (d, J=8.2 Hz, 1H), 7.34 (d, J=8.2 Hz, 1H), 2.87-2.77 (m, 1H), 1.22-1.14 (m, 2H), 0.92-0.86 (m, 2H).

Step B: (2S3R)-Methyl 3-cyclopropyl-3-(1'-(2-cyclopropyl-5-(trifluoromethyl) benzyl)spiro[chroman-2,4'-piperidin]-7-yl)-2-methylpropanoate To a solution of 2-cyclopropyl-5-(trifluoromethyl)benzaldehyde (29.9 mg, 0.140 mmol) and (2S,3R)-methyl 3-cyclopropyl-2-methyl-3-(spiro[chroman-2,4'-piperidin]-7-yl)-propanoate (40.0 mg, 0.116 mmol) in MeOH (2 mL) and THF (2 mL) was added titanium (IV) isopropoxide (99.0 mg, 0.349 mmol). The mixture was stirred at 60° C. for 12 h. Then NaCNBH$_4$ (36.6 mg, 0.582 mmol) was added at 25° C. The mixture was stirred at 25° C. for 2 h. Then H$_2$O (5 mL) was added, and the aqueous layer was extracted with DCM (30 mL×3). The combined organic layers was dried over sodium sulfate and filtered. The filtrate was concentrated in vacuo to give the title compound, which was used directly in the next step without purification. MS (ESI) m/z: 542.2 (M+H)$^+$

Step C: Sodium (2S,3R)-3-cyclopropyl-3-(1'-(2-cyclopropyl-5-(trifluoromethyl) benzyl)spiro[chroman-2,4'-piperidin]-7-yl)-2-methylpropanoate To a solution of (2S,3R)-methyl 3-cyclopropyl-3-(1'-(2-cyclopropyl-5-(trifluoromethyl)benzyl)-spiro-[chroman-2, 4'-piperidin]-7-yl)-2-methylpropanoate (53.0 mg, 98.0 umol) in a co-solvent of THF (2 ml), water (2 ml) and MeOH (2 ml) was added LiOH (117 mg, 4.9 mmol). The reaction mixture was stirred at 50° C. for 12 hours under $N_2$. Then the mixture was poured into water (2 mL) and citric acid was added to adjust the pH to 7. The mixture was extracted with EtOAc (5 mL×3). The combined organic layers were washed with brine (2 mL×3), dried over $Na_2SO_4$, filtered, and evaporated under reduced pressure to give a residue, which was purified by Prep-HPLC (base) to give the title compound. NaOH (1.0 eq, 0.5 M) was added to the title compound, and the mixture was stirred for 1 h at room temperature. Then the reaction mixture was lyophilized to give the sodium salt of the title compound. Prep HPLC conditions: a MS trigger instrument fitted with a Waters Xbridge Prep OBD C18 150*30 5 u using water (0.05% ammonia hydroxide v/v)-ACNas the eluents, Mobile phase A: water (0.05% ammonia hydroxide v/v), mobile phase B: acetonitrile, Gradient: 45-75% B, 0-2.0 min and FlowRate: 25 mL/min. MS (ESI) m/z: 528.2[M+H]$^+$ $^1$H NMR (400 MHz, CD$_3$OD): δ=7.74 (s, 1H), 7.54 (d, J=7.9 Hz, 1H), 7.21 (d, J=7.9 Hz, 1H), 7.02 (d, J=7.5 Hz, 1H), 6.75-6.65 (m, 2H), 4.03 (s, 2H), 2.96-2.69 (m, 7H), 2.31 (br. s., 1H), 2.01-1.72 (m, 7H), 1.12 (d, J=6.8 Hz, 3H), 0.93 (d, J=6.8 Hz, 3H), 0.79 (d, J=4.4 Hz, 2H), 0.62 (br. s., 1H), 0.44-0.28 (m, 2H), 0.05--0.04 (m, 1H)

Example 2

$^1$H NMR (400 MHz, CD$_3$OD) δ=7.43-7.36 (m, 1H), 7.35-7.26 (m, 1H), 7.14-7.04 (m, 1H), 6.78 (d, J=7.7 Hz, 1H), 6.65 (t, J=6.9 Hz, 1H), 3.94-3.85 (m, 1H), 3.00-2.90 (m, 1H), 2.83-2.72 (m, 3H), 2.57-2.42 (m, 3H), 2.26 (t, J=9.9 Hz, 1H), 1.93-1.57 (m, 6H), 1.36 (d, J=6.4 Hz, 3H), 1.12 (m, 1H), 0.88 (d, J=6.4 Hz, 3H), 0.61-0.51 (m, 1H), 0.40-0.21 (m, 2H), -0.01--0.11 (m, 1H)

Example 3

$^1$H NMR (400 MHz, CD$_3$OD) δ=7.41-7.34 (m, 1H), 7.34-7.27 (m, 1H), 7.14-7.05 (m, 1H), 6.79 (d, J=7.7 Hz, 1H), 6.66 (d, J=6.4 Hz, 1H), 3.65 (s, 2H), 2.83-2.73 (m, 3H), 2.72-2.64 (m, 2H), 2.63-2.54 (m, 2H), 2.26 (t, J=10.1 Hz, 1H), 1.88-1.78 (m, 4H), 1.73 (d, J=10.1 Hz, 2H), 1.17-1.05 (m, 1H), 0.88 (d, J=6.6 Hz, 3H), 0.61-0.51 (m, 1H), 0.39-0.20 (m, 2H), -0.01--0.11 (m, 1H)

TABLE 1

The compounds of Examples 2 and 3 were prepared in a similar manner to Example 1 using the appropriate starting material and reagents.

| Example | Structure | M.W. | Compound Name | LC/MS (ESI) observed [M + H]$^+$ |
|---|---|---|---|---|
| 2 | 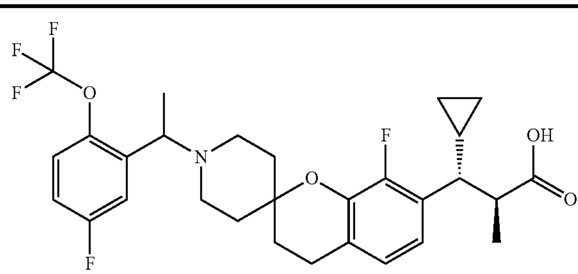 | 533.56 | (2S,3R)-3-cyclopropyl-3-(8-fluoro-1'-(1-(5-fluoro-2-(trifluoromethoxy)phenyl)ethyl)-spiro[chroman-2,4'-piperidin]-7-yl)-2-methylpropanoic acid | 554.3 |
| 3 | 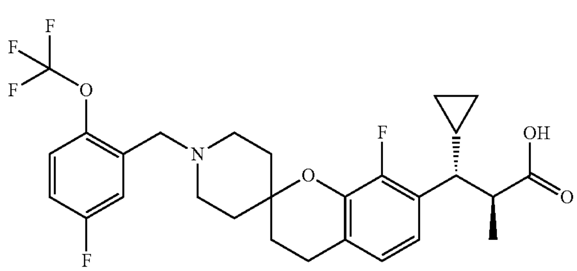 [SMILES: C[C@H](C(=O)O)[C@H](c1ccc2c(c1F)OC1(CC2)CCN(Cc2cc(F)ccc2OC(F)(F)F)CC1)C1CC1] | 539.53 | (2S,3R)-3-cyclopropyl-3-(8-fluoro-1'-(5-fluoro-2-(trifluoromethoxy)-benzyl)spiro[chroman-2,4'-piperidin]-7-yl)-2-methylpropanoic acid | 540.2 |

Example 4

(2S,3R)-3-(1'-(5-chloro-2-(trifluoromethoxy)benzyl)-8-fluorospiro[chroman-2,4'-piperidin]-7-yl)-3-cyclopropyl-2-methylpropanoic Acid

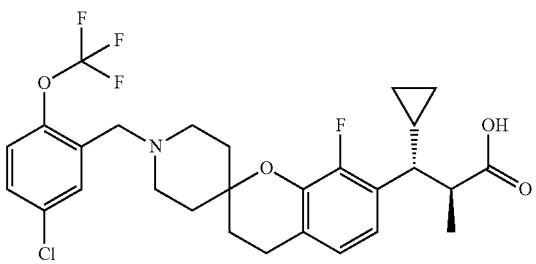 [SMILES: C[C@H](C(=O)O)[C@H](c1ccc2c(c1F)OC1(CC2)CCN(Cc2cc(Cl)ccc2OC(F)(F)F)CC1)C1CC1]

Step A: (2S,3R)-methyl 3-(1'-(5-chloro-2-(trifluoromethoxy)benzyl)-8-fluorospiro-[chroman-2,4'-piperidin]-7-yl)-3-cyclopropyl-2-methylpropanoate To a solution of 5-chloro-2-(trifluoromethoxy)benzaldehyde (47.7 mg, 0.212 mmol) and (2S,3R)-methyl 3-cyclopropyl-3-(8-fluorospiro[chroman-2,4'-piperidin]-7-yl)-2-methyl-propanoate (64 mg, 0.177 mmol) in MeOH (2 mL) and THF (2 mL) was added titanium (IV) isopropoxide (151 mg, 0.531 mmol). The mixture was stirred at 60° C. for 12 h. Then NaCNBH$_4$ (55.6 mg, 0.885 mmol) was added at 25° C. The mixture was stirred at 25° C. for 2 h. Then H$_2$O (5 mL) was added, and the aqueous layer was extracted with DCM (30×3 mL). The combined organic layers were dried over sodium sulfate, and then filtered. The filtrate was concentrated in vacuo to give the crude product, which was purified by preparative-TLC (SiO$_2$, petroleum ether:ethyl acetate=10:1) to give the title compound. LCMS (ESI) m/z: 570.2 [M+H]$^+$ Step B: (2S,3R)-3-(1'-(5-chloro-2-(trifluoromethoxy)benzyl)-8-fluorospiro [chroman-2,4'-piperidin]-7-yl)-3-cyclopropyl-2-methylpropanoic Acid To a solution of (2S,3R)-methyl 3-(1'-(5-chloro-2-(trifluoromethoxy)benzyl)-8-fluoro-spiro-[chroman-2,4'-piperidin]-7-yl)-3-cyclopropyl-2-methylpropanoate (35.0 mg, 0.0610 mmol) in MeOH (1 mL), THF (1 mL) and water (1 mL) was added LiOH (14.7 mg, 0.614 mmol) under nitrogen. The reaction mixture was stirred at 55° C. for 24 h. Then the reaction mixture was concentrated in vacuo to remove the solvent. Water (5 mL) was added to the resulting residue and citric acid was added to adjust the pH to pH ~5. Then the mixture was extracted with EtOAc (10 mL×3). The combined organic layers were washed with brine (10 mL), dried over anhydrous MgSO$_4$ and filtered. The filtrate was concentrated under reduced pressure. The resulting residue was purified by prep-HPLC (acid) to afford the title compound. Preparative HPLC conditions: MS trigger instrument fitted with a Phenomenex Synergi C18 150×30 mm×4 um water (0.1% TFA)-ACN as the eluents; mobile phase A: water (0.1% TFA); mobile phase B: acetonitrile; gradient: 35-55% B, 0-12.0 min; 100% B, 12.1-14.0 min; 10% B, 14.1-17 min; and flowRate: 25 mL/min. MS (ESI) m/z: 556.1 [M+H]$^+$ $^1$H NMR (400 MHz, CD$_3$OD) δ=7.54-7.48 (m, 1H), 7.45-7.38 (m, 1H), 7.24-7.17 (m, 1H), 6.97 (d, J=7.8 Hz, 1H), 6.65 (d, J=7.8 Hz, 1H), 6.60 (s, 1H), 4.23 (d, J=6.3 Hz, 1H), 3.65 (t, J=9.4 Hz, 1H), 3.47 (s, 1H), 3.07 (d, J=6.8 Hz, 1H), 2.94 (s, 1H), 2.85-2.67 (m, 3H), 2.66-2.55 (m, 1H), 2.07 (d, J=8.3 Hz, 2H), 1.93-1.70 (m, 4H), 1.60 (d, J=7.8 Hz, 1H), 1.42 (s, 3H), 1.33 (d, J=13.3 Hz, 1H), 1.12-1.03 (m, 1H), 0.89 (d, J=6.8 Hz, 3H), 0.61-0.52 (m, 1H), 0.40-0.23 (m, 2H), 0.00--0.09 (m, 1H)

Examples 5A and 5B (2S3R)-3-(1'-((RS)-1-(5-chloro-2-(trifluoromethyl)phenyl)ethyl)spiro[chroman-2,4'-piperidin]-7-yl)-3-cyclopropyl-2-methylpropanoic Acid

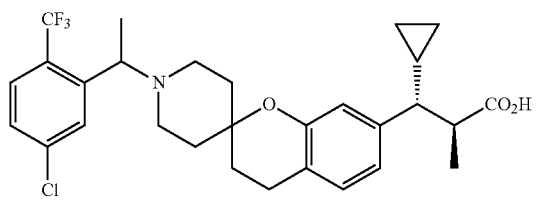 [SMILES: CC(c1cc(Cl)ccc1C(F)(F)F)N1CCC2(CCc3ccc([C@H](C4CC4)[C@H](C)C(=O)O)cc3O2)CC1]

Step A: (2S3R)-methyl 3-(1'-((RS)-1-(5-chloro-2-(trifluoromethyl)phenyl)ethyl) spiro[chroman-2,4'-piperidin]-7-yl)-3-cyclopropyl-2-methylpropanoate To a solution of (2S,3R)-methyl 3-cyclopropyl-2-methyl-3-(spiro[chroman-2,4'-piperidin]-7-yl)-propanoate (350 mg, 1.019 mmol), K$_2$CO$_3$ (704 mg, 5.10 mmol), and sodium iodide (305 mg, 2.04 mmol) in MeCN (6 mL) was added 1-(5-chloro-2-(trifluoro-methyl)phenyl)ethyl methanesulfonate (370 mg, 1.22 mmol). The reaction mixture was stirred at 80° C. for 6 h. Then water (15 mL) was added, and the mixture was extracted with EtOAc (30 mL×3). The combined organic layers were washed with brine (20 mL), dried (MgSO$_4$) and filtered. The filtrate was concentrated in vacuo to give the crude product, which was purified by prep-TLC (SiO$_2$, PE:EA=10:1, v/v) to give the title compound. MS (ESI) m/z: 550.3 [M+H]$^+$ Step B: (2S,3R)-3-(1'-((RS)-1-(5-chloro-2-(trifluoromethyl)phenyl)ethyl)spiro [chroman-2,4'-piperidin]-7-yl)-3-cyclopropyl-2-methylpropanoic Acid To a solution of (2S,3R)-methyl 3-(1'-((RS)-1-(5-chloro-2-(trifluoromethyl)phenyl)ethyl)-spiro[chroman-2,4'-piperidin]-7-yl)-3-cyclopropyl-2-methylpropanoate (300 mg, 0.545 mmol) in MeOH (3 mL), THF (3 mL) and water (3 mL) was added LiOH (261 mg, 10.9 mmol). The reaction mixture was stirred at 50° C. for 40 h. Then the reaction mixture was cooled to 25° C., and acidified with citric acid to adjust the pH to pH=5-6 and extracted with EtOAc (30 mL×3). The combined organic layers were dried (Na$_2$SO$_4$) and filtered. The filtrate was concentrated in vacuo to give the crude product, which was purified by prep-TLC (SiO$_2$, PE:EA=1:1, v/v) to give the title compound. To a solution of the title compound in MeCN (1 mL) and water (1 mL) was added an aqueous solution of NaOH (1.0 eq, 0.5 M), and the mixture was stirred for 1 hour at room temperature. Then the reaction mixture was lyophilized to give the sodium salt of the title compound. MS (ESI) m/z: 536.3 [M+H]$^+$ $^1$H NMR (400 MHz, CD$_3$OD) δ=7.94 (s, 1H), 7.65 (d, J=8.4 Hz, 1H), 7.43 (d, J=7.5 Hz, 1H), 6.96 (d, J=7.5 Hz, 1H), 6.68-6.57 (m, 2H), 3.81-3.68 (m, 1H), 3.12-2.97 (m, 1H), 2.80-2.68 (m, 3H), 2.54-2.41 (m, 2H), 2.41-2.29 (m, 1H), 1.95-1.69 (m, 6H), 1.66-1.52 (m, 1H), 1.33 (d, J=6.4 Hz, 3H), 1.14-1.04 (m, 1H), 0.90 (d, J=6.8 Hz, 3H), 0.63-0.52 (m, 1H), 0.37-0.24 (m, 2H), 0.06--0.13 (m, 1H)

Step C: (2S,3R)-3-(1'-((R or S)-1-(5-chloro-2-(trifluoromethyl)phenyl)ethyl)spiro [chroman-2,4'-piperidin]-7-yl)-3-cyclopropyl-2-methylpropanoic Acid

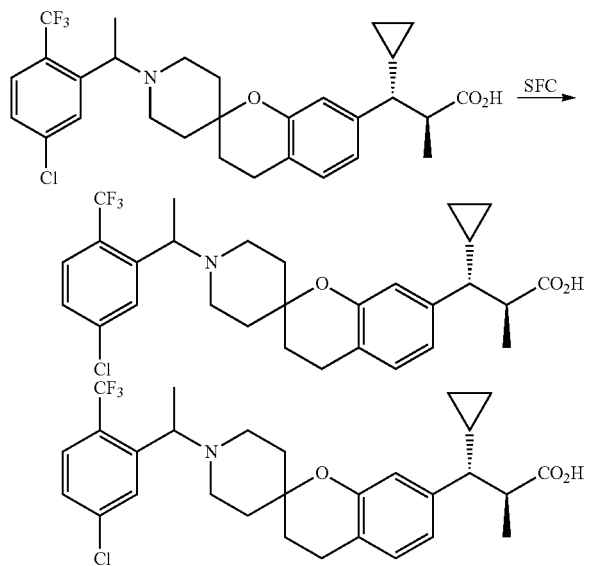

(2S,3R)-3-(1'-((RS)-1-(5-chloro-2-(trifluoromethyl)phenyl)ethyl)spiro[chroman-2,4'-piperidin]-7-yl)-3-cyclopropyl-2-methylpropanoic acid (150 mg, 0.280 mmol) was separated into its individual diastereoisomers via SFC (SFC conditions: Column: Chiralpak AD-3 150×4.6 mm I.D., 3 um Mobile phase: A: $CO_2$B:iso-propanol (0.05% DEA) Gradient: from 5% to 40% of B in 5 min and hold 40% for 2.5 min, then 5% of B for 2.5 min Flow rate: 2.5 mL/min Column temp.: 35° C.) to give the first peak (2S,3R)-3-(1'-((R or S)-1-(5-chloro-2-(trifluoromethyl)phenyl)ethyl)-spiro-[chroman-2,4'-piperidin]-7-yl)-3-cyclopropyl-2-methylpropanoic acid (Rt=3.145 min), which was purified by prep-HPLC(Neutral) to give Example 5A; and the second peak: (2S,3R)-3-(1'-((R or S)-1-(5-chloro-2-(trifluoromethyl)-phenyl)-ethyl)spiro[chroman-2,4'-piperidin]-7-yl)-3-cyclopropyl-2-methylpropanoic acid (Rt=3.277 min), which was purified by prep-HPLC (Neutral) to give Example 5B. Preparative HPLC conditions: a MS trigger instrument fitted with a Phenomenex Gemini C18 250×21.2 mm×5 um using water and acetonitrile as the eluents, Mobile phase A: water (10 mM $NH_4HCO_3$), Mobile phase B: acetonitrile, Gradient: 41-71% B, 0-12.0 min; 100% B, 12.1-14.0 min; 10% B, 14.1-17 min, FlowRate: 25 mL/min.

Example 5A

MS (ESI) m/z: 536.2 $[M+H]^+$ $^1$H NMR (400 MHz, $CD_3OD$) δ=7.93 (s, 1H), 7.64 (d, J=8.4 Hz, 1H), 7.41 (d, J=8.6 Hz, 1H), 6.95 (d, J=7.5 Hz, 1H), 6.66-6.58 (m, 2H), 3.77-3.68 (m, 1H), 3.08-2.98 (m, 1H), 2.78-2.68 (m, 3H), 2.52-2.40 (m, 2H), 2.39-2.29 (m, 1H), 1.94-1.84 (m, 2H), 1.79 (s, 4H), 1.63-1.50 (m, 1H), 1.32 (d, J=6.4 Hz, 3H), 1.12-1.03 (m, 1H), 0.89 (d, J=6.8 Hz, 3H), 0.61-0.51 (m, 1H), 0.37-0.23 (m, 2H), 0.02--0.09 (m, 1H).

Example 5B

MS (ESI) m/z: 536.2 $[M+H]^+$ $^1$H NMR (400 MHz, $CD_3OD$) δ=7.94 (s, 1H), 7.65 (d, J=8.6 Hz, 1H), 7.42 (d, J=8.4 Hz, 1H), 6.96 (d, J=7.7 Hz, 1H), 6.66-6.59 (m, 2H), 3.79-3.71 (m, 1H), 3.10-3.00 (m, 1H), 2.78-2.70 (m, 3H), 2.54-2.43 (m, 2H), 2.40-2.31 (m, 1H), 1.95-1.85 (m, 2H), 1.83-1.68 (m, 4H), 1.65-1.53 (m, 1H), 1.33 (d, J=6.4 Hz, 3H), 1.13-1.03 (m, 1H), 0.90 (d, J=6.8 Hz, 3H), 0.62-0.53 (m, 1H), 0.36-0.27 (m, 2H), 0.02--0.07 (m, 1H).

TABLE 2

The compounds of Examples 6-8 were prepared in a similar manner to Examples 5A and 5B using the appropriate starting material and reagents.

| Example | Structure | M.W. | Compound Name | LC/MS (ESI) observed $[M + H]^+$ |
|---|---|---|---|---|
| 6 | 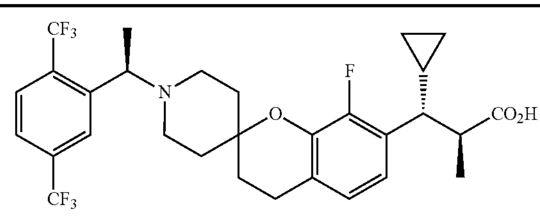 | 587.57 | (2S,3R)-3-(1'-((R)-1-(2,5-bis(trifluoromethyl)-phenyl)ethyl)-8-fluoro-spiro[chroman-2,4'-piperidin]-7-yl)-3-cyclopropyl-2-methyl-propanoic acid | 588.3 |
| 7 | 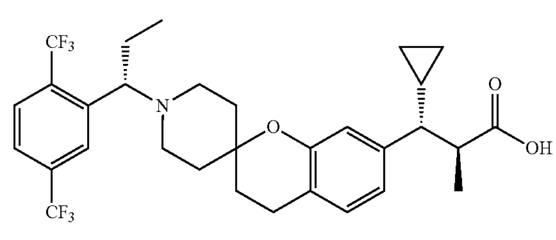 [SMILES: CC[C@@H](c1cc(C(F)(F)F)ccc1C(F)(F)F)N1CCC2(CCc3ccc([C@H](C4CC4)[C@H](C)C(=O)O)cc3O2)CC1] | 583.60 | sodium (2S,3R)-3-(1'-((S)-1-(2,5-bis(trifluoromethyl)phenyl)propyl)-spiro[chroman-2,4'-piperidin]-7-yl)-3-cyclopropyl-2-methyl-propanoic acid | 584.2 |

TABLE 2-continued

The compounds of Examples 6-8 were prepared in a similar manner to Examples 5A and 5B using the appropriate starting material and reagents.

| Example | Structure | M.W. | Compound Name | LC/MS (ESI) observed [M + H]+ |
|---|---|---|---|---|
| 8 | 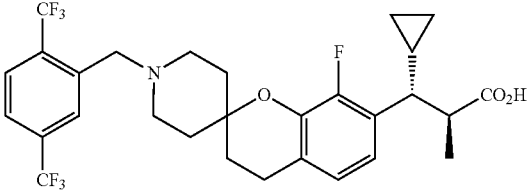 [SMILES: C[C@H](C(=O)O)[C@H](c1ccc2c(c1F)OC1(CC2)CCN(Cc2cc(C(F)(F)F)ccc2C(F)(F)F)CC1)C1CC1] | 573.54 | (2S,3R)-3-(1'-(2,5-bis-(trifluoromethyl)benzyl)-8-fluoro-spiro[chroman-2,4'-piperidin]-7-yl)-3-cyclopropyl-2-methyl-propanoic acid | 574.1 |

Example 6

¹H NMR (400 MHz, CDCl₃): δ=8.19 (s, 1H), 7.69 (d, J=8.2 Hz, 1H), 7.53 (d, J=8.2 Hz, 1H), 6.74 (d, J=7.8 Hz, 1H), 6.59 (t, J=7.0 Hz, 1H), 3.79 (d, J=5.5 Hz, 1H), 2.98-2.83 (m, 2H), 2.79-2.65 (m, 2H), 2.55-2.38 (m, 2H), 2.32-2.20 (m, 2H), 1.91 (d, J=12.5 Hz, 1H), 1.83-1.63 (m, 4H), 1.58-1.47 (m, 1H), 1.27 (d, J=6.3 Hz, 3H), 1.16 (br. s., 1H), 0.97 (d, J=6.7 Hz, 3H), 0.64-0.53 (m, 1H), 0.41-0.25 (m, 2H), 0.07--0.03 (m, 1H).

Example 7

¹H NMR (400 MHz, CDCl₃) δ=8.11 (s, 1H), 7.77 (d, J=8.2 Hz, 1H), 7.60 (d, J=7.9 Hz, 1H), 6.97 (d, J=7.5 Hz, 1H), 6.68-6.62 (m, 2H), 3.78 (s, 1H), 3.01-2.89 (m, 1H), 2.88-2.78 (m, 1H), 2.73 (s, 2H), 2.53-2.44 (m, 2H), 2.36-2.21 (m, 1H), 1.97-1.85 (m, 3H), 1.83-1.68 (m, 5H), 1.61-1.47 (m, 1H), 1.16-1.07 (m, 1H), 0.99 (d, J=6.6 Hz, 3H), 0.74-0.59 (m, 4H), 0.44-0.28 (m, 2H), 0.13--0.01 (m, 1H).

Example 8

¹H NMR (400 MHz, CDCl₃): δ=8.41 (s, 1H), 7.94-7.87 (m, 1H), 7.85-7.79 (m, 1H), 6.82 (d, J=8.2 Hz, 1H), 6.75-6.68 (m, 1H), 4.52 (s, 2H), 3.39 (br. s., 2H), 3.33-3.19 (m, 2H), 2.98-2.87 (m, 1H), 2.78 (t, J=6.3 Hz, 2H), 2.35 (t, J=10.2 Hz, 1H), 2.25 (t, J=13.5 Hz, 2H), 2.03 (d, J=14.5 Hz, 2H), 1.92 (t, J=6.5 Hz, 2H), 1.19 (br. s., 1H), 1.02 (d, J=7.0 Hz, 3H), 0.64 (br. s., 1H), 0.47-0.30 (m, 2H), 0.10-0.00 (m, 1H)

Example 9

(2S,3R)-3-(1'-((S)-1-(2,5-bis(trifluoromethyl)phenyl) propyl)spiro[chroman-2,4'-piperidin]-7-yl)-3-cyclopropyl-2-methylpropanoic Acid

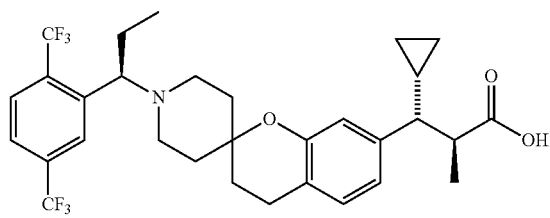 [SMILES: CC[C@H](c1cc(C(F)(F)F)ccc1C(F)(F)F)N1CCC2(CCc3ccc([C@H](C4CC4)[C@H](C)C(=O)O)cc3O2)CC1]

Step A: tert-butyl 7-((1R,2S)-1-cyclopropyl-3-methoxy-2-methyl-3-oxopropyl)-4-oxospiro [chroman-2,4'-piperidine]-1'-carboxylate To a solution of (2S,3R)-methyl 3-(4-acetyl-3-hydroxyphenyl)-3-cyclopropyl-2-methyl propanoate (3.00 g, 10.9 mmol) and tert-butyl 4-oxopiperidine-1-carboxylate (2.163 g, 10.86 mmol) in MeOH (30 mL) was added pyrrolidine (1.3 mL, 16.3 mmol). The resulting mixture was stirred at 60° C. for 4 hours under N₂. Then the reaction concentrated under reduced pressure to give a residue, which was purified via column chromatography (SiO₂, PE/EA=30:1 to 12:1, v/v) to give the title compound. MS (ESI) m/z: 402.2 [M+H]+

Step B: tert-butyl 7-((1R,2S)-1-cyclopropyl-3-methoxy-2-methyl-3-oxopropyl)-4-hydroxy spiro [chroman-2,4'-piperidine]-1'-carboxylate To a solution of tert-butyl 7-((1R,2S)-1-cyclopropyl-3-methoxy-2-methyl-3-oxopropyl)-4-oxo-spiro-[chroman-2,4'-piperidine]-1'-carboxylate (4.50 g, 9.83 mmol) in MeOH (50 mL) was added NaBH₄ (1.12 g, 29.5 mmol) at 0° C. The resulting mixture was stirred at 0° C. for 30 minutes. Then water (30 mL) was added and the mixture was concentrated under the reduced pressure to give a residue. The residue was extracted with EtOAc (50 mL×3). The combined organic layers were washed with brine (saturated, 10 mL), dried (Na₂SO₄) and filtered. The filtrate was concentrated to give the title compound, which was used to the next step without purification. MS (ESI) m/z: 404.2 [M−Boc+H]+

Step C: (2S,3R)-methyl 3-cyclopropyl-2-methyl-3-(spiro[chroman-2,4'-piperidin]-7-yl)propanoate To a solution of tert-butyl 7-((1R,2S)-1-cyclopropyl-3-methoxy-2-methyl-3-oxopropyl)-4-hydroxyspiro[chroman-2,4'-piperidine]-1'-carboxylate (550 mg, 1.20 mmol) and triethylsilane (2.0 mL, 1.20 mmol) in DCM (10 ml) was added TFA (2.0 mL, 26.0 mmol). The resulting mixture was stirred at 25° C. for 30 minutes. Then the mixture was poured into water (10 mL), neutralized with NaHCO₃ (aq.) to pH=7-8. The aqueous layer was separated and extracted with EtOAc (20 mL×3). The combined organic layers were washed with brine (saturated, 10 mL), dried (Na₂SO₄) and filtered. The filtrate was concentrated to give the title compound, which was used in the next step without purification. MS (ESI) m/z: 344.2 [M+H]+

Step D: (2S,3R)-methyl 3-(1'-((R)-1-(2,5-bis(trifluoromethyl)phenyl)propyl) spiro-[chroman-2,4'-piperidin]-7-yl)-3-cyclopropyl-2-methylpropanoate To a solution of (2S,3R)-methyl 3-cyclopropyl-2-methyl-3-(spiro[chroman-2,4'-piperidin]-7-yl)propanoate (500 mg, 1.46 mmol) and cesium carbonate (1.42 g, 4.37 mmol) in MeCN (5 mL) was added (S)-1-(2,5-bis(trifluoromethyl)phenyl)propyl methane-sulfonate (1.02 g, 2.91 mmol). The resulting mixture was stirred at 60° C. for 3 days under $N_2$. Then the reaction was added to water (10 mL). The aqueous layer was extracted with EtOAc (10 mL×3). The combined organic layers were washed with brine (10 mL×2), dried over $MgSO_4$ and filtered. The filtrate was concentrated under reduced pressure to give a residue, which was purified by column chromatography (PE/EtOAc=50:1 to 20:1, v/v) to give the title compound. MS (ESI) m/z: 598.3 [M+H]$^+$ Step E: (2S,3R)-3-(1'-((R)-1-(2,5-bis(trifluoromethyl)phenyl)propyl)spiro[chroman-2,4'-piperidin]-7-yl)-3-cyclopropyl-2-methylpropanoic Acid To a solution of (2S,3R)-methyl 3-(1'-((R)-1-(2,5-bis(trifluoromethyl)phenyl)propyl)spiro [chroman-2,4'-piperidin]-7-yl)-3-cyclopropyl-2-methylpropanoate (232 mg, 0.388 mmol) in a co-solvent of MeOH (3 mL), THF (3 mL) and water (3 mL) was added LiOH (186 mg, 7.76 mmol). The resulting mixture was stirred at 50° C. for 12 hours under $N_2$. Then the reaction was added to water (10 mL). The aqueous layer was separated, and extracted with EtOAc (10 mL×3). The combined organic layers were washed with brine (10 mL×2), dried over $MgSO_4$ and filtered. The filtrate was concentrated under reduced pressure to give a residue, which was purified by Prep-HPLC (Basic) to give the title compound. To a solution of the title compound in MeCN (1 mL) and water (1 mL) was added the solution of aqueous NaOH (1.0 eq, 0.5 M), and the mixture was stirred for 1 hour at room temperature. Then the reaction mixture was lyophilized to give the sodium salt of the title compound. HPLC Conditions: Instrument: ed; Method: Column: Waters Xbridge Prep OBD C18 150*30 5u; water (0.05% ammonia hydroxide v/v)-ACN Begin B 43, End B: 58; Gradient Time (min): 14, 100% B Hold Time (min): 2, FlowRate (ml/min): 25, Injections: 10. MS (ESI) m/z: 584.2[M+H]$^+$ $^1$H NMR (400 MHz, CDCl$_3$-d) δ=8.12 (s, 1H), 7.77 (d, J=8.2 Hz, 1H), 7.60 (d, J=8.2 Hz, 1H), 6.97 (d, J=7.4 Hz, 1H), 6.68-6.63 (m, 2H), 3.78 (s, 1H), 3.00-2.90 (m, 1H), 2.87-2.79 (m, 1H), 2.78-2.69 (m, 2H), 2.54-2.43 (m, 2H), 2.35-2.24 (m, 1H), 1.97-1.86 (m, 3H), 1.82-1.69 (m, 5H), 1.61-1.46 (m, 1H), 1.16-1.07 (m, 1H), 0.99 (d, J=6.7 Hz, 3H), 0.73-0.68 (m, 3H), 0.67-0.58 (m, 1H), 0.41-0.34 (m, 2H), 0.10-0.02 (m, 1H).

TABLE 3

The compound of Example 10 was prepared in a similar manner to Example 9 using the appropriate starting material and reagents.

| Example | Structure | M.W. | Compound Name | LC/MS (ESI) observed [M + H]$^+$ |
|---|---|---|---|---|
| 10 | 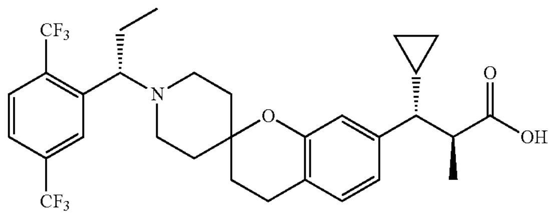 [SMILES: CC[C@@H](c1cc(C(F)(F)F)ccc1C(F)(F)F)N1CCC2(CCc3ccc([C@H](C4CC4)[C@H](C)C(=O)O)cc3O2)CC1] | 583.60 | Sodium (2S,3R)-3-(1'-((S)-1-(2,5-bis-(trifluoromethyl)phenyl)propyl)spiro[chroman-2,4'-piperidin]-7-yl)-3-cyclopropyl-2-methylpropanoic acid | 584.2 |

Example 10

$^1$H NMR (400 MHz, CDCl$_3$) δ=8.11 (s, 1H), 7.77 (d, J=8.2 Hz, 1H), 7.60 (d, J=7.9 Hz, 1H), 6.97 (d, J=7.5 Hz, 1H), 6.68-6.62 (m, 2H), 3.78 (s, 1H), 3.01-2.89 (m, 1H), 2.88-2.78 (m, 1H), 2.73 (s, 2H), 2.53-2.44 (m, 2H), 2.36-2.21 (m, 1H), 1.97-1.85 (m, 3H), 1.83-1.68 (m, 5H), 1.61-1.47 (m, 1H), 1.16-1.07 (m, 1H), 0.99 (d, J=6.6 Hz, 3H), 0.74-0.59 (m, 4H), 0.44-0.28 (m, 2H), 0.13--0.01 (m, 1H).

Example 11 sodium (2S,3R)-3-cyclopropyl-3-(1'-((R or S)-1-(2-cyclopropyl-5-(trifluoromethyl)-phenyl)ethyl)-8-fluorospiro[chroman-2,4'-piperidin]-7-yl)-2-methylpropanoate

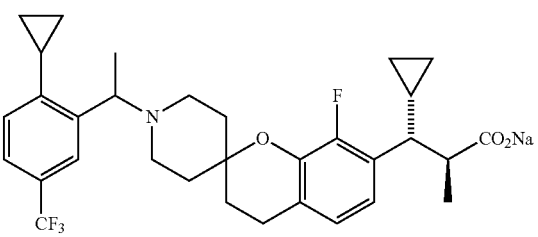

Step A:
1-(2-cyclopropyl-5-(trifluoromethyl)phenyl)ethanol

To a solution of 2-bromo-1-cyclopropyl-4-(trifluoromethyl)benzene (770 mg, 2.90 mmol) in THF (4 ml) was added butyllithium (1.74 ml, 4.36 mmol) at −78° C. The mixture was stirred at −78° C. for 30 min under nitrogen. Then acetaldehyde (320 mg, 7.26 mmol) was added dropwise at −78° C. The reaction mixture was stirred at −78° C. for 1 hour under nitrogen. Then the reaction was quenched with saturated NH$_4$Cl (3 mL) and water (2 mL). The mixture was extracted with EtOAc (20 mL×3). The combined organic layers were washed with brine (20 ml), dried over anhydrous $Na_2SO_4$ and filtered. The filtrate was evaporated under reduce pressure to give a residue, which was purified by silica gel chromatography ($SiO_2$, petroleum ether:ethyl acetate=20:1~10:1, v/v) to give the title compound. MS (ESI) m/z: 213.1 [M−OH]$^+$ $^1$H NMR (400 MHz, $CD_3OD$): δ=7.79 (s, 1H), 7.42 (d, J=7.9 Hz, 1H), 7.12 (d, J=8.2 Hz, 1H), 5.46 (q, J=6.4 Hz, 1H), 2.11-2.02 (m, 1H), 1.46 (d, J=6.4 Hz, 3H), 1.07-1.01 (m, 2H), 0.79-0.70 (m, 2H).

Step B: 2-(1-chloroethyl)-1-cyclopropyl-4-(trifluoromethyl)benzene

To a solution of 1-(2-cyclopropyl-5-(trifluoromethyl)phenyl)ethanol (400 mg, 1.74 mmol) in DCM (30 ml) was added $Et_3N$ (0.726 ml, 5.21 mmol) and MsCl (0.271 ml, 3.47 mmol). The reaction mixture was stirred at 30° C. for 12 h. Then the mixture was concentrated in vacuo to give the crude product, which was purified by column chromatography ($SiO_2$, petroleum ether:ethyl acetate=1:0, v/v) to give the title compound. $^1$H NMR (400 MHz, $CD_3OD$): δ=7.79 (s, 1H), 7.50 (d, J=8.2 Hz, 1H), 7.23 (d, J=8.2 Hz, 1H), 5.86 (q, J=6.8 Hz, 1H), 2.23-2.10 (m, 1H), 1.87 (d, J=6.8 Hz, 3H), 1.08 (dd, J=1.8, 8.4 Hz, 2H), 0.86-0.78 (m, 1H), 0.76-0.64 (m, 1H)

Step C: (2S,3R)-methyl 3-cyclopropyl-3-(1'-(1-(2-cyclopropyl-5-(trifluoromethyl) phenyl)ethyl)-8-fluorospiro[chroman-2,4'-piperidin]-7-yl)-2-methylpropanoate To a solution of (2S,3R)-methyl 3-cyclopropyl-3-(8-fluorospiro[chroman-2,4'-piperidin]-7-yl)-2-methyl-propanoate (151 mg, 0.238 mmol, Intermediate 1) and 2-(1-chloroethyl)-1-cyclopropyl-4-(trifluoromethyl)benzene (89.0 mg, 0.357 mmol) in acetonitrile (25 mL) was added $K_2CO_3$ (197 mg, 1.43 mmol) and sodium iodide (214 mg, 1.43 mmol). The reaction was stirred at 90° C. for 5 h. Then the reaction mixture was poured into water (10 mL), and the aqueous layer was extracted with EtOAc (30 mL×3). The combined organic layers were dried over sodium sulfate, and then filtered. The filtrate was concentrated in vacuo to give the crude product, which was purified by column chromatography ($SiO_2$, petroleum ether:ethyl acetate=20:1, v/v) to give the title compound. MS (ESI) m/z: 574.2 (M+H)$^+$ Step D: (2S,3R)-3-cyclopropyl-3-(1'-(1-(2-cyclopropyl-5-(trifluoromethyl)phenyl) ethyl)-8-fluorospiro[chroman-2,4'-piperidin]-7-yl)-2-methylpropanoic Acid To a solution of (2S,3R)-methyl 3-cyclopropyl-3-(1'-(1-(2-cyclopropyl-5-(trifluoro-methyl)phenyl)ethyl)-8-fluorospiro[chroman-2,4'-piperidin]-7-yl)-2-methylpropanoate (70.0 mg, 0.122 mmol) in a co-solvent of THF (2 ml), water (2 ml) and MeOH (2 ml) was added LiOH (146 mg, 6.10 mmol). The reaction mixture was stirred at 50° C. for 12 hours under $N_2$. Then the mixture was poured into water (2 mL) and citric acid was added to adjust the pH to pH 7. The mixture was extracted with EtOAc (5 mL×3). The combined organic layers were washed with brine (2 mL×3), dried over $Na_2SO_4$, and filtered. The filtrate was evaporated under reduced pressure to give a residue, which was purified via Prep-TLC ($SiO_2$, petroleum ether:ethyl acetate=1:1, v/v) to give the title compound. MS (ESI) m/z: 560.3 [M+H]$^+$ Step E: Sodium (2S,3R)-3-cyclopropyl-3-(1'-((R or S)-1-(2-cyclopropyl-5-(trifluoromethyl)phenyl) ethyl)-8-fluorospiro[chroman-2,4'-piperidin]-7-yl)-2-methylpropanoate (2S,3R)-3-cyclopropyl-3-(1'-(1-(2-cyclopropyl-5-(trifluoromethyl)-phenyl)ethyl)-8-fluorospiro[chroman-2,4'-piperidin]-7-yl)-2-methylpropanoic acid (70.0 mg, 0.125 mmol) was separated by SFC (Column: Chiralpak AD-3 150×4.6 mm I.D., 3 um Mobile phase: A: $CO_2$ B:iso-propanol (0.05% DEA) Gradient: from 5% to 40% of B in 5 min and hold 40% for 2.5 min, then 5% of B for 2.5 min Flow rate: 2.5 mL/min Column temp.: 35° C.) to give the title compound. To a solution of the title compound in MeCN (1 mL) and water (1 mL) was added an aqueous NaOH solution (1.0 eq, 0.5 M), and the mixture was stirred for 1 h at room temperature. Then the reaction mixture was lyophilized to give the sodium salt of the title compound. MS (ESI) m/z: 560.2 (M+H)$^+$ $t_{R\ (sfc)}$=3.307 min. $^1$H NMR (400 MHz, $CD_3OD$): δ=7.89 (s, 1H), 7.52 (d, J=7.9 Hz, 1H), 7.27 (d, J=8.2 Hz, 1H), 6.87 (d, J=7.9 Hz, 1H), 6.74 (t, J=7.1 Hz, 1H), 4.41 (q, J=6.2 Hz, 1H), 3.24 (d, J=11.0 Hz, 1H), 2.92-2.63 (m, 6H), 2.39-2.22 (m, 2H), 2.02 (d, J=11.9 Hz, 1H), 1.97-1.80 (m, 4H), 1.78-1.66 (m, 1H), 1.51 (d, J=6.6 Hz, 3H), 1.24-1.10 (m, 3H), 0.96 (d, J=6.8 Hz, 3H), 0.87-0.73 (m, 2H), 0.64 (br. s., 1H), 0.44 (dd, J=4.6, 9.3 Hz, 1H), 0.33 (td, J=4.5, 8.6 Hz, 1H), 0.06--0.04 (m, 1H)

TABLE 4

The compounds of Examples 12-16 were prepared in a similar manner to Example 11 using the appropriate starting material and reagents.

| Example | Structure | M.W. | Compound Name | LC/MS (ESI) observed [M + H]$^+$ |
|---|---|---|---|---|
| 12 | 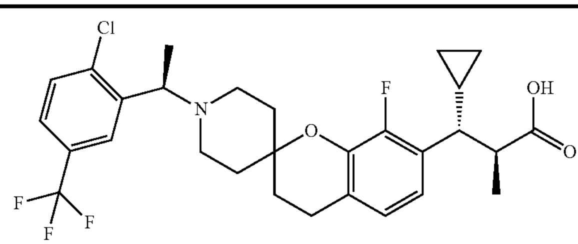 | 554.0 | (2S,3R)-3-(1'-((RS)-1-(2-chloro-5-(trifluoromethyl)phenyl)ethyl)-8-fluorospiro[chroman-2,4'-piperidin]-7-yl)-3-cyclopropyl-2-methylpropanoic acid | 554.2 |

TABLE 4-continued

The compounds of Examples 12-16 were prepared in a similar manner to Example 11 using the appropriate starting material and reagents.

| Example | Structure | M.W. | Compound Name | LC/MS (ESI) observed [M + H]+ |
|---|---|---|---|---|
| 13 | 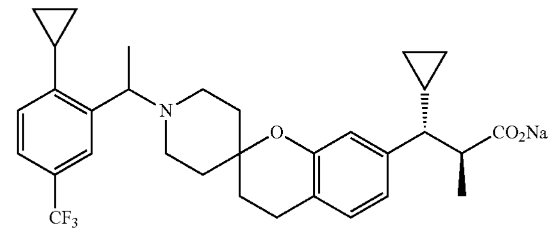 | 541.6 | sodium (2S,3R)-3-cyclopropyl-3-(1'-((R or S)-1-(2-cyclopropyl-5-(trifluoromethyl)phenyl)ethyl)spiro[chroman-2,4'-piperidin]-7-yl)-2-methylpropanoate | 542.2 |
| 14 | 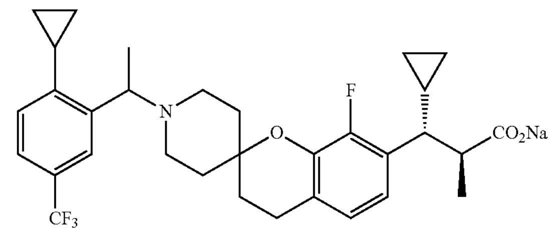 | 559.6 | sodium (2S,3R)-3-cyclopropyl-3-(1'-((S or R)-1-(2-cyclopropyl-5-(trifluoromethyl)phenyl)ethyl)-8-fluorospiro[chroman-2,4'-piperidin]-7-yl)-2-methylpropanoate | 560.2 |
| 15 | 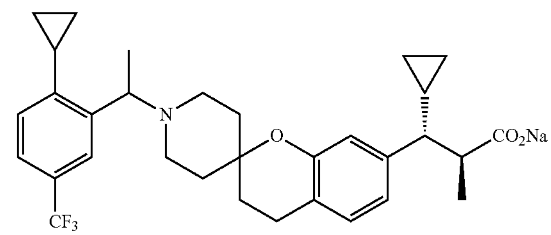 | 541.6 | sodium (2S,3R)-3-cyclopropyl-3-(1'-((S or R)-1-(2-cyclopropyl-5-(trifluoromethyl)phenyl)ethyl)spiro[chroman-2,4'-piperidin]-7-yl)-2-methylpropanoate | 542.2 |
| 16 | 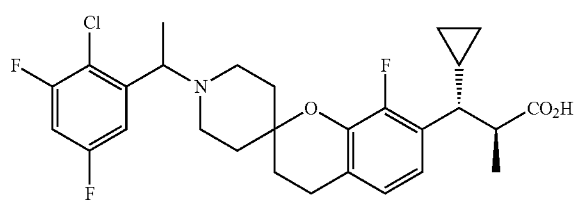 | 521.2 | (2S,3R)-3-cyclopropyl-2-methyl-3-((R or S)-2-(1-((S or R)-1-(2-(trifluoromethoxy)pyridin-3-yl)ethyl)piperidin-4-yl)chroman-7-yl)propanoic acid | 522.2 |

Example 12

$^1$H NMR (400 MHz, CDCl$_3$): δ=7.94 (s, 1H), 7.44 (q, J=8.2 Hz, 2H), 6.79 (d, J=7.8 Hz, 1H), 6.68-6.61 (m, 1H), 4.09-3.99 (m, 1H), 3.03-2.87 (m, 2H), 2.77 (t, J=6.3 Hz, 2H), 2.61-2.45 (m, 3H), 2.33 (t, J=10.2 Hz, 1H), 2.00-1.92 (m, 1H), 1.88-1.73 (m, 4H), 1.70-1.59 (m, 1H), 1.34 (d, J=6.3 Hz, 3H), 1.25-1.16 (m, 1H), 1.02 (d, J=5.9 Hz, 3H), 0.68-0.59 (m, 1H), 0.46-0.30 (m, 2H), 0.10-0.02 (m, 1H)

Example 13

MS (ESI) m/z: 542.2 (M+H)$^+$, t$_R$ $_{(sfc)}$=3.332 min, $^1$H NMR (400 MHz, CD$_3$OD): δ=7.92 (s, 1H), 7.55 (d, J=8.2 Hz, 1H), 7.29 (d, J=8.2 Hz, 1H), 7.03 (d, J=7.7 Hz, 1H), 6.77-6.64 (m, 2H), 4.48 (q, J=6.4 Hz, 1H), 3.27 (d, J=10.8 Hz, 1H), 2.94-2.63 (m, 6H), 2.28 (t, J=5.1 Hz, 1H), 2.07-1.83 (m, 6H), 1.77-1.67 (m, 1H), 1.54 (d, J=6.6 Hz, 3H), 1.21-1.07 (m, 3H), 0.95 (d, J=6.6 Hz, 3H), 0.82 (d, J=3.5 Hz, 2H), 0.69-0.57 (m, 1H), 0.47-0.27 (m, 2H), 0.09--0.03 (m, 1H)

Example 14

MS (ESI) m/z: 560.2 (M+H)$^+$, t$_R$ (sfc)=3.681 min, $^1$H NMR (400 MHz, CD$_3$OD): δ=7.91 (s, 1H), 7.53 (d, J=8.2 Hz, 1H), 7.28 (d, J=8.2 Hz, 1H), 6.88 (d, J=7.9 Hz, 1H), 6.75 (t, J=7.1 Hz, 1H), 4.44 (q, J=6.4 Hz, 1H), 3.27 (d, J=11.0 Hz, 1H), 2.91-2.66 (m, 6H), 2.39-2.22 (m, 2H), 2.04 (d, J=11.9 Hz, 1H), 1.96-1.82 (m, 4H), 1.79-1.69 (m, 1H), 1.58-1.48 (m, 3H), 1.24-1.12 (m, 3H), 0.96 (d, J=6.8 Hz, 3H), 0.87-0.75 (m, 2H), 0.70-0.60 (m, 1H), 0.45 (dd, J=4.9, 9.3 Hz, 1H), 0.39-0.29 (m, 1H), 0.06--0.03 (m, 1H)

Example 15

MS (ESI) m/z: 542.2 (M+H)$^+$, t$_R$ (sfc)=3.851 min, $^1$H NMR (400 MHz, CD$_3$OD): δ=7.89 (s, 1H), 7.52 (d, J=7.9 Hz, 1H), 7.27 (d, J=8.2 Hz, 1H), 7.01 (d, J=7.5 Hz, 1H), 6.74-6.62 (m, 2H), 4.46 (q, J=6.4 Hz, 1H), 3.25 (d, J=11.0 Hz, 1H), 2.87-2.62 (m, 6H), 2.31-2.21 (m, 1H), 2.04-1.81 (m, 6H), 1.74-1.65 (m, 1H), 1.52 (d, J=6.6 Hz, 3H), 1.17-

1.07 (m, 3H), 0.92 (d, J=6.8 Hz, 3H), 0.79 (d, J=3.5 Hz, 2H), 0.62 (d, J=4.0 Hz, 1H), 0.45-0.26 (m, 2H), 0.06--0.07 (m, 1H)

Example 16

$^1$H NMR (400 MHz, MeOH): δ=7.58 (dt, J=5.5, 8.4 Hz, 1H), 7.12 (t, J=8.8 Hz, 1H), 6.88 (d, J=8.2 Hz, 1H), 6.78-6.69 (m, 1H), 4.37 (q, J=7.0 Hz, 1H), 3.00-2.79 (m, 4H), 2.70-2.52 (m, 2H), 2.37-2.27 (m, 1H), 2.03-1.83 (m, 4H), 1.82-1.56 (m, 4H), 1.37 (br. s., 2H), 1.25-1.14 (m, 1H), 0.97 (d, J=7.0 Hz, 3H), 0.70-0.61 (m, 1H), 0.48-0.40 (m, 1H), 0.39-0.30 (m, 1H), 0.06--0.03 (m, 1H)

Example 17

(2S,3R)-3-(1'-((S or R)-1-(2-chloro-3,5-difluorophenyl)ethyl)-8-fluorospiro-[chroman-2,4'-piperidin]-7-yl)-3-cyclopropyl-2-methylpropanoic Acid

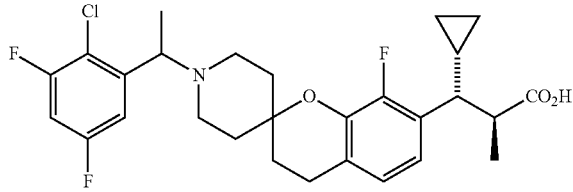 [SMILES: CC(c1cc(F)cc(F)c1Cl)N1CCC2(CCc3ccc([C@H](C4CC4)[C@H](C)C(=O)O)c(F)c3O2)CC1]

Step A: 2-chloro-3,5-difluorobenzaldehyde

To a solution of 1-bromo-2-chloro-3,5-difluorobenzene (904 mg, 4.0 mmol) in THF (40 mL) was added n-BuLi (2.4 mL, 6.0 mmol) in portions at −78° C. The reaction mixture was stirred at −78° C. for 30 min. Then DMF (0.619 mL, 8.0 mmol) was added, and the reaction mixture was stirred at −78° C. for 1 hour. The reaction was quenched with water (10 mL), and the mixture extracted with EtOAc (10 mL×3). The combined organic layers were washed with brine (20 mL), dried (Na$_2$SO$_4$), and filtered. The filtrate was evaporated under reduced pressure to give a residue, which was purified by column chromatography (silica gel eluting with PE/EA=50:1-20:1, v/v) to give the title compound. $^1$H NMR (400 MHz, CDCl$_3$): δ=10.32 (s, 1H), 7.66-7.55 (m, 1H), 7.03-6.92 (m, 1H)

Step B: 1-(2-chloro-3,5-difluorophenyl)ethanol

To a solution of 2-chloro-3,5-difluorobenzaldehyde (411 g, 2.33 mmol) in THF (30 mL) was added CH$_3$MgBr (3.1 mL, 9.30 mmol) in portions at 0° C. The reaction mixture was stirred at 0° C. for 1 hour. Then the reaction was quenched with water (10 mL), and extracted with EtOAc (10 mL×3). The combined organic layers were washed with brine (20 mL), dried (Na$_2$SO$_4$), and filtered. The filtrate was evaporated under reduced pressure to give a residue, which was purified by prep-TLC (SiO$_2$, PE/EA=10:1, v/v) to give the title compound. $^1$H NMR (400 MHz, CDCl$_3$): δ=7.34-7.18 (m, 1H), 6.92-6.72 (m, 1H), 5.23 (br. s., 1H), 1.61 (d, J=6.7 Hz, 3H).

Step C: 1-(2-chloro-3,5-difluorophenyl)ethyl methanesulfonate

To a solution of 1-(2-chloro-3,5-difluorophenyl)ethanol (96 mg, 0.500 mmol) in DCM (5 mL) were added MsCl (114 mg, 1.00 mmol) and Et$_3$N (101 mg, 1.00 mmol) at 0° C. The reaction was stirred at 25° C. for 2 hours, then quenched with water (10.00 mL), and extracted with EtOAc (10 mL×3). The combined organic layers were washed with brine (20 mL), dried (Na$_2$SO$_4$), and filtered. The filtrate was evaporated under reduced pressure to give the title compound, which was used directly in the next step. $^1$H NMR (400 MHz, CDCl$_3$): δ=7.43-7.33 (m, 1H), 6.94-6.84 (m, 1H), 6.07 (q, J=6.8 Hz, 1H), 2.92 (s, 3H), 1.85-1.73 (m, 3H)

Step D: (2S,3R)-methyl 3-(1'-(1-(2-chloro-3,5-difluorophenyl)ethyl)-8-fluorospiro [chroman-2,4'-piperidin]-7-yl)-3-cyclopropyl-2-methylpropanoate To a solution of 1-(2-chloro-3,5-difluorophenyl)ethyl methanesulfonate (113 mg, 0.420 mmol) in MeCN (10 mL) were added (2S,3R)-methyl 3-cyclopropyl-3-(8-fluorospiro-[chroman-2,4'-piperidin]-7-yl)-2-methylpropanoate (119 mg, 0.330 mmol), K$_2$CO$_3$ (228 mg, 1.65 mmol) and NaI (149 mg, 1.00 mmol). The reaction mixture was stirred at 90° C. for 5 hours. Then the mixture was diluted with water (10 mL), and extracted with EtOAc (10 mL×3). The combined organic layers were washed with brine (saturated 20 mL), dried over Na$_2$SO$_4$, and filtered. The filtrate was concentrated under reduced pressure to give a residue, which was purified by prep-TLC (SiO$_2$, PE/EA=5:1, v/v) to give the title compound. MS (ESI) m/z: 536.2[M+H]$^+$

Step E: (2S,3R)-3-(1'-(1-(2-chloro-3,5-difluorophenyl)ethyl)-8-fluorospiro [chroman-2,4'-piperidin]-7-yl)-3-cyclopropyl-2-methylpropanoic Acid To a solution of (2S,3R)-methyl 3-(2-(1-((R)-1-(2,5-bis(trifluoromethyl)phenyl)ethyl)-3-fluoroazetidin-3-yl)chroman-7-yl)-3-cyclopropyl-2-methylpropanoate (80.0 mg, 0.15 mmol) in CH$_3$OH (1 mL), THF (1 mL) and H$_2$O (1 mL) was added LiOH (252 mg, 6.0 mmol). The reaction mixture was stirred at 50° C. for 12 hours. Then the reaction mixture was poured into water (10 mL), and citric acid was added to adjust the pH to pH 7. Then the mixture was extracted with EtOAc (10 mL×3), and the combined organic layers were washed with brine (saturated, 20 mL), dried over Na$_2$SO$_4$ and filtered. The filtrate was concentrated under reduced pressure to give the title compound. MS (ESI) m/z: 522.2 [M+H]$^+$

Step F: (2S,3R)-3-(1'-((S or R)-1-(2-chloro-3,5-difluorophenyl)ethyl)-8-fluoro-spiro[chroman-2,4'-piperidin]-7-yl)-3-cyclopropyl-2-methylpropanoic Acid (2S,3R)-3-(1'-(1-(2-chloro-3,5-difluorophenyl)ethyl)-8-fluorospiro[chroman-2,4'-piperidin]-7-yl)-3-cyclopropyl-2-methylpropanoic acid (75 mg, 0.14 mmol) was separated into its individual diastereoisomers via SFC (SFC-E Column: Chiralpak AD-3 150×4.6 mm I.D., 3 um, mobile phase: A: CO$_2$B:iso-propanol (0.05% DEA), gradient: from 5% to 40% of B in 5 min and hold 40% for 2.5 min, then 5% of B for 2.5 min, Flow rate: 2.5 mL/min, Column temperature: 35° C.) to give (2S,3R)-3-(1'-((S or R)-1-(2-chloro-3,5-difluorophenyl)ethyl)-8-fluorospiro[chroman-2,4'-piperidin]-7-yl)-3-cyclopropyl-2-methylpropanoic acid, and (2S,3R)-3-(1'-((R or S)-1-(2-chloro-3,5-difluorophenyl)ethyl)-8-fluorospiro[chroman-2,4'-piperidin]-7-yl)-3-cyclopropyl-2-methylpropanoic acid. To a solution of each individual diastereoisomer of the title compound in MeCN (1 mL) and water (1 mL) was added a solution of aqueous NaOH (1.0 eq, 0.5 M), and the mixture was stirred for 1 h at room temperature. Then the reaction mixture was lyophilized to give the sodium salt of the diastereomer of the title compound. MS (ESI) m/z: 522.2[M+H]$^+$ $^1$H NMR (400 MHz, CD$_3$OD): δ=7.57 (dt, J=5.9, 8.4 Hz, 1H), 7.11 (t, J=8.8 Hz, 1H), 6.87 (d, J=7.8 Hz, 1H), 6.78-6.69 (m, 1H), 4.42-4.31 (m, 1H), 2.98-2.77 (m, 4H), 2.72-2.49 (m, 2H), 2.32 (t, J=10.2 Hz, 1H), 2.04-1.82 (m, 4H), 1.70 (d, J=7.0 Hz, 4H), 1.37 (br. s., 2H), 1.24-1.13 (m, 1H), 0.96 (d, J=7.0 Hz, 3H), 0.70-0.59 (m, 1H), 0.48-0.39 (m, 1H), 0.38-0.29 (m, 1H), 0.06--0.03 (m, 1H)

TABLE 5

The compounds of Examples 18-19 were prepared in a similar manner to Example 17 using the appropriate starting material and reagents.

| Example | Structure | M.W. | Compound Name | LC/MS (ESI) observed [M + 1]⁺ |
|---------|-----------|------|---------------|-------------------------------|
| 18 | 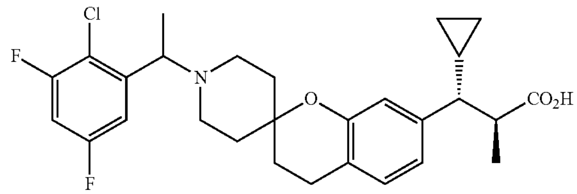 [SMILES: CC(c1cc(F)cc(F)c1Cl)N1CCC2(CCc3ccc([C@H](C4CC4)[C@H](C)C(=O)O)cc3O2)CC1] | 503.2 | (2S,3R)-3-cyclo-propyl-2-methyl-3-((S or R)-2-(1-((S or 5)-1-(2-(trifluoro-methoxy)pyridin-3-yl)ethyl)piperidin-4-yl)chroman-7-yl)propanoic acid | 504.2 |
| 19 | 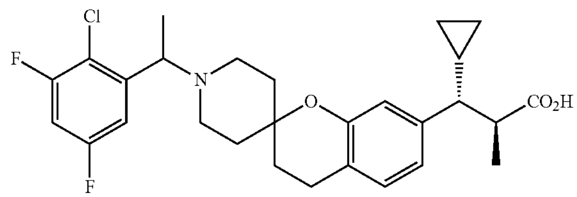 [SMILES: CC(c1cc(F)cc(F)c1Cl)N1CCC2(CCc3ccc([C@H](C4CC4)[C@H](C)C(=O)O)cc3O2)CC1] | 503.2 | (2S,3R)-3-cyclo-propyl-2-methyl-3-((S or R)-2-(1-(S or R)-1-(2-(trifluoromethoxy)-pyridin-3-yl)ethyl)-piperidin-4-yl)chroman-7-yl)-propanoic acid | 504.2 |

Example 18

¹H NMR (400 MHz, CD₃OD): δ=7.77-7.68 (m, 1H), 7.22 (t, J=9.4 Hz, 1H), 7.00 (d, J=7.7 Hz, 1H), 6.68 (d, J=7.5 Hz, 1H), 6.62 (s, 1H), 3.74 (br. s., 1H), 3.44 (d, J=12.1 Hz, 3H), 3.25-3.16 (m, 1H), 2.83-2.64 (m, 3H), 2.20-1.78 (m, 10H), 1.10-0.99 (m, 1H), 0.86 (d, J=6.8 Hz, 3H), 0.61-0.52 (m, 1H), 0.34-0.20 (m, 2H), −0.02−−0.11 (m, 1H)

Example 19

¹H NMR (400 MHz, CD₃OD): δ=7.63-7.55 (m, 1H), 7.14 (t, J=8.8 Hz, 1H), 7.04 (d, J=7.4 Hz, 1H), 6.72 (d, J=7.4 Hz, 1H), 6.56 (s, 1H), 4.37 (q, J=6.8 Hz, 1H), 2.94 (d, J=11.0 Hz, 1H), 2.88-2.73 (m, 3H), 2.71-2.52 (m, 2H), 1.98-1.80 (m, 5H), 1.71 (d, J=7.0 Hz, 3H), 1.54-1.38 (m, 3H), 1.18-1.08 (m, 1H), 0.96 (d, J=6.7 Hz, 3H), 0.71-0.60 (m, 1H), 0.46-0.32 (m, 2H), 0.07−−0.01 (m, 1H)

Example 20

(2S,3R)-3-(1'-(5-chloro-2-(difluoromethoxy)benzyl)-8-fluorospiro[chroman-2,4'-piperidin]-7-yl)-3-cyclopropyl-2-methylpropanoic Acid

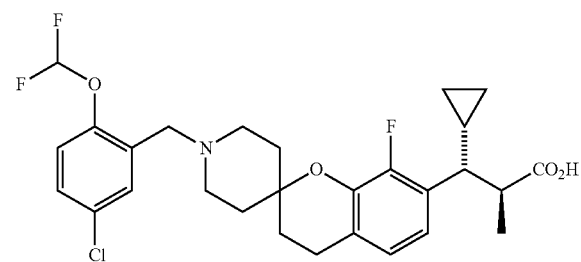 [SMILES: C[C@H](C(=O)O)[C@H](c1ccc2c(c1F)OC1(CC2)CCN(Cc2cc(Cl)ccc2OC(F)F)CC1)C1CC1]

Step A: difluoromethyl trifluoromethanesulfonate

TiCl₄ (0.512 mL, 4.64 mmol) was added dropwise to trifluoromethanesulfonic acid (49.5 mL, 557 mmol) under vigorous stirring at 25° C., and the mixture was kept at 25° C. for 5 min. Then the reaction mixture was evacuated at 10-15 Torr until gas evolution ceased (ca. 5-10 min). The mixture was cooled to −20° C., and trimethyl(trifluoromethyl)silane (66.0 g, 464 mmol) was added. The mixture was kept at −20° C. for 2 min, then the cooling bath was replaced with an ice/water bath for 2 min, and then with a water bath with 25° C. The reaction mixture was stirred at 25° C. for 2 h, and then distilled under a reduced pressure (6 kPa) at 25° C. to give the title compound. ¹H NMR (400 MHz, CDCl₃): δ=6.86 (t, J=68.1 Hz, 1H).

Step B: 5-chloro-2-(difluoromethoxy)benzaldehyde

Into a 20 mL vial was placed 5-chloro-2-hydroxybenzaldehyde (5.00 g, 31.9 mmol), acetonitrile (60 mL) and 6 M aqueous KOH (63.9 mL, 383 mmol). The mixture was stirred rapidly at 25° C. and difluoromethyl trifluoromethanesulfonate (30.0 g, 96.0 mmol) was added in one portion. The exothermic reaction was stirred vigorously for 2 minutes, then the reaction mixture was diluted with H₂O (30 mL) and extracted with EtOAc (100 mL×3). The combined organic layers were dried over MgSO₄, concentrated, and purified by flash column chromatography (silica gel, PE:EtOAc=10:1, v/v) to give the title compound. ¹H NMR (400 MHz, CDCl₃): δ=10.33 (s, 1H), 7.89 (d, J=2.7 Hz, 1H), 7.58 (dd, J=2.5, 8.8 Hz, 1H), 7.23 (d, J=9.0 Hz, 1H), 6.75 (t, J=72.0 Hz, 1H).

Step C: (2S,3R)-methyl 3-(1'-(5-chloro-2-(difluoromethoxy)benzyl)-8-fluoro-spiro[chroman-2,4'-piperidin]-7-yl)-3-cyclopropyl-2-methylpropanoate To a solution of 5-chloro-2-(difluoromethoxy)benzaldehyde (39.5 mg, 0.191 mmol) and (2S,3R)-methyl 3-cyclopropyl-3-(8-fluorospiro[chroman-2,4'-piperidin]-7-yl)-2-methyl-propanoate (80.0 mg, 0.159 mmol) in MeOH (1 mL) and THF (1 mL) was added titanium (IV) isopropoxide (0.142 mL, 0.478 mmol). The reaction mixture was stirred at 60° C. for 12 h and then cooled to room temperature. NaCNBH₃ (50.1 mg, 0.797 mmol) was added, and the mixture was stirred at 25° C. for 2 h. Then H₂O (5 mL) was added, and the mixture was extracted with DCM (5 mL×3). The combined organic layers were washed with brine (5 mL), dried over Na₂SO₄ and filtered. The filtrate was concentrated by rotary evaporator to give a residue, which was purified by preparative TLC (silica gel, PE:EtOAc=10:1, v/v) to give the title compound. MS (ESI) m/z: 552.1 [M+H]⁺

Step D: (2S,3R)-3-(1'-(5-chloro-2-(difluoromethoxy)benzyl)-8-fluorospiro-[chroman-2,4'-piperidin]-7-yl)-3-cyclopropyl-2-methylpropanoic Acid To a solution of (2S,3R)-methyl 3-(1'-(5-chloro-2-(difluoromethoxy)benzyl)-8-fluorospiro-[chroman-2,4'-piperidin]-7-yl)-3-cyclopropyl-2-methylpropanoate (40.0 mg, 72.0 μmol) in MeOH (0.5 mL), THF (0.5 mL) and water (0.5 mL) was added (2S,3R)-methyl 3-(1'-(5-chloro-2-(difluoromethoxy)benzyl)-8-fluorospiro-[chroman-2,4'-piperidin]-7-yl)-3-cyclopropyl-2-methylpropanoate (40.0 mg, 72.0 μmol). The reaction was heated to 55° C. for 18 hours, then cooled to room temperature and neutralized to pH 7 with concentrated HCl. The solvents were removed by rotary evaporator, and the resulting residue was dissolved in MeCN and DMSO and filtered. The filtrate was purified by preparative HPLC to give the title compound. The title compound was treated with 1 equivalent of aqueous NaOH (10 wt %) and lyophilized to give the sodium salt of the title compound. Preparative HPLC conditions: Column: Phenomenex Gemini C18 250*21.2 mm*5 um; Condition: water (10 mM NH₄HCO₃)-ACN; Begin B: 50; End B: 70; Gradient Time (min): 8; 100% B Hold Time (min): 2; FlowRate (ml/min): 25; Injections: 3.MS (ESI): m/z 538.1 [M+H]⁺ ¹H NMR (400 MHz, CD₃OD): δ=7.53 (d, J=2.3 Hz, 1H), 7.34 (dd, J=2.3, 8.6 Hz, 1H), 7.17 (d, J=9.0 Hz, 1H), 7.06-6.69 (m, 2H), 6.66 (d, J=5.5 Hz, 1H), 3.64 (s, 2H), 2.84-2.68 (m, 5H), 2.68-2.57 (m, 2H), 2.38-2.27 (m, 1H), 1.93-1.79 (m, 4H), 1.78-1.65 (m, 2H), 1.19-1.07 (m, 1H), 0.89 (d, J=7.0 Hz, 3H), 0.64-0.51 (m, 1H), 0.47-0.36 (m, 1H), 0.31-0.19 (m, 1H), 0.01--0.10 (m, 1H)

Example 21

(2S,3R)-3-(1'-(1-(5-chloro-2-(trifluoromethoxy)phenyl)ethyl)-8-fluorospiro[chroman-2,4'-piperidin]-7-yl)-3-cyclopropyl-2-methylpropanoic Acid

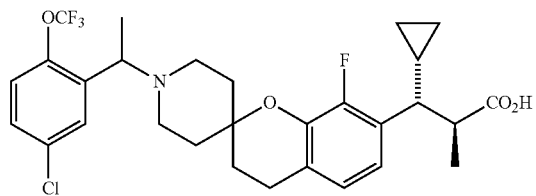 [SMILES: CC(c1cc(Cl)ccc1OC(F)(F)F)N1CCC2(CCc3ccc([C@H](C4CC4)[C@H](C)C(=O)O)c(F)c3O2)CC1]

Step A:
1-(5-chloro-2-(trifluoromethoxy)phenyl)ethyl methanesulfonate

To a solution of 5-chloro-2-(trifluoromethoxy)benzaldehyde (300 mg, 1.34 mmol) in THF (4 mL) was added methylmagnesium bromide (0.891 mL, 2.67 mmol) in a dry ice bath (−78° C.). The mixture was stirred for 1 hour at −78° C., then water (10 mL) and EtOAc (5 mL) were added. The organic layer was separated, and the aqueous layer was extracted with EtOAc (3 mL×3). The combined organic layers were dried over anhydrous sodium sulfate, filtered and concentrated under reduced pressure to afford the title compound, which was used in the next step without further purification.

Step B:
1-(5-chloro-2-(trifluoromethoxy)phenyl)ethyl methanesulfonate

To a solution of 1-(5-chloro-2-(trifluoromethoxy)phenyl)ethanol (200 mg, 0.830 mmol) in DCM (4 mL) was added Et₃N (0.348 mL, 2.49 mmol) and MsCl (0.130 mL, 1.66 mmol) at 0° C. The reaction was stirred at 16° C. for 1 h. Then the mixture was treated with water (10 mL) and DCM (5 mL). The organic layer was separated, and the aqueous layer was extracted with DCM (3 mL×3). The combined organic layers were dried over anhydrous sodium sulfate, filtered and concentrated under reduced pressure to afford the title compound, which was used in next step without further purification. ¹H NMR (400 MHz, CDCl₃): δ=7.57 (d, J=2.3 Hz, 1H), 7.38 (dd, J₁=2.5, J₂=8.8 Hz, 1H), 7.23 (br. s., 1H), 6.00 (q, J=6.5 Hz, 1H), 3.19-3.11 (m, 3H), 1.70 (d, J=6.7 Hz, 3H).

Step C: (2S,3R)-methyl 3-(1'-((RS)-1-(5-chloro-2-(trifluoromethoxy)phenyl)-ethyl)-8-fluorospiro[chroman-2,4'-piperidin]-7-yl)-3-cyclopropyl-2-methylpropanoate To a solution of (2S,3R)-methyl 3-cyclopropyl-3-(8-fluorospiro[chroman-2,4'-piperidin]-7-yl)-2-methylpropanoate (200 mg, 0.504 mmol) and 1-(5-chloro-2-(trifluoromethoxy)phenyl)ethyl methanesulfonate (241 mg, 0.755 mmol) in acetonitrile (5 mL) were added Cs₂CO₃ (492 mg, 1.51 mmol) and sodium iodide (226 mg, 1.51 mmol) at 16° C. The reaction was stirred at 75° C. for 1.5 h, then water (10 mL) and EtOAc (5 mL) were added. The organic layer was separated. The aqueous layer was extracted with ethyl acetate (5 mL×2). The combined organic layers were dried over anhydrous sodium sulfate, filtered and concentrated under reduced pressure to afford the crude product, which was purified by preparative-TLC (silica gel, PE:EtOAc=5:1, v/v) to afford the title compound. MS (ESI) m/z: 584.2 [M+H]⁺

Step D: (2S,3R)-3-(1'-(1-(5-chloro-2-(trifluoromethoxy)phenyl)ethyl)-8-fluorospiro-[chroman-2,4'-piperidin]-7-yl)-3-cyclopropyl-2-methylpropanoic Acid To a solution of (2S,3R)-methyl 3-(1'-(1-(5-chloro-2-(trifluoromethoxy)-phenyl)ethyl)-8-fluoro-spiro[chroman-2,4'-piperidin]-7-yl)-3-cyclopropyl-2-methylpropanoate (186 mg, 0.191 mmol) in MeOH (2.00 mL), THF (2 mL) and water (2 mL) was added LiOH (45.8 mg, 1.91 mmol) at room temperature. The reaction was stirred at 50° C. for 20 h, then the mixture pH was adjusted to pH 6 with citric acid, and EtOAc (5 mL) was added. The organic layer was separated. The aqueous layer was extracted with EtOAc (3 mL×3). The combined organic layers were dried over anhydrous sodium sulfate, filtered and concentrated under reduced pressure to afford the crude product, which was purified by preparative HPLC (Preparative HPLC Conditions: a MS trigger instrument fitted with a Phenomenex Gemini Column YMC-Actus Pro C18 150*30 5u; Condition water (0.1% TFA)-ACN Begin B 32 End B 62 Gradient Time (min) 11, 100% B Hold Time (min) 1.1, FlowRate (mL/min) 40) and dried by lyophilization to afford the title compound. $^1$H NMR (400 MHz, CDCl$_3$): δ=7.87 (br. s., 1H), 7.49 (dd, J$_1$=2.0, J$_2$=8.6 Hz, 1H), 7.31 (d, J=8.2 Hz, 1H), 6.82 (d, J=7.8 Hz, 1H), 6.75-6.67 (m, 1H), 4.63 (d, J=6.7 Hz, 1H), 3.85 (d, J=10.2 Hz, 1H), 3.25-3.09 (m, 2H), 3.02 (d, J=11.0 Hz, 1H), 2.95-2.85 (m, 1H), 2.78 (br. s., 2H), 2.39-2.19 (m, 3H), 2.07 (d, J=14.5 Hz, 1H), 1.99-1.87 (m, 3H), 1.83 (d, J=6.7 Hz, 3H), 1.17 (br. s., 1H), 1.01 (d, J=6.7 Hz, 3H), 0.65 (br. s., 1H), 0.47-0.29 (m, 2H), 0.09--0.03 (m, 1H) LCMS: m/z 570.2 [M+H]$^+$ Example 22 sodium (2S,3R)-3-cyclopropyl-2-methyl-3-(1'-(2-(trifluoromethyl) pyridin-3-yl)spiro[chroman-2,4'-piperidin]-7-yl)propanoate

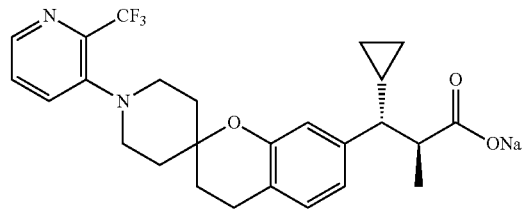

Step A: (2S,3R)-methyl 3-cyclopropyl-2-methyl-3-(1'-(2-(trifluoromethyl)pyridin-3-yl)spiro[chroman-2,4'-piperidin]-7-yl)propanoate To a solution of (2S,3R)-methyl 3-cyclopropyl-2-methyl-3-(spiro[chroman-2,4'-piperidin]-7-yl)-propanoate (50.0 mg, 0.146 mmol), 3-bromo-2-(trifluoromethyl)pyridine (36.2 mg, 0.160 mmol), Cs$_2$CO$_3$ (47.4 mg, 0.146 mmol) in toluene (5 ml) and t-BuOH (1 ml) was added 2-(dicyclohexylphosphino)-2',4',6'-triisopropylbiphenyl (6.94 mg, 15.0 umol) and Pd(OAc)$_2$ (3.27 mg, 15.0 umol) under N$_2$. The reaction was stirred at 120° C. for 12 hours under N$_2$. Then water (10 mL) was added and the mixture was extracted with EtOAc (10 mL×4). The combined organic layers were dried over sodium sulfate, and then filtered. The filtrate was concentrated in vacuo to give the crude product, which was purified by TLC (SiO$_2$, petroleum ether:ethyl acetate=10:1, v/v) to give the title compound. MS (ESI) m/z: 489.2 [M+H]$^+$ Step B: sodium(2S,3R)-3-cyclopropyl-2-methyl-3-(1'-(2-(trifluoromethyl)pyridin-3-yl)spiro[chroman-2,4'-piperidin]-7-yl)propanoate To a solution of (2S,3R)-methyl 3-cyclopropyl-2-methyl-3-(1'-(2-(trifluoromethyl)pyridin-3-yl)spiro[chroman-2,4'-piperidin]-7-yl)propanoate (50.0 mg, 0.102 mmol) in a co-solvent of THF (2 ml), water (2 ml) and MeOH (2 ml) was added LiOH (123 mg, 5.12 mmol). The reaction was stirred at 50° C. for 12 hours under N$_2$. Then the reaction mixture was poured into water (2 mL) and citric acid was added to adjust the pH to 7. The reaction mixture was extracted with EtOAc (5 mL×3). The combined organic layers were washed with brine (2 mL×3), dried over Na$_2$SO$_4$, and filtered. The filtrate was evaporated under reduced pressure to give a residue, which was purified with Prep-HPLC (base) to give the title compound. To a solution of the title compound in MeCN (1 mL) and water (1 mL) was added an aqueous NaOH solution (1.0 eq, 0.5 M), and the mixture was stirred for 1 h at room temperature. Then the reaction mixture was lyophilized to give the sodium salt of the title compound. Preparative HPLC conditions: a MS trigger instrument fitted with a Waters Xbridge Prep OBD C18 150*30 5u using water (0.05% ammonia hydroxide v/v)-ACN as the eluents, Mobile phase A: water (0.05% ammonia hydroxide v/v), mobile phase B: acetonitrile, gradient: 25-55% B, 2.0-10.0 min, flowRate: 25 mL/min. MS (ESI) m/z: 475.1 [M+H]$^+$ $^1$H NMR (400 MHz, CD$_3$OD): δ=8.37 (d, J=4.2 Hz, 1H), 8.03 (d, J=8.2 Hz, 1H), 7.63 (dd, J=4.6, 8.2 Hz, 1H), 6.97 (d, J=7.5 Hz, 1H), 6.71-6.61 (m, 2H), 3.26 (t, J=10.7 Hz, 2H), 2.95 (d, J=11.2 Hz, 2H), 2.80 (t, J=6.6 Hz, 2H), 2.71-2.61 (m, 1H), 1.99-1.77 (m, 7H), 1.12-1.02 (m, 1H), 0.86 (d, J=6.8 Hz, 3H), 0.62-0.50 (m, 1H), 0.38 (qd, J=4.8, 9.3 Hz, 1H), 0.25 (dt, J=4.3, 8.5 Hz, 1H), –0.06 (qd, J=5.0, 9.4 Hz, 1H)

Example 23

(2S,3R)-3-(1'-((2,5-bis(trifluoromethyl)phenyl)sulfonyl)spiro[chroman-2,4'-piperidin]-7-yl)-3-cyclopropyl-2-methylpropanoic Acid

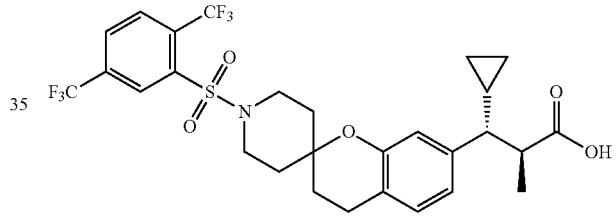

Step A: (2S,3R)-methyl 3-(1'-((2,5-bis(trifluoromethyl)phenyl)sulfonyl)spiro-[chroman-2,4'-piperidin]-7-yl)-3-cyclopropyl-2-methylpropanoate To a solution of (2S,3R)-methyl 3-cyclopropyl-2-methyl-3-(spiro[chroman-2,4'-piperidin]-7-yl)-propanoate (50.0 mg, 0.146 mmol) in CH$_2$Cl$_2$ (2 mL) was added Et$_3$N (0.041 mL, 0.291 mmol), DMAP (1.78 mg, 0.015 mmol) and 2,5-bis(trifluoromethyl)-benzene-1-sulfonyl chloride (45.5 mg, 0.146 mmol) at 15° C. The reaction was stirred at 15° C. for 0.5 h, then water (10 mL) and DCM (5 mL) were added. The organic layer was separated, and the aqueous layer was extracted with DCM (5 mL×3). The combined organic layers were dried over anhydrous sodium sulfate, filtered and concentrated under reduced pressure to afford the title compound, which was used in the next step without further purification. MS (ESI) m/z: 642.2 [M+H]$^+$.

Step B: (2S,3R)-3-(1'-((2,5-bis(trifluoromethyl)phenyl)sulfonyl)spiro[chroman-2,4'-piperidin]-7-yl)-3-cyclopropyl-2-methylpropanoic Acid To a solution of (2S,3R)-methyl 3-(1'-((2,5-bis(trifluoromethyl)phenyl)sulfonyl)spiro[chroman-2,4'-piperidin]-7-yl)-3-cyclopropyl-2-methylpropanoate (35.0 mg, 0.056 mmol) in THF (1 mL), MeOH (1 mL) and water (1 mL) was added LiOH (13.5 mg, 0.565 mmol) at room temperature. The reaction was stirred at 50° C. for 20 h. Then the pH of the reaction mixture was adjusted to pH 6 with citric acid, and EtOAc (5 mL) was added. The organic layer was separated. The aqueous layer was extracted with EtOAc (3 mL×3). The combined organic layers were dried over anhydrous sodium sulfate, filtered, concentrated under reduced pressure and lyophilized to afford the title compound. $^1$H NMR (400 MHz, CDCl$_3$): δ=8.41 (s, 1H), 8.11-8.03 (m, 1H), 7.97 (d, J=7.8 Hz, 1H), 6.99 (d, J=7.8 Hz, 1H), 6.67 (d, J=7.8 Hz, 1H), 6.61 (s, 1H), 3.70 (d, J=12.5 Hz, 1H), 3.24 (t, J=12.3 Hz, 1H), 2.82-2.72 (m, 1H), 1.92 (t, J=13.3 Hz, 3H), 1.86-1.79 (m, 2H), 1.77-1.66 (m, 1H), 1.13-1.02 (m, 1H), 0.97 (d, J=6.7 Hz, 1H), 0.66-0.56 (m, 1H), 0.35 (t, J=5.7 Hz, 1H), 0.07--0.03 (m, 1H) MS (ESI) m/z: 606.1 [M+H]$^+$ Example 24 (2S,3R)-3-(1'-(3-chloro-2-fluoro-5-(trifluoromethyl)benzyl)spiro[chroman-2,4'-piperidin]-7-yl)-3-cyclopropyl-2-methylpropanoic Acid

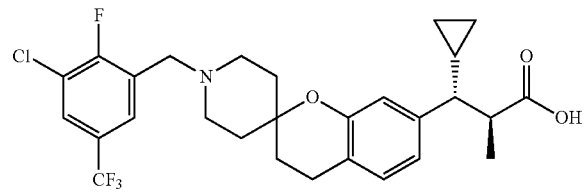 [SMILES: C[C@H](C(=O)O)[C@H](c1ccc2c(c1)OC1(CC2)CCN(Cc2cc(C(F)(F)F)cc(Cl)c2F)CC1)C1CC1]

Step A: (2S,3R)-methyl 3-(1'-(3-chloro-2-fluoro-5-(trifluoromethyl)benzyl)spiro [chroman-2,4'-piperidin]-7-yl)-3-cyclopropyl-2-methylpropanoate To a solution of (2S,3R)-methyl 3-cyclopropyl-2-methyl-3-(spiro[chroman-2,4'-piperidin]-7-yl)-propanoate (50.0 mg, 0.146 mmol), K$_2$CO$_3$ (60.4 mg, 0.437 mmol) and sodium iodide (43.6 mg, 0.291 mmol) in MeCN (3 mL) was added 1-(bromomethyl)-3-chloro-2-fluoro-5-(trifluoromethyl)benzene (46.7 mg, 0.160 mmol). The reaction mixture was stirred at 80° C. for 5 h. Then water (10 mL) was added, and the reaction mixture was extracted with ethyl acetate (15 mL×3). The combined organic layers were washed with brine (10 mL), dried over MgSO$_4$ and filtered. The filtrate was evaporated under reduced pressure to give the crude product, which was purified by prep-TLC (SiO$_2$, PE:EA=10:1, v/v) to give the title compound. MS (ESI) m/z: 554.3 [M+H]$^+$ Step B: (2S,3R)-3-(1'-(3-chloro-2-fluoro-5-(trifluoromethyl)benzyl)spiro[chroman-2,4'-piperidin]-7-yl)-3-cyclopropyl-2-methylpropanoic Acid To a solution of (2S,3R)-methyl 3-(1'-(3-chloro-2-fluoro-5-(trifluoromethyl)benzyl)spiro[chroman-2,4'-piperidin]-7-yl)-3-cyclopropyl-2-methylpropanoate (50.0 mg, 0.09 mmol) in MeOH (1 mL), THF (1 mL) and water (1 mL) was added LiOH (43.2 mg, 1.81 mmol). The reaction mixture was stirred at 50° C. under N$_2$ for 16 h. Then the reaction mixture was cooled to 25° C., acidified with citric acid to pH=5-6, and extracted with EtOAc (10 mL×3). The combined organic layers were dried (MgSO$_4$) and filtered. The filtrate was concentrated in vacuo to give crude product, which was purified by prep-HPLC(TFA) to give the title compound. (Preparative-HPLC conditions: a MS trigger instrument fitted with a YMC-Actus Pro C18 150×30×5 um using water and acetonitrile as the eluents; mobile phase A: water (0.1% TFA); mobile phase B: acetonitrile, gradient: 26-56% B, 0-11.0 min; 100% B, 11.1-13.0 min; 10% B, 13.1-16 min, flowRate: 40 mL/min.) To a solution of the title compound in MeCN (1 mL) and water (1 mL) was added aqueous solution of NaOH (1.0 eq, 0.5 M), and the mixture was stirred for 1 hour at room temperature. The reaction mixture was lyophilized to give the sodium salt of the title compound. MS (ESI) m/z: 540.1 [M+H]$^+$ 1H NMR (400 MHz, CD$_3$OD) δ=8.13 (d, J=5.1 Hz, 1H), 8.01 (d, J=4.4 Hz, 1H), 7.06 (d, J=7.7 Hz, 1H), 6.81-6.71 (m, 2H), 4.64 (s, 2H), 3.63-3.45 (m, 4H), 2.86-2.72 (m, 3H), 2.21-2.10 (m, 2H), 2.01-1.82 (m, 5H), 1.15-1.06 (m, 1H), 0.93 (d, J=6.8 Hz, 3H), 0.68-0.56 (m, 1H), 0.42-0.25 (m, 2H), 0.05--0.05 (m, 1H)

Example 25

(2S,3R)-3-(1'-((2-chloro-5-(trifluoromethyl)phenyl)sulfonyl)spiro[chroman-2,4'-piperidin]-7-yl)-3-cyclopropyl-2-methylpropanoic Acid

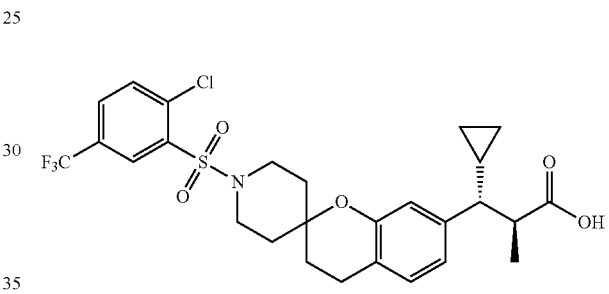

Step A: (2S,3R)-methyl 3-(1'-((2-chloro-5-(trifluoromethyl)phenyl)sulfonyl)spiro [chroman-2,4'-piperidin]-7-yl)-3-cyclopropyl-2-methylpropanoate To a solution of (2S,3R)-methyl 3-cyclopropyl-2-methyl-3-(spiro[chroman-2,4'-piperidin]-7-yl)-propanoate (80.0 mg, 0.233 mmol), TEA (0.032 mL, 0.233 mmol) and DMAP (2.85 mg, 0.023 mmol) in DCM (2 mL) was added 2-chloro-5-(trifluoromethyl)-benzene-1-sulfonyl chloride (65.0 mg, 0.233 mmol) in DCM (0.4 mL) dropwise at 25° C. The reaction mixture was stirred for 20 min at 25° C., then water (8 mL) was added and the mixture was extracted with DCM (3 mL×3). The combined organic layers were washed with brine (10 mL), dried over anhydrous Na$_2$SO$_4$ and filtered. The filtrate was concentrated in vacuo to give a residue, which was purified by prep-TLC (SiO$_2$, PE:EtOAc=10:1, v/v) to afford the title compound. MS (ESI) m/z: 586.1 [M+H]$^+$ Step B: (2S,3R)-3-(1'-((2-chloro-5-(trifluoromethyl)phenyl)sulfonyl)spiro[chroman-2,4'-piperidin]-7-yl)-3-cyclopropyl-2-methylpropanoic Acid To a solution of (2S,3R)-methyl 3-(1'-((2-chloro-5-(trifluoromethyl)phenyl) sulfonyl)spiro[chroman-2,4'-piperidin]-7-yl)-3-cyclopropyl-2-methylpropanoate (126 mg, 0.215 mmol) in MeOH (1.5 mL), THF (1.5 mL) and water (1.5 mL) was added lithium hydroxide (103 mg, 4.30 mmol) under N$_2$ atmosphere. The reaction mixture was stirred for 18 hours at 55° C. Then water (5 mL) was added, the mixture pH was adjusted with citric acid to pH 6-7, and the mixture was extracted with EtOAc (5 mL×3). The combined organic layers were washed with brine (5 mL), dried over anhydrous $Na_2SO_4$ and filtered. The filtrate was evaporated under reduce pressure to give a residue, which was purified by Pre-HPLC (neutral) to give the title compound. LCMS (ESI) m/z: 594.2 [M+Na]$^+$ $^1$H NMR (400 MHz, $CD_3OD$) δ=8.27 (s, 1H), 7.94-7.90 (m, 1H), 7.88-7.83 (m, 1H), 6.95 (d, J=7.7 Hz, 1H), 6.63 (d, J=7.7 Hz, 1H), 6.55 (s, 1H), 3.68 (d, J=12.3 Hz, 2H), 3.27-3.18 (m, 2H), 2.74 (t, J=6.6 Hz, 2H), 2.70-2.63 (m, 1H), 1.92-1.76 (m, 5H), 1.73-1.63 (m, 2H), 1.07-0.97 (m, 1H), 0.85 (d, J=6.8 Hz, 3H), 0.59-0.49 (m, 1H), 0.33-0.20 (m, 2H), 0.04-0.14 (m, 1H)

aqueous $NH_4Cl$ (20 mL). The reaction mixture was extracted with ethyl acetate (30 mL×3). The combined organic layers were washed with brine (20 mL), dried over $MgSO_4$ and filtered. The filtrate was evaporated under reduced pressure to give the title compound, which was used in the next step without further purification. MS (ESI) m/z: 177.1 [M−18+H]$^+$ Step B: 2-fluoro-5-(trifluoromethyl)benzyl methanesulfonate To a solution of (2-fluoro-5-(trifluoromethyl)phenyl)methanol (300 mg, 1.545 mmol) and TEA (0.646 mL, 4.64

TABLE 6

The compound of Example 26 was prepared in a similar manner to Example 25 using the appropriate starting materials and reagents.

| Example | Structure | M.W. | Compound Name | LC/MS (ESI) observed [M + Na]$^+$ |
|---|---|---|---|---|
| 26 | 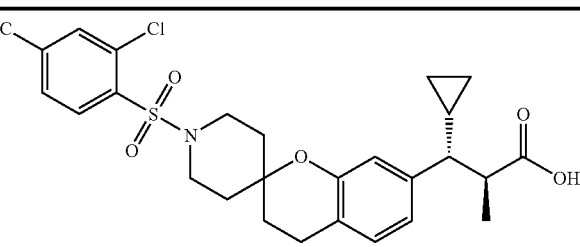 | 572.03 | (2S,3R)-3-(1'-((2-chloro-4-(trifluoromethyl)-phenyl)sulfonyl)spiro[chroman-2,4'-piperidin]-7-yl)-3-cyclopropyl-2-methylpropanoic acid | 594.2 |

Example 26

$^1$H NMR (400 MHz, $CD_3OD$) δ=8.23 (d, J=8.2 Hz, 1H), 7.96 (s, 1H), 7.81 (d, J=8.2 Hz, 1H), 6.94 (d, J=7.7 Hz, 1H), 6.62 (d, J=7.7 Hz, 1H), 6.56 (s, 1H), 3.68 (d, J=12.3 Hz, 2H), 3.26-3.18 (m, 2H), 2.77-2.62 (m, 3H), 1.91-1.75 (m, 5H), 1.72-1.62 (m, 2H), 1.07-0.97 (m, 1H), 0.84 (d, J=6.8 Hz, 3H), 0.57-0.48 (m, 1H), 0.32-0.18 (m, 2H), −0.05−−0.14 (m, 1H)

Example 27

(2S,3R)-3-cyclopropyl-3-(1'-(2-fluoro-5-(trifluoromethyl)benzyl)spiro-[chroman-2,4'-piperidin]-7-yl)-2-methylpropanoic Acid

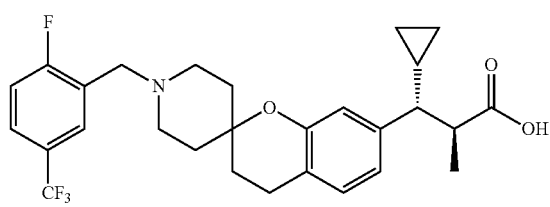 [SMILES: C[C@H](C(=O)O)[C@H](c1ccc2c(c1)OC1(CC2)CCN(Cc2cc(C(F)(F)F)ccc2F)CC1)C1CC1]

Step A: (2-fluoro-5-(trifluoromethyl)phenyl)methanol

To a solution of 2-fluoro-5-(trifluoromethyl)benzaldehyde (2.00 g, 10.4 mmol) in MeOH (20 mL) was added $NaBH_4$ (0.788 g, 20.8 mmol) at 0° C. The reaction was stirred at 0° C. under $N_2$ for 30 min, then quenched with saturated mmol) in DCM (3 mL) was added Ms-Cl (0.241 mL, 3.09 mmol) dropwise at 0° C. The reaction mixture was stirred at 20° C. under $N_2$ for 1 h. Then water (10 mL) was added to the reaction and the mixture was extracted with EtOAc (15 mL×2). The combined organic layers were washed with brine (10 mL), dried over $MgSO_4$, and filtered. The filtrate was concentrated in vacuo to give the title compound, which was used in the next step without further purification. $^1$H NMR (400 MHz, $CDCl_3$) δ=7.78-7.72 (m, 1H), 7.72-7.58 (m, 1H), 7.26-7.18 (m, 1H), 5.34 (s, 2H), 3.08 (s, 3H)

Step C: (2S,3R)-methyl 3-cyclopropyl-3-(1'-(2-fluoro-5-(trifluoromethyl)benzyl)spiro [chroman-2,4'-piperidin]-7-yl)-2-methylpropanoate To a solution of (2S,3R)-methyl 3-cyclopropyl-2-methyl-3-(spiro[chroman-2,4'-piperidin]-7-yl)propanoate (100 mg, 0.291 mmol), sodium iodide (87.0 mg, 0.582 mmol) and $K_2CO_3$ (121 mg, 0.873 mmol) in MeCN (2 mL) was added 2-fluoro-5-(trifluoromethyl)benzyl methanesulfonate (95.0 mg, 0.349 mmol). The reaction mixture was stirred at 85° C. for 4 h. Then water (10 mL) was added and the mixture was extracted with EA (15 mL×3). The combined organic layers were washed with brine (10 mL), dried over $MgSO_4$ and filtered. The filtrate was evaporated under reduced pressure to give the crude product, which was purified by prep-TLC ($SiO_2$, PE:EA=5:1, v/v) to give the title compound. MS (ESI) m/z: 520.3 [M+H]$^+$ Step D: (2S,3R)-3-cyclopropyl-3-(1'-(2-fluoro-5-(trifluoromethyl)benzyl)spiro [chroman-2,4'-piperidin]-7-yl)-2-methylpropanoic Acid To a solution of (2S,3R)-methyl 3-cyclopropyl-3-(1'-(2-fluoro-5-(trifluoromethyl)benzyl)spiro-[chroman-2,4'-piperidin]-7-yl)-2-methylpropanoate (40 mg, 0.077 mmol) in MeOH (1 mL), THF (1 mL) and water (1 mL) was added LiOH (36.9 mg, 1.54 mmol). The reaction mixture was stirred at 50° C. under $N_2$ for 16 h. Then the reaction mixture was cooled to 25° C., acidified with citric acid to pH=5-6 and extracted with EtOAc (10 mL×3). The combined organic layers were dried ($MgSO_4$) and filtered. The filtrate was concentrated in vacuo to give the crude product, which was purified by prep-HPLC (basic) to give the title compound. Preparative-HPLC conditions: a MS trigger instrument fitted with a Waters Xbridge Prep OBD C18 150×30×5 um using water and acetonitrile as the eluents, mobile phase A: water (0.05% ammonia hydroxide); mobile phase B: acetonitrile, gradient: 32-62% B, 0-10.0 min; 100% B, 10.1-12.0 min; 10% B, 12.1-15 min, flowRate: 25 mL/min. To a solution of the title compound in MeCN (1 mL) and water (1 mL) was added an aqueous solution of NaOH (1.0 eq, 0.5 M), and the mixture was stirred for 1 hour at room temperature. Then the reaction mixture was lyophilized to give the sodium salt of the title compound. MS (ESI) m/z: 506.2 [M+H]$^+$ $^1$H NMR (400 MHz, $CD_3OD$) δ=7.84 (d, J=5.1 Hz, 1H), 7.70-7.63 (m, 1H), 7.32 (t, J=8.9 Hz, 1H), 6.96 (d, J=7.7 Hz, 1H), 6.64 (d, J=7.7 Hz, 1H), 6.60 (s, 1H), 3.76 (s, 2H), 2.81-2.59 (m, 7H), 1.91-1.77 (m, 5H), 1.76-1.64 (m, 2H), 1.12-1.01 (m, J=4.9 Hz, 1H), 0.88 (d, J=6.8 Hz, 3H), 0.62-0.53 (m, 1H), 0.39-0.23 (m, 2H), 0.01--0.08 (m, 1H)

Example 29

$^1$H NMR (400 MHz, $CD_3OD$) δ=7.47 (s, 1H), 7.29-7.19 (m, 2H), 6.95 (d, J=7.7 Hz, 1H), 6.63 (d, J=7.7 Hz, 1H), 6.51 (s, 1H), 4.15-4.02 (m, 1H), 3.02-2.93 (m, 1H), 2.79-2.65 (m, 4H), 2.63-2.48 (m, 2H), 1.92-1.74 (m, 6H), 1.69-1.59 (m, 1H), 1.47 (d, J=6.8 Hz, 3H), 1.10-0.99 (m, 1H), 0.87 (d, J=6.8 Hz, 3H), 0.62-0.52 (m, 1H), 0.30 (ddd, J=4.4, 8.9, 17.4 Hz, 2H), −0.01--0.10 (m, 1H)

Example 30

(2S,3R)-3-cyclopropyl-3-((S)-2-(1-((S or R)-1-(2-fluoro-5-(trifluoromethyl)phenyl) ethyl)azetidin-3-yl)chroman-7-yl)-2-methylpropanoic Acid

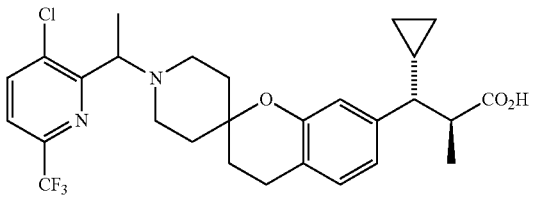

TABLE 7

The compounds of Examples 28-29 were prepared in a similar manner to Example 27 using the appropriate starting material and reagents.

| Example | Structure | M.W. | Compound Name | LC/MS (ESI) observed [M + 1]$^+$ |
|---|---|---|---|---|
| 28 | 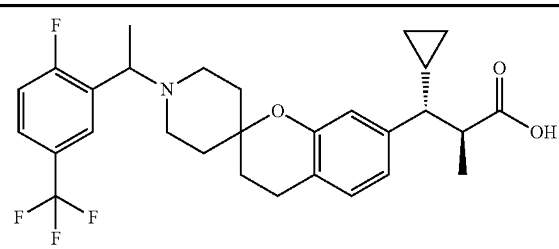 | 519.57 | (2S,3R)-3-cyclopropyl-3-(1'-((RS)-1-(2-fluoro-5-(trifluoromethyl)phenyl) ethyl)spiro[chroman-2,4'-piperidin]-7-yl)-2-methylpropanoic acid | 520.2 |
| 29 | 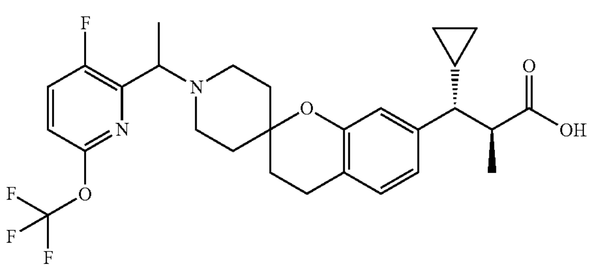 [SMILES: CC(c1nc(OC(F)(F)F)ccc1F)N1CCC2(CCc3ccc([C@H](C4CC4)[C@H](C)C(=O)O)cc3O2)CC1] | 535.57 | (2S,3R)-3-cyclopropyl-3-(1'-((RS)-1-(2-fluoro-5-(trifluoromethoxy)phenyl) ethyl)spiro[chroman-2,4'-piperidin]-7-yl)-2-methylpropanoic acid | 536.2 |

Example 28

$^1$H NMR (400 MHz, $CD_3OD$) δ=7.89-7.83 (m, 1H), 7.69-7.62 (m, 1H), 7.32 (t, J=9.3 Hz, 1H), 6.96 (d, J=7.7 Hz, 1H), 6.63 (d, J=7.7 Hz, 1H), 6.52 (s, 1H), 4.13-4.04 (m, 1H), 3.03-2.94 (m, 1H), 2.80-2.45 (m, J=6.6, 6.6 Hz, 6H), 1.93-1.74 (m, 6H), 1.69-1.58 (m, 1H), 1.48 (d, J=6.6 Hz, 3H), 1.10-1.00 (m, 1H), 0.87 (d, J=6.8 Hz, 3H), 0.61-0.52 (m, 1H), 0.37-0.23 (m, 2H), −0.02--0.10 (m, 1H)

Step A: 3-chloro-N-methoxy-N-methyl-6-(trifluoromethyl)picolinamide

To a solution of 3-chloro-6-(trifluoromethyl)picolinic acid (300 mg, 1.33 mmol), N, O-dimethylhydroxylamine hydrochloride (194 mg, 1.99 mmol) and DIEA (515 mg, 4.00 mmol) in DCM (5 mL) was added HATU (607 mg, 1.60 mmol) at 25° C. The reaction was stirred at 25° C. for 2 hours, then quenched with water (10 mL), and extracted with EtOAc (10 mL×3). The combined organic layers were washed with brine (10 mL), dried over MgSO$_4$ and filtered. The filtrate was concentrated under reduced pressure to give the crude product, which was purified by prep-TLC (SiO$_2$, PE:EtOAc=5:1, v/v) to give the title compound. MS (ESI) m/z: 269.1 [M+H]$^+$ Step B: 1-(3-chloro-6-(trifluoromethyl)pyridin-2-yl) ethanone To a solution of 3-chloro-N-methoxy-N-methyl-6-(trifluoromethyl)picolinamide (300 mg, 1.12 mmol) in THF (4 mL) was added CH$_3$MgBr (0.180 mL, 4.48 mmol) at 0° C. The reaction was stirred at 25° C. for 2 hours, then quenched with saturated aqueous NH$_4$Cl (10 mL) and extracted with EtOAc (10 mL×3). The combined organic layers were washed with brine (saturated, 10 mL), dried over MgSO$_4$ and filtered. The filtrate was concentrated under reduced pressure to give the crude product, which was purified by prep-TLC (SiO$_2$, PE:EtOAc=5:1, v/v) to give the title compound. MS (ESI) m/z: 304.0[M+H]$^+$ Step C: 1-(3-chloro-6-(trifluoromethyl)pyridin-2-yl) ethanol To a solution of 1-(3-chloro-6-(trifluoromethyl)pyridin-2-yl)ethanone (168 mg, 0.750 mmol) in MeOH (4 mL) was added NaBH$_4$ (57.0 mg, 1.50 mmol) at 0° C. The reaction mixture was stirred at 25° C. for 1 hour. Then the reaction was quenched with water (10 mL), and extracted with EtOAc (10 mL×3). The combined organic layers were washed with brine (saturated, 10 mL), dried over MgSO$_4$ and filtered. The filtrate was concentrated under reduced pressure to give the title compound, which was used in the next step without further purification. MS (ESI) m/z: 226 [M+H]$^+$ Step D: 1-(3-chloro-6-(trifluoromethyl)pyridin-2-yl)ethyl methanesulfonate To a solution of 1-(3-chloro-6-(trifluoromethyl)pyridin-2-yl)ethanol (145 mg, 0.640 mmol), and TEA (0.270 mL, 1.92 mmol) in DCM (3 mL) was added MsCl (0.0750 mL, 0.960 mmol) at 0° C. The mixture was stirred for 1 hour at 0° C. Then the reaction was quenched with water (5 mL) and extracted with EtOAc (5 mL×3). The combined organic layers were washed with brine (saturated, 10 mL), dried over MgSO$_4$ and filtered. The filtrate was concentrated under reduced pressure to give the title compound, which was used in the next step without further purification. MS (ESI) m/z: 304.0 [M+H]$^+$.

Step E: (2S,3R)-methyl 3-(1'-(1-(3-chloro-6-(trifluoromethyl)pyridin-2-yl)ethyl)spiro [chroman-2,4'-piperidin]-7-yl)-3-cyclopropyl-2-methylpropanoate To a solution of 1-(3-chloro-6-(trifluoromethyl)pyridin-2-yl)ethyl methanesulfonate (144 mg, 0.470 mmol) and (2S,3R)-methyl 3-cyclopropyl-2-methyl-3-(spiro-[chroman-2,4'-piperidin]-7-yl)propanoate (110 mg, 0.320 mmol) in MeCN (3 mL) was added DIEA (207 mg, 1.60 mmol) at 25° C. The reaction was stirred at 85° C. for 3 hours, then quenched with water (5 mL) and extracted with EtOAc (5 mL×3). The combined organic layers were washed with brine (saturated, 10 mL), dried over MgSO$_4$ and filtered. The filtrate was concentrated under reduced pressure to give the crude product, which was purified by prep-TLC (SiO$_2$, PE:EtOAc=5:1, v/v) to give the title compound. MS (ESI) m/z: 550.2[M+H]$^+$ Step F: (2S,3R)-3-(1'-(1-(3-chloro-6-(trifluoromethyl)pyridin-2-yl)ethyl)spiro [chroman-2,4'-piperidin]-7-yl)-3-cyclopropyl-2-methylpropanoic Acid To a solution of (2S,3R)-methyl 3-(1'-(1-(3-chloro-6-(trifluoromethyl)pyridin-2-yl) ethyl)-spiro[chroman-2,4'-piperidin]-7-yl)-3-cyclopropyl-2-methylpropanoate (106 mg, 0.190 mmol) in a co-solvent of water (2 mL), THF (2 mL) and MeOH (2 mL) was added LiOH (45.5 mg, 1.90 mmol) at 25° C. The reaction was stirred at 55° C. for 12 hours. Then the reaction mixture was acidified with citric acid to pH 5, diluted with water (5 mL) and extracted with EtOAc (5 mL×3). The combined organic layers were washed with brine (saturated, 10 mL), dried over MgSO$_4$ and filtered. The filtrate was concentrated under reduced pressure to give the crude product, which was purified by prep-HPLC (Neutral) to give the title compound. Preparative HPLC conditions: a MS trigger instrument fitted with a Phenomenex Gemini C18 250*21.2 mm*5 um using water and acetonitrile as the eluents, mobile phase A: water (10 mM NH$_4$HCO$_3$)-ACN, mobile phase B: acetonitrile, gradient: 25-55% B, 0-12.0 min, 100% B, 12.0-14.0 min, flowRate: 25 mL/min. MS (ESI) m/z: 537.2 [M+H]$^+$ Step G: (2S,3R)-3-(1'-((R or S)-1-(3-chloro-6-(trifluoromethyl)pyridin-2-yl)ethyl) spiro[chroman-2,4'-piperidin]-7-yl)-3-cyclopropyl-2-methylpropanoic Acid (2S,3R)-3-(1'-(1-(3-chloro-6-(trifluoromethyl)pyridin-2-yl)ethyl)spiro[chroman-2,4'-piperidin]-7-yl)-3-cyclopropyl-2-methylpropanoic acid (63.0 mg, 0.117 mmol) were separated into individual diastereoisomers by SFC (SFC separation conditions: Column: Chiralpak AD-3 150×4.6 mm I.D., 3 um; Mobile phase: A: CO$_2$B:methanol (0.05% DEA). Gradient: from 5% to 40% of B in 5 min and hold 40% for 2.5 min, then 5% of B for 2.5 min; Flow rate: 2.5 mL/min; Column temperature: 35° C.) to give the first peak (2S,3R)-3-(1'-((R or S)-1-(3-chloro-6-(trifluoromethyl)-pyridin-2-yl)-ethyl)-spiro[chroman-2,4'-piperidin]-7-yl)-3-cyclopropyl-2-methyl-propanoic acid (Example 30), and the second peak (2S,3R)-3-(1'-((S or R)-1-(3-chloro-6-(trifluoro-methyl)-pyridin-2-yl)-ethyl)spiro-[chroman-2,4'-piperidin]-7-yl)-3-cyclopropyl-2-methylpropanoic acid (Example 31). To a solution of each individual diastereoisomer of the title compound in MeCN (1 mL) and water (1 mL) was added a solution of aqueous NaOH (1.0 equivalent, 0.5 M), and the mixture was stirred for 1 hour at room temperature. Then the reaction mixture was lyophilized to give the sodium salt of the diastereoisomer of the title compound.

TABLE 8

The compounds of Examples 31-32 were prepared in a similar manner to Example 30 using the appropriate starting material and reagents.

| Example | Structure | M.W. | Compound Name | LC/MS (ESI) observed [M + 1]+ |
|---|---|---|---|---|
| 30 | 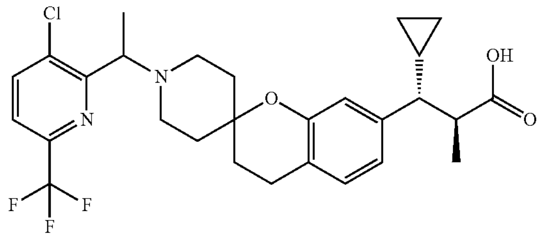 [SMILES: CC(c1nc(C(F)(F)F)ccc1Cl)N1CCC2(CCc3ccc([C@H](C4CC4)[C@H](C)C(=O)O)cc3O2)CC1] | 537.01 | (2S,3R)-3-cyclopropyl-3-((S)-2-(1-((S or R)-1-(2-fluoro-5-(trifluoromethyl)phenyl)ethyl)azetidin-3-yl)chroman-7-yl)-2-methylpropanoic acid | 537.2 |
| 31 | 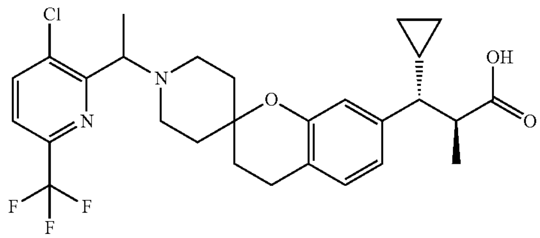 [SMILES: CC(c1nc(C(F)(F)F)ccc1Cl)N1CCC2(CCc3ccc([C@H](C4CC4)[C@H](C)C(=O)O)cc3O2)CC1] | 537.01 | (2S,3R)-3-cyclopropyl-3-((S)-2-(1-((R or S)-1-(2-fluoro-5-(trifluoromethyl)phenyl)ethyl)azetidin-3-yl)chroman-7-yl)-2-methylpropanoic acid | 537.2 |
| 32 | 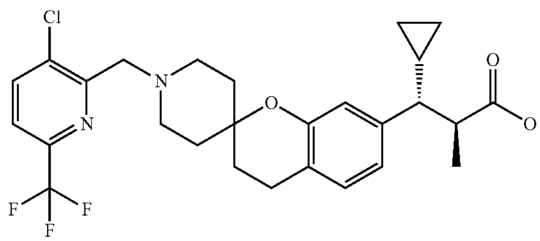 [SMILES: C[C@H](C(=O)O)[C@H](c1ccc2c(c1)OC1(CC2)CCN(Cc2nc(C(F)(F)F)ccc2Cl)CC1)C1CC1] | 522.99 | (2S,3R)-3-(1'-((3-chloro-6-(trifluoromethyl)-pyridin-2-yl)methyl)-spiro-[chroman-2,4'-piperidin]-7-yl)-3-cyclopropyl-2-methylpropanoic acid | 523.2 |

Example 30

MS (ESI) m/z: 537.2 [M+H]+ 1H NMR (400 MHz, CDCl3): δ=7.92-7.80 (m, 1H), 7.60-7.48 (m, 1H), 6.98 (d, J=1.0 Hz, 1H), 6.69-6.54 (m, 2H), 4.61-4.49 (m, 1H), 2.96-2.76 (m, 4H), 2.75-2.68 (m, 2H), 2.67-2.58 (m, 1H), 1.89 (t, J=9.8 Hz, 2H), 1.80-1.74 (m, 2H), 1.72-1.59 (m, 2H), 1.51 (s, 2H), 1.37-1.22 (m, 2H), 1.14-1.06 (m, 1H), 1.04-0.84 (m, 3H), 0.68-0.56 (m, 1H), 0.45-0.27 (m, 2H), 0.10--0.01 (m, 1H)

Example 31

1H NMR (400 MHz, CDCl3): δ=7.85 (d, J=8.2 Hz, 1H), 7.55 (d, J=8.2 Hz, 1H), 6.96 (d, J=7.8 Hz, 1H), 6.70-6.51 (m, 2H), 4.66-4.56 (m, 1H), 3.06-2.78 (m, 4H), 2.77-2.67 (m, 2H), 2.66-2.58 (m, 1H), 1.98-1.85 (m, 2H), 1.85-1.73 (m, 3H), 1.72-1.57 (m, 2H), 1.51 (d, J=6.3 Hz, 2H), 1.31-1.23 (m, 1H), 1.13-1.04 (m, 1H), 1.02-0.83 (m, 3H), 0.67-0.56 (m, 1H), 0.43-0.29 (m, 2H), 0.10-0.00 (m, 1H)

Example 32

1H NMR (400 MHz, CD3OD): δ=8.08 (d, J=8.4 Hz, 1H), 7.73 (d, J=8.2 Hz, 1H), 6.93 (d, J=7.7 Hz, 1H), 6.67-6.59 (m, 2H), 3.93 (s, 2H), 2.86-2.80 (m, 2H), 2.79-2.67 (m, 4H), 2.63-2.55 (m, 1H), 1.90-1.79 (m, 4H), 1.76-1.66 (m, 2H), 1.33-1.28 (m, 1H), 1.08-1.00 (m, 1H), 0.82 (d, J=6.8 Hz, 3H), 0.58-0.48 (m, 1H), 0.46-0.36 (m, 1H), 0.27-0.15 (m, 1H), -0.03--0.15 (m, 1H)

Example 33

(2S,3R)-3-(1'-((R or S)-1-(5-chloro-2-(difluoromethoxy)phenyl)ethyl)-8-fluorospiro-[chroman-2,4'-piperidin]-7-yl)-3-cyclopropyl-2-methylpropanoic Acid

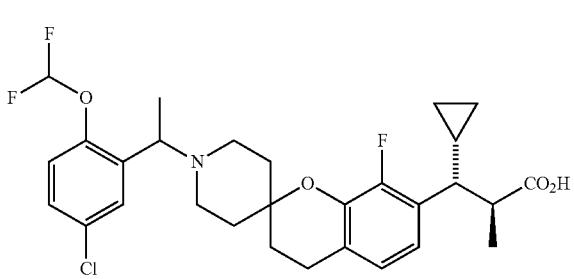

Step A:
1-(5-chloro-2-(difluoromethoxy)phenyl)ethanol

A solution of 5-chloro-2-(difluoromethoxy)benzaldehyde (100 mg, 0.484 mmol) in THF (1 mL) was cooled to 0° C.

under a nitrogen atmosphere. Methylmagnesium bromide (0.323 mL, 0.968 mmol) was added dropwise over 2 min, and the resulting suspension was stirred at 0° C. for 2 h. Then saturated aqueous NH$_4$Cl (2 mL) was added, and the mixture was extracted with EtOAc (5 mL×3). The combined organic layers were washed with brine (5 mL), dried over Na$_2$SO$_4$ and filtered. The filtrate was concentrated by rotary evaporator to give the title compound, which was used directly in the next step. $^1$H NMR (400 MHz, CDCl$_3$): δ=7.43 (d, J=2.3 Hz, 1H), 7.11 (dd, J=2.3, 8.6 Hz, 1H), 6.91 (d, J=8.6 Hz, 1H), 6.41 (t, J=73.6 Hz, 1H), 5.05 (q, J=6.4 Hz, 1H), 2.37 (br. s, 1H), 1.34 (d, J=6.7 Hz, 3H)

Step B: 4-chloro-2-(1-chloroethyl)-1-(difluoromethoxy)benzene

A solution of 1-(5-chloro-2-(difluoromethoxy)phenyl)ethanol (107 mg, 0.481 mmol) and Et$_3$N (0.201 mL, 1.44 mmol) in DCM (1 ml) was cooled to 0° C. Then Ms-Cl (56.0 µL, 0.721 mmol) was added dropwise over 2 min, and the reaction was stirred at 25° C. for 12 h. Then saturated aqueous NaHCO$_3$. (2 mL) was added, and the reaction mixture was extracted with DCM (5 mL×3). The combined organic layers were washed with brine (5 mL), dried over anhydrous Na$_2$SO$_4$ and filtered. The filtrate was concentrated by rotary evaporator to give a residue, which was purified by preparative TLC (silica gel, PE:EtOAc=10:1, v/v) to give the title compound. $^1$H NMR (400 MHz, CDCl$_3$): δ=7.52 (d, J=2.3 Hz, 1H), 7.21 (dd, J=2.3, 8.6 Hz, 1H), 7.00 (d, J=8.6 Hz, 1H), 6.45 (td, J=72.0, 74.3 Hz, 1H), 5.35 (q, J=6.7 Hz, 1H), 1.73 (d, J=7.0 Hz, 3H)

Step C: (2S,3R)-methyl 3-(1'-(1-(5-chloro-2-(difluoromethoxy)phenyl)-ethyl)-8-fluorospiro-[chroman-2,4'-piperidin]-7-yl)-3-cyclopropyl-2-methylpropanoate A suspension of 4-chloro-2-(1-chloroethyl)-1-(difluoromethoxy)-benzene (68.0 mg, 0.282 mmol), (2S,3R)-methyl 3-cyclopropyl-3-(8-fluorospiro-[chroman-2,4'-piperidin]-7-yl)-2-methylpropanoate (112 mg, 0.310 mmol), K$_2$CO$_3$ (117 mg, 0.846 mmol) and sodium iodide (85.0 mg, 0.564 mmol) in acetonitrile (2 mL) was heated to 85° C. for 18 h. Then the reaction was cooled to room temperature, diluted with water (10 mL) and extracted with EtOAc (10 mL×3). The combined organic layers were washed with brine (10 mL), dried over Na$_2$SO$_4$ and filtered. The filtrate was concentrated by rotary evaporator to give the title compound, which was directly used in the next step. MS (ESI): m/z 566.2 [M+H]$^+$ Step D: (2S,3R)-3-(1'-(1-(5-chloro-2-(difluoromethoxy)phenyl)ethyl)-8-fluoro-spiro-[chroman-2,4'-piperidin]-7-yl)-3-cyclopropyl-2-methylpropanoic Acid To a solution of (2S,3R)-methyl 3-(1'-(1-(5-chloro-2-(difluoromethoxy)phenyl)ethyl)-8-fluoro-spiro[chroman-2,4'-piperidin]-7-yl)-3-cyclopropyl-2-methylpropanoate (200 mg, 0.208 mmol) in MeOH (0.5 mL), THF (0.5 mL) and water (0.5 mL) was added lithium hydroxide monohydrate (131 mg, 3.13 mmol). The reaction was heated to 55° C. for 12 hours, then cooled to room temperature and neutralized to pH 7 by the dropwise addition of concentrated HCl. The solvents were removed by rotary evaporator to give a residue, which was dissolved in MeCN and DMSO and filtered. The filtrate was purified by preparative HPLC to give the title compound. Preparative HPLC conditions: Column: Waters XSELECT C18 150*30 mm*5 um; Condition: water (0.1% TFA)-ACN; Begin B: 27; End B: 57; Gradient Time (min): 10; 100% B Hold Time (min): 2; FlowRate (mL/min): 25; Injections: 6. MS (ESI): m/z 552.2 [M+H]$^+$ Step E: (2S,3R)-3-(1'-((R or S)-1-(5-chloro-2-(difluoromethoxy)phenyl)ethyl)-8-fluoro-spiro-[chroman-2,4'-piperidin]-7-yl)-3-cyclopropyl-2-methylpropanoic Acid, and (2S,3R)-3-(1'-((S or R)-1-(5-chloro-2-(difluoromethoxy)phenyl)ethyl)-8-fluoro-spiro[chroman-2,4'-piperidin]-7-yl)-3-cyclopropyl-2-methylpropanoic Acid (2S,3R)-3-(1'-(1-(5-chloro-2-(difluoromethoxy)phenyl)ethyl)-8-fluorospiro[chroman-2,4'-piperidin]-7-yl)-3-cyclopropyl-2-methylpropanoic acid (68.0 mg, 0.123 mmol) was separated into individual diastereoisomers via SFC (SFC conditions: Column: AD (250 mm*30 mm, 5 um); Condition Base-EtOH; Begin B: 20%; FlowRate (mL/min) 60 mL/min; injections 80) to give (2S,3R)-3-(1'-((R or S)-1-(5-chloro-2-(difluoro-methoxy)phenyl)ethyl)-8-fluorospiro-[chroman-2,4'-piperidin]-7-yl)-3-cyclopropyl-2-methylpropanoic acid, and (2S,3R)-3-(1'-((S or R)-1-(5-chloro-2-(difluoro-methoxy)phenyl)-ethyl)-8-fluorospiro-[chroman-2,4'-piperidin]-7-yl)-3-cyclo-propyl-2-methylpropanoic acid. The individual diastereoisomers of the title compound were treated respectively with 1 equivalent of aqueous NaOH (10 wt %) and lyophilized to give the corresponding sodium salt of the title compound. MS (ESI): m/z 552.2 [M+H]$^+$ $^1$H NMR (400 MHz, CD$_3$OD): δ=7.60 (d, J=2.2 Hz, 1H), 7.34 (dd, J=2.4, 8.8 Hz, 1H), 7.19 (d, J=8.8 Hz, 1H), 7.07-6.69 (m, 2H), 6.66 (d, J=7.7 Hz, 1H), 4.17-4.06 (m, 1H), 3.05-2.95 (m, 1H), 2.86-2.72 (m, 3H), 2.70-2.53 (m, 3H), 2.35-2.24 (m, 1H), 1.98-1.62 (m, 6H), 1.41 (d, J=6.8 Hz, 3H), 1.20-1.08 (m, 1H), 0.89 (d, J=6.8 Hz, 3H), 0.64-0.53 (m, 1H), 0.43-0.33 (m, 1H), 0.32-0.22 (m, 1H), 0.00-−0.09 (m, 1H)

TABLE 9

The compound of Example 34 was prepared in a similar manner to Example 33 using the appropriate starting material and reagents.

| Example | Structure | M.W. | Compound Name | LC/MS (ESI) observed [M + H]+ |
|---|---|---|---|---|
| 34 | 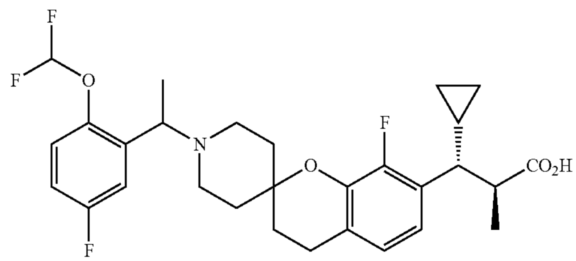 [SMILES: CC(c1cc(F)ccc1OC(F)F)N1CCC2(CCc3ccc([C@H](C4CC4)[C@H](C)C(=O)O)c(F)c3O2)CC1] | 552.0 | (2S,3R)-3-(1'-((S or R)-1-(5-chloro-2-(difluoromethoxy)phenyl)ethyl)-8-fluorospiro-[chroman-2,4'-piperidin]-7-yl)-3-cyclopropyl-2-methylpropanoic acid | 552.2 |

Example 34

$^1$H NMR (400 MHz, CD$_3$OD): δ=7.62 (d, J=2.3 Hz, 1H), 7.36 (dd, J=2.3, 9.0 Hz, 1H), 7.20 (d, J=9.0 Hz, 1H), 7.09-6.69 (m, 2H), 6.67 (d, J=7.8 Hz, 1H), 4.18 (q, J=6.7 Hz, 1H), 3.06 (d, J=11.3 Hz, 1H), 2.89-2.58 (m, 6H), 2.34-2.23 (m, 1H), 1.98-1.64 (m, 6H), 1.45 (d, J=6.7 Hz, 3H), 1.21-1.06 (m, 1H), 0.90 (d, J=6.7 Hz, 3H), 0.63-0.53 (m, 1H), 0.42-0.33 (m, 1H), 0.32-0.22 (m, 1H), 0.01--0.09 (m, 1H)

Example 35 sodium (2S,3R)-3-cyclopropyl-2-methyl-3-(1'-(2-(trifluoromethyl)phenyl)-spiro[chroman-2,4'-piperidin]-7-yl)propanoate

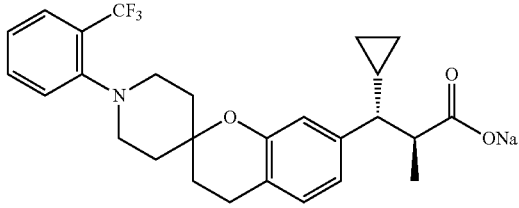

Step A: (2S,3R)-methyl 3-cyclopropyl-2-methyl-3-(1'-(2-(trifluoromethyl)phenyl) spiro[chroman-2,4'-piperidin]-7-yl)propanoate To a solution of (2S,3R)-methyl 3-cyclopropyl-2-methyl-3-(spiro[chroman-2,4'-piperidin]-7-yl)propanoate (50.0 mg, 0.146 mmol), 1-bromo-2-(trifluoromethyl)benzene (49.1 mg, 0.218 mmol), Cs$_2$CO$_3$ (95.0 mg, 0.291 mmol) in toluene (5 ml) and t-BuOH (1 ml) was added chloro(2-dicyclohexylphosphino-2',4',6'-tri-i-propyl-1,1'-biphenyl)(2'-amino-1,1'-biphenyl-2-yl) palladium(II) (11.4 mg, 15.0 umol) under N$_2$. The mixture was stirred at 120° C. for 12 hours under N$_2$. Then water (10 mL) was added and the mixture was extracted with EtOAc (20 mL×3). The combined organic layers were dried over sodium sulfate, and then filtered. The filtrate was concentrated in vacuo to give the crude product, which was purified by TLC (SiO$_2$, petroleum ether:ethyl acetate=10:1, v/v) to give the title compound. MS (ESI) m/z: 488.3 [M+H]+

Step B: sodium (2S,3R)-3-cyclopropyl-2-methyl-3-(1'-(2-(trifluoromethyl)phenyl) spiro[chroman-2,4'-piperidin]-7-yl)propanoate To a solution of (2S,3R)-methyl 3-cyclopropyl-2-methyl-3-(1'-(2-(trifluoromethyl)phenyl)spiro[chroman-2,4'-piperidin]-7-yl)propanoate (20.0 mg, 41.0 umol) in a co-solvent of THF (2 ml), water (2 ml) and MeOH (2 ml) was added LiOH (49.1 mg, 2.05 mmol). The reaction mixture was stirred at 50° C. for 12 hours under N$_2$. Then the reaction mixture was poured into water (2 mL), citric acid was added to adjust pH to 7, and the mixture was extracted with EtOAc (5 mL×3). The combined organic layers were washed with brine (2 mL×3), dried over Na$_2$SO$_4$, and filtered. The filtrate was evaporated under reduced pressure to give a residue, which was purified via Prep-HPLC (base) to give the title compound. To the solution of the title compound in MeCN (1 mL) and water (1 mL) was added an aqueous NaOH solution (1.0 eq, 0.5 M), and the mixture was stirred for 1 h at room temperature. Then the reaction mixture was lyophilized to give the sodium salt of the title compound. Preparative HPLC conditions: a MS trigger instrument fitted with a Waters Xbridge Prep OBD C18 150*30 5u using water (0.05% ammonia hydroxide v/v)-ACN as the eluents, mobile phase A: water (0.05% ammonia hydroxide v/v), mobile phase B: acetonitrile, gradient: 30-60% B, 2.0-10.0 min, flowRate: 25 mL/min. MS (ESI) m/z: 474.2[M+H]+ $^1$H NMR (400 MHz, CD$_3$OD): δ=7.67-7.51 (m, 3H), 7.27 (t, J=7.3 Hz, 1H), 6.98 (d, J=7.7 Hz, 1H), 6.70-6.62 (m, 2H), 3.20 (t, J=10.4 Hz, 2H), 2.90-2.67 (m, 5H), 1.95-1.76 (m, 7H), 1.08 (dd, J=4.1, 8.7 Hz, 1H), 0.89 (d, J=6.8 Hz, 3H), 0.62-0.53 (m, 1H), 0.41-0.23 (m, 2H), 0.01--0.07 (m, 1H)

Example 36

(2S,3R)-3-cyclopropyl-2-methyl-3-(1'-(1-methyl-3-(trifluoromethyl)-1H-indazol-4-yl)spiro[chroman-2,4'-piperidin]-7-yl)propanoic Acid

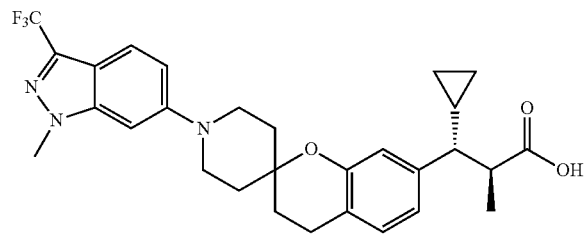 [SMILES: C[C@H](C(=O)O)[C@H](c1ccc2c(c1)OC1(CC2)CCN(c2ccc3c(C(F)(F)F)nn(C)c3c2)CC1)C1CC1]

Step A: (2S,3R)-methyl 3-cyclopropyl-2-methyl-3-(1'-(1-methyl-3-(trifluoromethyl)-1H-indazol-4-yl)spiro[chroman-2,4'-piperidin]-7-yl)propanoate To a solution of (2S,3R)-methyl 3-cyclopropyl-2-methyl-3-(spiro[chroman-2,4'-piperidin]-7-yl)-propanoate (70 mg, 0.200 mmol) and 4-bromo-1-methyl-3-(trifluoromethyl)-1H-indazole (83.7 mg, 0.300 mmol) in toluene (3 mL) were added 2$^{nd}$ Generation SPHOS Precatalyst (14.4 mg, 0.020 mmol) and potassium 2-methylpropan-2-olate (38.8 mg, 0.4 mmol) at 19° C. The reaction was heated under microwave radiation at 120° C. for 30 min. Then the reaction was quenched with water (2 mL), and the aqueous layer was extracted with EtOAc (2 mL×3). The combined organic layers were washed with brine (10 mL), dried over anhydrous MgSO$_4$ and filtered. The filtrate was concentrated under reduced pressure to give a residue, which was purified by prep-TLC (SiO$_2$, PE:EtOAc=3:1, v/v) to give the title compound. MS (ESI) m/z: 542.3 [M+H]$^+$

Step B: (2S,3R)-3-cyclopropyl-2-methyl-3-(1'-(1-methyl-3-(trifluoromethyl)-1H-indazol-4-yl)spiro[chroman-2,4'-piperidin]-7-yl)propanoic Acid To a suspension of (2S,3R)-methyl 3-cyclopropyl-2-methyl-3-(1'-(1-methyl-3-(trifluoromethyl)-1H-indazol-4-yl)-spiro[chroman-2,4'-piperidin]-7-yl)propanoate (52 mg, 0.096 mmol) in MeOH (1 mL), THF (1 mL) and water (1 mL) was added lithium hydroxide monohydrate (173 mg, 4.11 mmol). The reaction was heated to 55° C. for 12 hours, then concentrated in vacuo to remove the solvent, and water (2 mL) was added. Citric acid was added to the mixture to adjust the pH to pH 5, and the mixture was extracted with EtOAc (2 mL×3). The combined organic layers were dried over anhydrous MgSO$_4$ and filtered. The filtrate was concentrated under reduced pressure to give a residue, which was purified by HPLC (neutral) to give the title compound. To a solution of the title compound in MeCN (1 mL) and water (1 mL) was added an aqueous solution of NaOH (1.0 eq, 0.5 M), and the mixture was stirred for 1 hour at room temperature. Then the reaction mixture was lyophilized to give the sodium salt of the title compound. Preparative HPLC conditions: a MS trigger instrument fitted with a Phenomenex Gemini C18 250*21.2 mm*5 um using water and acetonitrile as the eluents, Mobile phase A: water (10 mM NH$_4$HCO$_3$)-ACN, Mobile phase B: acetonitrile, Gradient: 39-69% B, 0-12.0 min; 100% B, 12.0-14 min, Flow-Rate: 25 mL/min. MS (ESI) m/z: 528.3 [M+H]$^+$ $^1$H NMR (400 MHz, CD$_3$OD): δ=7.52-7.42 (m, 1H), 7.35 (d, J=8.4 Hz, 1H), 7.10 (d, J=7.5 Hz, 1H), 7.00 (d, J=7.5 Hz, 1H), 6.68-6.64 (m, 2H), 4.10 (s, 3H), 3.23-3.15 (m, 2H), 3.12-3.03 (m, 2H), 2.84-2.72 (m, 3H), 1.96-1.85 (m, 7H), 1.16-1.04 (m, 1H), 0.92 (d, J=6.8 Hz, 3H), 0.62-0.53 (m, 1H), 0.37-0.26 (m, 2H), 0.06--0.07 (m, 1H)

TABLE 10

The compounds of Examples 37-38 were prepared in a similar manner to Example 36 using the appropriate starting material and reagents.

| Example | Structure | M.W. | Compound Name | LC/MS (ESI) observed [M + H]$^+$ |
|---|---|---|---|---|
| 37 | 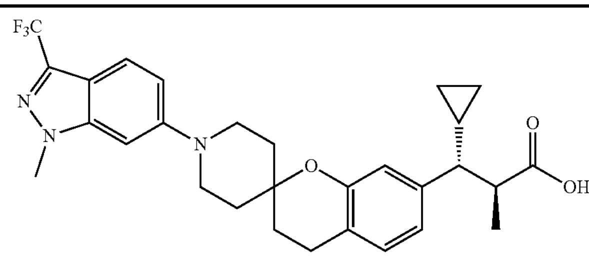 | 527.6 | (2S,3R)-3-cyclopropyl-2-methyl-3-(1'-(1-methyl-3-(trifluoromethyl)-1H-indazol-6-yl)spiro[chroman-2,4'-piperidin]-7-yl)-propanoic acid | 528.3 |
| 38 | 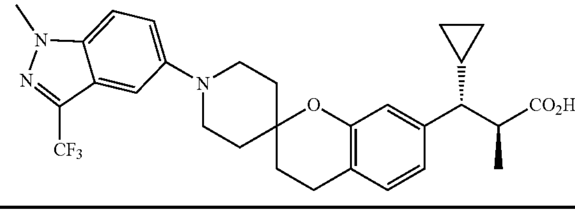 | 527.6 | (2S,3R)-3-cyclopropyl-2-methyl-3-(1'-(1-methyl-3-(trifluoromethyl)-1H-indazol-5-yl)spiro[chroman-2,4'-piperidin]-7-yl)propanoic acid | 528.3 |

Example 37

$^1$H NMR (400 MHz, CD$_3$OD): δ=7.59 (d, J=9.0 Hz, 1H), 7.17 (d, J=1.0 Hz, 1H), 7.00 (d, J=7.8 Hz, 1H), 6.95 (s, 1H), 6.70-6.62 (m, 2H), 4.04 (s, 3H), 3.69-3.58 (m, 2H), 3.37-

3.32 (m, 1H), 3.30-3.26 (m, 1H), 2.86-2.67 (m, 3H), 2.02-1.93 (m, 2H), 1.92-1.78 (m, 5H), 1.12-1.02 (m, 1H), 0.90 (d, J=7.0 Hz, 3H), 0.61-0.52 (m, 1H), 0.36-0.25 (m, 2H), 0.01-0.07 (m, 1H).

Example 38

$^1$H NMR (400 MHz, CD$_3$OD): δ=7.87-7.72 (m, 3H), 7.04 (d, J=7.7 Hz, 1H), 6.79 (s, 1H), 6.71 (d, J=7.7 Hz, 1H), 4.18 (s, 3H), 3.77 (t, J=11.5 Hz, 2H), 3.62 (d, J=11.9 Hz, 2H), 2.85 (t, J=6.6 Hz, 2H), 2.80-2.71 (m, 1H), 2.22-2.15 (m, 2H), 2.11-2.02 (m, 2H), 1.99-1.86 (m, 3H), 1.16-1.05 (m, 1H), 0.91 (d, J=6.8 Hz, 3H), 0.63-0.55 (m, 1H), 0.36-0.27 (m, 2H), 0.03--0.06 (m, 1H)

Example 39

(2S,3R)-3-cyclopropyl-2-methyl-3-(1'-(5-(trifluoromethyl)pyridin-3-yl)Spiro [chroman-2,4'-piperidin]-7-yl)propanoic Acid

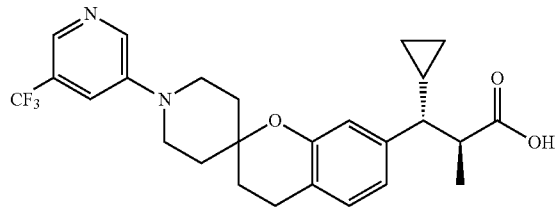 [SMILES: C[C@H](C(=O)O)[C@H](c1ccc2c(c1)OC1(CC2)CCN(c2cncc(C(F)(F)F)c2)CC1)C1CC1]

Step A: (2S3R)-3-cyclopropyl-2-methyl-3-(1'-(5-(trifluoromethyl)pyridin-3-yl) spiro[chroman-2,4'-piperidin]-7-yl)propanoic Acid To a solution of (2S,3R)-methyl 3-cyclopropyl-2-methyl-3-(spiro[chroman-2,4'-piperidin]-7-yl)propanoate (50 mg, 0.146 mmol) in toluene (2.5 mL) and t-BuOH (0.5 mL) were added sodium tert-butoxide (13.9 mg, 0.146 mmol), 3-bromo-5-(trifluoromethyl)pyridine (36.2 mg, 0.160 mmol) and chloro(2-dicyclohexylphosphino-2',4',6'-tri-i-propyl-1,1'-biphenyl)-(2'-amino-1,1'-biphenyl-2-yl) palladium (II) (115 mg, 0.146 mmol) at 25° C. The reaction mixture was degassed and purged with N$_2$. Then the reaction was heated to 120° C. for 12 h. The reaction mixture was filtered and the filtrate was subsequently evaporated under reduced pressure to give a residue, which was purified by prep-TLC (SiO$_2$, PE:EtOAc=5:1, v/v) to give the title compound. MS (ESI) m/z: 489.2 [M+H]$^+$ Step B: (2S,3R)-3-cyclopropyl-2-methyl-3-(1'-(5-(trifluoromethyl)pyridin-3-yl) spiro[chroman-2,4'-piperidin]-7-yl)propanoic Acid To a solution of (2S,3R)-methyl 3-cyclopropyl-2-methyl-3-(1'-(5-(trifluoromethyl)pyridin-3-yl)spiro[chroman-2,4'-piperidin]-7-yl)propanoate (45.0 mg, 0.0920 mmol) in MeOH (1 mL), THF (1 mL) and water (1 mL) was added LiOH (22.0 mg, 0.921 mmol) under nitrogen. The reaction was stirred at 55° C. for 12 h, and then concentrated in vacuo to give a residue. Water (5 mL) was added to the resulting residue and citric acid was added to the mixture to adjust the pH to pH 5. Then the mixture was extracted with EtOAc (10 mL×3). The combined organic layers were washed with brine (10 mL), dried over anhydrous MgSO$_4$ and filtered. The filtrate was concentrated under reduced pressure to give a residue, which was purified by prep-HPLC (neutral) to afford the title compound. Preparative HPLC conditions: a MS trigger instrument fitted with a Phenomenex Gemini C18 25×21.2 mm×5 um as the eluents, Mobile phase A: water (10 mM NH$_4$HCO$_3$)-ACN, mobile phase B: acetonitrile, Gradient: 31-61% B, 0-12.0 min; 100% B, 12.1-14.0 min; 10% B, 14.1-17 min, FlowRate: 25 mL/min. MS (ESI) m/z: 475.2 [M+H]$^+$ $^1$H NMR (400 MHz, CD$_3$OD) δ=7.81 (s, 1H), 7.67 (s, 1H), 7.56-7.50 (m, 1H), 6.89 (d, J=7.9 Hz, 1H), 6.77 (s, 1H), 4.51 (s, 2H), 3.46 (s, 4H), 2.84 (d, J=6.2 Hz, 3H), 2.29 (t, J=10.3 Hz, 1H), 2.17 (d, J=14.6 Hz, 2H), 1.93 (s, 3H), 1.30 (s, 2H), 1.15 (s, 1H), 0.91 (d, J=6.4 Hz, 3H), 0.60 (s, 1H), 0.42-0.22 (m, 2H), −0.04 (s, 1H)

Example 40 (2S,3R)-3-cyclopropyl-2-methyl-3-(1'-(2-(trifluoromethyl)pyridin-4-yl)spiro-[chroman-2,4'-piperidin]-7-yl)propanoic Acid

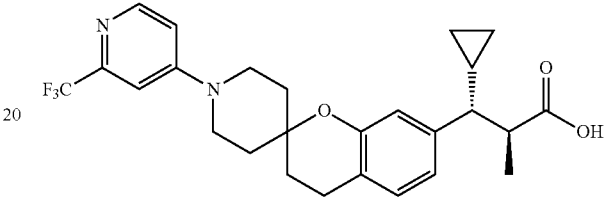

Step A: (2S,3R)-methyl 3-cyclopropyl-2-methyl-3-(1'-(2-(trifluoromethyl)pyridin-4-yl) spiro[chroman-2,4'-piperidin]-7-yl)propanoate To a suspension of 4-bromo-2-(tri-fluoromethyl)pyridine (118 mg, 0.524 mmol), (2S,3R)-methyl 3-cyclopropyl-2-methyl-3-(spiro[chroman-2,4'-piperidin]-7-yl)propanoate (150 mg, 0.437 mmol) and Cs$_2$CO$_3$ (285 mg, 0.873 mmol) in toluene (4 mL) and t-BuOH (0.8 mL) was added chloro (2-dicyclohexylphosphino-2',4',6'-tri-i-propyl-1,1'-biphenyl)(2'-amino-1,1'-biphenyl-2-yl) palladium (ii) (34.4 mg, 0.0440 mmol) under N$_2$ atmosphere. The reaction mixture was stirred for 20 h at 120° C., then water (10 mL) was added and the mixture was extracted with EtOAc (5 mL×3). The combined organic layers were washed with brine (10 mL), dried over anhydrous Na$_2$SO$_4$ and filtered. The filtrate was concentrated in vacuo to give a residue, which was purified by prep-TLC (SiO$_2$, PE:EtOAc=5:1, v/v) to afford the title compound. MS (ESI) m/z: 489.3 [M+H]$^+$ Step B: (2S,3R)-3-cyclopropyl-2-methyl-3-(1'-(2-(trifluoromethyl)pyridin-4-yl)spiro [chroman-2,4'-piperidin]-7-yl)propanoic Acid To a solution of (2S,3R)-methyl 3-cyclopropyl-2-methyl-3-(1'-(2-(trifluoromethyl)pyridin-4-yl)spiro[chroman-2,4'-piperidin]-7-yl)propanoate (90.0 mg, 0.184 mmol) in MeOH (1.5 mL), THF (1.5 mL) and water (1.5 mL) was added lithium hydroxide (88.0 mg, 3.68 mmol) under a N$_2$ atmosphere. The reaction was stirred for 22 hours at 55° C., then water (5 mL) was added, the mixture pH was adjusted with citric acid to pH 6-7, and the mixture was extracted with EtOAc (5 mL×3). The combined organic layers were washed with brine (5 mL), dried over anhydrous Na$_2$SO$_4$ and filtered. The filtrate was evaporated under reduced pressure to give a residue, which was purified by prep-HPLC (Neutral) to give the title compound. LC-MS (ESI) m/z: 475.2 [M+H]$^+$ $^1$H NMR (400 MHz, CD$_3$OD) δ=8.18 (d, J=6.2 Hz, 1H), 7.19 (d, J=2.2 Hz, 1H), 7.02-6.95 (m, 2H), 6.68-6.62 (m, 2H), 3.86 (d, J=13.2 Hz, 2H), 3.45 (t, J=11.8 Hz, 2H), 2.82-2.74 (m, 2H), 2.74-2.66 (m, 1H), 1.97-1.79 (m, 5H), 1.76-1.65 (m, 2H), 1.12-1.01 (m, 1H), 0.88 (d, J=6.8 Hz, 3H), 0.60-0.51 (m, 1H), 0.35-0.24 (m, 2H), 0.00--0.09 (m, 1H)

TABLE 11

The compounds of Examples 41-42 were prepared in a similar manner to Example 40 using the appropriate starting material and reagents.

| Example | Structure | M.W. | Compound Name | LC/MS (ESI) observed [M + H]+ |
|---|---|---|---|---|
| 41 | 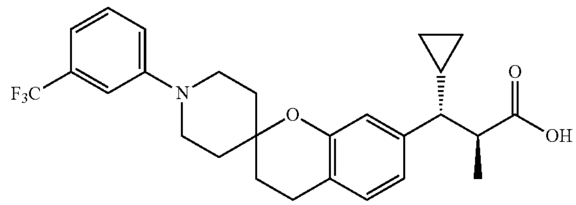 [SMILES: C[C@H](C(=O)O)[C@H](c1ccc2c(c1)OC1(CC2)CCN(c2cccc(C(F)(F)F)c2)CC1)C1CC1] | 473.52 | (2S,3R)-3-cyclopropyl-2-methyl-3-(1'-(3-(trifluoromethyl)phenyl)spiro[chroman-2,4'-piperidin]-7-yl)propanoic acid | 474.2 |
| 42 | 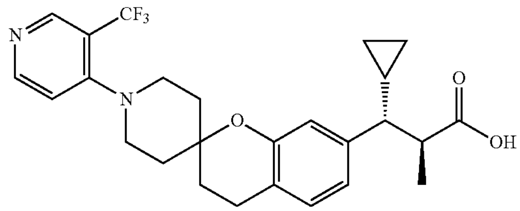 [SMILES: C[C@H](C(=O)O)[C@H](c1ccc2c(c1)OC1(CC2)CCN(c2ccncc2C(F)(F)F)CC1)C1CC1] | 474.51 | (2S,3R)-3-(1'-((2-chloro-4-(trifluoromethyl)phenyl)sulfonyl)spiro[chroman-2,4'-piperidin]-7-yl)-3-cyclopropyl-2-methylpropanoic acid | 475.2 |

Example 41

$^1$H NMR (400 MHz, CD$_3$OD) δ=7.44-7.34 (m, 1H), 7.26-7.17 (m, 2H), 7.08-6.97 (m, 2H), 6.70-6.61 (m, 2H), 3.56 (d, J=12.3 Hz, 2H), 3.30-3.23 (m, 2H), 2.85-2.69 (m, 3H), 2.00-1.75 (m, 7H), 1.16-1.03 (m, 1H), 0.91 (d, J=6.8 Hz, 3H), 0.63-0.52 (m, 1H), 0.38-0.25 (m, 2H), −0.02 (d, J=4.9 Hz, 1H)

Example 42

$^1$H NMR (400 MHz, CD$_3$OD) δ=8.58 (s, 1H), 8.45 (d, J=6.0 Hz, 1H), 7.23 (d, J=6.0 Hz, 1H), 7.00 (d, J=7.5 Hz, 1H), 6.70-6.64 (m, 2H), 3.43-3.36 (m, 4H), 2.85-2.68 (m, 3H), 1.99-1.78 (m, 7H), 1.14-1.03 (m, 1H), 0.90 (d, J=6.8 Hz, 3H), 0.62-0.53 (m, 1H), 0.38-0.25 (m, 2H), 0.02--0.06 (m, 1H)

Example 43

(2S,3R)-3-cyclopropyl-2-methyl-3-(1'-((S or R)-1-(3-(trifluoromethyl)-pyridin-2-yl)ethyl)spiro[chroman-2,4'-piperidin]-7-yl)propanoic Acid

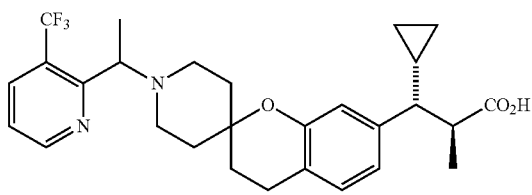 [SMILES: CC(c1ncccc1C(F)(F)F)N1CCC2(CCc3ccc([C@H](C4CC4)[C@H](C)C(=O)O)cc3O2)CC1]

Step A: 1-(3-(trifluoromethyl)pyridin-2-yl)ethanol

To a solution of 2-bromo-3-(trifluoromethyl)pyridine (450 mg, 2.00 mmol) in THF (20 mL) was added n-BuLi (1.2 mL, 3.00 mmol) at −78° C. in portions. The reaction was stirred at −78° C. for 30 min, then acetaldehyde (881 mg, 20 mmol) was added. The reaction mixture was stirred at −78° C. for 1 hour. Then the reaction was quenched with water (20 mL) and extracted with EtOAc (20 mL×3). The combined organic layers were washed with brine (50 mL), dried (Na$_2$SO$_4$), and filtered. The filtrate was evaporated under reduced pressure to get a residue, which was purified by TLC (SiO$_2$, PE/EA=3:1, v/v) to give the title compound. MS (ESI) m/z: 192.0[M+H]$^+$

Step B: 1-(3-(trifluoromethyl)pyridin-2-yl)ethyl methanesulfonate

To a solution of 3-(trifluoromethyl)pyridin-2-yl)ethanol (143 g, 0.750 mmol) in DCM (7.5 mL) were added MsCl (171 mg, 1.50 mmol) and Et$_3$N (152 mg, 1.50 mmol) at 0° C. The reaction was stirred at 25° C. for 2 hours, then quenched with water (10 mL), and extracted with EtOAc (10 mL×3). The combined organic layers were washed with brine (20 mL), dried (Na$_2$SO$_4$), and filtered. The filtrate was evaporated under reduced pressure to give the title compound, which was used directly in the next step. MS (ESI) m/z: 270.0[M+H]$^1$H NMR (400 MHz, CDCl$_3$): δ=8.90 (d, J=4.0 Hz, 1H), 8.02 (d, J=7.5 Hz, 1H), 7.50-7.41 (m, 1H), 6.17 (q, J=6.0 Hz, 1H), 2.97 (s, 3H), 1.78 (d, J=6.5 Hz, 3H)

Step C: (2S,3R)-methyl 3-cyclopropyl-2-methyl-3-(1'-(1-(3-(trifluoromethyl)-pyridin-2-yl)ethyl)spiro[chroman-2,4'-piperidin]-7-yl)propanoate To a solution of 1-(3-(tri-fluoromethyl)pyridin-2-yl)ethyl methanesulfonate (92.0 mg, 0.340 mmol) in MeCN (3 mL) were added (2S,3R)-methyl 3-cyclopropyl-2-methyl-3-(spiro-[chroman-2,4'-piperidin]-7-yl)propanoate (103 mg, 0.300 mmol), K$_2$CO$_3$ (207 mg, 1.50 mmol) and NaI (134 mg, 0.90 mmol). The reaction was stirred at 90° C. for 5 hours, then poured into water (20 mL), and extracted with EtOAc (20 mL×3). The combined organic layers were washed with brine (saturated 20 mL), dried over Na$_2$SO$_4$, and filtered. The filtrate was concentrated under reduced pressure to give a residue, which was purified by TLC (SiO$_2$, PE/EA=2:1, v/v) to give the title compound. MS (ESI) m/z: 517.3[M+H]$^+$ Step D: (2S,3R)-3-cyclopropyl-2-methyl-3-(1'-(1-(3-(trifluoromethyl)-pyridin-2-yl)ethyl)spiro[chroman-2,4'-piperidin]-7-yl)propanoic Acid To a solution of (2S,3R)-methyl 3-cyclopropyl-2-methyl-3-(1'-(1-(3-(trifluoromethyl)pyridin-2-yl)-ethyl)spiro[chroman-2,4'-piperidin]-7-yl)propanoate (78.0 mg, 0.151 mmol) in CH$_3$OH (1.5 mL), THF (1.5 mL, H$_2$O (1.5 mL) was added LiOH (285 mg, 6.8 mmol). The reaction was stirred at 55° C. for 12 hours. The reaction mixture was poured into water (10 mL), citric acid was added to adjust the mixture pH to pH 7, and the mixture was extracted with EtOAc (10 mL×3). The combined organic layers were washed with brine (saturated, 20 mL), dried over Na$_2$SO$_4$ and filtered. The filtrate was concentrated under reduced pressure to give the title compound.
MS (ESI) m/z: 503.7[M+H]$^+$ Step E: (2S,3R)-3-cyclopropyl-2-methyl-3-(1'-((S or R)-1-(3-(trifluoromethyl)-pyridin-2-yl)ethyl)spiro[chroman-2,4'-piperidin]-7-yl)propanoic Acid (2S,3R)-3-cyclopropyl-2-methyl-3-(1'-(1-(3-(trifluoromethyl)pyridin-2-yl)ethyl)spiro-[chroman-2,4'-piperidin]-7-yl)propanoic acid (103 mg, 0.151 mmol) was separated into individual diastereoisomers via SFC (SFC conditions: Instrument: SFC-E Column: Chiralpak AD-3 150×4.6 mm I.D., 3 um., 3 um, Mobile phase: A: CO$_2$B:iso-propanol (0.05% DEA), Gradient: from 5% to 40% of B in 5 min and hold 40% for 2.5 min, then 5% of B for 2.5 min, Flow rate: 2.5 mL/min, Column temperature: 35° C.) to give (2S,3R)-3-cyclopropyl-2-methyl-3-(1'-((S or R)-1-(3-(trifluoromethyl)pyridin-2-yl)-ethyl)spiro[chroman-2,4'-piperidin]-7-yl)propanoic acid, and (2S,3R)-3-cyclopropyl-2-methyl-3-(1'-((R or S)-1-(3-(trifluoromethyl)pyridin-2-yl)ethyl)spiro[chroman-2,4'-piperidin]-7-yl)propanoic acid. To a solution of each individual diastereoisomer in MeCN (1 mL) and water (1 mL) was added a solution of aq. NaOH (1.0 eq, 0.5 M), and the mixture was stirred for 1 h at room temperature. Then the reaction mixture was lyophilized to give the sodium salt of each diastereoisomer of the title compound. MS (ESI) m/z: 503.2[M+H]$^1$H NMR (400 MHz, CD$_3$OD): δ=8.99 (d, J=4.2 Hz, 1H), 8.27 (d, J=7.9 Hz, 1H), 7.65 (dd, J=5.0, 7.8 Hz, 1H), 7.05 (d, J=7.9 Hz, 1H), 6.78-6.70 (m, 2H), 4.51 (d, J=6.2 Hz, 1H), 3.13-3.01 (m, 2H), 2.88-2.72 (m, 4H), 2.10-2.02 (m, 1H), 1.96-1.87 (m, 4H), 1.85-1.75 (m, 1H), 1.63 (d, J=6.6 Hz, 3H), 1.42-1.34 (m, 2H), 1.20-1.09 (m, 1H), 0.99-0.91 (m, 3H), 0.71-0.60 (m, 1H), 0.50-0.39 (m, 1H), 0.38-0.28 (m, 1H), 0.05--0.02 (m, 1H)

TABLE 12

The compound of Example 44 was prepared in a similar manner to Example 43 using the appropriate starting material and reagents.

| Example | Structure | M.W. | Compound Name | LC/MS (ESI) observed [M + 1]$^+$ |
|---|---|---|---|---|
| 44 | 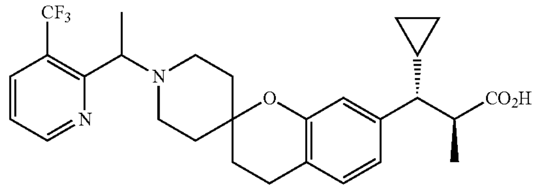 [SMILES: CC(c1ncccc1C(F)(F)F)N1CCC2(CCc3ccc([C@H](C4CC4)[C@H](C)C(=O)O)cc3O2)CC1] | 502.2 | (2S,3R)-3-cyclo-propyl-2-methyl-3-(1'-((R or S)-1-(3-(trifluoromethyl)pyridin-2-yl)ethyl)spiro-[chroman-2,4'-piperidin]-7-yl)propanoic acid | 503.2 |

Example 44

$^1$H NMR (400 MHz, CD$_3$OD): δ=8.98 (d, J=4.2 Hz, 1H), 8.26 (d, J=7.7 Hz, 1H), 7.64 (dd, J=5.0, 7.8 Hz, 1H), 7.05 (d, J=8.2 Hz, 1H), 6.78-6.71 (m, 2H), 4.47 (d, J=6.2 Hz, 1H), 3.03 (t, J=10.8 Hz, 2H), 2.89-2.67 (m, 4H), 2.10-2.03 (m, 1H), 2.00-1.96 (m, 1H), 1.95-1.86 (m, 3H), 1.85-1.74 (m, 1H), 1.62 (d, J=6.6 Hz, 3H), 1.37 (s, 2H), 1.20-1.09 (m, 1H), 0.94 (d, J=6.8 Hz, 3H), 0.69-0.59 (m, 1H), 0.49-0.40 (m, 1H), 0.38-0.29 (m, 1H), 0.07--0.02 (m, 1H)

Example 45

(2S,3R)-3-cyclopropyl-2-methyl-3-(1'-(5-(trifluoromethyl)pyridin-3-yl)Spiro [chroman-2,4'-piperidin]-7-yl)propanoic Acid

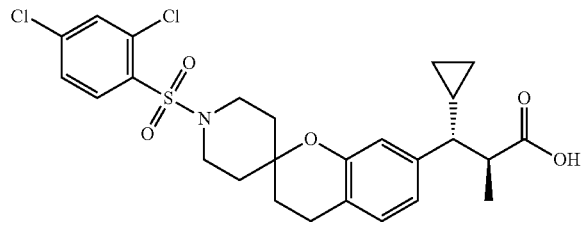 [SMILES: C[C@H](C(=O)O)[C@H](c1ccc2c(c1)OC1(CC2)CCN(S(=O)(=O)c2ccc(Cl)cc2Cl)CC1)C1CC1]

Step A: (2S3R)-methyl 3-cyclopropyl-3-(1'-((2,4-dichlorophenyl)sulfonyl)spiro [chroman-2,4'-piperidin]-7-yl)-2-methylpropanoate To a solution of (2S,3R)-methyl 3-cyclopropyl-2-methyl-3-(spiro[chroman-2,4'-piperidin]-7-yl)propanoate (50.0 mg, 0.146 mmol) and Et$_3$N (0.020 mL, 0.146 mmol) in DCM (1 mL) was added dropwise a solution of 2,4-dichlorobenzene-1-sulfonyl chloride (35.7 mg, 0.146 mmol) in DCM (0.5 mL) at 25° C. The reaction was stirred at 25° C. for 1 h, then quenched by the addition of water (5 mL) and extracted with DCM (10 mL×3). The organic layers were dried over Na$_2$SO$_4$ and filtered. The filtrate was concentrated in vacuo to give the title compound. MS (ESI) m/z: 552.2 [M+H]$^+$ Step B: (2S3R)-3-cyclopropyl-3-(1'-((2,4-dichlorophenyl)sulfonyl)spiro [chroman-2,4'-piperidin]-7-yl)-2-methylpropanoic Acid To a solution of (2S,3R)-methyl 3-cyclopropyl-3-(1'-((2,4-dichlorophenyl)sulfonyl)spiro[chroman-2,4'-piperidin]-7-yl)-2-methylpropanoate (60.0 mg, 0.109 mmol) in THF (1 mL) and water (1 mL) was added LiOH (26.0 mg, 1.08 mmol) under nitrogen. The reaction was stirred at 55° C. for 24 h, then concentrated in vacuo to remove the solvent. Water (5 mL) was added to the residue, then citric acid was added to adjust the pH of the mixture to adjust pH 5, and the mixture was extracted with EtOAc (10 mL×3). The combined organic layers were washed with brine (10 mL), dried over anhydrous MgSO$_4$ and filtered. The filtrate was concentrated under reduced pressure to give a residue, which was purified by prep-HPLC (neutral) to afford the title compound. Preparative HPLC conditions: a MS trigger instrument fitted with a Phenomenex Gemini C18 250×21.2 mm×5 um as the eluents, mobile phase A: water (10 mM NH$_4$HCO$_3$)-ACN, mobile phase B: acetonitrile, gradient: 38-68% B, 0-12.0 min, 100% B, 12.1-14.0 min, 10% B, 14.1-17 min, FlowRate: 25 mL/min. MS (ESI) m/z: 538.0 [M+H]$^+$ $^1$H NMR (400 MHz, CD$_3$OD) δ=8.03 (d, J=8.6 Hz, 1H), 7.73 (s, 1H), 7.54 (d, J=8.2 Hz, 1H), 6.95 (d, J=7.7 Hz, 1H), 6.64 (d, J=7.7 Hz, 1H), 6.58 (s, 1H), 3.67 (d, J=11.9 Hz, 2H), 3.21 (s, 2H), 2.75 (s, 2H), 2.69-2.59 (m, 1H), 1.91-1.78 (m, 5H), 1.74-1.62 (m, 2H), 1.04 (s, 1H), 0.84 (d, J=6.6 Hz, 3H), 0.54 (s, 1H), 0.39-0.19 (m, 1H), −0.08 (s, 1H)

Example 47

(2S,3R)-3-((R or S)-1-(2,5-bis(trifluoromethyl)benzyl)spiro[azepane-4,2'-chroman]-7'-yl)-3-cyclopropyl-2-methylpropanoic Acid

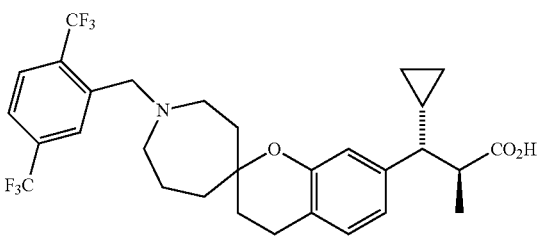 [SMILES: C[C@H](C(=O)O)[C@H](c1ccc2c(c1)OC1(CCCN(Cc3cc(C(F)(F)F)ccc3C(F)(F)F)CC1)CC2)C1CC1]

Step A: (RS)-tert-butyl 7'-((1R,2S)-1-cyclopropyl-3-methoxy-2-methyl-3-oxopropyl)-4'-oxospiro [azepane-4,2'-chroman]-1-carboxylate To a solution of (2S,3R)-methyl-3-(4-acetyl-2-fluoro-3-hydroxyphenyl)-3-cyclopropyl-2-methylpropanoate (1.00 g, 3.62 mmol) and tert-butyl 4-oxoazepane-1-carboxylate (1.16 g, 5.43 mmol) in dry MeOH (20 mL) was added pyrrolidine (536 mg, 7.24 mmol) at 15° C. The reaction was stirred at 60° C. for 30 hours. Then the solvent was removed under reduced pressure, and the resulting residue was purified by flash column chromatography (silica gel, PE:EtOAc=100:1 to 5:1, v/v) to give the title compound. MS (ESI) m/z: 494.3 [M+Na]$^+$ Step B: (R or S)-tert-butyl 7'-((1R,2S)-1-cyclopropyl-3-methoxy-2-methyl-3-oxopropyl)-4'-oxospiro [azepane-4,2'-chroman]-1-carboxylate (RS)-tert-butyl 7'-((1R,2S)-1-cyclopropyl-3-methoxy-2-methyl-3-oxopropyl)-4'-oxospiro[azepane-4,2'-chroman]-1-

TABLE 13

The compound of Example 46 was prepared in a similar manner to Example 45 using the appropriate starting material and reagents.

| Example | Structure | M.W. | Compound Name | LC/MS (ESI) observed [M + H]$^+$ |
|---|---|---|---|---|
| 46 | ![structure] | 538.4 | (2S,3R)-3-cyclopropyl-3-(1'-((2,5-dichlorophenyl)sulfonyl)spiro [chroman-2,4'-piperidin]-7-yl)-2-methyl-propanoic acid | 538.0 |

Example 46

$^1$H NMR (400 MHz, CD$_3$OD) δ=8.04 (s, 1H), 7.64 (s, 2H), 6.97 (d, J=7.5 Hz, 1H), 6.65 (d, J=7.3 Hz, 1H), 6.58 (s, 1H), 3.69 (d, J=12.1 Hz, 2H), 3.25 (d, J=12.3 Hz, 2H), 2.79-2.66 (m, 3H), 1.92-1.79 (m, 5H), 1.69 (t, J=10.8 Hz, 2H), 1.05 (s, 1H), 0.88 (d, J=6.4 Hz, 3H), 0.56 (s, 1H), 0.29 (d, J=6.0 Hz, 2H), −0.05 (s, 1H)

carboxylate (1.63 g, 3.46 mmol) was separated into individual diastereoisomers via SFC (SFC separation conditions: Column: Chiralcel OJ-3 150×4.6 mm I.D., 3 um, Mobile phase: A: CO$_2$B:ethanol (0.05% DEA), Gradient: from 5% to 40% of B in 5 min and hold 40% for 2.5 min, then 5% of B for 2.5 min, Flow rate: 2.5 mL/min, Column temperature: 35° C.) to afford (R or S)-tert-butyl 7'-((1R, 2S)-1-cyclopropyl-3-methoxy-2-methyl-3-oxopropyl)-4'-oxospiro-[azepane-4,2'-chroman]-1-carboxylate, and (R or S)-tert-butyl 7'-((1R,2S)-1-cyclopropyl-3-methoxy-2-methyl-3-oxopropyl)-4'-oxospiro[azepane-4,2'-chroman]-1-carboxylate. $^1$H NMR (400 MHz, CDCl$_3$): δ=7.79 (d, J=7.8 Hz, 1H), 6.81 (d, J=8.2 Hz, 1H), 6.77 (s, 1H), 3.73 (s, 4H), 3.61-3.50 (m, 1H), 3.38-3.26 (m, 2H), 2.87-2.62 (m, 3H), 2.24-2.13 (m, 2H), 1.94 (t, J=10.0 Hz, 2H), 1.73-1.57 (m, 3H), 1.47 (s, 9H), 1.09-1.00 (m, 1H), 0.96 (d, J=6.7 Hz, 3H), 0.64-0.54 (m, 1H), 0.40-0.22 (m, 2H), 0.05-0.04 (m, 1H).

Step C: (2' R or S)-tert-butyl 7'-((1R,2S)-1-cyclopropyl-3-methoxy-2-methyl-3-oxopropyl)-4'-hydroxyspiro[azepane-4,2'-chroman]-1-carboxylate To a solution of (R or S)-tert-butyl 7'-((1R,2S)-1-cyclopropyl-3-methoxy-2-methyl-3-oxopropyl)-4'-oxospiro-[azepane-4,2'-chroman]-1-carboxylate (300 mg, 0.636 mmol) in MeOH (5 mL) was added NaBH$_4$ (48.3 mg, 1.27 mmol) in portions at 0° C. The reaction was stirred at 0° C. for 1 hour, then quenched with water (6 mL) at 15° C., and extracted with EtOAc (6 mL×3). The combined organic layers were washed with brine (20 mL), dried over anhydrous MgSO$_4$ and filtered. The filtrate was concentrated under reduced pressure to give the title compound, which was used directly in the next step. LCMS (ESI): m/z 496.3 [M+Na]$^+$ $^1$H NMR (400 MHz, DMSO-d$_6$): δ=7.31 (d, J=7.8 Hz, 1H), 6.73 (d, J=7.8 Hz, 1H), 6.56 (br. s., 1H), 5.32-5.26 (m, 1H), 4.66-4.58 (m, 1H), 3.63 (s, 3H), 3.48-3.39 (m, 2H), 3.30-3.13 (m, 2H), 2.81-2.71 (m, 1H), 2.16-2.04 (m, 1H), 1.98-1.48 (m, 7H), 1.45-1.35 (m, 9H), 1.07-0.97 (m, 1H), 0.82 (d, J=6.7 Hz, 3H), 0.52-0.43 (m, 1H), 0.27-0.19 (m, 1H), 0.15-0.05 (m, 1H), 0.04-0.12 (m, 1H).

Step D: (2S,3R)-methyl 3-cyclopropyl-2-methyl-3-((R or S)-spiro[azepane-4,2'-chroman]-7'-yl)propanoate To a solution of (2'R or S)-tert-butyl 7'-((1R,2S)-1-cyclopropyl-3-methoxy-2-methyl-3-oxopropyl)-4'-hydroxyspiro-[azepane-4,2'-chroman]-1-carboxylate (280 mg, 0.603 mmol) in DCM (4 mL) and TFA (1.0 mL, 13.7 mmol) was added triethylsilane (1.0 mL, 6.72 mmol) dropwise within 3 min at 0° C. The reaction was stirred for 20 min under at 0° C. Then water (4 mL) was added, then NaHCO$_3$ solid was added to adjust the mixture pH to pH=7-8, and the aqueous layer was extracted with DCM (6 mL×3). The combined organic layers were washed with water (20 mL) and brine (20 mL), dried over anhydrous MgSO$_4$ and filtered. The filtrate was concentrated under reduced pressure to give the title compound, which was used directly in the next step. LCMS (ESI): m/z 358.2 [M+H]$^+$ Step E: (2S,3R)-methyl 3-((R or S)-1-(2,5-bis(trifluoromethyl)benzyl)spiro[azepane-4,2'-chroman]-7'-yl)-3-cyclopropyl-2-methylpropanoate To a solution of (2S,3R)-methyl-3-cyclopropyl-2-methyl-3-((R or S)-spiro[azepane-4,2'-chroman]-7'-yl)-propanoate (100 mg, 0.279 mmol) and 2,5-bis(trifluoromethyl)benzyl methane-sulfonate (180 mg, 0.559 mmol) in MeCN (3 mL) were added K$_2$CO$_3$ (116 mg, 0.837 mmol) and NaI (126 mg, 0.837 mmol). The reaction was stirred for 3 hours under N$_2$ atmosphere at 85° C. The reaction mixture was filtered, and the filtrate was concentrated and purified by prep-TLC (SiO$_2$, PE:EtOAc=10:1, v/v) to give the title compound. LC-MS (ESI): m/z 584.3 [M+H]$^+$ Step F: (2S,3R)-3-((R or S)-1-(2,5-bis(trifluoromethyl)benzyl)spiro[azepane-4,2'-chroman]-7'-yl)-3-cyclopropyl-2-methylpropanoic Acid To a suspension of (2S,3R)-methyl 3-((R or S)-1-(2,5-bis(trifluoromethyl)benzyl)spiro[azepane-4,2'-chroman]-7'-yl)-3-cyclopropyl-2-methylpropanoate (60 mg, 0.103 mmol) in MeOH (1.5 mL), THF (1.5 mL) and water (1.5 mL) was added lithium hydroxide monohydrate (173 mg, 4.11 mmol). The reaction was heated to 60° C. for 20 hours, and then concentrated in vacuo to remove the solvent. Then water (6 mL) was added to the residue, citric acid was added to adjust the mixture pH to pH 6, and the mixture was extracted with EtOAc (5 mL×3). The combined organic layers were washed with brine (10 mL), dried over anhydrous MgSO$_4$ and filtered. The filtrate was concentrated under reduced pressure to give a residue, which was purified by HPLC (neu) to give the title compound. To a solution of the title compound in MeCN (0.5 mL) and water (0.5 mL) was added aqueous solution of NaOH (1.0 eq, 0.5 M), and the mixture was stirred for 1 hour at room temperature. Then the reaction mixture was lyophilized to give the sodium salt of the title compound. Preparative HPLC conditions: a MS trigger instrument fitted with a Phenomenex Gemini C18 250*21.2 mm*5 um using water and acetonitrile as the eluents, mobile phase A: water (10 mM NH$_4$HCO$_3$), mobile phase B: acetonitrile, gradient: 41-71% B, 0-12 min; 100% B, 12-14 min, flowRate: 25 mL/min. LCMS (ESI): m/z 570.2 [M+H]$^+$ $^1$H NMR (400 MHz, CD$_3$OD): δ=8.26 (s, 1H), 7.87 (d, J=8.2 Hz, 1H), 7.73 (d, J=8.2 Hz, 1H), 6.95 (d, J=7.5 Hz, 1H), 6.62 (d, J=7.7 Hz, 1H), 6.58 (s, 1H), 3.87 (s, 2H), 2.84 (dd, J=9.3, 12.6 Hz, 1H), 2.80-2.63 (m, 5H), 2.60-2.50 (m, 1H), 2.09-1.80 (m, 8H), 1.69-1.57 (m, 1H), 1.12-1.00 (m, 1H), 0.88 (d, J=6.8 Hz, 3H), 0.61-0.52 (m, 1H), 0.39-0.23 (m, 2H), 0.00-0.09 (m, 1H).

TABLE 14

The compounds of Examples 48-52 were prepared in a similar manner to Example 47 using the appropriate starting material and reagents.

| Example | Structure | M.W. | Compound Name | LC/MS (ESI) observed [M + H]$^+$ |
|---|---|---|---|---|
| 48 | 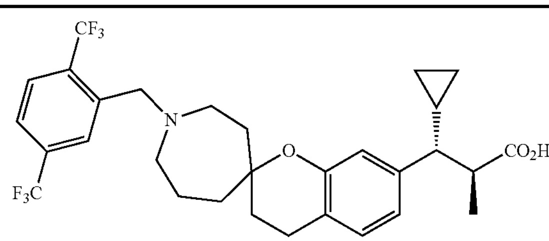 | 569.6 | sodium (2S,3R)-3-((R or S)-1-(2,5-bis (trifluoromethyl) benzyl)spiro[azepane-4,2'-chroman]-7'-yl)-3-cyclopropyl-2-methyl-propanoate | 570.2 |

TABLE 14-continued

The compounds of Examples 48-52 were prepared in a similar manner to Example 47 using the appropriate starting material and reagents.

| Example | Structure | M.W. | Compound Name | LC/MS (ESI) observed [M + H]+ |
|---|---|---|---|---|
| 49 | 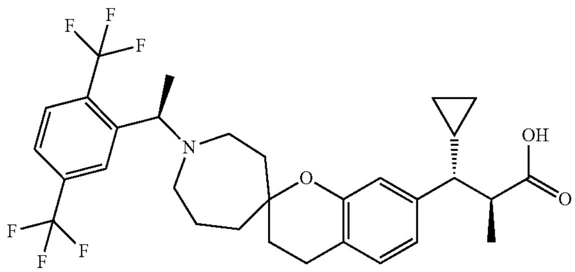 [SMILES: C[C@H](C(=O)O)[C@H](c1ccc2c(c1)OC1(CCCN([C@H](C)c3cc(C(F)(F)F)ccc3C(F)(F)F)CC1)CC2)C1CC1] | 583.60 | (2S,3R)-3-((R or S)-1-((R)-1-(2,5-bis (trifluoromethyl)phenyl) ethyl)spiro[azepane-4,2'-chroman]-7'-yl)-3-cyclopropyl-2-methylpropanoic acid | 584.2 |
| 50 | 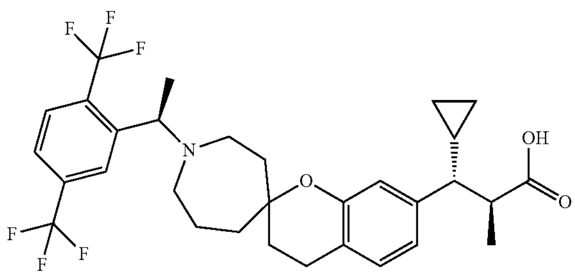 [SMILES: C[C@H](C(=O)O)[C@H](c1ccc2c(c1)OC1(CCCN([C@H](C)c3cc(C(F)(F)F)ccc3C(F)(F)F)CC1)CC2)C1CC1] | 583.60 | (2S,3R)-3-((S or R)-1-((R)-1-(2,5-bis (trifluoromethyl)phenyl) ethyl)spiro[azepane-4,2'-chroman]-7'-yl)-3-cyclopropyl-2-methylpropanoic acid | 584.2 |
| 51 | 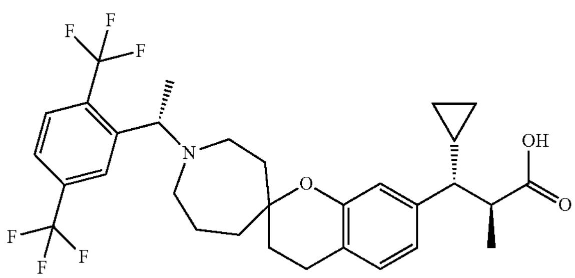 [SMILES: C[C@H](C(=O)O)[C@H](c1ccc2c(c1)OC1(CCCN([C@@H](C)c3cc(C(F)(F)F)ccc3C(F)(F)F)CC1)CC2)C1CC1] | 583.60 | (2S,3R)-3-((R or S)-1-((S)-1-(2,5-bis (trifluoromethyl)phenyl) ethyl)spiro[azepane-4,2'-chroman]-7'-yl)-3-cyclopropyl-2-methylpropanoic acid | 584.2 |
| 52 | 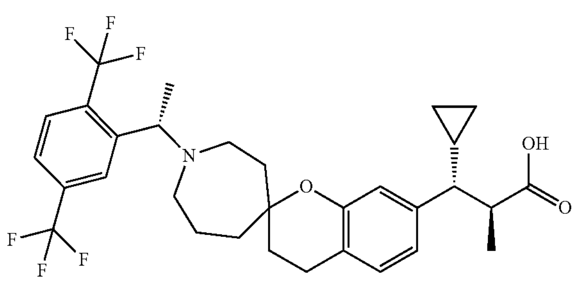 [SMILES: C[C@H](C(=O)O)[C@H](c1ccc2c(c1)OC1(CCCN([C@@H](C)c3cc(C(F)(F)F)ccc3C(F)(F)F)CC1)CC2)C1CC1] | 583.60 | (2S,3R)-3-((S or R)-1-((S)-1-(2,5-bis (trifluoromethyl)phenyl) ethyl)spiro[azepane-4,2'-chroman]-7'-yl)-3-cyclopropyl-2-methylpropanoic acid | 584.2 |

Example 48

$^1$H NMR (400 MHz, CD$_3$OD): δ=8.26 (s, 1H), 7.87 (d, J=8.2 Hz, 1H), 7.72 (d, J=7.9 Hz, 1H), 6.94 (d, J=7.5 Hz, 1H), 6.62 (d, J=7.7 Hz, 1H), 6.58 (s, 1H), 3.87 (s, 2H), 2.88-2.80 (m, 1H), 2.78-2.63 (m, 4H), 2.59-2.50 (m, 1H), 2.05-1.82 (m, 8H), 1.69-1.58 (m, 1H), 1.11-1.00 (m, 1H), 0.85 (d, J=6.6 Hz, 3H), 0.60-0.50 (m, 1H), 0.41-0.32 (m, 1H), 0.30-0.20 (m, 1H), 0.01-0.10 (m, 1H).

Example 49

1H NMR (400 MHz, CD$_3$OD): δ=8.26 (s, 1H), 7.86 (d, J=8.2 Hz, 1H), 7.72 (d, J=7.8 Hz, 1H), 6.93 (d, J=7.8 Hz, 1H), 6.60 (d, J=7.8 Hz, 1H), 6.55 (s, 1H), 4.14-4.02 (m, 1H), 3.09-2.97 (m, 1H), 2.93-2.80 (m, 1H), 2.78-2.54 (m, 4H), 2.47-2.36 (m, 1H), 2.06-1.74 (m, 7H), 1.70-1.56 (m, 2H), 1.33 (d, J=6.3 Hz, 3H), 1.12-0.99 (m, 1H), 0.87 (d, J=6.7 Hz, 3H), 0.62-0.49 (m, 1H), 0.37-0.23 (m, 2H), 0.03--0.10 (m, 1H)

Example 50

1H NMR (400 MHz, CD$_3$OD): δ=8.25 (s, 1H), 7.88 (d, J=8.2 Hz, 1H), 7.73 (d, J=8.2 Hz, 1H), 6.96 (d, J=7.7 Hz, 1H), 6.62 (d, J=7.7 Hz, 1H), 6.58 (s, 1H), 4.15-4.09 (m, 1H), 2.98-2.65 (m, 6H), 2.58-2.45 (m, 1H), 2.06-1.69 (m, 8H), 1.63-1.48 (m, 1H), 1.35 (d, J=6.4 Hz, 3H), 1.14-1.00 (m, 1H), 0.89 (d, J=6.8 Hz, 3H), 0.63-0.52 (m, 1H), 0.38-0.24 (m, 2H), 0.02--0.08 (m, 1H)

Example 51

¹H NMR (400 MHz, CD₃OD) δ=8.27 (s, 1H), 7.86 (d, J=8.2 Hz, 1H), 7.72 (d, J=8.2 Hz, 1H), 6.93 (d, J=7.7 Hz, 1H), 6.60 (d, J=7.7 Hz, 1H), 6.56 (s, 1H), 4.13-4.02 (m, 1H), 3.08-2.98 (m, 1H), 2.91-2.81 (m, 1H), 2.77-2.64 (m, 3H), 2.63-2.55 (m, 1H), 2.46-2.36 (m, 1H), 1.96 (dd, J=9.0, 12.8 Hz, 2H), 1.91-1.75 (m, 5H), 1.69-1.57 (m, 2H), 1.34 (d, J=6.4 Hz, 3H), 1.11-1.00 (m, 1H), 0.87 (d, J=6.8 Hz, 3H), 0.61-0.51 (m, 1H), 0.37-0.22 (m, 2H), 0.01--0.10 (m, 1H)

Example 52

¹H NMR (400 MHz, CD₃OD) δ=8.26 (s, 1H), 7.87 (d, J=8.2 Hz, 1H), 7.73 (d, J=8.2 Hz, 1H), 6.96 (d, J=7.7 Hz, 1H), 6.62 (d, J=7.5 Hz, 1H), 6.58 (s, 1H), 4.11 (d, J=5.5 Hz, 1H), 2.95-2.85 (m, 1H), 2.83-2.66 (m, 5H), 2.50 (t, J=8.9 Hz, 1H), 2.07-1.70 (m, 8H), 1.59-1.47 (m, 1H), 1.34 (d, J=6.4 Hz, 3H), 1.06 (br. s., 1H), 0.89 (d, J=6.4 Hz, 3H), 0.61-0.52 (m, 1H), 0.38-0.23 (m, 2H), 0.02--0.08 (m, 1H)

Example 53

(2S,3R)-3-cyclopropyl-2-methyl-3-(1'-((2-methyl-4-(trifluoromethyl)thiazol-5-yl)methyl)spiro[chroman-2,4'-piperidin]-7-yl)propanoic Acid

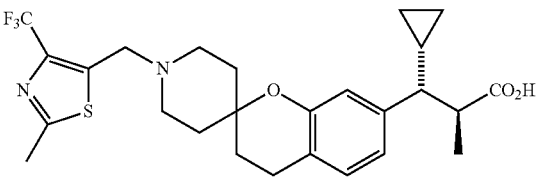 [SMILES: Cc1nc(C(F)(F)F)c(CN2CCC3(CCc4ccc([C@H](C5CC5)[C@H](C)C(=O)O)cc4O3)CC2)s1]

Step A: (2-methyl-4-(trifluoromethyl)thiazol-5-yl)methanol

To a solution of 2-methyl-4-(trifluoromethyl)thiazole-5-carboxylic acid (0.500 g, 2.37 mmol) in THF (8 mL) was added BH₃.DMS (0.474 ml, 4.74 mmol) dropwise over 3 min at 0° C. under nitrogen. The reaction was stirred at 0° C. for 0.5 h and at 20° C. for 12 h. Then the reaction was quenched slowly with MeOH (10 mL) at 0° C. The mixture was concentrated under reduced pressure to give the title compound, which was used directly in the next step without further purification. MS (ESI) m/z: 198.0 [M+H]⁺ ¹H NMR (400 MHz, DMSO-d6) δ=6.06 (br.s, 1H), 4.74 (br. s., 2H), 2.62 (s, 3H)

Step B: (2-methyl-4-(trifluoromethyl)thiazol-5-yl)methyl methanesulfonate

To a solution of (2-methyl-4-(trifluoromethyl)thiazol-5-yl)methanol (75.0 mg, 0.380 mmol) in DCM (3 mL) was added TEA (0.133 ml, 0.951 mmol). Then Ms-Cl (0.0440 mL, 0.571 mmol) was added dropwise over 1 min to the mixture at 0° C. under nitrogen. The reaction was stirred at 0° C. for 1 h. Then water (10 mL) was added to the reaction mixture at 0° C. and the mixture was extracted with DCM (5 mL×3). The combined organic layers were washed with brine (10 mL), dried over anhydrous MgSO₄ and filtered. The filtrate was concentrated in vacuo to give the title compound, which was used directly in the next step without further purification. MS (ESI) m/z: 276.0 [M+H]⁺

Step C: (2S,3R)-methyl 3-cyclopropyl-2-methyl-3-(1'-((2-methyl-4-(trifluoromethyl)-thiazol-5-yl) methyl)spiro[chroman-2,4'-piperidin]-7-yl)propanoate To a solution of (2S,3R)-methyl 3-cyclopropyl-2-methyl-3-(spiro[chroman-2,4'-piperidin]-7-yl)-propanoate (60.0 mg, 0.175 mmol) in MeCN (2 mL) were added sodium iodide (79.0 mg, 0.524 mmol), (2-methyl-4-(trifluoromethyl)thiazol-5-yl)methyl methanesulfonate (72.1 mg, 0.262 mmol) and K₂CO₃ (121 mg, 0.873 mmol) under nitrogen. The reaction was stirred at 80° C. for 12 h. Then water (10 mL) was added to the mixture and the mixture was extracted with EtOAc (10 mL×3). The combined organic layers were washed with brine (20 mL), dried over anhydrous MgSO₄ and filtered. The filtrate was concentrated in vacuo to give a residue, which was purified by prep-TLC (SiO₂, PE/EtOAc=5:1, v/v)) to give the title compound. MS (ESI) m/z: 523.2 [M+H]⁺

Step D: (2S,3R)-3-cyclopropyl-2-methyl-3-(1'-((2-methyl-4-(trifluoromethyl)-thiazol-5-yl)methyl)spiro [chroman-2,4'-piperidin]-7-yl)propanoic Acid To a solution of (2S,3R)-methyl 3-cyclopropyl-2-methyl-3-(1'-((2-methyl-4-(trifluoromethyl)-thiazol-5-yl)methyl) spiro[chroman-2,4'-piperidin]-7-yl)propanoate (63.0 mg, 0.121 mmol) in MeOH (1.5 mL), THF (1.5 mL) and water (1.5 mL) was added LiOH (87.0 mg, 3.62 mmol) under nitrogen. The reaction was stirred at 55° C. for 24 h, then concentrated in vacuo to remove the solvent. Water (15 mL) was added to the resulting residue, citric acid was added to adjust the mixture pH to pH-5, and the mixture was extracted with EtOAc (10 mL×3). The combined organic layers were washed with brine (15 mL), dried over anhydrous MgSO₄ and filtered. The filtrate was concentrated under reduced pressure to give a residue, which was purified by Prep HPLC (neutral) to give the title compound. Preparative HPLC conditions: a MS trigger instrument fitted with a Phenomenex Gemini C18 250*21.2 mm*5 um using water and acetonitrile as the eluents, mobile phase A: water (10 mM NH4HCO3)-ACN, mobile phase B: acetonitrile, gradient: 35-65% B, 0-11.0 min; 100% B, 11.1-13.0 min; 10% B, 13.1-16 min, flowRate: 25 mL/min. MS (ESI) m/z: 509.2 [M−H]⁺ ¹H NMR (400 MHz, CDCl₃) δ=6.99 (d, J=7.4 Hz, 1H), 6.71-6.61 (m, 2H), 3.83 (br. s., 2H), 2.89-2.79 (m, 1H), 2.79-2.65 (m, 7H), 2.65-2.56 (m, 2H), 1.97-1.76 (m, 5H), 1.73-1.59 (m, 2H), 1.18-1.06 (m, 1H), 1.00 (d, J=7.0 Hz, 3H), 0.68-0.58 (m, 1H), 0.44-0.32 (m, 2H), 0.12-0.00 (m, 1H)

Example 54

(2S,3R)-3-(1'-(1-(3,5-bis(trifluoromethyl)phenyl)ethyl)spiro[chroman-2,4'-piperidin]-7-yl)-3-cyclopropyl-2-methylpropanoic Acid

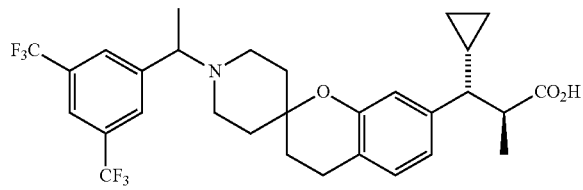 [SMILES: CC(c1cc(C(F)(F)F)cc(C(F)(F)F)c1)N1CCC2(CCc3ccc([C@H](C4CC4)[C@H](C)C(=O)O)cc3O2)CC1]

Step A: 1-(3,5-bis(trifluoromethyl)phenyl)ethanol

To a solution of 1-(3,5-bis-(trifluoromethyl)phenyl)ethanone (230 g, 0.90 mmol) in MeOH (9 mL) was added NaBH$_4$ (69.0 mg, 1.80 mmol) at 0° C. in portions. The reaction was stirred at 0° C. for 1 hour, then quenched by the addition of water (10 mL). The resulting mixture was extracted with EtOAc (10 mL×3). The combined organic layers were washed with brine (20 mL), dried (Na$_2$SO$_4$), and filtered. The filtrate was evaporated under reduced pressure to the title compound, which was used directly in the next step. $^1$H NMR (400 MHz, CDCl$_3$): δ=7.82 (s, 2H), 7.77 (s, 1H), 5.07-4.99 (m, 1H), 1.53 (d, J=6.3 Hz, 3H)

Step B: 1-(3,5-bis(trifluoromethyl)phenyl)ethyl methanesulfonate

To a solution of 3-(trifluoromethyl)pyridin-2-yl)ethanol (232 g, 0.900 mmol) in DCM (10 mL) were added MsCl (205 mg, 1.80 mmol) and Et$_3$N (182 mg, 1.80 mmol) at 20° C. The reaction was stirred at 20° C. for 2 hours, quenched by the addition of water (10 mL), and the mixture extracted with EtOAc (10 mL×3). The combined organic layers were washed with brine (20 mL), dried (Na$_2$SO$_4$), and filtered. The filtrate was evaporated under reduced pressure to give the title compound, which was used directly in the next step.

Step C: (2S3R)-methyl-3-(1'-(1-(3,5-bis(trifluoromethyl)phenyl)ethyl)spiro-[chroman-2,4'-piperidin]-7-yl)-3-cyclopropyl-2-methylpropanoate To a solution of 1-(3,5-bis(trifluoromethyl)phenyl)ethyl methanesulfonate (274 mg, 0.82 mmol) in MeCN (10 mL) were added (2S,3R)-methyl 3-cyclopropyl-2-methyl-3-(spiro-[chroman-2,4'-piperidin]-7-yl)propanoate (206 mg, 0.600 mmol), K$_2$CO$_3$ (414 mg, 3.00 mmol) and NaI (268 mg, 1.8 mmol). The reaction was stirred at 85° C. for 3 hours, then poured into water (10 mL), and extracted with EtOAc (10 mL×3). The combined organic layers were washed with brine (saturated 20 mL), dried over Na$_2$SO$_4$, and filtered. The filtrate was concentrated under reduced pressure to give a residue, which was purified by TLC (SiO$_2$, PE/EA=5:1, v/v) to give the title compound. MS (ESI) m/z: 584.2[M+H]$^+$

Step C: (2S,3R)-3-(1'-(1-(3,5-bis(trifluoromethyl)phenyl)ethyl)spiro[chroman-2,4'-piperidin]-7-yl)-3-cyclopropyl-2-methylpropanoic Acid To a solution of (2S,3R)-methyl 3-(1'-(1-(3,5-bis(trifluoromethyl)phenyl)ethyl)spiro[chroman-2,4'-piperidin]-7-yl)-3-cyclopropyl-2-methylpropanoate (201 mg, 0.345 mmol) in CH$_3$OH (2 mL), THF (2 mL), and H$_2$O (2 mL) was added LiOH (571 mg, 13.6 mmol). The reaction was stirred at 55° C. for 12 hours, then poured into water (10 mL). Citric acid was added to adjust the mixture pH to pH 7, and the mixture was extracted with EtOAc (10 mL×3). The combined organic layers were washed with brine (saturated, 20 mL), dried over Na$_2$SO$_4$ and filtered. The filtrate was concentrated under reduced pressure to give the crude product, which was purified by preparative HPLC to give the title compound. To a solution of the title compound in MeCN (1 mL) and water (1 mL) was added the solution of aqueous NaOH (1.0 eq, 0.5 M), and the mixture was stirred for 1 h at room temperature. Then the reaction mixture was lyophilized to give the sodium salt of the title compound. Preparative HPLC Conditions: Instrument: ee, Column: YMC-Actus Pro C18 150*30 5u, Condition: water (0.1% TFA)-ACN, Begin B: 28 100% B Hold Time (min): 1.1, FlowRate: 40 (ml/min). MS (ESI) m/z: 570.2[M+H]$^+$ $^1$H NMR (400 MHz, CD$_3$OD): δ=8.31 (s, 2H), 8.24 (s, 1H), 7.09 (d, J=7.7 Hz, 1H), 6.78 (d, J=7.5 Hz, 1H), 6.70 (s, 1H), 3.81 (br. s., 1H), 3.48-3.39 (m, 2H), 3.27 (br. s., 1H), 2.87 (t, J=6.5 Hz, 2H), 2.83-2.73 (m, 1H), 2.42-1.80 (m, 11H), 1.19-1.07 (m, 1H), 0.96 (d, J=6.8 Hz, 3H), 0.71-0.61 (m, 1H), 0.45-0.29 (m, 2H), 0.07--0.03 (m, 1H)

Example 55

(2S,3R)-3-(1'-(5-chloro-2-methoxypyridin-4-yl)spiro[chroman-2,4'-piperidin]-7-yl)-3-cyclopropyl-2-methylpropanoic Acid

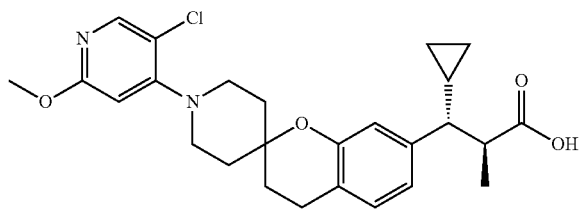 [SMILES: COc1cc(N2CCC3(CCc4ccc([C@H](C5CC5)[C@H](C)C(=O)O)cc4O3)CC2)c(Cl)cn1]

Step A: 4,5-dichloro-2-methoxypyridine

To a suspension of 4,5-dichloropyridin-2-ol (300 mg, 1.83 mmol), and silver carbonate (504 mg, 1.83 mmol) in CHCl$_3$ (4 mL) was added iodomethane (0.229 mL, 3.66 mmol). The reaction was stirred for 16 h at 55° C. under N$_2$ atmosphere. Then the reaction mixture was filtered and the filtrate was concentrated in vacuo to give a residue, which was purified by prep-TLC (SiO$_2$, PE:EtOAc=1:1, v/v) to afford the title compound. $^1$H NMR (400 MHz, CD$_3$OD) δ=8.21 (s, 1H), 7.00 (s, 1H), 3.90 (s, 3H)

Step B: (2S,3R)-methyl 3-(1'-(5-chloro-2-methoxypyridin-4-yl)spiro[chroman-2,4'-piperidin]-7-yl)-3-cyclopropyl-2-methylpropanoate To a solution of (2S,3R)-methyl 3-cyclopropyl-2-methyl-3-(spiro[chroman-2,4'-piperidin]-7-yl)propanoate (386 mg, 1.12 mmol) and 4,5-dichloro-2-methoxypyridine (100 mg, 0.562 mmol) in NMP (4 mL) was added TEA (0.235 mL, 1.69 mmol). The reaction was stirred for 16 h at 140° C. under N$_2$ atmosphere. Then water (20 mL) was added, and the mixture was extracted with EtOAc (15 mL×3). The combined organic layers were washed with brine (30 mL), dried over anhydrous Na$_2$SO$_4$ and filtered. The filtrate was evaporated under reduced pressure to give a residue, which was purified by Prep-TLC (SiO$_2$, PE:EA=1:1, v/v) to give the title compound. LCMS (ESI) m/z: 507.2 [M+Na]$^+$ Step C: (2S,3R)-3-(1'-(5-chloro-2-methoxypyridin-4-yl)spiro[chroman-2,4'-piperidin]-7-yl)-3-cyclopropyl-2-methylpropanoic Acid To a solution of (2S,3R)-methyl 3-(1'-(5-chloro-2-methoxypyridin-4-yl)spiro[chroman-2,4'-piperidin]-7-yl)-3-cyclopropyl-2-methylpropanoate (135 mg, 0.278 mmol) in MeOH (1.5 mL), THF (1.5 mL) and water (1.5 mL) was added lithium hydroxide (6.67 mg, 0.278 mmol) under N$_2$ atmosphere. The reaction was stirred for 16 hours at 55° C. Then water (10 mL) was added to the mixture, the pH of the mixture was adjusted with citric acid to pH 6-7, and the mixture was extracted with EtOAc (10 mL×3). The combined organic layers were washed with brine (15 mL), dried over anhydrous Na$_2$SO$_4$ and filtered. The filtrate was evaporated under reduced pressure to give a residue, which was purified by preparative—HPLC (neutral) to give the title compound. LCMS (ESI) m/z: 471.2 [M+H]$^+$ $^1$H NMR (400 MHz, CD$_3$OD) δ=7.90 (s, 1H), 6.98 (d, J=7.4 Hz, 1H), 6.69-6.59 (m, 2H), 6.40 (s, 1H), 3.84 (s, 3H), 3.39 (d, J=11.3 Hz, 2H), 3.16 (t, J=11.2 Hz, 2H), 2.84-2.66 (m, 3H), 1.98-1.77 (m, 7H), 1.13-1.00 (m, 1H), 0.89 (d, J=6.7 Hz, 3H), 0.61-0.50 (m, 1H), 0.37-0.21 (m, 2H), 0.02--0.10 (m, 1H)

Example 56 sodium (2S3R)-3-cyclopropyl-2-methyl-3-(1'-(2-(trifluoromethyl)pyrimidin-4-yl)spiro[chroman-2,4'-piperidin]-7-yl)propanoate

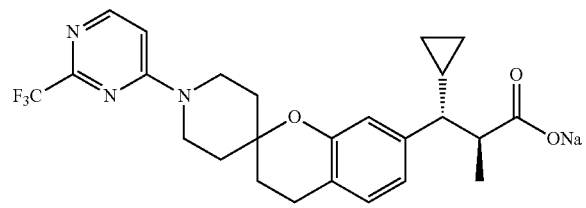

Step A: 4-bromo-2-(trifluoromethyl)pyrimidine

A mixture of 2-(trifluoromethyl)-pyrimidin-4-ol (200 mg, 1.22 mmol) and phosphoryl tribromide (419 mg, 1.46 mmol) was heated at 120° C. for 5.5 h. Then water (10 mL) was added and the mixture was extracted with EtOAc (20 mL×3). The combined organic layers were dried over sodium sulfate, and then filtered. The filtrate was concentrated in vacuo to give the crude product, which was purified by TLC (SiO$_2$, petroleum ether:ethyl acetate=10:1, v/v) to give the title compound. MS (ESI) m/z: 226.9 [M+H]$^+$ $^1$H NMR (400 MHz, CDCl$_3$ δ=8.65 (d, J=5.1 Hz, 1H), 7.72 (d, J=5.1 Hz, 1H).

Step B: (2S,3R)-methyl 3-cyclopropyl-2-methyl-3-(1'-(2-(trifluoromethyl)pyrimidin-4-yl)spiro[chroman-2,4'-piperidin]-7-yl)propanoate To a solution of (2S,3R)-methyl 3-cyclopropyl-2-methyl-3-(spiro[chroman-2,4'-piperidin]-7-yl)propanoate (80.0 mg, 0.233 mmol), 4-bromo-2-(trifluoromethyl)pyrimidine (106 mg, 0.466 mmol), Cs$_2$CO$_3$ (152 mg, 0.466 mmol) in toluene (5 ml) and t-BuOH (1 ml) was added chloro-(2-dicyclohexylphosphino-2',4',6'-tri-i-propyl-1,1'-biphenyl)(2'-amino-1,1'-biphenyl-2-yl) palladium(ii) (18.3 mg, 23.0 umol) under N$_2$. The reaction was stirred at 120° C. for 12 hours under N$_2$. Then water (10 mL) was added and the mixture was extracted with EtOAc (20 mL×3). The combined organic layer was dried over sodium sulfate and then filtered. The filtrate was concentrated in vacuo to give the crude product, which was purified by TLC (SiO$_2$, petroleum ether:ethyl acetate=3:1) to give the title compound. MS (ESI) m/z: 490.1 [M+H]$^+$ Step C: sodium (2S,3R)-3-cyclopropyl-2-methyl-3-(1'-(2-(trifluoromethyl)pyrimidin-4-yl)spiro[chroman-2,4'-piperidin]-7-yl)propanoate To a solution of (2S,3R)-methyl 3-cyclopropyl-2-methyl-3-(1'-(2-(trifluoromethyl)pyrimidin-4-yl)spiro[chroman-2,4'-piperidin]-7-yl)propanoate (70.0 mg, 0.143 mmol) in a co-solvent of THF (2 ml), water (2 ml) and MeOH (2 ml) was added LiOH (171 mg, 7.15 mmol). The reaction was stirred at 50° C. for 12 hours under N$_2$, and then poured into water (2 mL). Citric acid was added to adjust the mixture pH to pH 7, and the mixture was extracted with EtOAc (5 mL×3). The combined organic layers were washed with brine (2 mL×3), dried over Na$_2$SO$_4$, and filtered. The filtrate was evaporated under reduced pressure to give a residue, which was purified with Prep-HPLC (base) to give the title compound. To a solution of the title compound in MeCN (1 mL) and water (1 mL) was added an aqueous NaOH solution (1.0 eq, 0.5 M), and the mixture was stirred for 1 h at room temperature. Then the reaction mixture was lyophilized to give the sodium salt of the title compound. Preparative HPLC conditions: a MS trigger instrument fitted with a Waters Xbridge Prep OBD C18 150*30 5u using water (0.05% ammonia hydroxide v/v)-ACN as the eluents, mobile phase A: water (0.05% ammonia hydroxide v/v), mobile phase B: acetonitrile, Gradient: 24-54% B, 2.0-10.0 min, FlowRate: 25 mL/min. MS (ESI) m/z: 474.1 [M+H]$^+$ $_1$H NMR (400 MHz, CD$_3$OD): δ=8.25 (d, J=6.4 Hz, 1H), 7.05 (d, J=8.2 Hz, 1H), 6.98 (d, J=6.4 Hz, 1H), 6.75-6.70 (m, 2H), 4.40 (br. s., 2H), 3.54 (t, J=11.7 Hz, 2H), 2.87-2.73 (m, 3H), 2.03-1.85 (m, 5H), 1.78-1.66 (m, 2H), 1.18-1.08 (m, 1H), 0.95 (d, J=6.8 Hz, 3H), 0.67-0.57 (m, 1H), 0.42-0.29 (m, 2H), 0.06--0.05 (m, 1H)

Example 57

(2S,3R)-3-cyclopropyl-3-(1'-((R or S)-1-(5-cyclopropyl-2-(trifluoromethyl)phenyl)-ethyl)-spiro[chroman-2,4'-piperidin]-7-yl)-2-methylpropanoic Acid

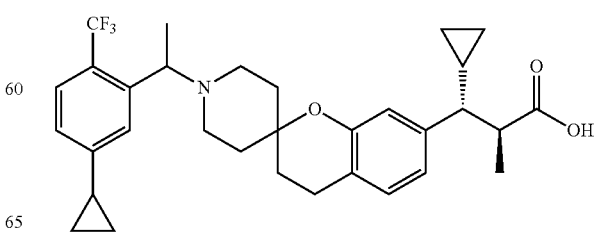

Step A: (2S,3R)-methyl 3-(1'-(1-(5-chloro-2-(trifluoromethyl)phenyl)ethyl)spiro-[chroman-2,4'-piperidin]-7-yl)-3-cyclopropyl-2-methylpropanoate A suspension of (2S,3R)-methyl 3-cyclopropyl-2-methyl-3-(spiro[chroman-2,4'-piperidin]-7-yl)-propanoate (100 mg, 0.291 mmol), 1-(5-chloro-2-(trifluoromethyl)phenyl)ethyl methanesulfonate (106 mg, 0.349 mmol), K₂CO₃ (121 mg, 0.873 mmol) and sodium iodide (87.0 mg, 0.582 mmol) in acetonitrile (2 mL) was heated to 85° C. for 18 h. Then the reaction mixture was cooled to room temperature, diluted with water (10 mL) and extracted with EtOAc (10 mL×3). The combined organic layers were washed with brine (10 mL), dried over Na₂SO₄ and filtered. The filtrate was concentrated by rotary evaporator to give a residue, which was purified by preparative TLC (silica gel, PE:EtOAc=5:1, v/v) to give the title compound. MS (ESI): m/z 550.1 [M+H]⁺

Step B: (2S,3R)-methyl 3-cyclopropyl-3-(1'-(1-(5-cyclopropyl-2-(trifluoromethyl)-phenyl)-ethyl)spiro [chroman-2,4'-piperidin]-7-yl)-2-methylpropanoate A flask containing (2S,3R)-methyl 3-(1'-(1-(5-chloro-2-(trifluoromethyl)phenyl)ethyl)spiro-[chroman-2,4'-piperidin]-7-yl)-3-cyclopropyl-2-methylpropanoate (132 mg, 0.240 mmol), cyclopropylboronic acid (41.2 mg, 0.480 mmol), 2-dicyclohexylphosphino-2',6'-dimethoxybiphenyl (9.85 mg, 24.0 μmol) and palladium(II) acetate (2.69 mg, 12.0 μmol) was evacuated and backfilled with nitrogen three times. To the flask was added dioxane (2.5 mL). The reaction was stirred at 20° C. under a nitrogen atmosphere for 1 h. Then tripotassium phosphate (204 mg, 0.960 mmol) and water (0.250 mL) were added. The reaction mixture was heated to 85° C. for 8 h, then diluted with water (3 mL) and extracted with EtOAc (5 mL×3). The combined organic layers were washed with brine (5 mL), dried over Na₂SO₄ and filtered. The filtrate was concentrated by rotary evaporator to give a residue, which was purified by preparative TLC (silica gel, PE:EtOAc=5:1, v/v) to give the title compound. MS (ESI): m/z 556.7 [M+H]⁺

Step C: (2S,3R)-3-cyclopropyl-3-(1'-(1-(5-cyclopropyl-2-(trifluoromethyl)phenyl)-ethyl)spiro[chroman-2,4'-piperidin]-7-yl)-2-methylpropanoic Acid To a solution of (2S,3R)-methyl-3-cyclopropyl-3-(1'-(1-(5-cyclopropyl-2-(trifluoromethyl)-phenyl)-ethyl)spiro [chroman-2,4'-piperidin]-7-yl)-2-methylpropanoate (128 mg, 0.230 mmol) in MeOH, THF and water was added lithium hydroxide monohydrate (145 mg, 3.46 mmol). The reaction was heated to 55° C. for 12 hours, then cooled to room temperature and neutralized to pH 7 with concentrated HCl. The solvents were removed by rotary evaporator, and the resulting residue was dissolved in MeCN and DMSO, and filtered. The filtrate was purified by preparative HPLC to give the title compound. The title compound was treated with 1 equivalent of aqueous NaOH (10 wt %) and lyophilized to give the corresponding sodium salt of the title compound. Preparative HPLC conditions: Column: Waters XSELECT C18 150*30 mm*5 um; Condition: water (0.1% TFA)-ACN; Begin B: 30; End B: 60; Gradient Time (min): 10; 100% B Hold Time (min): 2; FlowRate (mL/min): 25; Injections: 9. MS (ESI): m/z 542.1 [M+H]⁺

Step D: (2S,3R)-3-cyclopropyl-3-(1'-((R or S)-1-(5-cyclopropyl-2-(trifluoromethyl)-phenyl)ethyl)-spiro [chroman-2,4'-piperidin]-7-yl)-2-methylpropanoic Acid and (2S,3R)-3-cyclopropyl-3-(1'-((S or R)-1-(5-cyclopropyl-2-(trifluoromethyl)phenyl)-ethyl)-spiro[chroman-2,4'-piperidin]-7-yl)-2-methylpropanoic Acid (2S,3R)-methyl 3-cyclopropyl-3-(1'-(1-(5-cyclopropyl-2-(trifluoromethyl)phenyl)ethyl)spiro [chroman-2,4'-piperidin]-7-yl)-2-methylpropanoate (128 mg, 0.230 mmol) was separated into individual diastereoisomers via SFC (SFC conditions: Column: C2 250 mm*30 mm, 10 um; Condition: Base-MeOH; Begin B: 20%; End B: 20%; FlowRate (mL/min): 60; Injections: 170) to give (2S,3R)-3-cyclopropyl-3-(1'-((R or S)-1-(5-cyclopropyl-2-(trifluoromethyl)phenyl) ethyl)-spiro[chroman-2,4'-piperidin]-7-yl)-2-methylpropanoic acid, and (2S,3R)-3-cyclopropyl-3-(1'-((S or R)-1-(5-cyclopropyl-2-(trifluoromethyl)-phenyl)ethyl)-spiro[chroman-2,4'-piperidin]-7-yl)-2-methylpropanoic acid. The diastereoisomers of the title compound were individually treated with 1 equivalent of aqueous NaOH (10 wt %) and lyophilizated to give the corresponding sodium salt of the title compound. MS (ESI): m/z 542.2[M+H]⁺ ¹H NMR (400 MHz, CD₃OD): δ=7.62 (s, 1H), 7.53 (d, J=8.2 Hz, 1H), 7.09 (d, J=8.2 Hz, 1H), 6.95 (d, J=7.5 Hz, 1H), 6.67-6.59 (m, 2H), 3.91-3.81 (m, 1H), 3.21-3.11 (m, 1H), 2.81-2.68 (m, 3H), 2.66-2.42 (m, 3H), 2.05-1.70 (m, 7H), 1.69-1.57 (m, 1H), 1.40 (d, J=6.4 Hz, 3H), 1.15-1.01 (m, 3H), 0.89 (d, J=6.6 Hz, 3H), 0.82-0.75 (m, 2H), 0.63-0.52 (m, 1H), 0.39-0.24 (m, 2H), 0.02--0.09 (m, 1H)

TABLE 15

The compound of Example 58 was prepared in a similar manner to Example 57 using the appropriate starting material and reagents.

| Example | Structure | M.W. | Compound Name | LC/MS (ESI) observed [M + H]⁺ [M − H]⁺ |
|---|---|---|---|---|
| 58 | 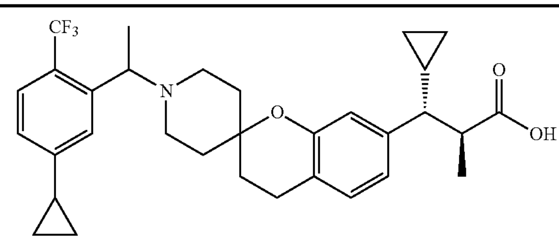 | 541.6 | (2S,3R)-3-cyclopropyl-3-(1'-((S or R)-1-(5-cyclopropyl-2-(trifluoromethyl)-phenyl)ethyl)-spiro[chroman-2,4'-piperidin]-7-yl)-2-methylpropanoic acid | 542.3 |

Example 58

$^1$H NMR (400 MHz, CD$_3$OD): δ=7.61 (s, 1H), 7.54 (d, J=8.4 Hz, 1H), 7.11 (d, J=8.2 Hz, 1H), 6.97 (d, J=7.5 Hz, 1H), 6.68-6.60 (m, 2H), 3.98-3.85 (m, 1H), 3.26-3.15 (m, 1H), 2.83-2.45 (m, 6H), 2.05-1.72 (m, 7H), 1.69-1.58 (m, 1H), 1.42 (d, J=6.4 Hz, 3H), 1.08 (d, J=6.6 Hz, 3H), 0.90 (d, J=6.6 Hz, 3H), 0.82-0.76 (m, 2H), 0.63-0.53 (m, 1H), 0.38-0.23 (m, 2H), 0.02--0.08 (m, 1H)

Example 59

(2S,3R)-3-(1'-(2,5-bis(trifluoromethyl)phenyl)spiro [chroman-2,4'-piperidin]-7-yl)-3-cyclopropyl-2-methylpropanoic Acid

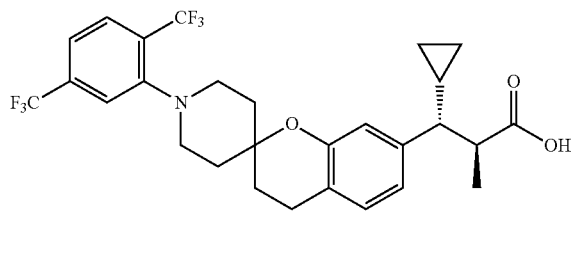 [SMILES: C[C@H](C(=O)O)[C@H](c1ccc2c(c1)OC1(CC2)CCN(c2cc(C(F)(F)F)ccc2C(F)(F)F)CC1)C1CC1]

Step: A: (2S,3R)-methyl 3-(1'-(2,5-bis(trifluoromethyl)phenyl)spiro[chroman-2,4'-piperidin]-7-yl)-3-cyclopropyl-2-methylpropanoate To a solution of (2S,3R)-methyl 3-cyclopropyl-2-methyl-3-(spiro[chroman-2,4'-piperidin]-7-yl)propanoate (176 mg, 0.512 mmol) and 2-bromo-1,4-bis(trifluoromethyl)benzene (100 mg, 0.341 mmol) in 1,4-dioxane (3 mL) were added Cs$_2$CO$_3$ (334 mg, 1.02 mmol) and chloro(2-di-cyclohexylphosphino-2',6'-dimethoxy-1,1'-biphenyl)[2-(2-aminoethylphenyl)]palladium(II) methyl-t-butyl ether adduct (51.9 mg, 0.068 mmol) at 15° C. The reaction mixture was stirred at 110° C. for 15 h, then filtered and purified by column chromatography (silica gel, PE:EtOAc=8:1, v/v) to afford the title compound. MS (ESI) m/z: 556.3[M+H]$^+$ Step: B: (2S,3R)-3-(1'-(2,5-bis(trifluoromethyl)phenyl)spiro[chroman-2,4'-piperidin]-7-yl)-3-cyclopropyl-2-methylpropanoic Acid To a solution of (2S,3R)-methyl-3-(1'-(2,5-bis(trifluoromethyl)phenyl)spiro[chroman-2,4'-piperidin]-7-yl)-3-cyclopropyl-2-methylpropanoate (80.0 mg, 0.096 mmol) in MeOH (2 mL), THF (2 mL) and water (2 mL) was added (2S,3R)-methyl 3-(1'-(2,5-bis(trifluoromethyl)phenyl)spiro[chroman-2,4'-piperidin]-7-yl)-3-cyclopropyl-2-methylpropanoate (80.0 mg, 0.096 mmol) at room temperature. The reaction was stirred for 20 h at 50° C. Then the reaction mixture was adjusted to pH 6 by citric acid, and EtOAc (5 mL) was added. The organic layer was separated. The aqueous layer was extracted with EtOAc (3 mL×3). The combined organic layers were dried over anhydrous sodium sulfate, and filtered. The filtrate was concentrated under reduced pressure to afford the crude product, which was purified by preparative-HPLC (Preparative HPLC Conditions: a MS trigger instrument fitted with a Phenomenex Gemini YMC-Actus Pro C18 150*30 5u using water and acetonitrile as the eluents, mobile phase A: water (0.1% TFA); mobile phase B: acetonitrile; Gradient: Begin B 25 End B 55 Gradient Time (min) 11 100% B Hold Time (min) 1.1; FlowRate: 40 mL/min) and lyophilized to afford the crude product (NMR Showed racemization), which was separated by SFC to afford the title compound. To a solution of the title compound (30.0 mg) in MeCN (1 mL) and water (1 mL) was added an aqueous solution of NaOH (1.0 eq, 0.5 M), and the mixture was stirred for 1 hour at room temperature. Then the reaction mixture was lyophilized to give the sodium salt of the title compound. MS (ESI): m/z 542.2 [M+H]$^+$ $^1$H NMR (400 MHz, CDCl$_3$): δ=7.75 (d, J=8.2 Hz, 1H), 7.66 (s, 1H), 7.45 (d, J=8.2 Hz, 1H), 7.00 (d, J=7.8 Hz, 1H), 6.75 (s, 1H), 6.67 (d, J=6.7 Hz, 1H), 3.20 (t, J=11.2 Hz, 2H), 2.94 (d, J=11.0 Hz, 2H), 2.88-2.73 (m, 3H), 2.01-1.77 (m, 7H), 1.20-1.08 (m, 1H), 1.01 (d, J=6.7 Hz, 3H), 0.68-0.58 (m, 1H), 0.37 (t, J=5.7 Hz, 2H), 0.12-0.02 (m, 1H).

Example 60

(2S,3R)-3-(1'-(5-cyano-2-(trifluoromethyl) benzyl) spiro[chroman-2,4'-piperidin]-7-yl)-3-cyclopropyl-2-methylpropanoic Acid

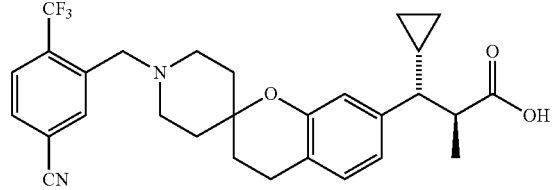 [SMILES: C[C@H](C(=O)O)[C@H](c1ccc2c(c1)OC1(CC2)CCN(Cc2cc(C#N)ccc2C(F)(F)F)CC1)C1CC1]

Step A: (5-chloro-2-(trifluoromethyl)phenyl)methanol

To a solution of 5-chloro-2-(trifluoromethyl)benzaldehyde (500 mg, 2.40 mmol) in MeOH (5 mL) was added NaBH$_4$ (182 mg, 4.80 mmol) at 0° C. The reaction was stirred at 25° C. for 1 hour, then quenched with water (3 mL) and extracted with EtOAc (5 mL×3). The combined organic layers were washed with brine (saturated, 5 mL), dried over MgSO$_4$ and filtered. The filtrate was concentrated under reduced pressure to give the title compound, which was used in the next step without purification. $^1$H NMR (400 MHz, CDCl$_3$): δ=7.77 (s, 1H), 7.58 (d, J=8.2 Hz, 1H), 7.37 (d, J=8.2 Hz, 1H), 4.89 (s, 2H)

Step B: 5-chloro-2-(trifluoromethyl)benzyl methanesulfonate

To a solution of (5-chloro-2-(trifluoromethyl)phenyl) methanol (400 mg, 1.90 mmol) and triethylamine (0.794 mL, 5.70 mmol) in DCM (8 mL) was added methanesulfonyl chloride (0.148 mL, 1.90 mmol) at 0° C. The reaction was stirred for 1 hour at 0° C., then quenched with water (10 mL) and extracted with DCM (10 mL×3). The combined organic layers were washed with brine (saturated, 10 mL), dried over MgSO$_4$ and filtered. The filtrate was concentrated under reduced pressure to give the title compound, which was used in the next step without purification.

Step C: (2S,3R)-methyl 3-(1'-(5-chloro-2-(trifluoromethyl)benzyl)spiro[chroman-2,4'-piperidin]-7-yl)-3-cyclopropyl-2-methylpropanoate To a solution of (2S,3R)-methyl 3-cyclopropyl-2-methyl-3-(spiro[chroman-2,4'-piperidin]-7-yl)propanoate (300 mg, 0.873 mmol), potassium carbonate (362 mg, 2.62 mmol) and sodium iodide (393 mg, 2.62 mmol) in MeCN (10 mL) was added 5-chloro-2-(trifluoromethyl)-benzyl methanesulfonate (378 mg, 1.31 mmol) at room temperature. The reaction was stirred at 85° C. for 2 hours, then quenched with water (10 mL) and extracted with EtOAc (10 mL×3). The combined organic layers were washed with brine (saturated, 10 mL), dried over MgSO$_4$ and filtered. The filtrate was concentrated under reduced pressure to give the crude product, which was purified by prep-TLC (SiO$_2$, PE:E-tOAc=10:1, v/v) to give the title compound.

MS (ESI)$_m$/z: 536.2[M+H]$^+$

Step D: (2S,3R)-methyl 3-(1'-(5-cyano-2-(trifluoromethyl)benzyl)spiro[chroman-2,4'-piperidin]-7-yl)-3-cyclopropyl-2-methylpropanoate To a solution of (2S,3R)-methyl 3-(1'-(5-chloro-2-(trifluoromethyl)benzyl)spiro[chroman-2,4'-piperidin]-7-yl)-3-cyclopropyl-2-methylpropanoate (250 mg, 0.466 mmol) and potassium hexacyanoferrate(II) trihydrate (985 mg, 2.33 mmol) in water (4 mL) and 1,4-dioxane (16 mL) were added dicyclohexyl(2',4',6'-triisopropyl-[1,1'-biphenyl]-2-yl)phosphine (44.5 mg, 0.0930 mmol) diacetoxypalladium (20.9 mg, 0.0930 mmol) and potassium carbonate (193 mg, 1.40 mmol) at room temperature. The reaction was stirred at 100° C. for 3 hours, then quenched with water (20 mL) and extracted with EtOAc (25 mL×3). The combined organic layers were washed with brine (saturated, 20 mL), dried over MgSO$_4$ and filtered. The filtrate was concentrated under reduced pressure to give the crude product, which was purified with prep-TLC (SiO$_2$, PE:EtOAc=5:1, v/v) to give the title compound. MS (ESI) m/z: 527.2[M+H]$^+$ Step E: (2S,3R)-3-(1'-(5-carbamoyl-2-(trifluoromethyl)benzyl)spiro[chroman-2,4'-piperidin]-7-yl)-3-cyclopropyl-2-methylpropanoic Acid To a solution of (2S,3R)-methyl 3-(1'-(5-cyano-2-(trifluoromethyl)benzyl)spiro [chroman-2,4'-piperidin]-7-yl)-3-cyclopropyl-2-methylpropanoate (190 mg, 0.361 mmol) in THF (10 mL) was added potassium trimethylsilanolate (926 mg, 7.22 mmol) at room temperature. The reaction was stirred at 60° C. for 3 hours, then quenched with water (10 mL), acidified with citric acid to pH 5 and extracted with EtOAc (10 mL×3). The combined organic layers were washed with brine (saturated, 10 mL), dried over MgSO$_4$ and filtered. The filtrate was concentrated under reduced pressure to give the title compound, which was used in the next step without purification. MS (ESI) m/z: 531.2[M+H]$^+$ Step F: (2S,3R)-3-(1'-(5-cyano-2-(trifluoromethyl)benzyl)spiro[chroman-2,4'-piperidin]-7-yl)-3-cyclopropyl-2-methylpropanoic Acid To a solution of (2S,3R)-3-(1'-(5-carbamoyl-2-(trifluoromethyl)benzyl)spiro[chroman-2,4'-piperidin]-7-yl)-3-cyclopropyl-2-methylpropanoic acid (200 mg, 0.377 mmol) in DCM (10 mL) were added triethylamine (0.525 mL, 3.77 mmol) and 2,2,2-trifluoroacetic anhydride (0.266 mL, 1.89 mmol) at 0° C. under a N$_2$ atmosphere. The reaction was stirred at 0° C. for 1 hour, then quenched with water (10 mL) and extracted with DCM (10 mL×3). The combined organic layers were washed with brine (saturated, 10 mL), dried over MgSO$_4$ and filtered. The filtrate was concentrated under reduced pressure to give the crude product, which was purified with preparative-HPLC (Neutral) to give the title compound. Preparative HPLC conditions: a MS trigger instrument fitted with a Phenomenex Gemini C18 250*21.2 mm*5 um using water and acetonitrile as the eluents, mobile phase A: water (10 mM NH4HCO3)-ACN, mobile phase B: acetonitrile, Gradient: 36-66% B, 0-12.0 min; 100% B, 12.0-14.0 min; 10% B, 13.1-16 min, FlowRate: 25 mL/min. MS (ESI) m/z: 513.3[M+H]$^+$ $^1$H NMR (400 MHz, CD$_3$OD): δ=8.25 (s, 1H), 7.90-7.76 (m, 2H), 6.97 (d, J=7.7 Hz, 1H), 6.68-6.60 (m, 2H), 3.76 (s, 2H), 2.81-2.69 (m, 3H), 2.68-2.53 (m, 4H), 1.88-1.73 (m, 6H), 1.40-1.21 (m, 1H), 1.14-1.04 (m, 1H), 0.90 (d, J=6.8 Hz, 3H), 0.64-0.52 (m, 1H), 0.41-0.22 (m, 2H), 0.04--0.08 (m, 1H)

Example 61 sodium (2S3R)-3-(1'-((5-chloro-2,2-dimethyl-2,3-dihydrobenzofuran-7-yl)methyl)-spiro[chroman-2,4'-piperidin]-7-yl)-3-cyclopropyl-2-methylpropanoate

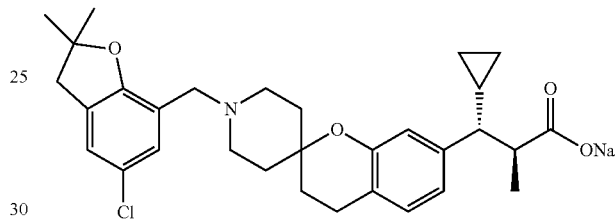

Step A: methyl 5-chloro-2-((2-methylallyl)oxy)benzoate

To a solution of 3-bromo-2-methylprop-1-ene (716 mg, 5.31 mmol) and methyl 5-chloro-2-hydroxybenzoate (900 mg, 4.82 mmol) in DMF (20 ml) was added Cs$_2$CO$_3$ (1.57 g, 4.82 mmol). The reaction was stirred at 80° C. for 12 h, then cooled to room temperature, poured into water, and extracted with ethyl acetate (20 mL×3). The combined extracts were washed with brine, dried over sodium sulfate and concentrated to give the crude product, which was purified by flash chromatography (SiO$_2$, petroleum ether:ethyl acetate=20:1, v/v) to give the title compound. $^1$H NMR (400 MHz, CDCl$_3$ δ=7.76 (d, J=2.7 Hz, 1H), 7.36 (dd, J=2.7, 9.0 Hz, 1H), 6.87 (d, J=9.0 Hz, 1H), 5.15 (s, 1H), 4.99 (br. s., 1H), 4.46 (s, 2H), 3.87 (s, 3H), 1.80 (br. s., 3H)

Step B: methyl 5-chloro-2-hydroxy-3-(2-methylallyl)benzoate

Methyl 5-chloro-2-((2-methylallyl)oxy)benzoate (250 mg, 1.04 mmol) was dissolved in NMP (2 ml). The reaction vessel was sealed and the reaction was heated in a microwave at 200° C. for 30 minutes. Then the reaction was cooled to room temperature, water (10 mL) was added, and the mixture was extracted with ethyl acetate (20 mL×3). The combined extracts were dried over sodium sulfate, concentrated and purified by prep-TLC (SiO$_2$, petroleum ether: ethyl acetate=10:1, v/v) to give the title compound. MS (ESI) m/z: 241.0 [M+H]$^+$ $^1$H NMR (400 MHz, CDCl$_3$) δ=10.98 (s, 1H), 7.71 (d, J=2.7 Hz, 1H), 7.30 (d, J=2.0 Hz, 1H), 4.87 (s, 1H), 4.70 (s, 1H), 3.96 (s, 3H), 3.36 (s, 2H), 1.75 (s, 3H)

Step C: Methyl 5-chloro-2,2-dimethyl-2,3-dihydrobenzofuran-7-carboxylate

Methyl 5-chloro-2-hydroxy-3-(2-methylallyl)benzoate (220 mg, 0.914 mmol) was dissolved in 98% formic acid (2 ml) and the reaction was stirred at 110° C. for 3 h. Then the reaction was cooled to room temperature and concentrated. The resulting residue was dissolved in ethyl acetate (20 mL), and washed with water (5 mL) and saturated sodium dicarbonate (5 mL). The organic layer was dried over sodium sulfate and concentrated to give the crude product, which was purified via flash chromatography (SiO$_2$, petroleum ether:ethyl acetate=20:1, v/v) to give the title compound. MS (ESI) m/z: 241.0 [M+H]$^+$ $^1$H NMR (400 MHz, CDCl$_3$) δ=7.69 (s, 1H), 7.25 (s, 1H), 3.89 (s, 3H), 3.01 (s, 2H), 1.54 (s, 6H)

Step D: (5-chloro-2,2-dimethyl-2,3-dihydrobenzofuran-7-yl)methanol

To a solution of methyl 5-chloro-2,2-dimethyl-2,3-dihydrobenzofuran-7-carboxylate (170 mg, 0.706 mmol) in THF (5 ml) was added LiAlH$_4$ (26.8 mg, 0.706 mmol) at 0° C. The reaction was stirred at 20° C. for 1 h, then quenched by addition of water (10 mL), and extracted with EtOAc (20 mL×3). The combined organic layers were dried over sodium sulfate, and then filtered. The filtrate was concentrated in vacuo to give the crude product, which was purified by preparative-TLC (SiO$_2$, petroleum ether:ethyl acetate=10:1, v/v) to give the title compound. MS (ESI) m/z: 195.0 [M−OH+H]$^+$

Step E: 5-chloro-7-(chloromethyl)-2,2-dimethyl-2,3-dihydrobenzofuran

To a solution of (5-chloro-2,2-dimethyl-2,3-dihydrobenzofuran-7-yl)methanol (30.0 mg, 0.141 mmol) in DCM (3 ml) was added Et$_3$N (39.0 ul, 0.282 mmol) and methanesulfonyl chloride (24.2 mg, 0.212 mmol) at 20° C. The reaction was stirred at 35° C. for 2 h. Then water (2 mL) was added, and the mixture was extracted with DCM (10 mL×3). The combined organic layers were dried over sodium sulfate, and then filtered. The filtrate was concentrated in vacuo to give the crude product, which was purified by TLC (SiO$_2$, petroleum ether:ethyl acetate=10:1, v/v) to give the title compound. $^1$H NMR (400 MHz, CDCl$_3$) δ=7.14 (s, 1H), 7.06 (s, 1H), 4.52 (s, 2H), 3.00 (s, 2H), 1.49 (s, 6H)

Step F: (2S,3R)-methyl 3-(1'-((5-chloro-2,2-dimethyl-2,3-dihydrobenzofuran-7-yl)-methyl)spiro[chroman-2,4'-piperidin]-7-yl)-3-cyclopropyl-2-methylpropanoate To a solution of 5-chloro-7-(chloromethyl)-2,2-dimethyl-2,3-dihydrobenzofuran (40.0 mg, 0.173 mmol) in MeCN (5 ml) was added sodium iodide (78.0 mg, 0.519 mmol), K$_2$CO$_3$ (120 mg, 0.865 mmol) and (2S,3R)-methyl 3-cyclopropyl-2-methyl-3-(spiro-[chroman-2,4'-piperidin]-7-yl) propanoate (59.4 mg, 0.173 mmol). The reaction was stirred at 90° C. for 5 h, then poured into water (10 mL) and extracted with EtOAc (10 mL×3). The combined organic layers were dried over sodium sulfate, and then filtered. The filtrate was concentrated in vacuo to give the crude product, which was purified by prep-TLC (SiO$_2$, petroleum ether:ethyl acetate=5:1, v/v) to give the title compound. MS (ESI) m/z: 538.3 [M+H]$^+$

Step G: sodium (2S,3R)-3-(1'-((5-chloro-2,2-dimethyl-2,3-dihydrobenzofuran-7-yl)-methyl)spiro[chroman-2,4'-piperidin]-7-yl)-3-cyclopropyl-2-methylpropanoate To a solution of (2S,3R)-methyl 3-(1'-((5-chloro-2,2-dimethyl-2,3-dihydrobenzo-furan-7-yl)methyl)spiro[chroman-2,4'-piperidin]-7-yl)-3-cyclopropyl-2-methylpropanoate (28.0 mg, 52.0 umol) in a co-solvent of THF (1 ml), water (1 ml) and MeOH (1 ml) was added LiOH (62.3 mg, 2.60 mmol). The reaction was stirred at 50° C. for 12 hours under N$_2$, then poured into water (2 mL). Citric acid was added to adjust the mixture pH to pH 7, and the mixture was extracted with EtOAc (5 mL×3). The combined organic layers were washed with brine (2 mL×3), dried over Na$_2$SO$_4$, and filtered. The filtrate was evaporated under reduced pressure to give a residue, which was purified with Prep-HPLC (neutral) to give the title compound.

To the solution of the title compound in MeCN (1 mL) and water (1 mL) was added an aqueous NaOH solution (1.0 eq, 0.5 M), and the mixture was stirred for 1 h at room temperature. Then the reaction mixture was lyophilized to give the sodium salt of the title compound. Preparative HPLC conditions: a MS trigger instrument fitted with a Phenomenex Gemini C18 250*21.2 mm*5 um using water (10 mM NH4HCO3)-ACN as the eluents, mobile phase A: water (10 mM NH4HCO3), mobile phase B: acetonitrile, Gradient: 30-60% B, 2.0-12.0 min, FlowRate: 25 mL/min. MS (ESI) m/z: 524.3 [M+H]$^+$ $^1$H NMR (400 MHz, CD$_3$OD): δ=7.18 (d, J=7.9 Hz, 2H), 6.97 (d, J=7.7 Hz, 1H), 6.69-6.60 (m, 2H), 3.84 (br. s., 2H), 3.07 (s, 2H), 3.02-2.84 (m, 4H), 2.77 (t, J=6.6 Hz, 2H), 2.67 (br. s., 1H), 1.99-1.69 (m, 7H), 1.46 (s, 6H), 1.08 (br. s., 1H), 0.86 (d, J=6.8 Hz, 3H), 0.56 (br. s., 1H), 0.36 (d, J=4.4 Hz, 1H), 0.25 (br. s., 1H), −0.06 (d, J=4.4 Hz, 1H)

Examples 62A and 62B (2S,3R)-3-(1'-((R or S)-1-(5-chloro-2-(2,2,2-trifluoroethoxy)phenyl)ethyl)spiro [chroman-2,4'-piperidin]-7-yl)-3-cyclopropyl-2-methylpropanoic Acid

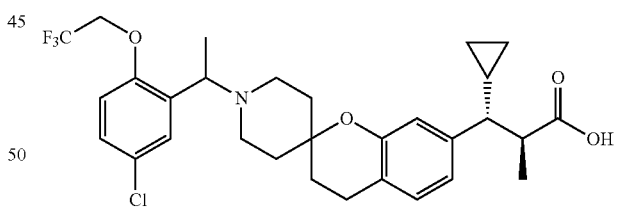

Step A: 1-(5-chloro-2-(2,2,2-trifluoroethoxy)phenyl) ethanone

To a solution of 1-(5-chloro-2-hydroxyphenyl)ethanone (500 mg, 2.93 mmol) in N-Methyl-2-pyrrolidinone (2 mL) was added Cs$_2$CO$_3$ (1.43 g, 4.40 mmol). The stirred mixture was cooled to 0° C. before addition of 2,2,2-trifluoroethyl trifluoromethanesulfonate (680 mg, 2.93 mmol) dropwise over 2 min. The reaction was allowed to warm to 20° C. and stirred for 3 h. Then water (20 mL) was added, and the mixture was extracted with ethyl acetate (20 mL×3). The combined organic layers were washed with brine (10 mL), dried over MgSO$_4$ and filtered. The filtrate was evaporated under reduced pressure to give the crude product, which was purified by prep-TLC (SiO$_2$, PE:EA=10:1, v/v) to give the title compound. MS (ESI) m/z: 253.0 [M+H]$^+$ Step B: (RS)-1-(5-chloro-2-(2,2,2-trifluoroethoxy) phenyl)ethanol To a solution of 1-(5-chloro-2-(2,2,2-trifluoroethoxy)phenyl)ethanone (600 mg, 2.38 mmol) in MeOH (10 mL) was added NaBH$_4$ (180 mg, 4.75 mmol) at 0° C. The reaction was stirred at 0° C. under N$_2$ protection for 30 min, then quenched with saturated NH$_4$Cl aqueous (15 mL), and extracted with ethyl acetate (20 mL×3). The combined organic layers were washed with brine (15 mL), dried over MgSO$_4$ and filtered. The filtrate was evaporated under reduced pressure to give the title compound, which was used in the next step without further purification. MS (ESI) m/z: 237.0 [M−18+H]$^+$ Step C: (RS)-2-(1-bromoethyl)-4-chloro-1-(2,2,2-trifluoroethoxy)benzene To a solution of (RS)-1-(5-chloro-2-(2,2,2-trifluoroethoxy)phenyl)ethanol (600 mg, 2.37 mmol) and Ph$_3$P (927 mg, 3.53 mmol) in DCM (6 mL) was added CBr$_4$ (1.17 g, 3.53 mmol). The reaction was stirred at 20° C. under N$_2$ protection for 2 h. Then the solvent was removed under reduced pressure to give the crude product, which was purified by prep-TLC (SiO$_2$, PE:EA=15:1, v/v) to give the title compound. $^1$H NMR (400 MHz, CDCl$_3$) δ=7.54 (d, J=2.3 Hz, 1H), 7.27-7.22 (m, 1H), 6.78 (d, J=8.6 Hz, 1H), 5.56 (q, J=7.0 Hz, 1H), 4.45-4.37 (m, 2H), 2.01 (d, J=7.0 Hz, 3H)

Step D: (2S,3R)-methyl 3-(1'-((RS)-1-(5-chloro-2-(2,2,2-trifluoroethoxy)phenyl)ethyl) spiro[chroman-2,4'-piperidin]-7-yl)-3-cyclopropyl-2-methylpropanoate To a solution of (2S,3R)-methyl 3-cyclopropyl-2-methyl-3-(spiro[chroman-2,4'-piperidin]-7-yl)propanoate (100 mg, 0.291 mmol) and (RS)-2-(1-bromoethyl)-4-chloro-1-(2,2,2-trifluoroethoxy)benzene (102 mg, 0.320 mmol) in MeCN (2 mL) was added K$_2$CO$_3$ (121 mg, 0.873 mmol). The reaction was stirred at 80° C. for 2 h. Then water (10 mL) was added, and the mixture was extracted with ethyl acetate (15 mL×3). The combined organic layers were washed with brine (10 mL), dried over MgSO$_4$ and filtered. The filtrate was evaporated under reduced pressure to give the crude product, which was purified by prep-TLC (SiO$_2$, PE:EA=10:1, v/v) to give the title compound. MS (ESI) m/z: 580.3 [M+H]$^+$ Step E: (2S,3R)-3-(1'-((RS)-1-(5-chloro-2-(2,2,2-trifluoroethoxy)phenyl)ethyl)spiro [chroman-2,4'-piperidin]-7-yl)-3-cyclopropyl-2-methylpropanoic Acid To a solution of (2S,3R)-methyl 3-(1'-((RS)-1-(5-chloro-2-(2,2,2-trifluoroethoxy) phenyl)ethyl)-spiro[chroman-2,4'-piperidin]-7-yl)-3-cyclopropyl-2-methylpropanoate (155 mg, 0.267 mmol) in MeOH (2 mL), THF (2 mL) and water (2 mL) was added LiOH (128 mg, 5.34 mmol). The reaction was stirred at 50° C. for 14 h, and then cooled to 25° C. The reaction mixture was acidified to pH=5-6 with citric acid and extracted with EtOAc (10 mL×3). The combined organic layers were dried (MgSO$_4$) and filtered. The filtrate was concentrated in vacuo to give the title compound. MS (ESI) m/z: 566.3 [M+H]$^+$ Step F: (2S,3R)-3-(1'-((R or S)-1-(5-chloro-2-(2,2,2-trifluoroethoxy)phenyl)ethyl) spiro[chroman-2,4'-piperidin]-7-yl)-3-cyclopropyl-2-methylpropanoic Acid (2S,3R)-3-(1'-((RS)-1-(5-chloro-2-(2,2,2-trifluoroethoxy)phenyl)ethyl)spiro [chroman-2,4'-piperidin]-7-yl)-3-cyclopropyl-2-methylpropanoic acid (150 mg, 0.265 mmol) was separated into individual diastereoisomers via SFC (SFC conditions: Column: Chiralpak AD-3 100×4.6 mm I.D., 3 um, mobile phase: A: CO$_2$ B:ethanol (0.05% DEA), Gradient: from 5% to 40% of B in 4.5 min and hold 40% for 2.5 min, then 5% of B for 1 min, Flow rate: 2.8 mL/min Column temperature: 40° C.) to give the first peak (2S,3R)-3-(1'-((R or S)-1-(5-chloro-2-(2,2,2-trifluoroethoxy)-phenyl)ethyl) spiro[chroman-2,4'-piperidin]-7-yl)-3-cyclopropyl-2-methylpropanoic acid Example 62A (Rt=2.313 min), which was further purified by prep-HPLC (base), and the second peak (2S,3R)-3-(1'-((S or R)-1-(5-chloro-2-(2,2,2-trifluoroethoxy)-phenyl)ethyl)spiro [chroman-2,4'-piperidin]-7-yl)-3-cyclopropyl-2-methylpropanoic acid Example 62B (Rt=3.087 min) which was further purified by prep-HPLC (base). Preparative-HPLC conditions: a MS trigger instrument fitted with a Waters Xbridge Prep OBD C18 150×30×5 um using water and acetonitrile as the eluents, mobile phase A: water (0.05% ammonia hydroxide); mobile phase B: acetonitrile, Gradient: 30-60% B, 0-10.0 min; 100% B, 10.1-12.0 min; 10% B, 12.1-15 min, FlowRate: 25 mL/min.) To a solution of each individual diastereoisomer of the title compound in MeCN (1 mL) and water (1 mL) was added an aqueous solution of NaOH (1.0 eq, 0.5 M), and the mixture was stirred for 1 hour at room temperature. Then the reaction mixture was lyophilized to give the sodium salt of each diastereoisomer of the title compound.

Example 62A

MS (ESI) m/z: 566.2 [M+H]$^+$ $^1$H NMR (400 MHz, CD$_3$OD) δ=7.53 (br. s., 1H), 7.35-7.28 (m, 1H), 7.08 (d, J=8.8 Hz, 1H), 6.95 (d, J=7.7 Hz, 1H), 6.64 (d, J=7.7 Hz, 1H), 6.55 (s, 1H), 4.61 (q, J=8.4 Hz, 2H), 4.33-4.23 (m, 1H), 3.14-3.01 (m, 1H), 2.81-2.59 (m, 6H), 1.96-1.74 (m, 6H), 1.71-1.60 (m, 1H), 1.46 (d, J=6.2 Hz, 3H), 1.12-0.99 (m, 1H), 0.86 (d, J=6.8 Hz, 3H), 0.61-0.49 (m, 1H), 0.36 (dd, J=4.5, 8.9 Hz, 1H), 0.29-0.19 (m, 1H), 0.00-−0.11 (m, 1H)

Example 62B

MS (ESI) m/z: 566.2 [M+H]$^+$ $^1$H NMR (400 MHz, CD$_3$OD) δ=7.53 (d, J=2.0 Hz, 1H), 7.33 (dd, J=2.3, 8.6 Hz, 1H), 7.09 (d, J=9.0 Hz, 1H), 6.96 (d, J=7.8 Hz, 1H), 6.65 (d, J=7.4 Hz, 1H), 6.55 (s, 1H), 4.63 (q, J=8.2 Hz, 2H), 4.38-4.27 (m, 1H), 3.17-3.07 (m, 1H), 2.81-2.65 (m, 6H), 1.96-1.76 (m, 6H), 1.69-1.60 (m, 1H), 1.48 (d, J=6.7 Hz, 3H), 1.10-1.01 (m, 1H), 0.86 (d, J=7.0 Hz, 3H), 0.63-0.50 (m, 1H), 0.39-0.31 (m, 1H), 0.30-0.20 (m, 1H), −0.01-−0.09 (m, 1H)

Example 63

(2S,3R)-3-cyclopropyl-2-methyl-3-(4'-(methyl(3-(trifluoromethyl)pyridin-2-yl)amino)spiro[chroman-2,1'-cyclohexan]-7-yl)propanoic Acid

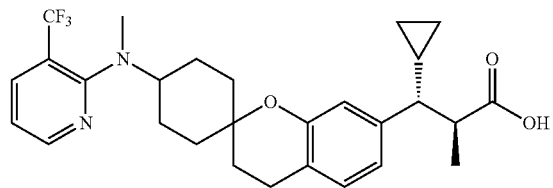 [SMILES: C[C@H](C(=O)O)[C@H](c1ccc2c(c1)OC1(CC2)CCC(N(C)c2ncccc2C(F)(F)F)CC1)C1CC1]

Step: A: (2S,3R)-methyl 3-(4'-((tert-butoxycarbonyl)amino)-4-oxospiro[chroman-2,1'-cyclohexan]-7-yl)-3-cyclopropyl-2-methylpropanoate To a solution of tert-butyl (4-oxocyclohexyl)carbamate (1.00 g, 4.69 mmol) and (2S,3R)-methyl 3-(4-acetyl-3-hydroxyphenyl)-3-cyclopropyl-2-methylpropanoate (1.30 g, 4.69 mmol) in MeOH (20 mL) was added pyrrolidine (0.516 mL, 7.03 mmol) at 15° C. The reaction was warmed to 70° C. for 1.5 h, then concentrated under reduced pressure to afford the crude product, which was purified by preparative-TLC (silica gel, PE:EtOAc=5:1, v/v) to afford the title compound. $^1$H NMR (400 MHz, CDCl$_3$): δ=7.84-7.77 (m, 1H), 6.85-6.79 (m, 1H), 6.77 (s, 1H), 4.52 (br. s., 1H), 3.75 (d, J=2.3 Hz, 3H), 3.52 (br. s., 1H), 2.89-2.81 (m, 1H), 2.79 (s, 1H), 2.67 (s, 1H), 2.47-2.40 (m, 1H), 2.18 (d, J=12.9 Hz, 2H), 2.04-1.80 (m, 5H), 1.49-1.43 (m, 12H), 1.06 (dd, J=2.5, 4.9 Hz, 1H), 0.98 (d, J=6.7 Hz, 3H), 0.60 (d, J=3.1 Hz, 1H), 0.38 (br. s., 1H), 0.32-0.24 (m, 1H), 0.02 (dd, $J_1$=4.7, $J_2$=9.0 Hz, 1H).

Step: B: (2S,3R)-methyl 3-(4'-((tert-butoxycarbonyl)amino)-4-oxospiro[chroman-2,1'-cyclohexan]-7-yl)-3-cyclopropyl-2-methylpropanoate (2S,3R)-methyl-3-(4'-((tert-butoxycarbonyl)amino)-4-oxospiro[chroman-2,1'-cyclohexan]-7-yl)-3-cyclopropyl-2-methylpropanoate (3.00 g, 6.36 mmol) was separated into individual diastereoisomers by SFC (SFC conditions: Column AD (250 mm*30 mm, 5 um); Condition Base-IPA Begin B 25% End B, Gradient Time (min); 100% B Hold Time (min); Flow Rate (ml/min) 70) and dried by lyophilization to afford (2S,3R)-methyl 3-(4'-((tert-butoxy-carbonyl)amino)-4-oxospiro[chroman-2,1'-cyclohexan]-7-yl)-3-cyclopropyl-2-methylpropanoate, and (2S,3R)-methyl 3-(4'-((tert-butoxycarbonyl)amino)-4-oxospiro[chroman-2,1'-cyclohexan]-7-yl)-3-cyclopropyl-2-methylpropanoate. MS (ESI) m/z: 494.2 [M+Na]$^+$ Step: B: (2S,3R)-methyl 3-(4'-((tert-butoxycarbonyl)amino)-4-hydroxyspiro-[chroman-2,1'-cyclohexan]-7-yl)-3-cyclopropyl-2-methylpropanoate To a solution of (2S,3R)-methyl 3-(4'-((tert-butoxycarbonyl)amino)-4-oxospiro[chroman-2,1'-cyclo-hexan]-7-yl)-3-cyclopropyl-2-methylpropanoate (1.00 g, 2.12 mmol) in MeOH (15 mL) was added sodium borohydride (0.241 g, 6.36 mmol) at 10° C. The reaction was stirred at 10° C. for 1 h, then water (10 mL) and ethyl acetate (10 mL) were added. The organic layer was separated. The aqueous layer was extracted with ethyl acetate (10 mL×3). The combined organic layers were dried over anhydrous sodium sulfate, filtered and concentrated under reduced pressure to afford the title compound. MS (ESI) m/z: 496.3 [M+Na]$^+$ $^1$H NMR (400 MHz, CDCl$_3$): δ=7.41 (d, J=7.8 Hz, 1H), 6.78 (dd, $J_1$=3.1, $J_2$=7.0 Hz, 1H), 6.66 (br. s., 1H), 4.88-4.79 (m, 1H), 3.76 (s, 3H), 2.86 (td, J=4.3, $J_2$=6.4, J3=10.1 Hz, 1H), 2.15-1.43 (m, 22H), 1.10 (d, J=5.1 Hz, 1H), 0.96 (d, J=7.0 Hz, 3H), 0.59 (br. s., 1H), 0.40-0.18 (m, 2H), 0.01 (dd, J=4.7, $J_2$=9.4 Hz, 1H).

Step: C: (2S,3R)-methyl 3-(4'-aminospiro[chroman-2,1'-cyclohexan]-7-yl)-3-cyclo-propyl-2-methylpropanoate To a solution of (2S,3R)-methyl 3-(4'-((tert-butoxy-carbonyl)amino)-4-hydroxyspiro[chroman-2,1'-cyclohexan]-7-yl)-3-cyclopropyl-2-methylpropanoate (800 mg, 1.69 mmol) in DCM (10 mL) were added triethylsilane (2 mL, 12.52 mmol) and TFA (2 mL, 26.0 mmol). The reaction was stirred at 14° C. for 0.5 h, then saturated sodium bicarbonate solution (10 mL) and DCM (10 mL) were added. The organic layer was separated. The aqueous layer was extracted with DCM (10 mL×3). The combined organic layers were dried over anhydrous sodium sulfate, filtered and concentrated under reduced pressure to afford the crude product, which was purified by preparative-TLC (silica gel, DCM:MeOH=6:1, v/v) to give the title compound. MS (ESI) m/z: 358.2 [M+H]$^+$ Step: D: (2S,3R)-methyl 3-cyclopropyl-2-methyl-3-(4'-((3-(trifluoromethyl)-pyridin-2-yl)amino)spiro[chroman-2,1'-cyclohexan]-7-yl)propanoate To a solution of 2-bromo-3-(trifluoromethyl)pyridine (91.0 mg, 0.403 mmol) and (2S,3R)-methyl 3-(4'-aminospiro[chroman-2,1'-cyclohexan]-7-yl)-3-cyclopropyl-2-methylpropanoate (120 mg, 0.336 mmol) in 1,4-dioxane (3 mL) were added Cs$_2$CO$_3$ (273 mg, 0.839 mmol), BINAP (41.8 mg, 0.067 mmol) and Pd$_2$(dba)$_3$ (61.5 mg, 0.067 mmol) at 15° C. The reaction was stirred at 105° C. for 15 h. Then the reaction mixture was filtered and concentrated under reduced pressure to afford the crude product, which was purified by preparative-TLC (silica gel, PE:EtOAc=6:1, v/v) to afford the title compound.

Step: E: (2S,3R)-methyl 3-cyclopropyl-2-methyl-3-(4'-(methyl(3-(trifluoromethyl)-pyridin-2-yl)amino)spiro[chroman-2,1'-cyclohexan]-7-yl)propanoate To a solution of (2S,3R)-methyl 3-cyclopropyl-2-methyl-3-(4'-((3-(trifluoromethyl)pyridin-2-yl)-amino)spiro[chroman-2,1'-cyclohexan]-7-yl)propanoate (50.0 mg, 0.099 mmol) in DMF (2 mL) was added NaH (39.8 mg, 0.995 mmol) at 20° C. The reaction was stirred at 20° C. for 10 minutes, then iodomethane (70.6 mg, 0.497 mmol) was added. The mixture was stirred at 20° C. for 1 hour, then concentrated and poured into water (5 mL). EtOAc (5 mL) was added to the mixture, and the organic layer was separated. The aqueous layer was extracted with EtOAc (5 mL×3). The combined organic layers were dried over Na$_2$SO$_4$, filtered and concentrated under reduced pressure to afford the title compound, which was used in next step without further purification. MS (ESI) m/z: 517.3 [M+H]$^+$.

Step: F: (2S,3R)-3-cyclopropyl-2-methyl-3-(4'-(methyl(3-(trifluoromethyl)-pyridin-2-yl)amino) spiro[chroman-2,1'-cyclohexan]-7-yl)propanoic Acid To a solution of (2S,3R)-methyl-3-cyclopropyl-2-methyl-3-(4'-(methyl(2-(trifluoro-methyl)-pyridin-3-yl)amino)spiro[chroman-2,1'-cyclohexan]-7-yl)propanoate (30.0 mg, 0.058 mmol) in MeOH (1 mL), THF (1 mL) and water (1 mL) was added LiOH (27.8 mg, 1.16 mmol) at room temperature. The reaction was stirred for 20 h at 60° C. Then the reaction mixture pH was adjusted to pH 6 with citric acid, and EtOAc (5 mL) was added. The organic layer was separated. The aqueous layer was extracted with EtOAc (3 mL×3). The combined organic layers were dried over anhydrous sodium sulfate, filtered and concentrated under reduced pressure to afford the crude product, which was purified by preparative-HPLC and lyophilized to afford the title compound. (Preparative HPLC conditions: a MS trigger instrument fitted with a Phenomenex Gemini YMC-Actus Pro C18 150*30 5u using water and acetonitrile as the eluents; mobile phase A: water (0.1% TFA), mobile phase B: acetonitrile; Gradient: Begin B 54 End B 84 Gradient Time (min) 11 100% B Hold Time (min) 1.1; FlowRate: 40 mL/min. MS (ESI): m/z=503.3 [M+H]$^+$ $^1$H NMR (400 MHz, CDCl$_3$): δ=11.71 (br. s., 1H), 8.42 (br. s., 1H), 8.13 (d, J=7.4 Hz, 1H), 7.03-6.90 (m, 2H), 6.66-6.56 (m, 2H), 4.07-3.80 (m, 1H), 3.10 (br. s., 3H), 2.85-2.63 (m, 3H), 2.18-2.03 (m, 2H), 1.98 (d, J=13.3 Hz, 2H), 1.86 (t, J=10.0 Hz, 1H), 1.77-1.62 (m, 4H), 1.49 (t, J=12.9 Hz, 2H), 1.06 (br. s., 1H), 0.95 (d, J=6.7 Hz, 3H), 0.56 (br. s., 1H), 0.30 (d, J=4.7 Hz, 2H), 0.01 (d, J=4.7 Hz, 1H)

TABLE 16

The compounds of Examples 64-70 were prepared in a similar manner to Example 63 using the appropriate starting material and reagents.

| Example | Structure | M.W. | Compound Name | LC/MS (ESI) observed [M + H]$^+$ |
|---|---|---|---|---|
| 64 | 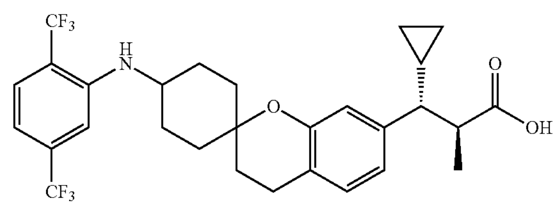 | 555.55 | (2S,3R)-3-(4'-((2,5-bis(trifluoromethyl)phenyl)amino)spiro[chroman-2,1'-cyclohexan]-7-yl)-3-cyclopropyl-2-methyl-propanoic acid | 556.3 |
| 65 | 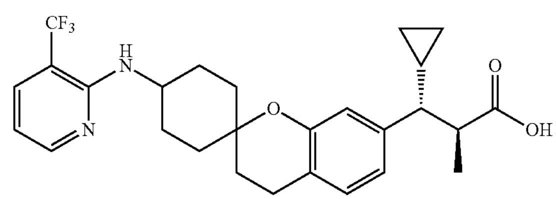 [SMILES: C[C@H](C(=O)O)[C@H](c1ccc2c(c1)OC1(CC2)CCC(Nc2ncccc2C(F)(F)F)CC1)C1CC1] | 488.54 | (2S,3R)-3-cyclopropyl-2-methyl-3-(4'-((3-(trifluoromethyl)pyridin-2-yl)amino)spiro-[chroman-2,1'-cyclohexan]-7-yl)propanoic acid | 487.1 |
| 66 | 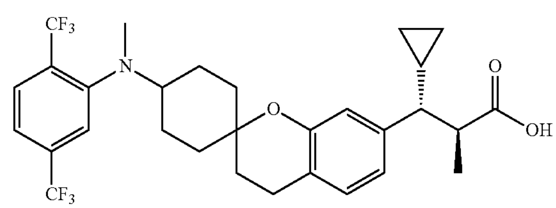 [SMILES: C[C@H](C(=O)O)[C@H](c1ccc2c(c1)OC1(CC2)CCC(N(C)c2cc(C(F)(F)F)ccc2C(F)(F)F)CC1)C1CC1] | 569.58 | (2S,3R)-3-(4'-((2,5-bis(trifluoromethyl)phenyl)(methyl)amino)spiro[chroman-2,1'-cyclohexan]-7-yl)-3-cyclopropyl-2-methylpropanoic acid | 570.3 |
| 67 | 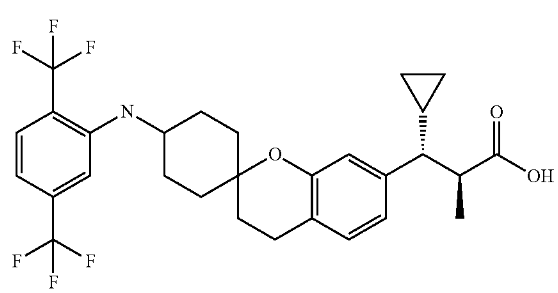 [SMILES: C[C@H](C(=O)O)[C@H](c1ccc2c(c1)OC1(CC2)CCC(Nc2cc(C(F)(F)F)ccc2C(F)(F)F)CC1)C1CC1] | 555.5 | (2S,3R)-3-(4'-((2,5-bis(trifluoromethyl)phenyl)amino)spiro[chroman-2,1'-cyclohexan]-7-yl)-3-cyclopropyl-2-methylpropanoic acid | 556.3 |

TABLE 16-continued

The compounds of Examples 64-70 were prepared in a similar manner to Example 63 using the appropriate starting material and reagents.

| Example | Structure | M.W. | Compound Name | LC/MS (ESI) observed [M + H]+ |
|---|---|---|---|---|
| 68 | 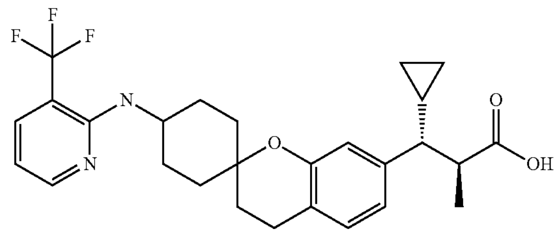 [SMILES: C[C@H](C(=O)O)[C@H](c1ccc2c(c1)OC1(CC2)CCC(Nc2ncccc2C(F)(F)F)CC1)C1CC1] | 488.5 | (2S,3R)-3-cyclopropyl-2-methyl-3-(4'-((3-(trifluoromethyl)pyridin-2-yl)amino)spiro-[chroman-2,1'-cyclohexan]-7-yl)propanoic acid | 489.2 |
| 69 | 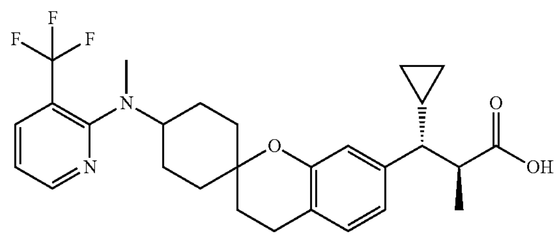 [SMILES: C[C@H](C(=O)O)[C@H](c1ccc2c(c1)OC1(CC2)CCC(N(C)c2ncccc2C(F)(F)F)CC1)C1CC1] | 502.5 | (2S,3R)-3-cyclopropyl-2-methyl-3-(4'-(methyl(3-(trifluoromethyl)pyridin-2-yl)amino)spiro[chroman-2,1'-cyclohexan]-7-yl)propanoic acid | 503.3 |
| 70 | 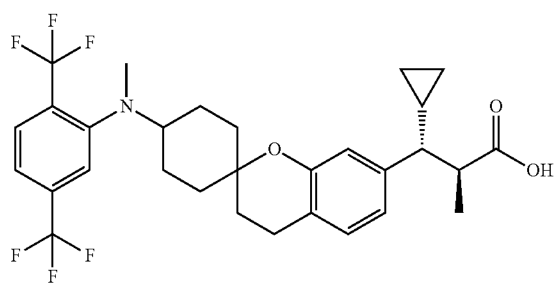 [SMILES: C[C@H](C(=O)O)[C@H](c1ccc2c(c1)OC1(CC2)CCC(N(C)c2cc(C(F)(F)F)ccc2C(F)(F)F)CC1)C1CC1] | 569.58 | (2S,3R)-3-(4'-((2,5-bis(trifluoromethyl)phenyl)(methyl)amino)spiro[chroman-2,1'-cyclohexan]-7-yl)-3-cyclopropyl-2-methylpropanoic acid | 570.2 |

Example 64

$^1$H NMR (400 MHz, CDCl$_3$): δ=7.47 (d, J=7.8 Hz, 1H), 6.94 (d, J=7.8 Hz, 1H), 6.90-6.81 (m, 2H), 6.66 (s, 1H), 6.60 (d, J=7.4 Hz, 1H), 3.37 (br. s., 1H), 2.84-2.67 (m, 3H), 1.98 (d, J=14.1 Hz, 2H), 1.92-1.81 (m, 3H), 1.76 (t, J=6.7 Hz, 2H), 1.67 (d, J=11.7 Hz, 2H), 1.52-1.40 (m, 2H), 1.07 (br. s., 1H), 0.95 (d, J=6.7 Hz, 3H), 0.62-0.49 (m, 1H), 0.30 (d, J=5.1 Hz, 2H), 0.01 (d, J=5.9 Hz, 1H).

Example 65

$^1$H NMR (400 MHz, CDCl$_3$): δ=8.25 (d, J=4.3 Hz, 1H), 7.64 (d, J=7.4 Hz, 1H), 6.98 (d, J=7.4 Hz, 1H), 6.72 (s, 1H), 6.65 (d, J=7.0 Hz, 1H), 6.61-6.54 (m, 1H), 4.79 (d, J=6.7 Hz, 1H), 4.11 (d, J=8.2 Hz, 1H), 2.90-2.79 (m, 1H), 2.76 (t, J=6.7 Hz, 2H), 2.04-1.87 (m, 5H), 1.79 (t, J=6.7 Hz, 2H), 1.75-1.62 (m, 2H), 1.58-1.45 (m, 2H), 1.12 (d, J=4.7 Hz, 1H), 1.00 (d, J=6.7 Hz, 3H), 0.62 (d, J=7.0 Hz, 1H), 0.37 (t, J=5.7 Hz, 2H), 0.06 (d, J=4.3 Hz, 1H)

Example 66

$^1$H NMR (400 MHz, CDCl$_3$): δ=7.75 (d, J=8.2 Hz, 1H), 7.58 (s, 1H), 7.42 (d, J=8.2 Hz, 1H), 6.97 (d, J=7.4 Hz, 1H), 6.61-6.60 (m, 1H), 6.70-6.58 (m, 2H), 3.04-2.94 (m, 1H), 2.90-2.80 (m, 1H), 2.78-2.70 (m, 5H), 2.00-1.82 (m, 5H), 1.73 (t, J=6.7 Hz, 2H), 1.63 (d, J=11.7 Hz, 2H), 1.32 (t, J=13.5 Hz, 2H), 1.19-1.06 (m, 1H), 1.01 (d, J=6.7 Hz, 3H), 0.69-0.56 (m, 1H), 0.42-0.28 (m, 2H), 0.07 (d, J=5.1 Hz, 1H)

Example 67

1H NMR (400 MHz, CD$_3$OD): δ=7.65 (d, J=7.9 Hz, 1H), 7.12 (s, 1H), 7.02 (d, J=7.5 Hz, 1H), 6.68 (d, J=7.9 Hz, 1H), 6.64 (s, 1H), 3.84 (s, 1H), 2.80 (t, J=6.7 Hz, 3H), 2.14 (d, J=8.4 Hz, 2H), 1.98-1.89 (m, 3H), 1.85-1.66 (m, 6H), 1.15-1.08 (m, 1H), 0.95 (d, J=6.8 Hz, 3H), 0.66-0.59 (m, 1H), 0.39-0.32 (m, 2H), 0.06--0.02 (m, 1H)

Example 68

1H NMR (400 MHz, CD$_3$OD): δ=8.19 (d, J=4.9 Hz, 1H), 8.02 (d, J=7.5 Hz, 1H), 6.98 (d, J=7.5 Hz, 1H), 6.84 (d, J=6.4 Hz, 1H), 6.63 (d, J=7.7 Hz, 1H), 6.57 (s, 1H), 4.13-4.08 (m, 1H), 2.75 (t, J=6.6 Hz, 3H), 2.06-1.97 (m, 5H), 1.86-1.76 (m, 5H), 1.29 (br. s., 1H), 1.07 (s, 1H), 0.90 (d, J=6.8 Hz, 3H), 0.61-0.54 (m, 1H), 0.31 (d, J=5.1 Hz, 2H), −0.02 (s, 1H)

Example 69

1H NMR (400 MHz, CD$_3$OD): δ=8.42 (d, J=4.2 Hz, 1H), 8.08 (d, J=7.5 Hz, 1H), 7.14-7.08 (m, 1H), 6.96 (d, J=7.7 Hz,

1H), 6.62 (d, J=7.7 Hz, 1H), 6.54 (s, 1H), 3.80 (s, 1H), 2.87 (s, 3H), 2.77-2.69 (m, 3H), 2.03-1.87 (m, 5H), 1.83 (d, J=11.2 Hz, 4H), 1.66 (d, J=12.8 Hz, 2H), 1.07 (d, J=4.9 Hz, 1H), 0.90 (d, J=6.8 Hz, 3H), 0.56 (d, J=9.0 Hz, 1H), 0.35-0.26 (m, 2H), −0.03 (d, J=5.1 Hz, 1H)

Example 70

1H NMR (400 MHz, CD$_3$OD): δ=7.94 (d, J=8.4 Hz, 1H), 7.85 (s, 1H), 7.66 (d, J=8.2 Hz, 1H), 7.01 (d, J=7.7 Hz, 1H), 6.66 (d, J=7.7 Hz, 1H), 6.59 (s, 1H), 3.30-3.24 (m, 1H), 2.82-2.72 (m, 6H), 1.97-1.85 (m, 7H), 1.66-1.65 (m, 4H), 1.15-1.07 (m, 1H), 0.95 (d, J=6.8 Hz, 3H), 0.63 (s, 1H), 0.42-0.30 (m, 2H), 0.02 (d, J=5.1 Hz, 1H)

Example 71

(2S,3R)-3-cyclopropyl-2-methyl-3-(1'-(2-(trifluoromethyl)imidazo[1,2-b]-pyridazin-6-yl)spiro[chroman-2,4'-piperidin]-7-yl)propanoic Acid

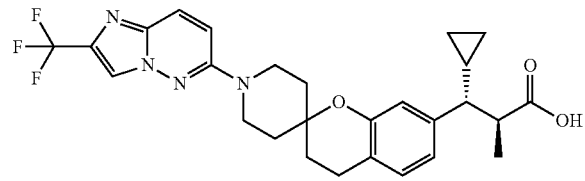 [SMILES: C[C@H](C(=O)O)[C@H](c1ccc2c(c1)OC1(CC2)CCN(c2ccc3nc(C(F)(F)F)cn3n2)CC1)C1CC1]

Step A: (2S,3R)-methyl 3-cyclopropyl-2-methyl-3-(1'-(2-(trifluoromethyl)imidazo [1,2-b]pyridazin-6-yl)spiro[chroman-2,4'-piperidin]-7-yl)propanoate To a solution of (2S,3R)-methyl 3-cyclopropyl-2-methyl-3-(spiro[chroman-2,4'-piperidin]-7-yl)-propanoate (50.0 mg, 0.146 mmol) and K$_2$CO$_3$ (60.4 mg, 0.437 mmol) in DMF (2 mL) was added 6-chloro-2-(trifluoromethyl)imidazo[1,2-b]pyridazine (38.7 mg, 0.175 mmol). The reaction was stirred at 120° C. under N$_2$ protection for 4 h, then diluted with ethyl acetate (40 mL), and washed with water (10 mL×2) and brine (10 mL). The organic layer was dried over MgSO$_4$ and filtered. The filtrate was concentrated in vacuo to give the crude product, which was purified by prep-TLC (SiO$_2$, PE:EA=2:1, v/v) to give the title compound. MS (ESI) m/z: 529.3 [M+H]$^+$ Step B: (2S,3R)-3-cyclopropyl-2-methyl-3-(1'-(2-(trifluoromethyl)imidazo[1,2-b] pyridazin-6-yl)spiro[chroman-2,4'-piperidin]-7-yl)propanoic Acid To a solution of (2S,3R)-methyl 3-cyclopropyl-2-methyl-3-(1'-(2-(trifluoromethyl)imidazo[1,2-b]-pyridazin-6-yl) spiro-[chroman-2,4'-piperidin]-7-yl)propanoate (70.0 mg, 0.132 mmol) in MeOH (2 mL), THF (2 mL) and water (2 mL) was added LiOH (63.4 mg, 2.65 mmol). The reaction was stirred at 50° C. for 14 h, then cooled to 25° C., acidified with citric acid to pH=5-6, and extracted with EtOAc (10 mL×3). The combined organic layers were dried (MgSO$_4$) and filtered. The filtrate was concentrated in vacuo to give the crude product, which was purified by preparative-HPLC (basic) to give the title compound. Preparative-HPLC conditions: a MS trigger instrument fitted with a Waters Xbridge Prep OBD C18 150×30×5 um using water and acetonitrile as the eluents, mobile phase A: water (0.05% ammonia hydroxide); mobile phase B: acetonitrile, Gradient: 30-60% B, 0-10.0 min; 100% B, 10.1-12.0 min; 10% B, 12.1-15 min, FlowRate: 25 mL/min. To a solution of the title compound in MeCN (1 mL) and water (1 mL) was added an aqueous solution of NaOH (1.0 eq, 0.5 M), and the mixture was stirred for 1 hour at room temperature. Then the reaction mixture was lyophilized to give the sodium salt of the title compound. MS (ESI) m/z: 515.1 [M+H]$^+$ $^1$H NMR (400 MHz, CD$_3$OD) δ=8.18 (s, 1H), 7.75 (d, J=10.2 Hz, 1H), 7.35 (d, J=9.8 Hz, 1H), 7.01 (d, J=7.8 Hz, 1H), 6.70-6.63 (m, 2H), 4.06 (d, J=13.3 Hz, 2H), 3.47 (t, J=12.1 Hz, 2H), 2.82-2.69 (m, 3H), 1.95-1.83 (m, 5H), 1.80-1.70 (m, 2H), 1.16-1.02 (m, 1H), 0.91 (d, J=6.7 Hz, 3H), 0.62-0.53 (m, 1H), 0.36-0.26 (m, 2H), 0.04-−0.07 (m, 1H)

Example 72

(2S,3R)-3-cyclopropyl-2-methyl-3-(1'-((1-methyl-3-(trifluoromethyl)-1H-pyrazol-4-yl)methyl)spiro[chroman-2,4'-piperidin]-7-yl)propanoic Acid

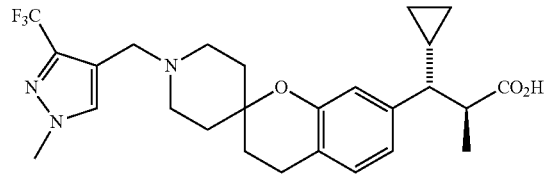 [SMILES: C[C@H](C(=O)O)[C@H](c1ccc2c(c1)OC1(CC2)CCN(Cc2cn(C)nc2C(F)(F)F)CC1)C1CC1]

Step A: (1-methyl-3-(trifluoromethyl)-1H-pyrazol-4-yl)methanol

To a solution of 1-methyl-3-(trifluoromethyl)-1H-pyrazole-4-carboxylic acid (400 mg, 2.06 mmol) in THF (6 mL) was added BH$_3$.DMS (0.412 mL, 4.12 mmol) dropwise over 1 min at 0° C. under nitrogen. The reaction was stirred at 0° C. for 0.5 h, at 20° C. for 0.5 h, and at 80° C. for 3 h. Then the reaction was quenched with MeOH (20 mL) at 0° C., and the mixture was concentrated under reduced pressure to give the title compound, which was used directly in the next step without further purification. MS (ESI) m/z: 181.0 [M+H]$^+$ $^1$H NMR (400 MHz, DMSO-d6) δ=7.81 (s, 1H), 5.12 (t, J=5.3 Hz, 1H), 4.40 (d, J=5.1 Hz, 2H), 3.88 (s, 3H).

Step B: 1-methyl-3-(trifluoromethyl)-1H-pyrazole-4-carbaldehyde

To a solution of (1-methyl-3-(trifluoromethyl)-1H-pyrazol-4-yl)methanol (300 mg, 1.67 mmol) in DCM (5 mL) was added DMP (1.06 g, 2.50 mmol). The reaction was stirred at 20° C. for 1 h, then quenched with 1N NaOH (15 mL) and water (10 mL). The mixture was extracted with DCM (10 mL×3). The combined organic layers were washed with brine (20 mL), dried over Na$_2$SO$_4$, filtered and concentrated under reduced pressure to give the title compound, which was used directly in the next step without further purification. MS (ESI) m/z: 220.0 [M+MeCN+H]$^+$
1H NMR (400 MHz, CDCl$_3$) δ=9.96 (s, 1H), 8.01 (s, 1H), 4.02 (s, 3H)

Step C: (2S,3R)-methyl 3-cyclopropyl-2-methyl-3-(1'-((1-methyl-3-(trifluoromethyl)-1H-pyrazol-4-yl)methyl)spiro[chroman-2,4'-piperidin]-7-yl)propanoate To a solution of (2S,3R)-methyl 3-cyclopropyl-2-methyl-3-(spiro[chroman-2,4'-piperidin]-7-yl)-propanoate (100 mg, 0.291 mmol) in MeOH (2 mL) and THF (2 mL) was added titanium(IV) isopropoxide (414 mg, 1.46 mmol) under nitrogen. The reaction was stirred at 60° C. for 3 h, then sodium cyanoborohydride (54.9 mg, 0.873 mmol) was added at 20° C. The reaction was stirred at 20° C. for 3h, then quenched with water (10 mL). The resulting mixture was extracted with EtOAc (10 mL×3). The combined organic layers were washed with brine (20 mL), dried over $Na_2SO_4$ and filtered. The filtrate was concentrated under reduced pressure to give the title compound, which was used directly in the next step without further purification. MS (ESI) m/z: 506.2 [M+H]$^+$ Step D: (2S,3R)-3-cyclopropyl-2-methyl-3-(1'-((1-methyl-3-(trifluoromethyl)-1H-pyrazol-4-yl)methyl) spiro[chroman-2,4'-piperidin]-7-yl)propanoic Acid To a solution of (2S,3R)-methyl 3-cyclopropyl-2-methyl-3-(1'-((1-methyl-3-(trifluoro-methyl)-1H-pyrazol-4-yl) methyl)spiro[chroman-2,4'-piperidin]-7-yl)propanoate (150 mg, 0.297 mmol) in MeOH (1.5 mL), THF (1.5 mL) and water (1.5 mL) was added LiOH (71.1 mg, 2.97 mmol) under nitrogen. The reaction mixture was stirred at 55° C. for 14 h., then concentrated in vacuo to give a residue. Water (15 mL) was added to the residue and citric acid was added to adjust the pH of the mixture to pH-5. Then the mixture was extracted with EtOAc (10 mL×3). The combined organic layers were washed with brine (15 mL), dried over anhydrous $MgSO_4$ and filtered. The filtrate was concentrated under reduced pressure to give a residue, which was purified by Preparative HPLC (neutral) to give the title compound. Preparative HPLC conditions: a MS trigger instrument fitted with a Phenomenex Gemini C18 250*21.2 mm*5 um using water and acetonitrile as the eluents, mobile phase A: water (10 mM NH4HCO3)-ACN, mobile phase B: acetonitrile, Gradient: 20-50% B, 0-11.0 min; 100% B, 11.1-13.0 min; 10% B, 13.1-16 min, FlowRate: 25 mL/min. MS (ESI) m/z: 490.2 [M−H]$^+$ $^1$H NMR (400 MHz, $CD_3OD$) δ=7.79 (s, 1H), 6.98 (d, J=7.7 Hz, 1H), 6.67 (d, J=7.7 Hz, 1H), 6.63 (s, 1H), 3.95 (s, 3H), 3.73 (s, 2H), 2.90-2.63 (m, 7H), 1.95-1.86 (m, 3H), 1.85-1.79 (m, 2H), 1.78-1.68 (m, 2H), 1.16-1.03 (m, 1H), 0.90 (d, J=6.8 Hz, 3H), 0.64-0.53 (m, 1H), 0.40-0.25 (m, 2H), 0.03-−0.08 (m, 1H)

Example 73

(2S,3R)-3-((R or S)-1'-((R)-1-(2,5-bis(trifluoromethyl)phenyl)ethyl)spiro-[chroman-2,3'-piperidin]-7-yl)-3-cyclopropyl-2-methylpropanoic Acid

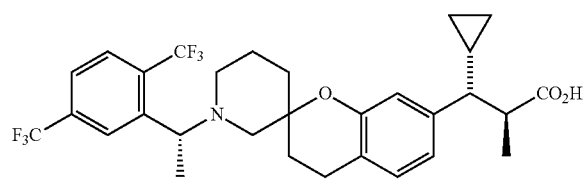 [SMILES: C[C@H](C(=O)O)[C@H](c1ccc2c(c1)OC1(CCCN([C@H](C)c3cc(C(F)(F)F)ccc3C(F)(F)F)C1)CC2)C1CC1]

Step A: tert-butyl 7-((1R,2S)-1-cyclopropyl-3-methoxy-2-methyl-3-oxopropyl)-4-oxospiro[chroman-2,3'-piperidine]-1'-carboxylate To a solution of (2S,3R)-methyl 3-(4-acetyl-3-hydroxyphenyl)-3-cyclopropyl-2-methylpropanoate (750 mg, 2.71 mmol) in MeOH (10 mL) were added pyrrolidine (0.269 mL, 3.26 mmol) and tert-butyl 3-oxopiperidine-1-carboxylate (811 mg, 4.07 mmol). The reaction was stirred at 60° C. for 3h, then the solvent was removed under reduced pressure to give the crude product, which was purified by prep-TLC ($SiO_2$, PE:EA=10:1, v/v) to give the title compound. MS (ESI) m/z: 480.2 [M+Na]$^+$ Step B: (R or S)-tert-butyl 7-((1R,2S)-1-cyclopropyl-3-methoxy-2-methyl-3-oxopropyl)-4-oxospiro [chroman-2,3'-piperidine]-1'-carboxylate Tert-butyl 7-((1R,2S)-1-cyclopropyl-3-methoxy-2-methyl-3-oxopropyl)-4-oxospiro[chroman-2,3'-piperidine]-1'-carboxylate (1.20 g, 2.62 mmol) was separated into individual diastereoisomers via SFC (SFC conditions: Column: Chiralcel OJ-3 150×4.6 mm I.D., 3 um Mobile phase: A: $CO_2$:methanol (0.05% DEA), Gradient: from 5% to 40% of B in 5 min and hold 40% for 2.5 min, then 5% of B for 2.5 min, Flow rate: 2.5 mL/min, Column temp.: 35° C.) to give the first peak S or R) tert-butyl-7-((1R,2S)-1-cyclopropyl-3-methoxy-2-methyl-3-oxopropyl)-4-oxospiro[chroman-2,3'-piperidine]-1'-carboxylate, and the second peak R or S)-tert-butyl 7-((1R,2S)-1-cyclopropyl-3-methoxy-2-methyl-3-oxopropyl)-4-oxospiro[chroman-2,3'-piperidine]-1'-carboxylate.

Step B: (2S or 2R)-tert-butyl 7-((1R,2S)-1-cyclopropyl-3-methoxy-2-methyl-3-oxopropyl)-4-hydroxyspiro[chroman-2,3'-piperidine]-1'-carboxylate To a solution of (R or S)-tert-butyl 7-((1R,2S)-1-cyclopropyl-3-methoxy-2-methyl-3-oxopropyl)-4-oxospiro[chroman-2,3'-piperidine]-1'-carboxylate (400 mg, 0.874 mmol) was added sodium borohydride (99.0 mg, 2.62 mmol) in MeOH (5 mL) at 10° C. The reaction was stirred at 10° C. for 30 min, then quenched with water (20 mL), and extracted with DCM (20 mL×3). The combined organic layers were dried over $Na_2SO_4$ and filtered. The filtrate was concentrated in vacuo to give the title compound. MS (ESI) m/z: 482.2 [M+Na]$^+$ Step C: (2S,3R)-methyl 3-cyclopropyl-2-methyl-3-((R or S)-spiro[chroman-2,3'-piperidin]-7-yl)propanoate To a solution of (2S or 2R)-tert-butyl 7-((1R,2S)-1-cyclopropyl-3-methoxy-2-methyl-3-oxopropyl)-4-hydroxyspiro-[chroman-2,3'-piperidine]-1'-carboxylate (300 mg, 0.653 mmol) in DCM (10 mL) were added triethylsilane (2.0 mL, 12.5 mmol) and TFA (2.0 mL, 26.0 mmol). The reaction was stirred at 14° C. for 0.5 h, then saturated sodium bicarbonate solution (10 mL) and EtOAc (10 mL) were added. The organic layer was separated. The aqueous layer was extracted with ethyl acetate (10 mL×3). The combined organic layers were dried over anhydrous sodium sulfate, filtered and concentrated under reduced pressure to afford the crude product, which was purified by preparative-TLC (silica gel, DCM:MeOH=5:1, v/v) to afford the title compound. MS (ESI) m/z: 344.2 [M+H]$^+$ Step D: (2S,3R)-methyl 3-((S or R)-1'-((R)-1-(2,5-bis(trifluoromethyl)phenyl)ethyl) spiro[chroman-2,3'-piperidin]-7-yl)-3-cyclopropyl-2-methylpropanoate To a solution of 2S,3R)-methyl 3-cyclopropyl-2-methyl-3-((R or S)-spiro[chroman-2,3'-piperidin]-7-yl) propanoate (70 mg, 0.204 mmol) in MeCN (3 mL) were added K$_2$CO$_3$ (141 mg, 1.019 mmol) and (S)-1-(2,5-bis(trifluoromethyl)phenyl)ethyl methanesulfonate (137 mg, 0.408 mmol) under a N$_2$ atmosphere. The reaction was stirred for 5 hours at 85° C., then water (8 mL) was added, and the mixture was extracted with EtOAc (15 mL×3). The combined organic layers ware washed with brine (10 mL), dried over anhydrous Na$_2$SO$_4$ and filtered. The filtrate was concentrated in vacuo to give a residue, which was purified by preparative-TLC (SiO$_2$, PE:EtOAc=10:1, v/v) to afford the title compound. MS (ESI) m/z: 584.3 [M+H]$^+$ Step E: (2S,3R)-3-((R or S)-1'-((R)-1-(2,5-bis(trifluoromethyl)phenyl)ethyl)spiro [chroman-2,3'-piperidin]-7-yl)-3-cyclopropyl-2-methylpropanoic Acid To a solution of (2S,3R)-methyl 3-((R or S)-1'-((R)-1-(2,5-bis(trifluoromethyl)phenyl)ethyl)-spiro[chroman-2,3'-piperidin]-7-yl)-3-cyclopropyl-2-methylpropanoate (82.0 mg, 0.141 mmol) in THF (1 mL) and water (1 mL) was added LiOH (67.3 mg, 2.81 mmol) under nitrogen. The reaction was stirred at 55° C. for 12 h, then concentrated in vacuo to give a residue. Water (5 mL) was added to the residue, citric acid was added to adjust the pH of the mixture to pH 5, and the mixture was extracted with EtOAc (10 mL×3). The combined organic layers were washed with brine (10 mL), dried over anhydrous MgSO$_4$ and filtered. The filtrate was concentrated under reduced pressure to give a residue, which was purified by preparative-HPLC (acid) to afford the title compound. Preparative HPLC conditions: a MS trigger instrument fitted with a Phenomenex Synergi C18 150×30 mm×4 um as the eluents, mobile phase A: water (0.1% TFA)-ACN, mobile phase B: ACN, Gradient: 40-60% B, 0-4.0 min; 100% B, 4.0-6.0 min; 10% B, 6.0-7.0 min, FlowRate: 25 mL/min. MS (ESI) m/z: 570.3 [M+H]$^+$ $^1$H NMR (400 MHz, CD$_3$OD) δ=8.65 (s, 1H), 8.15-8.10 (m, 1H), 8.07-8.02 (m, 1H), 7.06 (d, J=7.5 Hz, 1H), 6.82 (s, 1H), 6.76 (d, J=7.5 Hz, 1H), 4.76 (br. s., 1H), 4.01 (br. s., 1H), 3.41 (d, J=11.7 Hz, 1H), 3.14 (s, 1H), 2.94-2.75 (m, 4H), 2.07 (d, J=12.3 Hz, 2H), 1.99-1.92 (m, 3H), 1.85 (s, 4H), 1.62 (d, J=11.7 Hz, 1H), 1.15-1.05 (m, 1H), 0.93 (d, J=6.6 Hz, 3H), 0.62 (d, J=4.9 Hz, 1H), 0.42-0.24 (m, 2H), 0.07--0.07 (m, 1H)

TABLE 17

The compounds of Examples 74 and 75 were prepared in a similar manner to Example 73 using the appropriate starting material and reagents.

| Example | Structure | M.W. | Compound Name | LC/MS (ESI) observed [M + H]$^+$ |
|---|---|---|---|---|
| 74 | 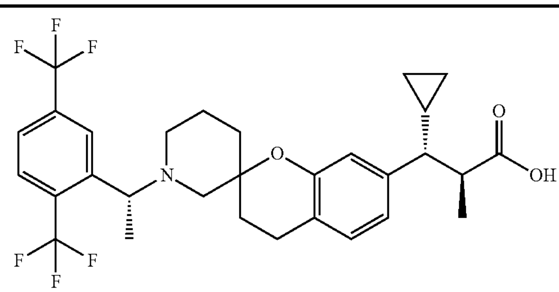 | 569.5 | (2S,3R)-3-((S or R)-1'-((R)-1-(2,5-bis(trifluoromethyl)phenyl)ethyl)spiro[chroman-2,3'-piperidin]-7-yl)-3-cyclopropyl-2-methylpropanoic acid | 596.2 |
| 75 | 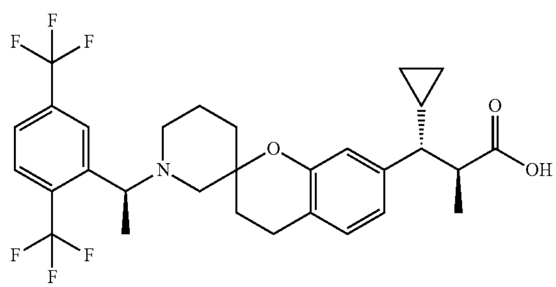 [SMILES: C[C@H](C(=O)O)[C@H](c1ccc2c(c1)OC1(CCCN([C@@H](C)c3cc(C(F)(F)F)ccc3C(F)(F)F)C1)CC2)C1CC1] | 569.5 | (2S,3R)-3-((S or R)-1'-((S)-1-(2,5-bis(trifluoromethyl)phenyl)ethyl)spiro[chroman-2,3'-piperidin]-7-yl)-3-cyclopropyl-2-methylpropanoic acid | 596.2 |

Example 74

$^1$H NMR (400 MHz, CD$_3$OD) δ=8.30 (s, 1H), 8.11 (d, J=8.4 Hz, 1H), 8.00 (d, J=8.2 Hz, 1H), 7.00 (d, J=7.5 Hz, 1H), 6.78 (s, 1H), 6.73 (s, 1H), 4.03-3.83 (m, 1H), 3.28-3.10 (m, 3H), 2.87-2.78 (m, 1H), 2.77-2.63 (m, 2H), 2.24 (d, J=13.9 Hz, 1H), 2.14-1.55 (m, 10H), 1.07 (d, J=5.1 Hz, 1H), 0.90 (d, J=6.8 Hz, 3H), 0.60 (s, 1H), 0.38-0.25 (m, 2H), 0.00--0.08 (m, 1H)

Example 75

$^1$H NMR (400 MHz, CD$_3$OD) δ=8.31 (s, 1H), 8.11 (d, J=8.4 Hz, 1H), 8.01 (d, J=8.2 Hz, 1H), 7.00 (d, J=7.5 Hz, 1H), 6.77 (s, 1H), 6.73 (s, 1H), 4.00-3.84 (m, 1H), 3.25 (s, 2H), 2.93-2.58 (m, 4H), 2.25 (d, J=11.5 Hz, 1H), 2.12-2.06 (m, 1H), 2.00-1.60 (m, 9H), 1.06 (d, J=4.9 Hz, 1H), 0.89 (d, J=6.8 Hz, 3H), 0.60 (s, 1H), 0.40-0.24 (m, 2H), 0.02--0.07 (m, 1H)

Example 76

(2S,3R)-3-cyclopropyl-3-(1'-(5-cyclopropyl-2-(trifluoromethoxy)benzyl)spiro[chroman-2,4'-piperidin]-7-yl)-2-methylpropanoic Acid

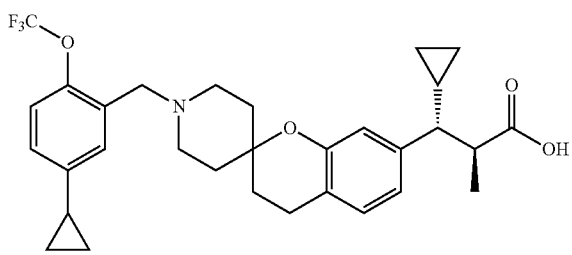 [SMILES: C[C@H](C(=O)O)[C@H](c1ccc2c(c1)OC1(CC2)CCN(Cc2cc(C3CC3)ccc2OC(F)(F)F)CC1)C1CC1]

Step A: (5-chloro-2-(trifluoromethoxy)phenyl)methanol

To a solution of 5-chloro-2-(trifluoromethoxy)benzaldehyde (300 mg, 1.34 mmol) in MeOH (0.5 mL) was added NaBH$_4$ (76.0 mg, 2.00 mmol) at 0° C. The reaction was stirred for 1 h, then saturated aqueous NH$_4$Cl (5 mL) was added, and the mixture was extracted with EtOAc (10 mL×3). The combined organic layers were washed with brine (10 mL), dried over Na$_2$SO$_4$ and filtered. The filtrate was concentrated by rotary evaporator to give the title compound, which was used directly in the next step. MS (ESI): m/z 249.8 [M+Na]$^+$

Step B: 5-chloro-2-(trifluoromethoxy)benzyl methanesulfonate

A solution of (5-chloro-2-(trifluoromethoxy)phenyl)methanol (349 mg, 1.54 mmol) and triethyl-amine (0.644 mL, 4.62 mmol) in DCM (10 mL) was cooled to 0° C. Methane-sulfonyl chloride (0.180 mL, 2.31 mmol) was added dropwise over 2 min. The reaction was stirred at 20° C. for 3 h, then saturated aqueous NaHCO$_3$ (20 mL) was added, and the mixture was extracted with DCM (50 mL×3). The combined organic layers were washed with brine (50 mL), dried over anhydrous Na$_2$SO$_4$ and filtered. The filtrate was concentrated by rotary evaporator to give the title compound, which was used directly in the next step.

Step C: (2S,3R)-methyl 3-(1'-(5-chloro-2-(trifluoromethoxy)benzyl)spiro[chroman-2,4'-piperidin]-7-yl)-3-cyclopropyl-2-methylpropanoate A suspension of 5-chloro-2-(trifluoromethoxy)benzyl methanesulfonate (469 mg, 1.54 mmol), (2S,3R)-methyl 3-cyclopropyl-2-methyl-3-(spiro[chroman-2,4'-piperidin]-7-yl)-propanoate (529 mg, 1.54 mmol) and Cs$_2$CO$_3$ (1254 mg, 3.85 mmol) in acetonitrile (15 mL) was heated to 80° C. for 18 h. Then the reaction was cooled to room temperature and filtered. The filter cake was washed with EtOAc (10 mL). The filtrate was concentrated by rotary evaporator to give a residue, which was purified by flash column chromatography (silica gel, PE:EtOAc=100:1~50:1, v/v) to give the title compound. MS (ESI): m/z 552.0 [M+H]$^+$ $^1$H NMR (400 MHz, CDCl$_3$): δ=7.61-7.56 (m, 1H), 7.22-7.18 (m, 1H), 7.13 (d, J=8.2 Hz, 1H), 6.95 (d, J=7.4 Hz, 1H), 6.65-6.57 (m, 2H), 3.70 (s, 3H), 3.56 (s, 2H), 2.83-2.68 (m, 3H), 2.62-2.46 (m, 4H), 1.89-1.74 (m, 5H), 1.71-1.59 (m, 2H), 1.08-0.98 (m, 1H), 0.92 (d, J=7.0 Hz, 3H), 0.56-0.46 (m, 1H), 0.37-0.26 (m, 1H), 0.24-0.16 (m, 1H), 0.05--0.05 (m, 1H)

Step D: (2S,3R)-methyl 3-cyclopropyl-3-(1'-(5-cyclopropyl-2-(trifluoromethoxy)-benzyl)-spiro[chroman-2,4'-piperidin]-7-yl)-2-methylpropanoate A flask containing (2S,3R)-methyl 3-(1'-(5-chloro-2-(trifluoromethoxy)benzyl)spiro-[chroman-2,4'-piperidin]-7-yl)-3-cyclopropyl-2-methylpropanoate (100 mg, 0.181 mmol), cyclopropylboronic acid (31.1 mg, 0.362 mmol), 2-dicyclohexylphosphino-2',6'-dimethoxybiphenyl (7.44 mg, 0.0180 mmol), tripotassium phosphate (154 mg, 0.725 mmol) and palladium(II) acetate (2.03 mg, 9.06 μmol) was evacuated and backfilled with nitrogen three times. To the flask was added dioxane (1.5 mL) and water (0.15 mL). The reaction was heated to 85° C. for 24 h, then diluted with water (5 mL) and extracted with EtOAc (10 mL×3). The combined organic layers were washed with brine (10 mL), dried over Na$_2$SO$_4$ and filtered. The filtrate was concentrated by rotary evaporator to give a residue, which was purified by preparative TLC (silica gel, PE:EtOAc=5:1, v/v) to give the title compound. MS (ESI): m/z 558.2 [M+H]$^+$

Step E: (2S,3R)-3-cyclopropyl-3-(1'-(5-cyclopropyl-2-(trifluoromethoxy)-benzyl)-spiro[chroman-2,4'-piperidin]-7-yl)-2-methylpropanoic Acid To a solution of (2S,3R)-methyl 3-cyclopropyl-3-(1'-(5-cyclopropyl-2-(trifluoromethoxy)benzyl)-spiro[chroman-2,4'-piperidin]-7-yl)-2-methylpropanoate (84.0 mg, 0.151 mmol) in MeOH (1 mL), THF (1 mL) and water (1 mL) was added lithium hydroxide hydrate (95.0 mg, 2.26 mmol). The reaction was heated to 55° C. for 12 hours, then cooled to room temperature and neutralized to pH 7 with concentrated HCl. The solvents were removed by rotary evaporator to give a residue, which was dissolved in MeCN and DMSO and filtered. The filtrate was purified by preparative HPLC to give the title compound. The title compound was treated with 1 equivalent of aqueous NaOH (10 wt %) and lyophilizated to give the sodium salt of the title compound. Preparative HPLC conditions: Column: Waters XSELECT C18 150*30 mm*5 um; Condition: water (0.1% TFA)-ACN; Begin B: 36; End B: 66; Gradient Time (min): 10; 100% B Hold Time (min): 2; FlowRate (mL/min): 25; Injections: 7. MS (ESI): m/z 542.1 [M−H]$^-$ $^1$H NMR (400 MHz, CD$_3$OD): δ=7.42 (s, 1H), 7.39-7.29 (m, 2H), 7.03 (d, J=8.2 Hz, 1H), 6.75-6.69 (m, 2H), 4.53-4.40 (m, 2H), 3.52-3.36 (m, 4H), 2.87-2.68 (m, 3H), 2.17-1.80 (m, 8H), 1.13-1.02 (m, 3H), 0.90 (d, J=6.8 Hz, 3H), 0.80-0.73 (m, 2H), 0.64-0.54 (m, 1H), 0.38-0.23 (m, 2H), 0.02--0.09 (m, 1H)

TABLE 18

The compound of Example 77 was prepared in a similar manner to Example 76 using the appropriate starting material and reagents.

| Example | Structure | M.W. | Compound Name | LC/MS (ESI) observed [M + H]+ |
|---|---|---|---|---|
| 77 | 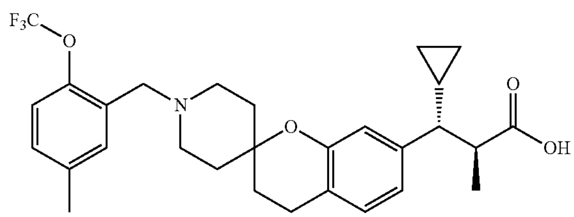 [SMILES: Cc1ccc(OC(F)(F)F)c(CN2CCC3(CCc4ccc([C@H](C5CC5)[C@H](C)C(=O)O)cc4O3)CC2)c1] | 517.58 | (2S,3R)-3-cyclopropyl-2-methyl-3-(1'-(5-methyl-2-(trifluoromethoxy)benzyl)spiro[chroman-2,4'-piperidin]-7-yl)propanoic acid | 518.3 |

Example 77

¹H NMR (400 MHz, CD₃OD): δ=7.43 (s, 1H), 7.27-7.16 (m, 2H), 6.97 (d, J=7.7 Hz, 1H), 6.65 (d, J=7.7 Hz, 1H), 6.62 (s, 1H), 3.79 (s, 2H), 2.88-2.65 (m, 7H), 2.37 (s, 3H), 1.94-1.68 (m, 7H), 1.15-1.02 (m, 1H), 0.89 (d, J=6.8 Hz, 3H), 0.64-0.51 (m, 1H), 0.40-0.23 (m, 2H), 0.02--0.09 (m, 1H)

Example 78

(2S,3R)-3-(1'-((R or S)-1-(5-chloro-2-fluorophenyl)ethyl)spiro[chroman-2,4'-piperidin]-7-yl)-3-cyclopropyl-2-methylpropanoic Acid

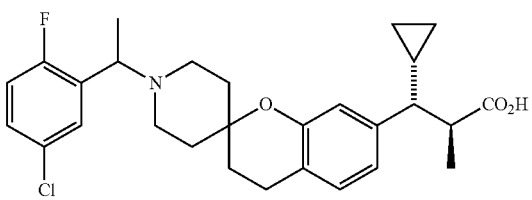 [SMILES: CC(c1cc(Cl)ccc1F)N1CCC2(CCc3ccc([C@H](C4CC4)[C@H](C)C(=O)O)cc3O2)CC1]

Step A: (5-chloro-2-fluorophenyl)methanol

To a solution of 5-chloro-2-fluorobenzoic acid (600 mg, 3.44 mmol) in THF (10 mL) was added BH₃.DMS (0.687 mL, 6.87 mmol) dropwise over 2 min at 0° C. under nitrogen. The reaction was stirred at 0° C. for 0.5 h, at 20° C. for 0.5 h, and at 80° C. for 2 h. Then the reaction was quenched by the dropwise addition of MeOH (20 mL) at 0° C. The resulting mixture was concentrated under reduced pressure to give the title compound, which was used directly in the next step without further purification. 1H NMR (400 MHz, DMSO-d6) δ=7.52-7.43 (m, 1H), 7.40-7.31 (m, 1H), 7.21 (t, J=9.2 Hz, 1H), 5.40 (t, J=5.7 Hz, 1H), 4.53 (d, J=5.7 Hz, 2H)

Step B: 5-chloro-2-fluorobenzaldehyde

To a solution of (5-chloro-2-fluorophenyl)-methanol (450 mg, 2.80 mmol) in DCM (8 mL) was added DMP (1.78 g, 4.20 mmol). The reaction was stirred at 20° C. for 1 h, then quenched by the addition of 1N NaOH (15 mL) and water (15 mL), and extracted with DCM (20 mL×3). The combined organic layers were washed with brine (40 mL), dried over Na₂SO₄ and filtered. The filtrate was concentrated under reduced pressure to give a residue, which was purified by prep-TLC (SiO₂, PE:EtOAc=5:1, v/v) to give the title compound. ¹H NMR (400 MHz, DMSO-d₆) δ=10.15 (s, 1H), 7.92-7.75 (m, 2H), 7.49 (t, J=9.6 Hz, 1H)

Step C: 1-(5-chloro-2-fluorophenyl)ethanol

To a solution of 5-chloro-2-fluorobenzaldehyde (200 mg, 1.261 mmol) in THF (3 mL) was added methylmagnesium bromide (1.05 mL, 3.15 mmol) dropwise at 0° C. under nitrogen. The reaction was stirred at 0° C. for 0.5 h and at 20° C. for 1 h. Then the reaction mixture was poured slowly into saturated NH₄Cl solution (5 mL) at 0° C., and water (5 mL) was added. The mixture was extracted with EtOAc (10 mL×2). The combined organic layers were washed with brine (10 mL), dried over Na₂SO₄ and filtered. The filtrate was concentrated under reduced pressure to give a residue, which was purified by prep-TLC (SiO₂, PE:EtOAc=5:1, v/v) to give the title compound. ¹H NMR (400 MHz, DMSO-d₆) δ=7.49 (dd, J=2.5, 6.3 Hz, 1H), 7.39-7.28 (m, 1H), 7.19 (t, J=9.3 Hz, 1H), 5.45 (d, J=4.6 Hz, 1H), 5.00-4.89 (m, 1H), 1.32 (d, J=6.4 Hz, 3H)

Step D: 1-(5-chloro-2-fluorophenyl)ethyl methanesulfonate

To a solution of 1-(5-chloro-2-fluorophenyl)ethanol (196 mg, 1.12 mmol) in DCM (3 mL) was added TEA (0.469 mL, 3.37 mmol), followed by the dropwise addition of MsCl (0.175 mL, 2.245 mmol) over 1 min at 0° C. under nitrogen. The reaction was stirred at 0° C. for 1 h. Then water (10 mL) was added to the mixture at 0° C. and the mixture was extracted with DCM (5 mL×3). The combined organic layers were washed with brine (10 mL), dried over anhydrous MgSO₄ and filtered. The filtrate was concentrated in vacuo to give the title compound, which was used directly in the next step without further purification. ¹H NMR (400 MHz, DMSO-d₆) δ=7.61 (dd, J=2.3, 6.1 Hz, 1H), 7.54-7.45 (m, 1H), 7.33 (t, J=9.5 Hz, 1H), 5.90 (q, J=6.6 Hz, 1H), 3.20 (s, 3H), 1.64 (d, J=6.6 Hz, 3H)

Step E: (2S,3R)-methyl 3-(1'-((RS)-1-(5-chloro-2-fluorophenyl)ethyl)spiro[chroman-2,4'-piperidin]-7-yl)-3-cyclopropyl-2-methylpropanoate To a solution of (2S,3R)-methyl 3-cyclopropyl-2-methyl-3-(spiro[chroman-2,4'-piperidin]-7-yl)-propanoate (125 mg, 0.364 mmol) in MeCN (3 mL) were added sodium iodide (164 mg, 1.09 mmol), 1-(5-chloro-2-fluorophenyl)ethyl methanesulfonate (184 mg, 0.728 mmol) and K$_2$CO$_3$ (251 mg, 1.82 mmol) under nitrogen. The reaction was stirred at 80° C. for 12 h. Then water (10 mL) was added to the reaction mixture and the mixture was extracted with EtOAc (10 mL×3). The combined organic layers were washed with brine (20 mL), dried over anhydrous MgSO$_4$ and filtered. The filtrate was concentrated in vacuo to give a residue, which was purified by prep-TLC (SiO$_2$, PE/EtOAc=10:1, v/v)) to give the title compound. MS (ESI) m/z: 500.3 [M+H]$^+$ Step F: (2S,3R)-3-(1'-((RS)-1-(5-chloro-2-fluorophenyl)ethyl)spiro[chroman-2,4'-piperidin]-7-yl)-3-cyclopropyl-2-methylpropanoic Acid To a solution of (2S,3R)-methyl-3-(1'-(1-(5-chloro-2-fluorophenyl)ethyl)spiro[chroman-2,4'-piperidin]-7-yl)-3-cyclopropyl-2-methylpropanoate (125 mg, 0.250 mmol) in MeOH (1.5 mL), THF (1.5 mL) and water (1.5 mL) was added LiOH (180 mg, 7.50 mmol) under nitrogen. The reaction mixture was stirred at 55° C. for 24 h, then concentrated in vacuo to give a residue. Water (15 mL) was added to the residue and citric acid was added to adjust the pH of the mixture to pH-5. Then the mixture was extracted with EtOAc (10 mL×3). The combined organic layers were washed with brine (15 mL), dried over anhydrous MgSO$_4$ and filtered. The filtrate was concentrated under reduced pressure to give the title compound, which was used directly in the next step without further purification. MS (ESI) m/z: 486.2 [M+H]$^+$ Step G: (2S,3R)-3-(1'-((R or S)-1-(5-chloro-2-fluorophenyl)ethyl)spiro[chroman-2,4'-piperidin]-7-yl)-3-cyclopropyl-2-methylpropanoic Acid (2S,3R)-3-(1'-((RS)-1-(5-chloro-2-fluorophenyl)ethyl)spiro[chroman-2,4'-piperidin]-7-yl)-3-cyclopropyl-2-methylpropanoic acid (85.0 mg, 0.175 mmol) was separated into individual diastereoisomers using SFC (SPc Conditions: Instrument: Berger MultiGram™ SFC, Mettler Toledo Co, Ltd SFC-AD (12#116) Method: Column: Chiralpak AD-3 100×4.6 mm I.D., 3 um, mobile phase: A: CO$_2$B:ethanol (0.05% DEA), Gradient: from 5% to 40% of B in 4.5 min and hold 40% for 2.5 min, then 5% of B for 1 min, Flow rate: 2.8 mL/min, Column temp: 40° C.) to give the first peak (2S,3R)-3-(1'-((R or S)-1-(5-chloro-2-fluorophenyl)ethyl)spiro[chroman-2,4'-piperidin]-7-yl)-3-cyclopropyl-2-methylpropanoic acid, and the second peak (2S,3R)-3-(1'-((S or R)-1-(5-chloro-2-fluorophenyl)ethyl)spiro[chroman-2,4'-piperidin]-7-yl)-3-cyclopropyl-2-methylpropanoic acid. To a solution of each individual diastereoisomer of the title compound in MeCN (1 mL) and water (1 mL) was added an aqueous solution of NaOH (1.0 eq, 0.5 M), and the mixture was stirred for 1 h at room temperature. Then the reaction mixture was lyophilized to give the sodium salt of each diastereoisomer of the title compound. Example 78A: MS (ESI) m/z: 486.2 [M−H]$^+$ $^1$H NMR (400 MHz, CD$_3$OD) δ=7.56-7.49 (m, 1H), 7.37-7.28 (m, 1H), 7.13 (t, J=9.4 Hz, 1H), 6.96 (d, J=7.8 Hz, 1H), 6.63 (d, J=7.8 Hz, 1H), 6.54 (s, 1H), 4.08-3.99 (m, 1H), 2.97 (d, J=10.6 Hz, 1H), 2.80-2.48 (m, 6H), 1.95-1.70 (m, 6H), 1.66 (d, J=10.2 Hz, 1H), 1.46 (d, J=6.7 Hz, 3H), 1.12-0.99 (m, 1H), 0.88 (d, J=6.7 Hz, 3H), 0.62-0.51 (m, 1H), 0.38-0.22 (m, 2H), 0.01--0.10 (m, 1H) Example 78B: MS (ESI) m/z: 486.2 [M−H]$^{+1}$ $^1$H NMR (400 MHz, CD$_3$OD) δ=7.58-7.49 (m, 1H), 7.38-7.28 (m, 1H), 7.13 (t, J=9.2 Hz, 1H), 6.96 (d, J=7.8 Hz, 1H), 6.63 (d, J=7.4 Hz, 1H), 6.53 (s, 1H), 4.10-3.98 (m, 1H), 2.98 (d, J=10.6 Hz, 1H), 2.82-2.49 (m, 6H), 1.95-1.71 (m, 6H), 1.70-1.58 (m, 1H), 1.46 (d, J=6.7 Hz, 3H), 1.12-0.99 (m, 1H), 0.88 (d, J=6.7 Hz, 3H), 0.62-0.51 (m, 1H), 0.40-0.22 (m, 2H), 0.01--0.11 (m, 1H)

Example 79

(2S,3R)-3-cyclopropyl-3-(1'-((R or S)-1-(3,5-dichloro-2-(difluoromethoxy)phenyl)-ethyl)spiro[chroman-2,4'-piperidin]-7-yl)-2-methylpropanoic Acid

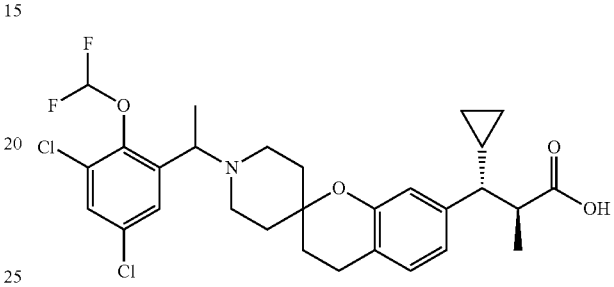

Step A:
3,5-dichloro-2-(difluoromethoxy)benzaldehyde

Into a 10 mL vial was placed 3,5-dichloro-2-hydroxybenzaldehyde (140 mg, 0.733 mmol), acetonitrile (3.5 mL), THF (3.50 mL) and 2.5 M aqueous KOH (3.52 mL, 8.80 mmol). The resulting yellow mixture was cooled to −70° C. and stirred rapidly. Then difluoromethyl trifluoromethanesulfonate (1375 mg, 4.40 mmol) was added at once. The reaction was stirred vigorously for 1 h at −70° C. and at 0° C. for 20 min. Then the reaction solvent was removed by rotary evaporator to give a residue, which was diluted with 10 mL of brine and extracted with EtOAc (10 mL×3). The combined organic layers were dried over MgSO$_4$ and filtered. The filtrate was concentrate by rotary evaporator to give a residue, which was purified by preparative TLC (silica gel, PE:EtOAc=10:1, v/v) to give the title compound. MS (ESI): m/z 278.9 [M+K]$^+$ Step B:
3,5-dichloro-2-(difluoromethoxy)benzaldehyde To a solution of 3,5-dichloro-2-(difluoromethoxy)benzaldehyde (135 mg, 0.560 mmol) in THF (5 mL) was added methylmagnesium bromide (0.280 mL, 0.840 mmol) at 0° C. The resulting solution was stirred at 0° C. for 20 min and at 10° C. for 2 h. Then the reaction was quenched with saturated aqueous NH$_4$Cl (5 mL). The mixture was extracted with EtOAc (5 mL×3). The combined organic layers were washed with brine (5 mL×2), dried over Na$_2$SO$_4$ and filtered. The filtrate was concentrated by rotary evaporator to give a residue, which was purified by preparative HPLC to give the title compound. Preparative HPLC conditions: Column: Waters XSELECT C18 150*30 mm*5 um; Condition: water (0.1% TFA)-ACN; Begin B: 35; End B: 65; Gradient Time (min): 10; 100% B Hold Time (min): 2; FlowRate (ml/min): 25; Injections: 5. $^1$H NMR (400 MHz, CDCl$_3$): δ=7.53 (d, J=1.8 Hz, 1H), 7.38 (d, J=1.8 Hz, 1H), 6.57 (dd, J=73.2, 75.6 Hz, 1H), 5.30 (q, J=6.3 Hz, 1H), 1.48 (d, J=6.2 Hz, 3H)

Step C: 1-(3,5-dichloro-2-(difluoromethoxy)phenyl)ethyl methanesulfonate

A solution of 1-(3,5-dichloro-2-(difluoromethoxy)phenyl)ethanol (40.0 mg, 0.156 mmol) and Et$_3$N (0.0650 mL, 0.467 mmol) in DCM (2 mL) was cooled to 0° C. Ms-Cl (0.018 mL, 0.233 mmol) was added dropwise over 2 min. The reaction was stirred at 20° C. for 2 h, then saturated aqueous NaHCO$_3$. (5 mL) was added. The mixture was extracted with DCM (5 mL×3). The combined organic layers were washed with brine (5 mL), dried over anhydrous Na$_2$SO$_4$ and filtered. The filtrate was concentrated by rotary evaporator to give the title compound, which was used directly in the next step.

Step D: (2S,3R)-methyl 3-cyclopropyl-3-(1'-(1-(3,5-dichloro-2-(difluoromethoxy)-phenyl)-ethyl)spiro[chroman-2,4'-piperidin]-7-yl)-2-methylpropanoate A suspension of 1-(3,5-dichloro-2-(difluoromethoxy)phenyl)ethyl methanesulfonate (65.0 mg, 0.194 mmol), (2S,3R)-methyl 3-cyclopropyl-2-methyl-3-(spiro[chroman-2,4'-piperidin]-7-yl)propanoate (73.3 mg, 0.213 mmol) and Cs$_2$CO$_3$ (126 mg, 0.388 mmol) in MeCN (1 mL) was heated to 80° C. for 18 h. The reaction was cooled to room temperature and filtered. The filter cake was washed with EtOAc (3 mL). The filtrate was concentrated by rotary evaporator to give a residue, which was purified by preparative TLC (silica gel, PE:EtOAc=10:1, v/v) to give the title compound. MS (ESI): m/z 582.2 [M+H]$^+$

Step E: (2S,3R)-3-cyclopropyl-3-(1'-(1-(3,5-dichloro-2-(difluoromethoxy)phenyl)-ethyl)-spiro[chroman-2,4'-piperidin]-7-yl)-2-methylpropanoic Acid To a solution of (2S,3R)-methyl 3-cyclopropyl-3-(1'-(1-(3,5-dichloro-2-(difluoromethoxy)-phenyl)-ethyl)spiro[chroman-2,4'-piperidin]-7-yl)-2-methylpropanoate (114, 0.196 mmol) in water (0.5 mL), THF (0.5 mL) and MeOH (0.5 mL) was added lithium hydroxide monohydrate (123 mg, 2.94 mmol). The reaction was heated to 55° C. for 12 hours, then cooled to room temperature and neutralized to pH 7 with concentrated HCl. The solvents were removed by rotary evaporator to give a residue, which was dissolved in MeCN and DMSO and filtered. The filtrate was purified by preparative HPLC to give the title compound. Preparative HPLC conditions: Column: Waters XSELECT C18 150*30 mm*5 um; Condition: water (0.1% TFA)-ACN; Begin B: 27; End B: 57; Gradient Time (min): 10; 100% B Hold Time (min): 2; FlowRate (mL/min): 25; Injections: 7. MS (ESI): m/z 568.1 [M+H]$^+$

Step F: (2S,3R)-3-cyclopropyl-3-(1'-((R or S)-1-(3,5-dichloro-2-(difluoro-methoxy)-phenyl)-ethyl)spiro[chroman-2,4'-piperidin]-7-yl)-2-methylpropanoic Acid, and (2S,3R)-3-cyclopropyl-3-(1'-((S or R)-1-(3,5-dichloro-2-(difluoromethoxy)phenyl)-ethyl) spiro-[chroman-2,4'-piperidin]-7-yl)-2-methylpropanoic Acid (2S,3R)-3-cyclopropyl-3-(1'-(1-(3,5-dichloro-2-(difluoromethoxy)phenyl)ethyl)spiro[chroman-2,4'-piperidin]-7-yl)-2-methylpropanoic acid (30.0 mg, 0.0530 mmol) was separated into individual diastereoisomers by SFC (SFC separation conditions: Column: AD (250 mm*30 mm, 5 um); Condition: Base-MeOH; FlowRate (mL/min): 60 mL/min) and further purified by preparative HPLC to give (2S,3R)-3-cyclopropyl-3-(1'-((R or S)-1-(3,5-dichloro-2-(difluoromethoxy)-phenyl)-ethyl)spiro[chroman-2,4'-piperidin]-7-yl)-2-methylpropanoic acid, and (2S,3R)-3-cyclopropyl-3-(1'-((S or R)-1-(3,5-dichloro-2-(difluoromethoxy)phenyl)-ethyl)spiro[chroman-2,4'-piperidin]-7-yl)-2-methylpropanoic acid. Preparative HPLC conditions: Column: Waters Xbridge Prep OBD C18 150*30 5 um; Condition: water (0.05% ammonia hydroxide v/v)-ACN; Begin B: 35; End B: 65; Gradient Time (min): 10; 100% B Hold Time (min): 2; FlowRate (mL/min): 25; Injections: 2. MS (ESI): m/z 568.2 [M+H]$^+$ $^1$H NMR (400 MHz, CD$_3$OD): δ=7.59 (d, J=2.2 Hz, 1H), 7.53 (d, J=2.2 Hz, 1H), 7.05-6.66 (m, 2H), 6.63 (d, J=7.7 Hz, 1H), 6.58 (s, 1H), 4.05 (q, J=6.5 Hz, 1H), 2.96-2.87 (m, 1H), 2.79-2.66 (m, 3H), 2.59-2.47 (m, 3H), 1.92-1.56 (m, 7H), 1.36 (d, J=6.6 Hz, 3H), 1.13-1.02 (m, 1H), 0.89 (d, J=6.8 Hz, 3H), 0.63-0.53 (m, 1H), 0.38-0.24 (m, 2H), 0.02--0.09 (m, 1H)

TABLE 19

The compound of Example 80 was prepared in a similar manner to Example 79 using the appropriate starting material and reagents.

| Example | Structure | M.W. | Compound Name | LC/MS (ESI) observed [M + H]$^+$ |
|---|---|---|---|---|
| 80 | 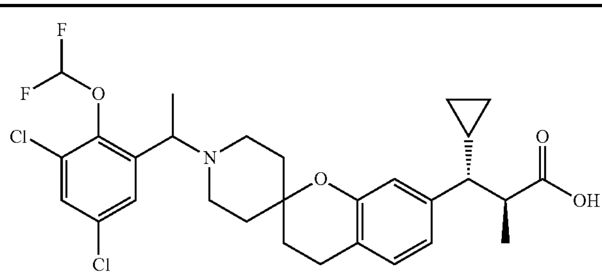 | 568.48 | (2S,3R)-3-cycloprop-3-(1'-((S or R)-1-(3,5-dichloro-2-(difluoromethoxy)phenyl)-ethyl)spiro[chroman-2,4'-piperidin]-7-yl)-2-methylpropanoic acid | 568.2 |

Example 80

$^1$H NMR (400 MHz, CD$_3$OD): δ=7.59 (d, J=2.4 Hz, 1H), 7.51 (d, J=2.4 Hz, 1H), 7.05-6.65 (m, 2H), 6.63 (d, J=7.7 Hz, 1H), 6.58 (s, 1H), 4.01 (q, J=6.5 Hz, 1H), 2.96-2.83 (m, 1H), 2.79-2.62 (m, 3H), 2.56-2.44 (m, 3H), 1.94-1.54 (m, 7H), 1.35 (d, J=6.8 Hz, 3H), 1.12-1.00 (m, 1H), 0.87 (d, J=6.8 Hz, 3H), 0.61-0.50 (m, 1H), 0.41-0.31 (m, 1H), 0.31-0.21 (m, 1H), 0.00--0.11 (m, 1H)

Example 81

(2S,3R)-3-((1R,5S)-3-((R)-1-(2,5-bis(trifluoromethyl)phenyl)ethyl)-3-azaspiro[-bicyclo[3.2.1]octane-8,2'-chroman]-7'-yl)-3-cyclopropyl-2-methyl-propanoic Acid

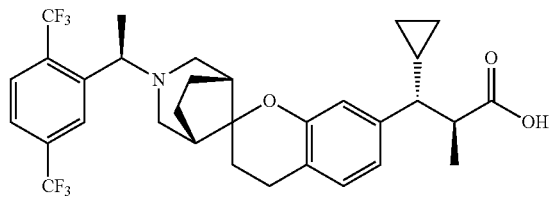 [SMILES: C[C@H](C(=O)O)[C@H](c1ccc2c(c1)OC1(CC2)[C@@H]2CC[C@H]1CN([C@H](C)c1cc(C(F)(F)F)ccc1C(F)(F)F)C2)C1CC1]

Step A: (1R,5S)-tert-butyl 7'-((1R,2S)-1-cyclopropyl-3-methoxy-2-methyl-3-oxopropyl)-4'-oxo-3-azaspiro[bicyclo[3.2.1]octane-8,2'-chroman]-3-carboxylate To a solution of (2S,3R)-methyl 3-(4-acetyl-3-hydroxyphenyl)-3-cyclopropyl-2-methyl-propanoate (1.50 g, 5.43 mmol) and (1R,5S)-tert-butyl 8-oxo-3-azabicyclo[3.2.1]-octane-3-carboxylate (1.28 g, 5.70 mmol) in MeOH (10 mL) was added pyrrolidine (1.35 mL, 16.3 mmol). The reaction mixture was stirred at 55° C. for 23 h. The solvent was removed under reduced pressure to give the crude product, which was purified by column chromatography (SiO$_2$, PE:EA=100:1 to PE:EA=20:1, v/v) to give the title compound. MS (ESI) m/z: 469.2 [M−56+MeCN+1]$^+$ Step B: (1R,5S)-tert-butyl 7'-((1R,2S)-1-cyclopropyl-3-methoxy-2-methyl-3-oxopropyl)-4'-oxo-3-azaspiro[bicyclo[3.2.1]octane-8,2'-chroman]-3-carboxylate The compound (1R,5S)-tert-butyl 7'-((1R,2S)-1-cyclopropyl-3-methoxy-2-methyl-3-oxo-propyl)-4'-oxo-3-azaspiro[bicyclo[3.2.1]octane-8,2'-chroman]-3-carboxylate (2.10 g, 4.34 mmol) was separated into individual diastereoisomers by SFC (SFC conditions: Column: Lux Cellulose-2 150×4.6 mm I.D., 3 m, mobile phase: A: CO$_2$B: ethanol (0.05% DEA), gradient: from 5% to 40% of B in 5.5 min and hold 40% for 3 min, then 5% of B for 1.5 min, Flow rate: 2.5 mL/min Column temperature: 40° C.) to give the first peak (Rt=3.726 min) (1R,5S)-tert-butyl-7'-((1R,2S)-1-cyclopropyl-3-methoxy-2-methyl-3-oxopropyl)-4'-oxo-3-azaspiro[bicyclo[3.2.1]octane-8,2'-chroman]-3-carboxylate, and the second peak (Rt=3.859 min) (1R,5S)-tert-butyl 7'-((1R,2S)-1-cyclopropyl-3-methoxy-2-methyl-3-oxopropyl)-4'-oxo-3-azaspiro[bicyclo[3.2.1]octane-8,2'-chroman]-3-carboxylate. MS (ESI) m/z: 469.2 [M−56+MeCN+1]$^+$ $^1$H NMR (400 MHz, CDCl$_3$) δ=7.82 (d, J=8.2 Hz, 1H), 6.88-6.82 (m, 2H), 3.74 (s, 3H), 3.67-3.59 (m, 1H), 3.49-3.40 (m, 1H), 3.37-3.30 (m, 1H), 2.78 (s, 3H), 2.27-2.13 (m, 2H), 2.01-1.93 (m, 1H), 1.79 (br. s., 2H), 1.71-1.61 (m, 2H), 1.49 (s, 10H), 1.06 (br. s., 1H), 0.97 (d, J=6.7 Hz, 3H), 0.60 (br. s., 1H), 0.42-0.23 (m, 2H), 0.02 (br s, 1H)

Step C: (1R,5S)-tert-butyl 7'-((1R,2S)-1-cyclopropyl-3-methoxy-2-methyl-3-oxopropyl)-4'-hydroxy-3-azaspiro[bicyclo[3.2.1]octane-8,2'-chroman]-3-carboxylate To a solution of (1R,5S)-tert-butyl 7'-((1R,2S)-1-cyclopropyl-3-methoxy-2-methyl-3-oxopropyl)-4'-oxo-3-azaspiro[bicyclo[3.2.1]octane-8,2'-chroman]-3-carboxylate (440 mg, 0.910 mmol) in MeOH (10 mL) was added NaBH$_4$ (51.6 mg, 1.36 mmol) in portions. The reaction was stirred at 18° C. for 30 min. Then water (30 mL) was added to the mixture slowly, and the mixture was extracted with EtOAc (30 mL×3). The combined organic layers were washed with brine (60 mL), dried over anhydrous Na$_2$SO$_4$ and filtered. The filtrate was concentrated in vacuo to give the title compound, which was used directly in the next step. MS (ESI) m/z: 508.3 [M+Na]$^+$ Step D: (2S,3R)-methyl 3-cyclopropyl-2-methyl-3-((1R,5S)-3-azaspiro[bicycle [3.2.1]octane-82'-chroman]-7'-yl)propanoate To a solution of (1R,5S)-tert-butyl 7'-((1R,2S)-1-cyclopropyl-3-methoxy-2-methyl-3-oxopropyl)-4'-hydroxy-3-aza-spiro[bicyclo[3.2.1]octane-8,2'-chroman]-3-carboxylate (460 mg, 0.947 mmol) in DCM (5 mL) were added triethylsilane (2.5 mL, 15.6 mmol) and TFA (2.5 mL, 32.4 mmol). The reaction was stirred at 25° C. for 1 h, then the solvent was removed under reduced pressure to give a residue. Saturated aqueous NaHCO$_3$ was added to the residue to adjust the mixture pH to pH 9-10. Then the mixture was extracted with EtOAc (20 mL×3). The combined organic layers were washed with brine (30 mL), dried (MgSO$_4$) and filtered. The filtrate was concentrated in vacuo to give the title compound, which was used in the next step directly without further purification. MS (ESI) m/z: 370.2 [M+H]$^+$ Step E: (2S,3R)-methyl 3-((1R,5S)-3-((R)-1-(2,5-bis(trifluoromethyl)phenyl)ethyl)-3-azaspiro[bicyclo [3.2.1]octane-8,2'-chroman]-7'-yl)-3-cyclopropyl-2-methylpropanoate To a solution of (S)-1-(2,5-bis(trifluoromethyl)phenyl) ethyl methanesulfonate (123 mg, 0.365 mmol) in MeCN (2 mL) were added (2S,3R)-methyl 3-cyclopropyl-2-methyl-3-((1R,5 S)-3-azaspiro[bicyclo[3.2.1]octane-8,2'-chroman]-7'-yl)propanoate (90 mg, 0.244 mmol) and DIPEA (0.213 mL, 1.22 mmol) under a N$_2$ atmosphere. The reaction was stirred for 48 hours at 85° C. under a N$_2$ atmosphere, then concentrated in vacuo to give a residue, which was purified by Prep-TLC (SiO$_2$, PE:EtOAc=10:1, v/v) to afford the title compound. MS (ESI) m/z: 610.4 [M+H]$^+$ Step F: (2S,3R)-3-((1R,5S)-3-((R)-1-(2,5-bis(trifluoromethyl)phenyl)ethyl)-3-azaspiro[bicyclo[3.2.1] octane-8,2'-chroman]-7'-yl)-3-cyclopropyl-2-methyl-propanoic Acid To a solution of (2S,3R)-methyl 3-((1R,5S)-3-((R)-1-(2, 5-bis(trifluoromethyl)-phenyl)ethyl)-3-azaspiro[bicyclo [3.2.1]octane-8,2'-chroman]-7'-yl)-3-cyclopropyl-2-methylpropanoate (110 mg, 0.180 mmol) in MeOH (1.5 mL), THF (1.5 mL) and water (1.5 mL) was added lithium hydroxide (86 mg, 3.61 mmol) under N$_2$ atmosphere. The reaction mixture was stirred for 12 hours at 60° C. Then water (10 mL) was added and the mixture pH was adjusted with citric acid to pH 6-7. The mixture was extracted with EtOAc (10 mL×3). The combined organic layers were washed with brine (15 mL), dried over anhydrous Na2SO4 and filtered. The filtrate was evaporated under reduce pressure to give a residue, which was purified by Prep-HPLC (TFA) to give the title compound. LCMS (ESI) m/z 596.2 [M+H]+ $^1$H NMR (400 MHz, CD$_3$OD) δ=8.46 (br. s., 1H), 8.08-7.85 (m, 2H), 7.00 (d, J=7.4 Hz, 1H), 6.67 (d, J=7.4 Hz, 1H), 6.55 (s, 1H), 2.90-2.66 (m, 4H), 2.40-2.08 (m, 6H), 1.96-1.51 (m, 6H), 1.11-0.99 (m, 1H), 0.87 (d, J=6.7 Hz, 3H), 0.60-0.50 (m, 1H), 0.33-0.21 (m, 2H), −0.01--0.12 (m, 1H)

2H), 3.83 (br. s, 1H), 2.89-2.84 (m, 2H), 2.77-2.67 (m, 3H), 2.57 (d, J=10.4 Hz, 1H), 2.09-1.99 (m, 2H), 1.99-1.59 (m, 8H), 1.27 (d, J=6.4 Hz, 3H), 1.08-0.97 (m, 1H), 0.87 (d, J=6.6 Hz, 3H), 0.59-0.49 (m, 1H), 0.34-0.20 (m, 2H), 0.00--0.10 (m, 1H)

Example 83

$^1$H NMR (400 MHz, CD$_3$OD) δ=8.27 (s, 1H), 7.81 (d, J=8.4 Hz, 1H), 7.68 (d, J=7.9 Hz, 1H), 6.95 (d, J=7.9 Hz, 1H), 6.64-6.58 (m, 2H), 3.95-3.84 (m, 1H), 2.96-2.88 (m,

TABLE 20

The compounds of Examples 82-86 were prepared in a similar manner to Example 81 using the appropriate starting material and reagents.

| Example | Structure | M.W. | Compound Name | LC/MS (ESI) observed [M + Na]+ |
|---|---|---|---|---|
| 82 | 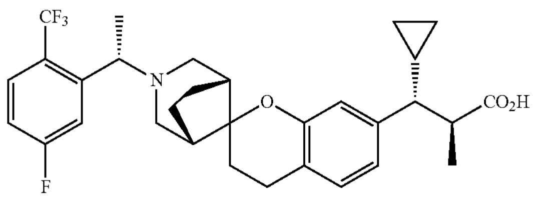 [SMILES: C[C@H](C(=O)O)[C@H](c1ccc2c(c1)OC1(CC2)[C@@H]2CC[C@H]1CN([C@@H](C)c1cc(F)ccc1C(F)(F)F)C2)C1CC1] | 545.61 | (2S,3R)-3-cyclopropyl-3-((1R,5S)-3-((S)-1-(5-fluoro-2-(trifluoro-methyl)phenyl)ethyl)-3-azaspiro[bicyclo[3.2.1]oc-tane-8,2'-chroman]-7'-yl)-2-methylpropanoic acid | 546.3 |
| 83 | 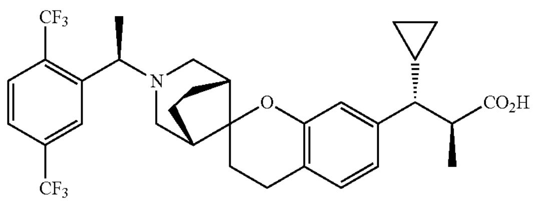 [SMILES: C[C@H](C(=O)O)[C@H](c1ccc2c(c1)OC1(CC2)[C@@H]2CC[C@H]1CN([C@H](C)c1cc(C(F)(F)F)ccc1C(F)(F)F)C2)C1CC1] | 595.62 | (2S,3R)-3-((1R,5S)-3-((R)-1-(2,5-bis(trifluoro-methyl)phenyl)ethyl)-3-azaspiro[bicyclo[3.2.1]oc-tane-8,2'-chroman]-7'-yl)-3-cyclopropyl-2-methylpropanoic acid | 594.2 |
| 84 | 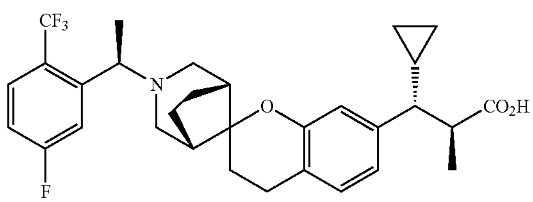 [SMILES: C[C@H](C(=O)O)[C@H](c1ccc2c(c1)OC1(CC2)[C@@H]2CC[C@H]1CN([C@H](C)c1cc(F)ccc1C(F)(F)F)C2)C1CC1] | 545.61 | (2S,3R)-3-cyclopropyl-3-((1R,5S)-3-((R)-1-(5-fluoro-2-(trifluoro-methyl)phenyl)ethyl)-3-azaspiro[bicyclo[3.2.1]oc-tane-8,2'-chroman]-7'-yl)-2-methylpropanoic acid | 546.3 |
| 85 | 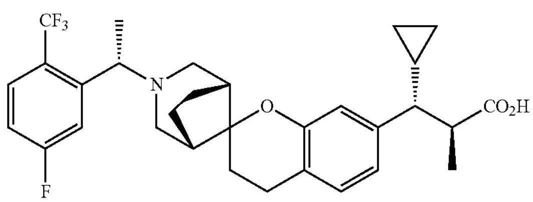 [SMILES: C[C@H](C(=O)O)[C@H](c1ccc2c(c1)OC1(CC2)[C@@H]2CC[C@H]1CN([C@@H](C)c1cc(F)ccc1C(F)(F)F)C2)C1CC1] | 545.61 | (2S,3R)-3-cyclopropyl-3-((1R,5S)-3-((S)-1-(5-fluoro-2-(trifluoro-methyl)phenyl)ethyl)-3-azaspiro[bicyclo[3.2.1]oc-tane-8,2'-chroman]-7'-yl)-2-methylpropanoic acid | 546.3 |
| 86 | 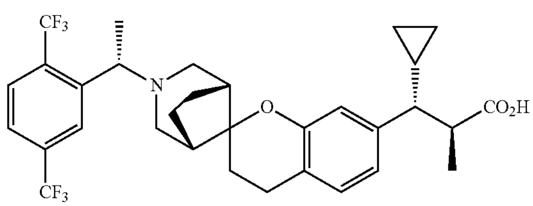 [SMILES: C[C@H](C(=O)O)[C@H](c1ccc2c(c1)OC1(CC2)[C@@H]2CC[C@H]1CN([C@@H](C)c1cc(C(F)(F)F)ccc1C(F)(F)F)C2)C1CC1] | 595.62 | (2S,3R)-3-((1R,5S)-3-((S)-1-(2,5-bis(trifluoro-methyl)phenyl)ethyl)-3-azaspiro[bicyclo[3.2.1]oc-tane-8,2'-chroman]-7'-yl)-3-cyclopropyl-2-methylpropanic acid | 594.2 |

Example 82

$^1$H NMR (400 MHz, CD$_3$OD) δ=7.67-7.60 (m, 2H), 7.11-7.04 (m, 1H), 6.94 (d, J=7.7 Hz, 1H), 6.63-6.58 (m, 2H), 2.81-2.68 (m, 3H), 2.63-2.54 (m, 1H), 2.10-1.53 (m, 10H), 1.30 (d, J=6.4 Hz, 3H), 1.11-1.01 (m, 1H), 0.88 (d, J=6.8 Hz, 3H), 0.62-0.50 (m, 1H), 0.36-0.22 (m, 2H), −0.01--0.09 (m, 1H)

Example 84

$^1$H NMR (400 MHz, CD$_3$OD) δ=8.27 (s, 1H), 7.83 (d, J=8.4 Hz, 1H), 7.69 (d, J=8.2 Hz, 1H), 6.95 (d, J=7.5 Hz, 1H), 6.61 (d, J=7.7 Hz, 1H), 6.50 (s, 1H), 3.95-3.82 (m, 1H), 3.13-3.01 (m, 1H), 2.82-2.61 (m, 4H), 2.39-2.29 (m, 1H), 2.23-2.11 (m, 4H), 2.10-1.79 (m, 5H), 1.59-1.49 (m, 1H), 1.30 (d, J=6.4 Hz, 3H), 1.11-0.98 (m, 1H), 0.87 (d, J=6.8 Hz, 3H), 0.60-0.49 (m, 1H), 0.34-0.22 (m, 2H), 0.00--0.12 (m, 1H)

Example 85

$^1$H NMR (400 MHz, CD$_3$OD) δ=7.94-7.82 (m, 2H), 7.43-7.32 (m, 1H), 7.00 (d, J=7.9 Hz, 1H), 6.68 (d, J=7.5 Hz, 1H), 6.55 (s, 1H), 2.96-2.63 (m, 4H), 2.44-2.12 (m, 6H), 2.02-1.58 (m, 6H), 1.10-0.97 (m, 1H), 0.86 (d, J=6.8 Hz, 3H), 0.60-0.48 (m, 1H), 0.34-0.21 (m, 2H), −0.03--0.13 (m, 1H)

Example 86

$^1$H NMR (400 MHz, CD$_3$OD) δ=8.46 (br. s., 1H), 8.08-7.89 (m, 2H), 7.01 (d, J=7.8 Hz, 1H), 6.67 (d, J=7.4 Hz, 1H), 6.55 (s, 1H), 2.88-2.66 (m, 4H), 2.39-2.10 (m, 6H), 2.01-1.80 (m, 3H), 1.71-1.53 (m, 3H), 1.09-1.00 (m, 1H), 0.87 (d, J=7.0 Hz, 3H), 0.59-0.51 (m, 1H), 0.33-0.21 (m, 2H), −0.02--0.11 (m, 1H)

Example 87

((2S,3R)-3-cyclopropyl-2-methyl-3-(3'-((3-(trifluoromethyl)pyridin-2-yl)amino)spiro[chroman-2,1'-cyclobutan]-7-yl)propanoic Acid

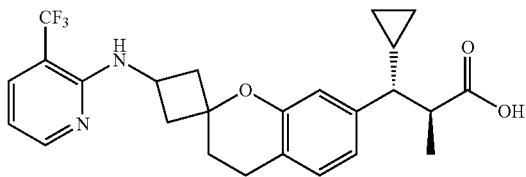 [SMILES: C[C@H](C(=O)O)[C@H](c1ccc2c(c1)OC1(CC2)CC(Nc2ncccc2C(F)(F)F)C1)C1CC1]

Step A: (2S,3R)-methyl 3-(3'-((tert-butoxycarbonyl)amino)-4-oxospiro[chroman-2,1'-cyclobutan]-7-yl)-3-cyclopropyl-2-methylpropanoate To a solution of (2S,3R)-methyl 3-(4-acetyl-3-hydroxyphenyl)-3-cyclopropyl-2-methylpropanoate (1.50 g, 5.43 mmol) and tert-butyl (3-oxocyclobutyl)carbamate (2.01 g, 10.9 mmol) in MeOH (10 mL) was added pyrrolidine (2.24 mL, 27.1 mmol). The reaction mixture was stirred at 55° C. for 23 h. Then the solvent was removed under reduced pressure to give the crude product, which was purified by column chromatography (SiO$_2$, PE:EA=100:1 to PE:EA=20:1, v/v) to give the title compound. MS (ESI) m/z: 466.2 [M+Na]$^+$ $^1$H NMR (400 MHz, CDCl$_3$) δ=7.79 (d, J=7.9 Hz, 1H), 6.83 (d, J=8.2 Hz, 1H), 6.77 (d, J=12.6 Hz, 1H), 5.31 (s, 1H), 4.76 (br. s., 1H), 3.73 (s, 3H), 2.89-2.78 (m, 3H), 2.71 (br. s., 2H), 2.26-2.16 (m, 1H), 2.11-2.01 (m, 1H), 1.94 (t, J=10.0 Hz, 1H), 1.44 (s, 9H), 1.09-0.99 (m, 1H), 0.95 (d, J=6.6 Hz, 3H), 0.60 (d, J=4.0 Hz, 1H), 0.41-0.22 (m, 2H), 0.04--0.05 (m, 1H)

Step B: (2S,3R)-methyl 3-(3'-((tert-butoxycarbonyl)amino)-4-oxospiro[chroman-2,1'-cyclobutan]-7-yl)-3-cyclopropyl-2-methylpropanoate (2S,3R)-methyl 3-(3'-((tert-butoxycarbonyl)amino)-4-oxospiro[chroman-2,1'-cyclobutan]-7-yl)-3-cyclopropyl-2-methylpropanoate (1.76 g, 3.97 mmol) was separated into individual diastereoisomers by SFC (SFC conditions: Column: Chiralpak AD-3 100×4.6 mm I.D., 3 um, mobile phase: A: CO$_2$B:ethanol (0.05% DEA), Gradient: from 5% to 40% of B in 4.5 min and hold 40% for 2.5 min, then 5% of B for 1 min, Flow rate: 2.8 mL/min Column temperature: 40° C.) to give the first peak (Rt=2.502 min) (2S,3R)-methyl 3-(3'-((tert-butoxycarbonyl)amino)-4-oxospiro[chroman-2,1'-cyclobutan]-7-yl)-3-cyclopropyl-2-methylpropanoate, and the second peak (3.218 min) (2S,3R)-methyl 3-(3'-((tert-butoxycarbonyl)amino)-4-oxospiro[chroman-2,1'-cyclobutan]-7-yl)-3-cyclopropyl-2-methylpropanoate. Peak 1: MS (ESI) m/z: 466.3 [M+H]+; Peak 2: MS (ESI) m/z: 466.3 [M+H]+

Step C: (2S,3R)-methyl 3-(3'-((tert-butoxycarbonyl)amino)-4-hydroxyspiro [chroman-2,1'-cyclobutan]-7-yl)-3-cyclopropyl-2-methylpropanoate To a solution of (2S,3R)-methyl 3-(3'-((tert-butoxycarbonyl)amino)-4-oxospiro-[chroman-2,1'-cyclobutan]-7-yl)-3-cyclopropyl-2-methylpropanoate (780 mg, 1.76 mmol) in MeOH (10 mL) was added NaBH$_4$ (100 mg, 2.64 mmol) in portions. The reaction mixture was stirred at 18° C. for 30 min. Then water (30 mL) was added slowly and the mixture was extracted with EtOAc (30 mL×3). The combined organic layers were washed with brine (60 mL), dried over anhydrous Na$_2$SO$_4$ and filtered. The filtrate was concentrated in vacuo to give the title compound, which was used directly in the next step. MS (ESI) m/z: 468.2 [M+Na]$^+$ $^1$H NMR (400 MHz, CDCl$_3$) δ=7.31-7.27 (m, 1H), 6.74 (d, J=7.8 Hz, 1H), 6.66 (s, 1H), 4.79 (br. s., 1H), 4.45 (br. s., 1H), 3.74 (s, 3H), 2.85-2.75 (m, 1H), 2.73-2.60 (m, 2H), 2.28-2.17 (m, 2H), 2.16-2.09 (m, 1H), 1.86 (t, J=10.0 Hz, 1H), 1.66 (br. s., 1H), 1.63-1.63 (m, 1H), 1.45 (s, 9H), 1.09-0.99 (m, 1H), 0.94 (d, J=6.7 Hz, 3H), 0.56 (br. s., 1H), 0.38-0.29 (m, 1H), 0.27-0.19 (m, 1H), 0.05--0.06 (m, 1H)

Step D: (2S,3R)-methyl 3-(3'-aminospiro[chroman-2,1'-cyclobutan]-7-yl)-3-cyclopropyl-2-methylpropanoate To a solution of (2S,3R)-methyl 3-(3'-((tert-butoxycarbonyl)amino)-4-hydroxyspiro[chroman-2,1'-cyclobutan]-7-yl)-3-cyclopropyl-2-methylpropanoate (540 mg, 1.21 mmol) in DCM (5 mL) was added triethylsilane (2.5 mL, 15.6 mmol) and TFA (2.5 mL, 32.4 mmol). The reaction mixture was stirred at 20° C. for 20 min. Then the solvent was removed under reduced pressure to give a residue. Saturated aqueous NaHCO$_3$ was added to the residue to adjust the pH to pH 9-10. The resulting mixture was extracted with EtOAc (20 mL×3). The combined organic layers were washed with brine (30 mL), dried (MgSO$_4$) and filtered. The filtrate was concentrated in vacuo to give the title compound, which was used in next step directly without further purification. MS (ESI) m/z: 371.2 [M+MeCN+H]$^+$

Step E: (2S,3R)-methyl 3-cyclopropyl-2-methyl-3-(3'-((3-(trifluoromethyl)pyridin-2-yl)amino)spiro [chroman-2,1'-cyclobutan]-7-yl)propanoate To a solution of 2-fluoro-3-(trifluoromethyl)pyridine (626 mg, 3.79 mmol) and (2S,3R)-methyl 3-cyclopropyl-2- methyl-3-(3'-((3-(trifluoromethyl)pyridin-2-yl)amino)spiro[chroman-2,1'-cyclobutan]-7-yl)propanoate (220 mg, 0.450 mmol) in NMP (4 mL) was added TEA (0.530 mL, 3.79 mmol). The mixture was stirred at 110° C. for 16 h. Then water (20 mL) was added, and the mixture was extracted with EtOAc (15 mL×3). The combined organic layers were washed with brine (30×mL), dried over anhydrous Na₂SO₄ and filtered. The filtrate was evaporated under reduced pressure to give a residue, which was purified by Prep-TLC (SiO₂, PE:EA=5:1, v/v) to give the title compound. LCMS (ESI) m/z: 475.2 [M+H]⁺

Step E: (2S,3R)-3-cyclopropyl-2-methyl-3-(3'-((3-(trifluoromethyl)pyridin-2-yl)amino)spiro[chroman-2,1'-cyclobutan]-7-yl)propanoic Acid To a solution of (2S,3R)-methyl 3-cyclopropyl-2-methyl-3-(3'-((3-(trifluoromethyl)pyridin-2-yl)-amino)spiro[chroman-2,1'-cyclobutan]-7-yl)propanoate (75.0 mg, 0.158 mmol) in MeOH (1.5 mL), THF (1.5 mL) and water (1.5 mL) was added lithium hydroxide (76 mg, 3.16 mmol) under a N₂ atmosphere. The reaction was stirred for 12 hours at 60° C. Then water (10 mL) was added, the mixture pH was adjusted with citric acid to pH 6-7, and the mixture was extracted with EtOAc (10 mL×3). The combined organic layers were washed with brine (15 mL), dried over anhydrous Na₂SO₄ and filtered. The filtrate was evaporated under reduced pressure to give a residue, which was purified by Pre-HPLC (base) to give the title compound. LC-MS (ESI) m/z 461.1 [M+H]⁺ ¹H NMR (400 MHz, CD₃OD) δ=8.21 (d, J=4.4 Hz, 1H), 7.73 (d, J=7.5 Hz, 1H), 6.91 (d, J=7.5 Hz, 1H), 6.71-6.58 (m, 3H), 4.76 (t, J=7.6 Hz, 1H), 2.77-2.57 (m, 5H), 2.17-2.09 (m, 2H), 2.01-1.85 (m, 3H), 1.10-0.99 (m, 1H), 0.83 (d, J=6.8 Hz, 3H), 0.53 (br. s., 1H), 0.44-0.35 (m, 1H), 0.27-0.18 (m, 1H), −0.03-−0.13 (m, 1H)

Example 89

(2S,3R)-3-cyclopropyl-2-methyl-3-(3'-(methyl(3-(trifluoromethyl)pyridin-2-yl)amino)spiro[chroman-2,1'-cyclobutan]-7-yl)propanoic Acid

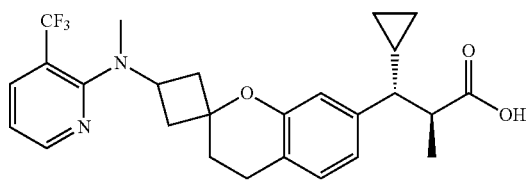

Step A: (2S,3R)-methyl 3-cyclopropyl-2-methyl-3-(3'-((3-(trifluoromethyl)pyridin-2-yl)amino)spiro[chroman-2,1'-cyclobutan]-7-yl)propanoate To a solution of (2S,3R)-methyl 3-cyclopropyl-2-methyl-3-(3'-((3-(trifluoromethyl)pyridin-2-yl)-amino)spiro[chroman-2,1'-cyclobutan]-7-yl)propanoate (150 mg, 0.316 mmol) and iodomethane (44.9 mg, 0.316 mmol) in DMF (4 mL) was added NaH (13.9 mg, 0.348 mmol) under a N₂ atmosphere. The reaction was stirred for 40 min at 20° C., then quenched with water (5 mL) and extracted with EtOAc (10 mL×3). The combined organic layers were washed with brine (15 mL), dried over anhydrous Na₂SO₄ and filtered. The filtrate was evaporated under reduced pressure to give the title compound, which was used directly in the next step. LCMS (ESI) m/z 511.2 [M+Na]⁺

Step B: (2S,3R)-3-cyclopropyl-2-methyl-3-(3'-(methyl(3-(trifluoromethyl)pyridine-2-yl)amino)spiro[chroman-2,1'-cyclobutan]-7-yl)propanoic Acid To a solution of (2S,3R)-methyl 3-cyclopropyl-2-methyl-3-(3'-(methyl(3-(trifluoromethyl)-pyridin-2-yl)amino)spiro

TABLE 21

The compound of Example 88 was prepared in a similar manner to Example 87 using the appropriate starting material and reagents.

| Example | Structure | M.W. | Compound Name | LC/MS (ESI) observed [M + H]⁺ |
|---|---|---|---|---|
| 88 | 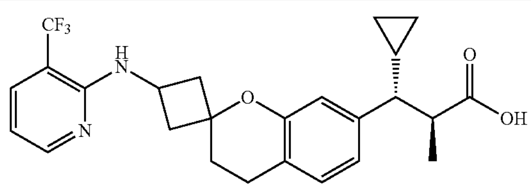 [SMILES: C[C@H](C(=O)O)[C@H](c1ccc2c(c1)OC1(CC2)CC(Nc2ncccc2C(F)(F)F)C1)C1CC1] | 460.49 | (2S,3R)-3-cyclopropyl-3-((1R,5S)-3-((R)-1-(5-fluoro-2-(trifluoromethyl)phenyl)ethyl)-3-azaspiro[bicyclo[3.2.1]octane-8,2'-chroman]-7'-yl)-2-methylpropanoic acid | 461.1 |

Example 88

¹H NMR (400 MHz, CD₃OD) δ=8.20 (d, J=4.2 Hz, 1H), 7.73 (d, J=7.5 Hz, 1H), 6.93 (d, J=7.7 Hz, 1H), 6.71-6.58 (m, 2H), 6.56 (s, 1H), 4.34-4.24 (m, 1H), 2.82-2.75 (m, 2H), 2.70-2.59 (m, 3H), 2.25-2.15 (m, 2H), 1.97 (t, J=6.3 Hz, 2H), 1.85 (t, J=9.9 Hz, 1H), 1.07-0.97 (m, 1H), 0.84 (d, J=6.8 Hz, 3H), 0.57-0.48 (m, 1H), 0.36-0.18 (m, 2H), −0.04-−0.13 (m, 1H)

[chroman-2,1'-cyclobutan]-7-yl)propanoate (100 mg, 0.205 mmol) in MeOH (1.5 mL), THF (1.5 mL) and water (1.5 mL) was added lithium hydroxide (98.0 mg, 4.09 mmol) under N₂ atmosphere. The reaction mixture was stirred at 60° C. for 12 h. Then water (10 mL) was added, the mixture pH was adjusted with citric acid to pH 6-7, and the mixture was extracted with EtOAc (10 mL×3). The combined organic layers were washed with brine (15 mL), dried over anhydrous Na$_2$SO$_4$ and filtered. The filtrate was evaporated under reduced pressure to give a residue, which was purified by Prep-HPLC to give the title compound. LCMS (ESI) m/z 475.1 [M+H]$^+$ $^1$H NMR (400 MHz, CD$_3$OD) δ=8.44 (d, J=4.0 Hz, 1H), 7.99 (d, J=1.0 Hz, 1H), 7.17-7.10 (m, 1H), 6.89 (d, J=7.5 Hz, 1H), 6.64-6.56 (m, 2H), 4.36-4.27 (m, 1H), 2.74 (s, 3H), 2.71-2.58 (m, 3H), 2.47-2.37 (m, 2H), 2.02-1.83 (m, 5H), 1.12-0.96 (m, 1H), 0.83 (d, J=6.8 Hz, 3H), 0.53 (br. s., 1H), 0.41-0.32 (m, 1H), 0.28-0.17 (m, 1H), −0.04−−0.15 (m, 1H)

TABLE 22

The compound of Example 90 was prepared in a similar manner to Example 89 using the appropriate starting material and reagents.

| Example | Structure | M.W. | Compound Name | LC/MS (ESI) observed [M + H]$^+$ |
|---|---|---|---|---|
| 90 | 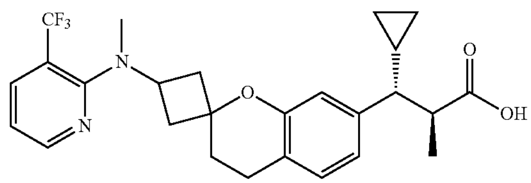 [SMILES: C[C@H](C(=O)O)[C@H](c1ccc2c(c1)OC1(CC2)CC(N(C)c2ncccc2C(F)(F)F)C1)C1CC1] | 474.52 | (2S,3R)-3-cyclo-propyl-2-methyl-3-(3'-(methyl(3-(trifluoro-methyl)pyridin-2-yl)amino)spiro[chro-man-2,1'-cyclobutan]-7-yl)propanoic acid | 475.1 |

Example 90

$^1$H NMR (400 MHz, CD$_3$OD) δ=8.41 (d, J=3.7 Hz, 1H), 7.97 (d, J=7.5 Hz, 1H), 7.13-7.05 (m, 1H), 6.89 (d, J=7.5 Hz, 1H), 6.60 (d, J=7.7 Hz, 1H), 6.55 (s, 1H), 3.87-3.76 (m, 1H), 2.82-2.70 (m, 5H), 2.64-2.53 (m, 1H), 2.46-2.36 (m, 2H), 2.20-2.09 (m, 2H), 1.96-1.80 (m, 3H), 1.07-0.95 (m, 1H), 0.80 (d, J=6.8 Hz, 3H), 0.56-0.45 (m, 1H), 0.40-0.30 (m, 1H), 0.25-0.14 (m, 1H), −0.06−−0.16 (m, 1H)

Example 91

(2S,3R)-3-(3'-((1-(2,5-bis(trifluoromethyl)phenyl) ethyl)amino)spiro[chroman-2,1'-cyclobutan]-7-yl)-3-cyclopropyl-2-methylpropanoic Acid

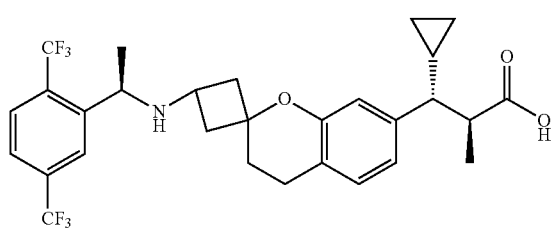 [SMILES: C[C@H](C(=O)O)[C@H](c1ccc2c(c1)OC1(CC2)CC(N[C@H](C)c2cc(C(F)(F)F)ccc2C(F)(F)F)C1)C1CC1]

Step A: (2S,3R)-methyl 3-(3'-(((S)-1-(2,5-bis(trifluoromethyl)phenyl)ethyl)-amino)spiro[chroman-2,1'-cyclobutan]-7-yl)-3-cyclopropyl-2-methylpropanoate To a solution of (S)-1-(2,5-bis(trifluoromethyl)phenyl) ethyl methanesulfonate (306 mg, 0.911 mmol) in MeCN (2 mL) were added (2S,3R)-methyl 3-(3'-aminospiro-[chroman-2,1'-cyclobutan]-7-yl)-3-cyclopropyl-2-methylpropanoate (200 mg, 0.607 mmol) and K$_2$CO$_3$ (420 mg, 3.04 mmol) under a N$_2$ atmosphere. The reaction was stirred for 24 hours at 85° C. under a N$_2$ atmosphere. Then the reaction mixture was filtered, and the filtrate was concentrated in vacuo to give a residue, which was purified by preparative-TLC (SiO$_2$, PE:EtOAc=10:1, v/v) to afford the title compound. MS (ESI) m/z: 570.2 [M+H]$^+$ Step B: (2S,3R)-3-(3'-(((S)-1-(2,5-bis(trifluoromethyl)phenyl)ethyl)amino) spiro[chroman-2,1'-cyclobutan]-7-yl)-3-cyclopropyl-2-methylpropanoic Acid To a solution of (2S,3R)-methyl 3-(3'-(((R)-1-(2,5-bis (trifluoromethyl)phenyl)ethyl)-amino) spiro[chroman-2,1'-cyclobutan]-7-yl)-3-cyclopropyl-2-methylpropanoate (100 mg, 0.176 mmol) in THF (1.5 mL) and water (1.5 mL) was added lithium hydroxide (84.0 mg, 3.51 mmol) under a N$_2$ atmosphere. The reaction was stirred for 12 hours at 60° C. Then water (10 mL) was added, the mixture pH was adjusted with citric acid to pH 6-7, and the mixture was extracted with EtOAc (10 mL×3). The combined organic layers were washed with brine (15 mL), dried over anhydrous Na$_2$SO$_4$ and filtered. The filtrate was evaporated under reduced pressure to give a residue, which was purified by preparative-HPLC (basic) to give the title compound. LCMS (ESI) m/z 556.3[M+H]$^+$ $^1$H NMR (400 MHz, CD$_3$OD) δ=8.18 (s, 1H), 7.84 (d, J=8.2 Hz, 1H), 7.71 (d, J=8.4 Hz, 1H), 6.88 (d, J=7.7 Hz, 1H), 6.57 (d, J=7.7 Hz, 1H), 6.48 (s, 1H), 4.26-4.19 (m, 1H), 3.31 (br. s., 1H), 2.71-2.57 (m, 3H), 2.36-2.27 (m, 1H), 2.16-2.07 (m, 1H), 1.94-1.66 (m, 6H), 1.34 (d, J=6.4 Hz, 3H), 1.06-0.94 (m, 1H), 0.83 (d, J=6.8 Hz, 3H), 0.55-0.47 (m, 1H), 0.30-0.18 (m, 2H), −0.05−−0.14 (m, 1H)

TABLE 23

The compound of Examples 92-94 were prepared in a similar manner to Example 91 using the appropriate starting material and reagents.

| Example | Structure | M.W. | Compound Name | LC/MS (ESI) observed [M + H]+ |
|---|---|---|---|---|
| 92 | 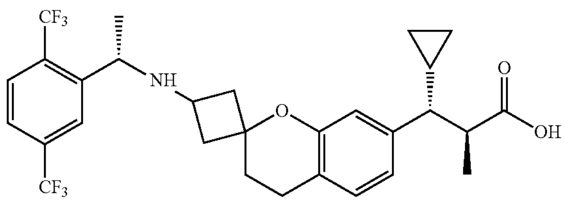 [SMILES: C[C@H](NC1CC2(CCc3ccc([C@H](C4CC4)[C@H](C)C(=O)O)cc3O2)C1)c1cc(C(F)(F)F)ccc1C(F)(F)F] | 555.55 | (2S,3R)-3-(3'-(((S)-1-(2,5-bis(trifluoromethyl)phenyl)ethyl)amino)spiro[chroman-2,1'-cyclobutan]-7-yl)-3-cyclopropyl-2-methylpropanoic acid | 556.3 |
| 93 | 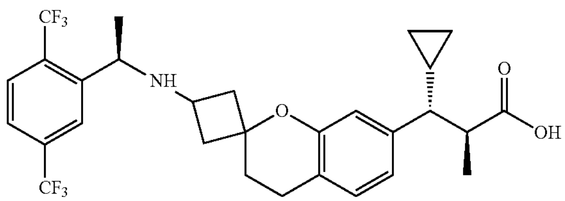 [SMILES: C[C@H](C(=O)O)[C@H](c1ccc2c(c1)OC1(CC2)CC(N[C@H](C)c2cc(C(F)(F)F)ccc2C(F)(F)F)C1)C1CC1] | 555.55 | (2S,3R)-3-(3'-(((R)-1-(2,5-bis(trifluoromethyl)phenyl)ethyl)amino)spiro[chroman-2,1'-cyclo-butan]-7-yl)-3-cyclopropyl-2-methylpropanic acid | 556.3 |
| 94 | 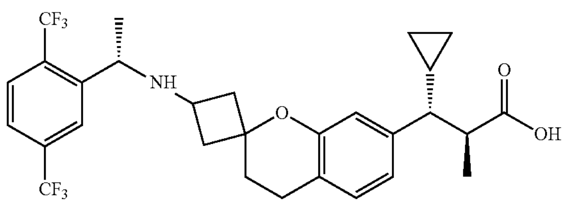 [SMILES: C[C@H](NC1CC2(CCc3ccc([C@H](C4CC4)[C@H](C)C(=O)O)cc3O2)C1)c1cc(C(F)(F)F)ccc1C(F)(F)F] | 555.55 | (2S,3R)-3-(3'-(((S)-1-(2,5-bis(trifluoromethyl)phenyl)ethyl)amino)spiro[chroman-2,1'-cyclobutan]-7-yl)-3-cyclopropyl-2-methylpropanoic acid | 556.3 |

Example 92

$^1$H NMR (400 MHz, CD$_3$OD) δ=8.17 (s, 1H), 7.83 (s, 1H), 7.72 (d, J=8.2 Hz, 1H), 6.87 (s, 1H), 6.57 (d, J=7.7 Hz, 1H), 6.48 (s, 1H), 4.27-4.19 (m, 1H), 3.36-3.29 (m, 1H), 2.70-2.59 (m, 3H), 2.37-2.28 (m, 1H), 2.16-2.07 (m, 1H), 1.95-1.66 (m, 6H), 1.34 (d, J=6.4 Hz, 3H), 1.05-0.94 (m, 1H), 0.83 (d, J=6.8 Hz, 3H), 0.55-0.47 (m, 1H), 0.29-0.19 (m, 2H), −0.06−−0.14 (m, 1H)

Example 93

$^1$H NMR (400 MHz, CD$_3$OD) δ=8.20 (s, 1H), 7.84 (d, J=8.4 Hz, 1H), 7.70 (d, J=8.2 Hz, 1H), 6.86 (s, 1H), 6.60-6.54 (m, 1H), 6.49 (s, 1H), 4.30-4.21 (m, 1H), 3.29-3.28 (m, 1H), 2.79-2.70 (m, 1H), 2.69-2.60 (m, 3H), 2.40-2.31 (m, 1H), 2.14-1.99 (m, 2H), 1.91-1.68 (m, 4H), 1.33 (d, J=6.6 Hz, 3H), 1.06-0.95 (m, 1H), 0.88-0.80 (m, 3H), 0.56-0.47 (m, 1H), 0.32-0.19 (m, 2H), −0.06−−0.14 (m, 1H)

Example 94

$^1$H NMR (400 MHz, CD$_3$OD) δ=8.20 (s, 1H), 7.83 (s, 1H), 7.72 (s, 1H), 6.87 (d, J=7.9 Hz, 1H), 6.59-6.55 (m, 1H), 6.49 (s, 1H), 4.30-4.20 (m, 1H), 3.29-3.28 (m, 1H), 2.78-2.59 (m, 3H), 2.39-2.31 (m, 1H), 2.14-1.99 (m, 2H), 1.90-1.68 (m, 4H), 1.33 (d, J=6.4 Hz, 3H), 1.05-0.95 (m, 1H), 0.83 (d, J=6.8 Hz, 3H), 0.57-0.47 (m, 1H), 0.32-0.17 (m, 2H), −0.07−−0.15 (m, 1H)

Example 95

(2S,3R)-3-(3'-((2,5-bis(trifluoromethyl)benzyl)amino)spiro[chroman-2,1'-cyclobutan]-7-yl)-3-cyclopropyl-2-methylpropanoic Acid

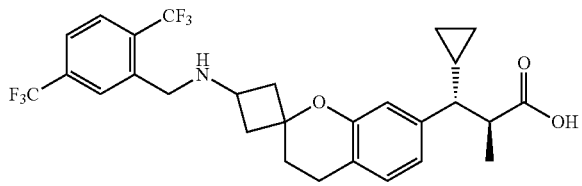 [SMILES: C[C@H](C(=O)O)[C@H](c1ccc2c(c1)OC1(CC2)CC(NCc2cc(C(F)(F)F)ccc2C(F)(F)F)C1)C1CC1]

Step A: (2S,3R)-methyl 3-(3'-((2,5-bis(trifluoromethyl)benzyl)amino)spiro[chroman-2,1'-cyclobutan]-7-yl)-3-cyclopropyl-2-methylpropanoate To a solution of (2S,3R)-methyl 3-(3'-aminospiro[chroman-2,1'-cyclobutan]-7-yl)-3-cyclopropyl-2-methylpropanoate (250 mg, 0.759 mmol) and K$_2$CO$_3$ (315 mg, 2.28 mmol) in MeCN (2 mL) was added 2,5-bis(trifluoromethyl) benzyl methanesulfonate (293 mg, 0.911 mmol). The reaction was stirred at 80° C. under a N$_2$ for 5 hours. Then water (5 mL) was added to the reaction, and the resulting mixture was extracted with ethyl acetate (10 mL×3). The combined organic layers were washed with brine (10 mL), dried over MgSO$_4$ and filtered. The filtrate was evaporated under reduced pressure to give the crude product, which was purified with prep-TLC (SiO$_2$, PE:EA=5:1, v/v) to give the title compound. MS (ESI) m/z: 556.3 [M+H]$^+$ Step B: (2S,3R)-3-(3'-((2,5-bis(trifluoromethyl)benzyl)amino)spiro[chroman-2,1'-cyclobutan]-7-yl)-3-cyclopropyl-2-methylpropanoic Acid To a solution of (2S,3R)-methyl 3-(3'-((2,5-bis(trifluoromethyl)benzyl)amino)spiro[chroman-2,1'-cyclobutan]-7-yl)-3-cyclopropyl-2-methylpropanoate (40.0 mg, 0.072 mmol) in MeOH (1 mL), THF (1 mL) and water (1 mL) was added LiOH (34.5 mg, 1.44 mmol). The reaction mixture was stirred at 50° C. for 14 h, then acidified with citric acid to pH=5-6 and extracted with EtOAc (10 mL×3). The combined organic layers were dried (MgSO$_4$) and filtered. The filtrate was concentrated in vacuo to give the crude product, which was purified by prep-HPLC(base) to give the title compound. Preparative HPLC conditions: a MS trigger instrument fitted with a Waters Xbridge Prep OBD C18 150×30×5 um using water and acetonitrile as the eluents, mobile phase A: water (0.05% ammonia hydroxide); mobile phase B: acetonitrile, Gradient: 31-61% B, 0-10.0 min; 100% B, 10.1-12.0 min; 10% B, 12.1-15 min, FlowRate: 25 mL/min. To a solution of the title compound in MeCN (1 mL) and water (1 mL) was added an aqueous solution of NaOH (1.0 eq, 0.5 M), and the mixture was stirred for 1 hour at room temperature. Then the reaction mixture was lyophilized to give the sodium salt of the title compound. MS (ESI) m/z: 542.3 [M+H]$^+$ $^1$H NMR (400 MHz, CD$_3$OD) δ=8.12 (s, 1H), 7.90 (d, J=8.2 Hz, 1H), 7.77 (d, J=8.2 Hz, 1H), 6.94 (d, J=7.7 Hz, 1H), 6.63 (d, J=7.7 Hz, 1H), 6.55 (s, 1H), 3.98 (s, 2H), 3.17-3.04 (m, 1H), 2.76 (t, J=6.3 Hz, 2H), 2.72-2.62 (m, 1H), 2.48 (t, J=9.8 Hz, 2H), 2.14-2.03 (m, 2H), 1.95-1.80 (m, 3H), 1.05 (d, J=4.6 Hz, 1H), 0.88 (d, J=6.8 Hz, 3H), 0.61-0.50 (m, 1H), 0.38-0.22 (m, 2H), −0.01--0.10 (m, 1H)

Example 97

(2S,3R)-3-(3'-((2,5-bis(trifluoromethyl)benzyl)(methyl)amino)spiro[chroman-2,1'-cyclobutan]-7-yl)-3-cyclopropyl-2-methylpropanoic Acid

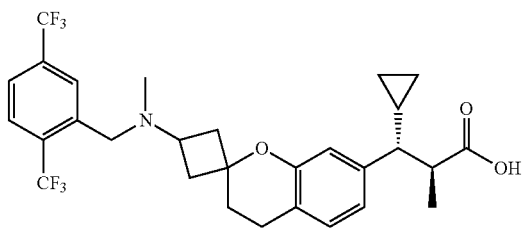 [SMILES: C[C@H](C(=O)O)[C@H](c1ccc2c(c1)OC1(CC2)CC(N(C)Cc2cc(C(F)(F)F)ccc2C(F)(F)F)C1)C1CC1]

Step A: (2S,3R)-methyl 3-(3'-((2,5-bis(trifluoromethyl)benzyl)(methyl)amino)spiro [chroman-2,1'-cyclobutan]-7-yl)-3-cyclopropyl-2-methylpropanoate To a solution of (2S,3R)-methyl 3-(3'-((2,5-bis(trifluoromethyl)benzyl)amino)spiro[chroman-2,1'-cyclobutan]-7-yl)-3-cyclopropyl-2-methylpropanoate (60 mg, 0.108 mmol) and MeI (10.1 μl, 0.162 mmol) in DMF (2 mL) was added NaH (4.75 mg, 0.119 mmol) at 20° C. The reaction was stirred at 20° C. under N$_2$ for 1 h, then quenched with saturated aqueous NH$_4$Cl (5 mL) and extracted with ethyl acetate (10 mL×3). The combined organic layers were washed with brine (10 mL), dried over MgSO$_4$ and filtered. The filtrate was evaporated under reduced pressure to give the title compound, which was used in the next step without purification. MS (ESI) m/z: 570.3 [M+H]$^+$

TABLE 24

The compound of Example 96 was prepared in a similar manner to Example 95 using the appropriate starting material and reagents.

| Example | Structure | M.W. | Compound Name | LC/MS (ESI) observed [M + H]$^+$ |
|---|---|---|---|---|
| 96 | 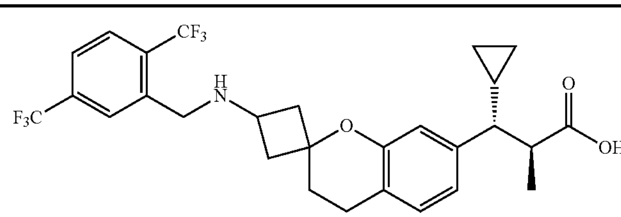 | 541.53 | sodium (2S,3R)-3-(3'-((2,5-bis(trifluoromethyl)benzyl)amino)spiro[chroman-2,1'-cyclobutan]-7-yl)-3-cyclopropyl-2-methylpropanoic acid | 542.3 |

Example 96

$^1$H NMR (400 MHz, CD$_3$OD) δ=8.11 (s, 1H), 7.91 (d, J=8.2 Hz, 1H), 7.78 (d, J=7.9 Hz, 1H), 6.95 (d, J=7.7 Hz, 1H), 6.64 (d, J=7.7 Hz, 1H), 6.58 (s, 1H), 3.97 (s, 2H), 3.65 (q, J=7.4 Hz, 1H), 2.79-2.70 (m, 3H), 2.50-2.42 (m, 2H), 1.96 (t, J=6.4 Hz, 4H), 1.86 (t, J=9.8 Hz, 1H), 1.14-1.00 (m, 1H), 0.89 (d, J=6.8 Hz, 3H), 0.63-0.52 (m, 1H), 0.36-0.27 (m, 2H), −0.03 (d, J=5.5 Hz, 1H).

Step B: (2S,3R)-3-(3'-((2,5-bis(trifluoromethyl)benzyl)(methyl)amino)spiro[chroman-2,1'-cyclobutan]-7-yl)-3-cyclopropyl-2-methylpropanoic Acid To a solution of (2S,3R)-methyl 3-(3'-((2,5-bis(trifluoromethyl)benzyl)(methyl)amino)spiro[chroman-2,1'-cyclobutan]-7-yl)-3-cyclopropyl-2-methylpropanoate (57.0 mg, 0.100 mmol) in MeOH (1 mL), THF (1 mL) and water (1 mL) was added LiOH (47.9 mg, 2.00 mmol). The reaction was stirred at 50° C. for 14 h. The reaction mixture was cooled to 25° C., then acidified with citric acid to pH=5-6 and extracted with EtOAc (10 mL×3). The combined organic layers were dried (MgSO$_4$) and filtered. The filtrate was concentrated in vacuo to give the crude product, which was purified by prep-HPLC (base) to give the title compound. Preparative HPLC conditions: a MS trigger instrument fitted with a Waters Xbridge Prep OBD C18 150×30×5 um using water and acetonitrile as the eluents, mobile phase A: water (0.05% ammonia hydroxide), mobile phase B: acetonitrile, Gradient: 36-66% B, 0-10.0 min; 100% B, 10.1-12.0 min; 10% B, 12.1-15 min, FlowRate: 25 mL/min. To a solution of the title compound in MeCN (1 mL) and water (1 mL) was added an aqueous solution of NaOH (1.0 eq, 0.5 M), and the mixture was stirred for 1 hour at room temperature. Then the reaction mixture was lyophilized to give the sodium salt of the title compound. MS (ESI) m/z: 556.3 [M+H]$^+$ $^1$H NMR (400 MHz, CD$_3$OD) δ=8.22 (s, 1H), 7.88 (d, J=8.2 Hz, 1H), 7.74 (d, J=8.2 Hz, 1H), 6.94 (d, J=7.7 Hz, 1H), 6.63 (d, J=7.7 Hz, 1H), 6.60 (s, 1H), 3.66 (s, 2H), 2.84-2.73 (m, 3H), 2.72-2.62 (m, 1H), 2.38 (t, J=9.0 Hz, 2H), 2.20-2.12 (m, 2H), 2.08 (s, 3H), 1.94 (t, J=6.1 Hz, 2H), 1.87 (t, J=9.8 Hz, 1H), 1.13-1.00 (m, 1H), 0.87 (d, J=6.8 Hz, 3H), 0.63-0.50 (m, 1H), 0.40-0.31 (m, 1H), 0.31-0.20 (m, 1H), −0.05 (td, J=4.7, 9.3 Hz, 1H)

Example 99

(2S,3R)-3-(3'-((1-(2,5-bis(trifluoromethyl)phenyl)ethyl)(methyl)amino)spiro[chroman-2,1'-cyclobutan]-7-yl)-3-cyclopropyl-2-methylpropanoic Acid

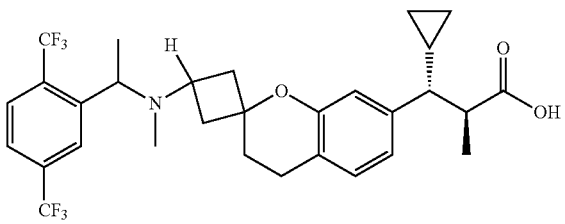 [SMILES: CC(c1cc(C(F)(F)F)ccc1C(F)(F)F)N(C)C1CC2(CCc3ccc([C@H](C4CC4)[C@H](C)C(=O)O)cc3O2)C1]

Step A: (2S3R)-methyl 3-(3'-(((R)-1-(2,5-bis(trifluoromethyl)phenyl)ethyl)(methyl)-amino)spiro[chroman-2,1'-cyclobutan]-7-yl)-3-cyclopropyl-2-methyl-propanoate To a solution of (2S,3R)-methyl 3-(3'-((1-(2,5-bis(trifluoromethyl)phenyl)ethyl)amino)-spiro[chroman-2,1'-cyclobutan]-7-yl)-3-cyclopropyl-2-methylpropanoate (100 mg, 0.176 mmol) in DMF (2 mL) were added iodomethane (0.033 mL, 0.527 mmol) and NaH (21.1 mg, 0.527 mmol). The mixture was stirred at 0° C. for 1 h, then quenched with water (10 mL) and extracted with EtOAc (15 mL×3). The organic layers was washed by water (10 mL×3), dried over Na$_2$SO$_4$ and filtered. The filtrate was concentrated in vacuo

TABLE 25

The compound of Example 98 was prepared in a similar manner to Example 97 using the appropriate starting material and reagents.

| Example | Structure | M.W. | Compound Name | LC/MS (ESI) observed [M + H]$^+$ |
|---|---|---|---|---|
| 98 | 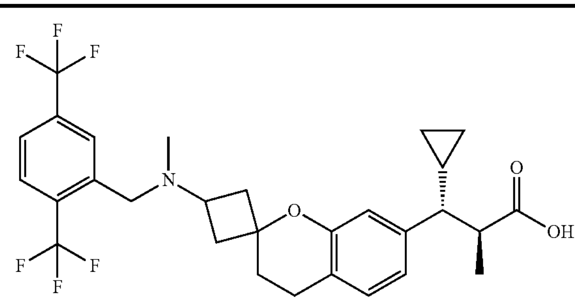 | 555.55 | sodium (2S,3R)-3-(3'-((2,5-bis(trifluoromethyl)benzyl)(methyl)amino)spiro[chroman-2,1'-cyclobutan]-7-yl)-3-cyclopropyl-2-methylpropanoic acid | 556.3 |

Example 98

$^1$H NMR (400 MHz, CD$_3$OD) δ=8.20 (s, 1H), 7.89 (d, J=8.2 Hz, 1H), 7.75 (d, J=7.9 Hz, 1H), 6.93 (d, J=7.7 Hz, 1H), 6.64 (d, J=7.7 Hz, 1H), 6.60 (s, 1H), 3.65 (s, 2H), 3.30-3.25 (m, 1H), 2.75 (t, J=6.3 Hz, 2H), 2.70-2.59 (m, 1H), 2.44-2.33 (m, 2H), 2.07 (s, 3H), 2.06-2.01 (m, 2H), 1.98 (t, J=6.4 Hz, 2H), 1.88 (t, J=9.9 Hz, 1H), 1.11-0.98 (m, 1H), 0.85 (br d, J=6.8 Hz, 3H), 0.60-0.50 (m, 1H), 0.38 (br dd, J=4.7, 9.2 Hz, 1H), 0.32-0.18 (m, 1H), 0.01-−0.12 (m, 1H).

to give the title compound, which was used in the next step without further purification. MS (ESI) m/z: 584.3 [M+H]$^+$ Step B: (2S,3R)-3-(3'-(((R)-1-(2,5-bis(trifluoromethyl)phenyl)ethyl)(methyl)amino)-spiro[chroman-2,1'-cyclobutan]-7-yl)-3-cyclopropyl-2-methylpropanoic Acid To a solution of (2S,3R)-methyl 3-(3'-(((R)-1-(2,5-bis(trifluoromethyl)phenyl)ethyl)(methyl)amino)-spiro[chroman-2,1'-cyclobutan]-7-yl)-3-cyclopropyl-2-methylpropanoate (45 mg, 0.077 mmol) in MeOH (1 mL), THF (1 mL)

and water (1 mL) was added lithium hydroxide (18.47 mg, 0.771 mmol) under nitrogen. The reaction was stirred at 55° C. for 12 h, and then concentrated in vacuo to remove the solvent. Water (5 mL) was added to the resulting residue, then citric acid was added to adjust the mixture pH to pH 5, and the mixture was extracted with EtOAc (10 mL×3). The combined organic layers were washed with brine (10 mL), dried over anhydrous MgSO$_4$ and filtered. The filtrate was concentrated under reduced pressure. The resulting residue was purified by Prep HPLC (acid) to give the title compound. Preparative HPLC Conditions: a MS trigger instrument fitted with a Phenomenex Gemini C18 250×21.2 mm×5 um as the eluents, mobile phase A: water (0.1% TFA)-ACN, mobile phase B: ACN, Gradient: 40-60% B, 0-12.0 min; 100% B, 12.0-14.0 min; 10% B, 14.0-17.0 min, FlowRate: 25 mL/min. MS (ESI) m/z: 570.3 [M+H]$^+$ $^1$H NMR (400 MHz, CD$_3$OD) δ=8.32-8.23 (m, 1H), 8.13-8.08 (m, 1H), 8.06-8.01 (m, 1H), 7.01-6.95 (m, 1H), 6.72-6.67 (m, 1H), 6.62-6.57 (m, 1H), 4.87-4.81 (m, 1H), 4.40-4.29 (m, 1H), 2.99-2.60 (m, 9H), 1.99-1.73 (m, 7H), 1.05 (s, 1H), 0.88 (d, J=6.6 Hz, 3H), 0.61-0.55 (m, 1H), 0.31 (s, 2H), −0.01--0.07 (m, 1H)

0.88 (d, J=6.8 Hz, 3H), 0.58 (d, J=5.7 Hz, 1H), 0.35-0.24 (m, 2H), −0.06 (d, J=5.1 Hz, 1H)

Example 102

(2S,3R)-3-cyclopropyl-3-(1'-((R or S)-1-(2-methoxy-5-(trifluoromethyl)pyridin-3-yl)ethyl)spiro-[chroman-2,4'-piperidin]-7-yl)-2-methylpropanoic Acid

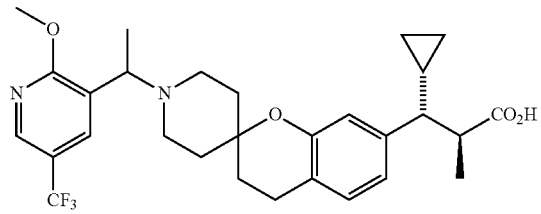

TABLE 26

The compounds of Examples 100-101 were prepared in a similar manner to Example 99 using the appropriate starting material and reagents.

| Example | Structure | M.W. | Compound Name | LC/MS (ESI) observed [M + H]$^+$ |
|---|---|---|---|---|
| 100 | 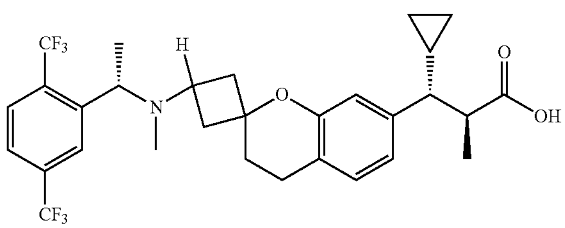 [SMILES: C[C@H](C(=O)O)[C@H](c1ccc2c(c1)OC1(CC2)CC(N(C)[C@@H](C)c2cc(C(F)(F)F)ccc2C(F)(F)F)C1)C1CC1] | 569.58 | (2S,3R)-3-(3'-(((S)-1-(2,5-bis(trifluoromethyl)phenyl)ethyl)(methyl)amino)spiro[chroman-2,1'-cyclobutan]-7-yl)-3-cyclopropyl-2-methylpropanic acid | 570.3 |
| 101 | 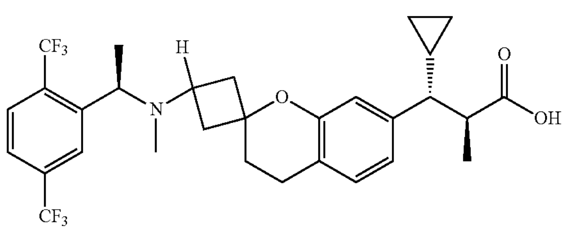 [SMILES: C[C@H](C(=O)O)[C@H](c1ccc2c(c1)OC1(CC2)CC(N(C)[C@H](C)c2cc(C(F)(F)F)ccc2C(F)(F)F)C1)C1CC1] | 569.58 | (2S,3R)-3-(3'-(((R)-1-(2,5-bis(trifluoromethyl)phenyl)methyl)amino)spiro-[chroman-2,1'-cyclobutan]-7-yl)-3-cyclopropyl-2-methylpropanoic acid | 570.3 |

Example 100

$^1$H NMR (400 MHz, CD$_3$OD) δ=8.35-8.26 (m, 1H), 8.13-8.08 (m, 1H), 8.06-8.01 (m, 1H), 7.00-6.95 (m, 1H), 6.71-6.66 (m, 1H), 6.62-6.55 (m, 1H), 4.36 (s, 2H), 2.92-2.61 (m, 8H), 2.06-1.72 (m, 8H), 1.05 (s, 1H), 0.88 (d, J=6.8 Hz, 3H), 0.58 (s, 1H), 0.34-0.26 (m, 2H), −0.02--0.08 (m, 1H)

Example 101

$^1$H NMR (400 MHz, CD$_3$OD) δ=8.36 (s, 1H), 8.11 (s, 1H), 8.04 (s, 1H), 6.98 (d, J=7.5 Hz, 1H), 6.68 (d, J=7.3 Hz, 1H), 6.57 (s, 1H), 4.87 (s, 1H), 3.87 (s, 1H), 2.93-2.66 (m, 8H), 2.32 (s, 1H), 2.03-1.73 (m, 7H), 1.09-1.02 (m, 1H),

Step A: 1-(2-chloro-5-(trifluoromethyl)pyridin-3-yl)ethanol

To a solution of 2-chloro-5-(trifluoromethyl)nicotinaldehyde (272 mg, 1.30 mmol) in THF (2 ml) was added methylmagnesium bromide (0.865 ml, 2.60 mmol). The reaction was stirred at 20° C. for 1 hour, then quenched with water (10 mL) and extracted with EtOAc (10 mL×3). The combined organic layers were washed with brine (30 mL), dried (Na$_2$SO$_4$), filtered. The filtrate was evaporated under reduced pressure to give the title compound, which was used directly in the next step without purification. MS (ESI) m/z: 226.0 [M+H]$^+$ $^1$H NMR (400 MHz, CDCl$_3$): δ=8.56 (br. s., 1H), 8.23 (s, 1H), 5.31-5.22 (m, 1H), 1.54 (d, J=6.4 Hz, 3H)

Step B: 1-(2-methoxy-5-(trifluoromethyl)pyridin-3-yl)ethanol

To a solution of 1-(2-chloro-5-(trifluoromethyl)pyridin-3-yl)ethanol (270 mg, 1.20 mmol) in 1,4-dioxane (2 ml) was added sodium methanolate (194 mg, 3.59 mmol). The reaction was stirred at 90° C. for 5 hours, then quenched with aqueous HCl, diluted with water (10 mL) and extracted with EtOAc (10 mL×3). The combined organic layers were washed with brine (25 mL), dried ($Na_2SO_4$), and filtered. The filtrate was evaporated under reduced pressure to give the crude product, which was purified by prep-TLC ($SiO_2$, PE/EA=10:1, v/v) to give the title compound. MS (ESI) m/z: 222.0 $[M+H]^+$

Step C: 1-(2-methoxy-5-(trifluoromethyl)pyridin-3-yl)ethyl methanesulfonate

To a solution of 1-(2-methoxy-5-(trifluoromethyl)pyridin-3-yl)ethanol (201 mg, 0.909 mmol) in DCM (10 mL) were added methanesulfonyl chloride (208 mg, 1.82 mmol) and triethylamine (184 mg, 1.82 mmol). The reaction was stirred at 30° C. for 1 hour, then diluted with water (10 mL) and extracted with DCM (10 mL×3). The combined organic layers were washed with brine (20 mL), dried ($Na_2SO_4$), and filtered. The filtrate was evaporated under reduced pressure to give the title compound, which was used directly in the next step without purification. $^1$H NMR (400 MHz, $CDCl_3$): δ=8.41 (s, 1H), 7.88 (s, 1H), 5.97 (q, J=6.4 Hz, 1H), 4.03 (s, 3H), 2.99 (s, 3H), 1.67 (d, J=6.4 Hz, 3H)

Step D: (2S,3R)-methyl 3-cyclopropyl-3-(1'-(1-(2-methoxy-5-(trifluoromethyl)-pyridin-3-yl)ethyl)spiro[chroman-2,4'-piperidin]-7-yl)-2-methylpropanoate To a solution of 1-(2-methoxy-5-(trifluoromethyl)pyridin-3-yl)ethyl methanesulfonate (190 mg, 0.635 mmol) in MeCN (10 mL) were added (2S,3R)-methyl 3-cyclopropyl-2-methyl-3-(spiro[chroman-2,4'-piperidin]-7-yl)propanoate (218 mg, 0.635 mmol), sodium iodide (285 mg, 1.91 mmol) and $K_2CO_3$ (439 mg, 3.17 mmol). The reaction was stirred at 85° C. for 5 hours, then diluted with water (10 mL) and extracted with EtOAc (10 mL×3). The combined organic layers were washed with brine (30 mL), dried ($Na_2SO_4$), and filtered. The filtrate was evaporated under reduced pressure to give the crude product, which was purified by prep-TLC ($SiO_2$, PE/EA=5:1, v/v) to give the title compound. MS (ESI) m/z: 547.2 $[M+H]^+$

Step E: (2S,3R)-3-cyclopropyl-3-(1'-(1-(6-methoxy-3-(trifluoromethyl)pyridin-2-yl)-ethyl)spiro[chroman-2,4'-piperidin]-7-yl)-2-methylpropanoic Acid To a solution of (2S,3R)-methyl 3-cyclopropyl-3-(1'-(1-(6-methoxy-3-(trifluoromethyl) pyridin-2-yl)-ethyl)spiro[chroman-2,4'-piperidin]-7-yl)-2-methylpropanoate (129 mg, 0.236 mmol) in MeOH (1 mL), THF (1 mL) and water (1 mL) was added lithium hydroxide (170 mg, 7.08 mmol). The reaction was stirred at 55° C. for 12 hours. Then the reaction mixture was poured into water (10 mL), citric acid was added to adjust the mixture pH to 7, and the mixture was extracted with EtOAc (10 mL×3). The combined organic layers were washed with brine (saturated, 30 mL), dried over $Na_2SO_4$ and filtered. The filtrate was concentrated under reduced pressure to give the crude product, which was purified by prep-TLC ($SiO_2$, PE/EA=1:1, v/v) to give the title compound. MS (ESI) m/z: 533.3 $[M+H]^+$

Step F: (2S,3R)-3-cyclopropyl-3-(1'-((R or S)-1-(2-methoxy-5-(trifluoromethyl) pyridin-3-yl)ethyl)spiro[chroman-2,4'-piperidin]-7-yl)-2-methylpropanoic Acid (2S,3R)-3-cyclopropyl-3-(1'-(1-(2-methoxy-5-(trifluoromethyl)pyridin-3-yl) ethyl)spiro[chroman-2,4'-piperidin]-7-yl)-2-methylpropanoic acid (91.0 mg, 0.171 mmol) was separated into individual diastereoisomers by SFC (SFC conditions: Column: Chiralpak AD-3 150×4.6 mm I.D., 3 um Mobile phase: A: $CO_2$B:iso-propanol (0.05% DEA) Gradient: from 5% to 40% of B in 5 min and hold 40% for 2.5 min, then 5% of B for 2.5 min Flow rate: 2.5 mL/min Column temp.: 35° C.) to give the first peak (2S,3R)-3-cyclopropyl-3-(1'-((R or S)-1-(2-methoxy-5-(trifluoromethyl)-pyridin-3-yl)-ethyl)spiro[chroman-2,4'-piperidin]-7-yl)-2-methylpropanoic acid (Rt=3.067 min). To a solution of (2S,3R)-3-cyclopropyl-3-(1'-((R or S)-1-(2-methoxy-5-(trifluoromethyl)pyridin-3-yl)ethyl)spiro-[chroman-2,4'-piperidin]-7-yl)-2-methylpropanoic acid (12.0 mg, 0.021 mmol) in MeCN (1 mL) and water (1 mL) were added the solution of aq. NaOH (1.0 eq, 0.5 M), and the mixture was stirred for 1 h at 20° C. Then the reaction mixture was lyophilized to give the sodium salt of the title compound. MS (ESI) m/z: 533.3 $[M+H]^+$ $^1$H NMR (400 MHz, $CD_3OD$): δ=8.43 (br. s., 1H), 8.07 (br. s., 1H), 6.96 (d, J=7.7 Hz, 1H), 6.64 (d, J=7.5 Hz, 1H), 6.56 (s, 1H), 4.17 (d, J=6.4 Hz, 1H), 4.05 (s, 3H), 3.09 (d, J=11.0 Hz, 1H), 2.79-2.62 (m, 6H), 1.95-1.76 (m, 6H), 1.66 (br. s., 1H), 1.45 (d, J=6.6 Hz, 3H), 1.06 (br. s., 1H), 0.87 (d, J=6.8 Hz, 3H), 0.56 (br. s., 1H), 0.38-0.20 (m, 2H), −0.05 (br. s., 1H)

TABLE 27

The following Example 103 was prepared in a similar manner to Example 102 using the appropriate starting material and reagents.

| Example | Structure | M.W. | Compound Name | LC/MS (ESI) observed $[M + H]^+$ |
|---|---|---|---|---|
| 103 | 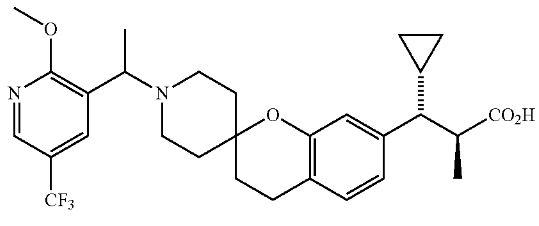 [SMILES: COc1ncc(C(F)(F)F)cc1C(C)N1CCC2(CCc3ccc([C@H](C4CC4)[C@H](C)C(=O)O)cc3O2)CC1] | 532.2 | (2S,3R)-3-cyclopropyl-3-(1'-((S or R)-1-(2-methoxy-5-(trifluoromethyl)pyridin-3-yl)ethyl)spiro[chroman-2,4'-piperidin]-7-yl)-2-methylpropanoic acid | 533.2 |

Example 103

$^1$H NMR (400 MHz, CD$_3$OD): δ=8.53 (br. s., 1H), 8.16 (d, J=1.6 Hz, 1H), 7.04 (d, J=7.8 Hz, 1H), 6.72 (d, J=7.8 Hz, 1H), 6.65 (s, 1H), 4.31 (d, J=6.7 Hz, 1H), 4.13 (s, 3H), 3.22 (d, J=11.3 Hz, 1H), 2.91-2.69 (m, 6H), 2.06-1.82 (m, 6H), 1.80-1.72 (m, 1H), 1.55 (d, J=7.0 Hz, 3H), 1.17-1.09 (m, 1H), 0.95 (d, J=7.0 Hz, 3H), 0.68-0.59 (m, 1H), 0.44-0.32 (m, 2H), 0.05--0.02 (m, 1H)

Example 104 sodium (2S,3R)-3-cyclopropyl-3-(1'-((R or S)-1-(6-methoxy-3-(trifluoromethyl) pyridin-2-yl)ethyl)spiro[chroman-2,4'-piperidin]-7-yl)-2-methylpropanoate

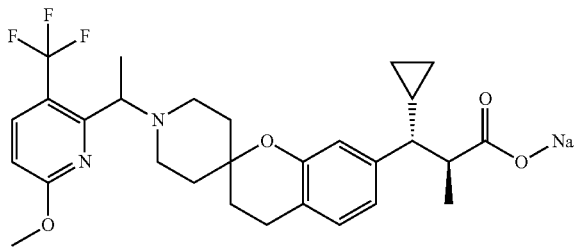

Step A: 6-chloro-N-methoxy-N-methyl-3-(trifluoromethyl)picolinamide

To a solution of 6-chloro-3-(trifluoromethyl)picolinic acid (1.00 g, 4.43 mmol) in DCM (15 ml) was added Et$_3$N (1.85 ml, 13.3 mmol), HATU (2.53 g, 6.65 mmol) and N,O-dimethylhydroxylamine HCl (519 mg, 5.32 mmol). The reaction was stirred at 20° C. for 12 h, then concentrated in vacuo to give the crude product, which was purified by column chromatography (SiO$_2$, petroleum ether:ethyl acetate=20:1-10:1, v/v) to give the title compound. MS (ESI) m/z: 268.9 [M+H]$^+$

Step B: 1-(6-chloro-3-(trifluoromethyl)pyridin-2-yl)ethanone

To a solution of 6-chloro-N-methoxy-N-methyl-3-(trifluoromethyl)picolinamide (500 mg, 1.86 mmol) in THF (10 ml) was added methylmagnesium bromide (6.20 ml, 18.6 mmol) at 0° C. The reaction mixture was stirred at 0° C. for 1 h, then quenched with water (10 mL), and extracted with EtOAc (20 mL×3). The combined organic layers were dried over sodium sulfate, and then filtered. The filtrate was concentrated in vacuo to give the crude product, which was purified by column chromatography (SiO$_2$, petroleum ether:ethyl acetate=20:1-10:1, v/v) to give the title compound. MS (ESI) m/z: 224.0 [M+H]$^+$ $^1$H NMR (400 MHz, CDCl$_3$) δ=8.02 (d, J=8.2 Hz, 1H), 7.55 (d, J=8.2 Hz, 1H), 2.66 (s, 3H)

Step C: 1-(6-chloro-3-(trifluoromethyl)pyridin-2-yl)ethanol

To a solution of 1-(6-chloro-3-(trifluoromethyl)pyridin-2-yl)ethanone (270 mg, 1.21 mmol) in MeOH (8 ml) was added NaBH$_4$ (228 mg, 6.04 mmol) at 20° C. The reaction was stirred at 20° C. for 2 h, then quenched with water (10 mL) and extracted with EtOAc (20 mL×3). The combined organic layers were dried over sodium sulfate, and then filtered. The filtrate was concentrated in vacuo to give the crude product, which was purified by column chromatography (SiO$_2$, petroleum ether:ethyl acetate=10:1-5:1, v/v) to give the title compound. $^1$H NMR (400 MHz, CDCl$_3$) δ=7.88 (d, J=8.2 Hz, 1H), 7.35 (d, J=8.2 Hz, 1H), 5.13 (dd, J=6.5, 9.2 Hz, 1H), 3.50 (d, J=10.2 Hz, 1H), 1.46 (d, J=6.3 Hz, 3H)

Step D: 1-(6-methoxy-3-(trifluoromethyl)pyridin-2-yl)ethanol

To a solution of 1-(6-chloro-3-(trifluoromethyl)pyridin-2-yl)ethanol (200 mg, 0.887 mmol) in MeOH (1 ml) was added sodium methoxide (144 mg, 2.66 mmol). The reaction was stirred at 60° C. for 6 h. Then water (20 mL) was added, and the mixture was extracted with EtOAc (20 mL×3). The combined organic layers were dried over sodium sulfate, and then filtered. The filtrate was concentrated in vacuo to give the crude product, which was purified by column chromatography (SiO$_2$, petroleum ether:ethyl acetate=10:1-5:1, v/v) to give the title compound. MS (ESI) m/z: 222.0 [M+H]$^+$

Step E: 1-(6-methoxy-3-(trifluoromethyl)pyridin-2-yl)ethyl methanesulfonate

To a solution of 1-(6-methoxy-3-(trifluoromethyl)pyridin-2-yl)ethanol (150 mg, 0.678 mmol) in DCM (5 ml) was added Et$_3$N (0.284 ml, 2.04 mmol) and methanesulfonyl chloride (155 mg, 1.36 mmol). The reaction was stirred at 20° C. for 1 h. Then water (10 mL) was added, and the mixture was extracted with DCM (10 mL×2). The combined organic layers were dried over sodium sulfate, and then filtered. The filtrate was concentrated in vacuo to give the title compound, which was used in the next step without further purification. MS (ESI) m/z: 300.0 (M+H)$^+$

Step F: (2S,3R)-methyl 3-cyclopropyl-3-(1'-(1-(6-methoxy-3-(trifluoromethyl) pyridin-2-yl)ethyl)spiro[chroman-2,4'-piperidin]-7-yl)-2-methylpropanoate To a solution of 1-(6-methoxy-3-(trifluoromethyl)pyridin-2-yl)ethyl methanesulfonate (170 mg, 0.568 mmol) in MeCN (15 ml) was added K$_2$CO$_3$ (471 mg, 3.41 mmol), sodium iodide (255 mg, 1.70 mmol) and (2S,3R)-methyl 3-cyclopropyl-2-methyl-3-(spiro-[chroman-2,4'-piperidin]-7-yl)propanoate (234 mg, 0.682 mmol). The reaction was stirred at 85° C. for 6 h, then poured into water (10 mL) and extracted with EtOAc (10 mL×3). The combined organic layers were dried over sodium sulfate, and then filtered. The filtrate was concentrated in vacuo to give the crude product, which was purified by prep-TLC (SiO$_2$, petroleum ether:ethyl acetate=5:1, v/v) to give the title compound. MS (ESI) m/z: 547.3[M+H]$^+$

Step G: (2S,3R)-3-cyclopropyl-3-(1'-(1-(6-methoxy-3-(trifluoromethyl)pyridin-2-yl) ethyl)spiro[chroman-2,4'-piperidin]-7-yl)-2-methylpropanoic Acid To a solution of (2S,3R)-methyl-3-cyclopropyl-3-(1'-(1-(6-methoxy-3-(trifluoromethyl)-pyridin-2-yl)-ethyl)spiro[chroman-2,4'-piperidin]-7-yl)-2-methylpropanoate (40.0 mg, 73.0 umol) in MeOH (1 ml), THF (1 ml) and water (1 ml) was added LiOH (88.0 mg, 3.66 mmol). The reaction mixture was stirred at 55° C. for 4 hours under N$_2$. Then the reaction mixture was poured into water (2 mL), citric acid was added to adjust the mixture pH to pH 7, and the mixture was extracted with EtOAc (5 mL×3). The combined organic layers were washed with brine (2 mL), dried over $Na_2SO_4$, (d, J=11.0 Hz, 2H), 2.80-2.63 (m, 3H), 1.97-1.79 (m, 6H), 1.76-1.65 (m, 1H), 1.57 (d, J=6.7 Hz, 3H), 1.11-1.00 (m, 1H), 0.86 (d, J=6.7 Hz, 3H), 0.62-0.51 (m, 1H), 0.40-0.21 (m, 2H), −0.06 (dd, J=4.7, 9.0 Hz, 1H)

TABLE 28

The compound of Examples 105-107 were prepared in a similar manner to Example 104 using the appropriate starting material and reagents.

| Example | Structure | M.W. | Compound Name | LC/MS (ESI) observed [M + H]+ |
|---|---|---|---|---|
| 105 | 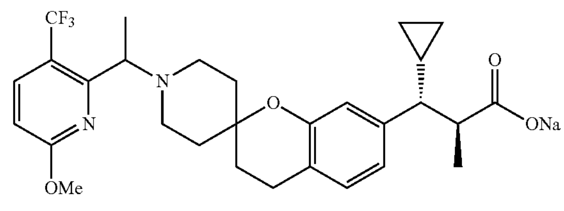 | 554.58 | sodium (2S,3R)-3-cyclopropyl-3-(1'-((S or R)-1-(6-methoxy-3-(trifluoromethyl)pyridin-2-yl)ethyl)-spiro[chroman-2,4'-piperidin]-7-yl)-2-methylpropanoate | 533.3 |
| 106 | 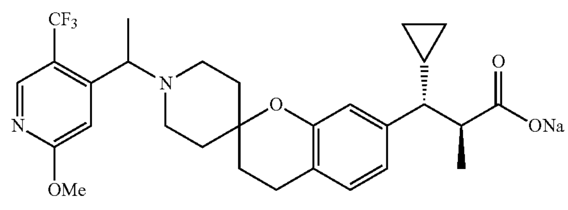 | 554.58 | sodium (2S,3R)-3-cyclopropyl-3-(1'-((R or S)-1-(2-methoxy-5-(trifluoromethyl)pyridin-4-yl)ethyl)spiro[chroman-2,4'-piperidin]-7-yl)-2-methylpropanoate | 533.2 |
| 107 | | 554.58 | sodium (2S,3R)-3-cyclopropyl-3-(1'-((S or R)-1-(2-methoxy-5-(trifluoromethyl)pyridin-4-yl)ethyl)spiro[chroman-2,4'-piperidin]-7-yl)-2-methylpropanoate | 533.2 | and filtered. The filtrate was evaporated under reduced pressure to give a residue, which was purified by prep-TLC ($SiO_2$, petroleum ether: ethyl acetate=1:1, v/v) to give the title compound. MS (ESI) m/z: 533.3 [M+H]+

Step H: sodium (2S,3R)-3-cyclopropyl-3-(1'-((R or S)-1-(6-methoxy-3-(trifluoro-methyl)-pyridin-2-yl)ethyl)spiro[chroman-2,4'-piperidin]-7-yl)-2-methylpropanoate (2S,3R)-3-cyclopropyl-3-(1'-(1-(6-methoxy-3-(trifluoromethyl)pyridin-2-yl)ethyl)spiro[chroman-2,4'-piperidin]-7-yl)-2-methylpropanoic acid (70.0 mg, 0.131 mmol) was separated by SFC (SPF conditions: Method Set: AD-3-EtOH-DEA-5-40, 25 mL Vial: 2:D, 6 Channel Name: 280.0 nm Injection Volume: 5.00 ul, Proc. Chnl. Descr.: PDA 280.0 nm Run Time: 10 Minutes) to give the title compound. To a solution of the title compound in MeCN (1 mL) and water (1 mL) was added an aqueous NaOH solution (1.0 eq, 0.5 M), and the mixture was stirred for 1 h at room temperature. Then the reaction mixture was lyophilized to give the sodium salt of the title compound. MS (ESI) m/z: 533.3 (M+H)+, Rt (SFC)=2.666 min $^1$H NMR (400 MHz, $CD_3OD$): δ=7.98 (d, J=9.0 Hz, 1H), 6.97 (d, J=7.8 Hz, 1H), 6.89 (d, J=9.0 Hz, 1H), 6.65 (d, J=7.4 Hz, 1H), 6.59 (s, 1H), 4.40 (d, J=6.7 Hz, 1H), 4.05 (s, 3H), 3.28-3.18 (m, 2H), 2.93 (d, J=11.0 Hz, 2H), 2.80-2.63 (m, 3H), 1.97-1.79 (m, 6H), 1.76-1.65 (m, 1H), 1.57 (d, J=6.7 Hz, 3H), 1.11-1.00 (m, 1H), 0.86 (d, J=6.7 Hz, 3H), 0.62-0.51 (m, 1H), 0.40-0.21 (m, 2H), −0.06 (dd, J=4.7, 9.0 Hz, 1H)

Example 105

MS (ESI) m/z: 533.3 (M+H)+, $t_R$ (sfc)=2.911 min $^1$H NMR (400 MHz, $CD_3OD$): δ=7.98 (d, J=8.6 Hz, 1H), 6.97 (d, J=7.8 Hz, 1H), 6.89 (d, J=9.0 Hz, 1H), 6.66 (d, J=7.8 Hz, 1H), 6.59 (s, 1H), 4.42 (d, J=6.3 Hz, 1H), 4.05 (s, 3H), 3.29-3.19 (m, 2H), 2.94 (br. s., 2H), 2.80-2.64 (m, 3H), 1.96-1.80 (m, 6H), 1.75-1.66 (m, 1H), 1.57 (d, J=6.7 Hz, 3H), 1.11-1.01 (m, 1H), 0.87 (d, J=7.0 Hz, 3H), 0.62-0.52 (m, 1H), 0.40-0.21 (m, 2H), −0.02--0.11 (m, 1H)

Example 106

MS (ESI) m/z: 533.2 (M+H)+, $t_R$ (sfc)=2.707 min $^1$H NMR (400 MHz, $CD_3OD$): δ=8.42 (s, 1H), 7.26 (s, 1H), 7.01-6.92 (m, 1H), 6.67-6.57 (m, 2H), 3.97 (s, 3H), 3.69 (d, J=5.9 Hz, 1H), 3.01 (d, J=10.6 Hz, 1H), 2.80-2.67 (m, 3H), 2.55-2.34 (m, 3H), 1.95-1.68 (m, 6H), 1.65-1.54 (m, 1H), 1.33 (d, J=6.7 Hz, 3H), 1.15-1.03 (m, 1H), 0.90 (d, J=7.0 Hz, 3H), 0.64-0.52 (m, 1H), 0.37-0.23 (m, 2H), 0.02--0.07 (m, 1H)

Example 107

MS (ESI) m/z: 533.2 (M+H)+, $t_R$ (sfc)=2.825 min $^1$H NMR (400 MHz, $CD_3OD$): δ=8.42 (s, 1H), 7.26 (s, 1H), 6.96 (d, J=7.4 Hz, 1H), 6.66-6.55 (m, 2H), 3.97 (s, 3H), 3.69 (d, J=6.3 Hz, 1H), 3.01 (d, J=10.2 Hz, 1H), 2.74 (d, J=5.9

Hz, 3H), 2.56-2.35 (m, 3H), 1.93-1.68 (m, 6H), 1.66-1.54 (m, 1H), 1.32 (d, J=6.7 Hz, 3H), 1.13-1.02 (m, 1H), 0.90 (d, J=6.7 Hz, 3H), 0.62-0.53 (m, 1H), 0.31 (d, J=6.3 Hz, 2H), 0.03--0.10 (m, 1H)

Example 108

(2S,3R)-3-(1'-((R or S)-1-(3-chloro-2-fluoro-5-(trifluoromethyl)phenyl)ethyl)spiro-[chroman-2,4'-piperidin]-7-yl)-3-cyclopropyl-2-methylpropanoic Acid

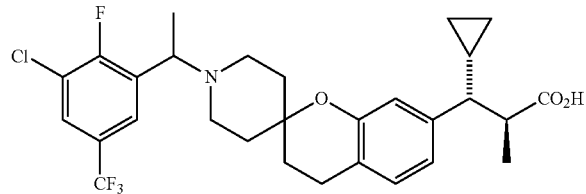 [SMILES: CC(c1cc(C(F)(F)F)cc(Cl)c1F)N1CCC2(CCc3ccc([C@H](C4CC4)[C@H](C)C(=O)O)cc3O2)CC1]

Step A: 1-(3-chloro-2-fluoro-5-(trifluoromethyl)phenyl)ethanol

To a solution of 3-chloro-2-fluoro-5-(trifluoromethyl)benzaldehyde (260 mg, 1.15 mmol) in THF (2 mL) was added methylmagnesium bromide (0.765 mL, 2.30 mmol) under nitrogen. The reaction was stirred at 20° C. for 1 hour, then quenched with water (5 mL) and extracted with EtOAc (5 mL×3). The combined organic layers were washed with brine (20 mL), dried ($Na_2SO_4$), and filtered. The filtrate was evaporated under reduced pressure to give the title compound, which was used directly in the next step without purification. $^1$H NMR (400 MHz, $CDCl_3$): δ=7.76 (d, J=4.7 Hz, 1H), 7.61 (d, J=5.1 Hz, 1H), 5.26 (d, J=6.3 Hz, 1H), 1.54 (d, J=6.3 Hz, 3H)

Step B: 1-(2-chloro-3-fluoro-5-(trifluoromethyl)phenyl)ethyl methanesulfonate

To a solution of 1-(2-chloro-3-fluoro-5-(trifluoromethyl)phenyl)ethanol (267 mg, 1.10 mmol) in DCM (2 mL) were added methanesulfonyl chloride (252 mg, 2.20 mmol) and triethylamine (223 mg, 2.20 mmol). The reaction was stirred at 20° C. for 1 hour, then diluted with water (5 mL) and extracted with DCM (5 mL×3). The combined organic layers were washed with brine (20 mL), dried ($Na_2SO_4$), and filtered. The filtrate was evaporated under reduced pressure to give the title compound, which was used directly in the next step without purification. $^1$H NMR (400 MHz, $CDCl_3$): δ=7.70 (d, J=6.3 Hz, 1H), 7.66 (d, J=4.7 Hz, 1H), 6.04 (q, J=6.7 Hz, 1H), 3.02 (s, 3H), 1.75 (d, J=6.3 Hz, 3H)

Step C: (2S,3R)-methyl 3-(1'-(1-(2-chloro-3-fluoro-5-(trifluoromethyl)phenyl)ethyl)-spiro[chroman-2,4'-piperidin]-7-yl)-3-cyclopropyl-2-methylpropanoate To a solution of 1-(2-chloro-3-fluoro-5-(trifluoromethyl)phenyl)ethyl methanesulfonate (200 mg, 0.624 mmol) in MeCN (10 mL) were added (2S,3R)-methyl-3-cyclopropyl-2-methyl-3-(spiro[chroman-2,4'-piperidin]-7-yl)propanoate (214 mg, 0.624 mmol), sodium iodide (280 mg, 1.87 mmol) and $K_2CO_3$ (431 mg, 3.12 mmol). The reaction was stirred at 85° C. for 5 h, then diluted with water (10 mL) and extracted with EtOAc (10 mL×3). The combined organic layers were washed with brine (30 mL), dried ($Na_2SO_4$), and filtered. The filtrate was evaporated under reduced pressure to give a crude product, which was purified by prep-TLC ($SiO_2$, PE/EA=5:1, v/v) to give the title compound. MS (ESI) m/z: 568.3 $[M+H]^+$ Step D: (2S,3R)-3-(1'-(1-(3-chloro-2-fluoro-5-(trifluoromethyl)phenyl)ethyl)-spiro-[chroman-2,4'-piperidin]-7-yl)-3-cyclopropyl-2-methylpropanoic Acid To a solution of (2S,3R)-methyl 3-(1'-(1-(3-chloro-2-fluoro-5-(trifluoromethyl) phenyl)-ethyl)-spiro-[chroman-2,4'-piperidin]-7-yl)-3-cyclopropyl-2-methylpropanoate (220 mg, 0.387 mmol) in MeOH (1 mL), THF (1 mL) and water (1 mL) was added lithium hydroxide (278 mg, 11.6 mmol). The reaction was stirred at 55° C. for 12 hours. Then the reaction mixture was poured into water (10 mL), citric acid was added to adjust the pH of the mixture to pH 7, and the mixture was extracted with EtOAc (10 mL×3). The combined organic layers were washed with brine (saturated, 30 mL), dried over $Na_2SO_4$ and filtered. The filtrate was concentrated under reduced pressure to give the crude product, which was purified by prep-TLC ($SiO_2$, PE/EA=1:1, v/v) to give the title compound. MS (ESI) m/z: 554.1 $[M+H]^+$ 1H NMR (400 MHz, $CD_3OD$): δ=7.84 (t, J=6.4 Hz, 2H), 7.00 (d, J=7.7 Hz, 1H), 6.67 (d, J=7.7 Hz, 1H), 6.58 (s, 1H), 4.10 (q, J=6.6 Hz, 1H), 2.98 (d, J=10.6 Hz, 1H), 2.82-2.71 (m, 3H), 2.67-2.50 (m, 3H), 1.96-1.75 (m, 6H), 1.73-1.62 (m, 1H), 1.50 (d, J=6.6 Hz, 3H), 1.16-1.04 (m, 1H), 0.93 (d, J=6.8 Hz, 3H), 0.66-0.57 (m, 1H), 0.40-0.28 (m, 2H), 0.05--0.05 (m, 1H)

TABLE 29

The compound of Example 109 was prepared in a similar manner to Example 108 using the appropriate starting material and reagents.

| Example | Structure | M.W. | Compound Name | LC/MS (ESI) observed $[M + 1]^+$ |
|---|---|---|---|---|
| 109 | 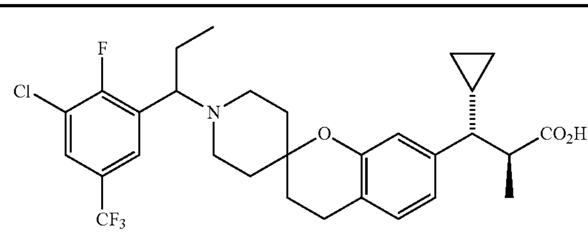 | 567.2 | (2S,3R)-3-(1'-(1-(3-chloro-2-fluoro-5-(trifluromethyl)phenyl)propyl)spiro[chroman-2,4'-piperidin]-7-yl)-3-cyclopropyl-2-methylpropanoic acid | 568.2 |

Example 109

$^1$H NMR (400 MHz, CD$_3$OD): δ=8.12 (d, J=5.7 Hz, 1H), 7.98 (d, J=4.2 Hz, 1H), 7.00 (d, J=7.7 Hz, 1H), 6.68 (d, J=7.7 Hz, 1H), 6.59 (br. s., 1H), 3.74 (br. s., 1H), 3.41-3.29 (m, 3H), 2.82-2.63 (m, 3H), 2.46-2.34 (m, 1H), 2.30-1.67 (m, 9H), 1.08-0.97 (m, 1H), 0.86 (d, J=6.8 Hz, 3H), 0.80 (t, J=7.2 Hz, 3H), 0.63-0.51 (m, 1H), 0.37-0.20 (m, 2H), −0.07 (br. s., 1H)

Example 110

(2S,3R)-3-(1'-(1-(5-chloro-2-(trifluoromethoxy)phenyl)propyl)spiro[chroman-2,4'-piperidin]-7-yl)-3-cyclopropyl-2-methylpropanoic Acid

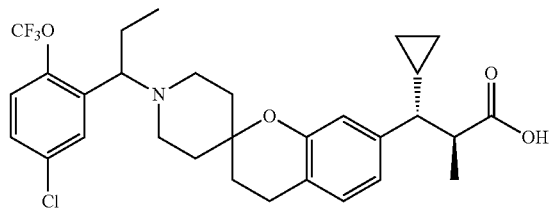

Step A:
1-(5-chloro-2-(trifluoromethoxy)phenyl)propan-1-ol

To a solution of 5-chloro-2-(trifluoromethoxy)benzaldehyde (600 mg, 2.67 mmol) in THF (5 mL) was added dropwise ethylmagnesium bromide (1.78 mL, 5.34 mmol) at 0° C. The mixture was stirred at 0° C. for 0.5 h, then quenched with water (5 mL), and extracted with EtOAc (10 mL×3). The combined organic layers were dried over Na$_2$SO$_4$ and filtered. The filtrate was concentrated in vacuo to give a residue, which was purified by prep—TLC (SiO$_2$, PE:EtOAc=10:1, v/v) to give the title compound.

Step B:
1-(5-chloro-2-(trifluoromethoxy)phenyl)propyl methanesulfonate

To a solution of 1-(5-chloro-2-(trifluoromethoxy)phenyl)propan-1-ol (150 mg, 0.589 mmol) and Et$_3$N (0.246 ml, 1.76 mmol) in DCM (3 mL) was added dropwise Ms-Cl (0.0920 ml, 1.17 mmol) at 0° C. The reaction was stirred at 0° C. for 0.5 h, then quenched with water (5 mL), and extracted with EtOAc (10 mL×3). The combined organic layers were dried over Na$_2$SO$_4$ and filtered. The filtrate was concentrated in vacuo to give the title compound, which was used in the next step without further purification.

Step C: (2S,3R)-methyl 3-(1'-(1-(5-chloro-2-(trifluoromethoxy)phenyl)propyl)spiro [chroman-2,4'-piperidin]-7-yl)-3-cyclopropyl-2-methylpropanoate To a solution of (2S,3R)-methyl 3-cyclopropyl-2-methyl-3-(spiro[chroman-2,4'-piperidin]-7-yl)-propanoate (229 mg, 0.667 mmol) in MeCN (3 mL) were added K$_2$CO$_3$ (231 mg, 1.66 mmol), sodium iodide (250 mg, 1.66 mmol) and 1-(5-chloro-2-(trifluoromethoxy)-phenyl)propyl methanesulfonate (185 mg, 0.556 mmol) under nitrogen. The reaction mixture was stirred at 80° C. for 12 h, then purified by prep-TLC (SiO$_2$, PE:EtOAc=3:1) to give the title compound. MS (ESI) m/z: 580.2 [M+H]$^+$ Step D: (2S,3R)-3-(1'-(1-(5-chloro-2-(trifluoromethoxy)phenyl)propyl)spiro [chroman-2,4'-piperidin]-7-yl)-3-cyclopropyl-2-methylpropanoic Acid To a solution of (2S,3R)-methyl 3-(1'-(1-(5-chloro-2-(trifluoromethoxy)phenyl)propyl)spiro-[chroman-2,4'-piperidin]-7-yl)-3-cyclopropyl-2-methylpropanoate (202 mg, 0.348 mmol) in MeOH (1 mL), THF (1 mL) and water (1 mL) was added lithium hydroxide (167 mg, 6.96 mmol) under nitrogen. The reaction mixture was stirred at 55° C. for 24 h, then concentrated in vacuo to remove the solvent. Water (5 mL) was added to the resulting residue, then citric acid was added to adjust the mixture pH to pH 5, and the mixture was extracted with EtOAc (10 mL×3). The combined organic layers were washed with brine (10 mL), dried over anhydrous MgSO$_4$ and filtered. The filtrate was concentrated under reduced pressure to give a residue, which was purified by prep-HPLC (acid) to afford the title compound. Preparative HPLC conditions: Preparative HPLC with MS trigger instrument fitted with a Phenomenex Synergi C18 150×30 mm×4 um as the eluents, mobile phase A: water (0.1% TFA)-ACN, mobile phase B: ACN, gradient: 40-60% B, 0-12.0 min; 100% B, 12.0-14.0 min, 10% B, 14.0-17.0 min, FlowRate: 25 mL/min. MS (ESI) m/z: 566.3 [M+H]$^+$ $^1$H NMR (400 MHz, CD$_3$OD) δ=7.94 (s, 1H), 7.79 (d, J=8.4 Hz, 1H), 7.66 (d, J=8.8 Hz, 1H), 7.10 (d, J=7.6 Hz, 1H), 6.78 (d, J=8.0 Hz, 1H), 6.64 (s, 1H), 4.91-4.84 (m, 1H), 3.83 (d, J=9.9 Hz, 1H), 3.37-3.21 (m, 2H), 2.88 (s, 2H), 2.82-2.75 (m, 1H), 2.51-2.43 (m, 1H), 2.17-2.15 (m, 1H), 2.08-1.88 (m, 9H), 1.13 (d, J=2.6 Hz, 3H), 0.96 (d, J=6.8 Hz, 3H), 0.89 (t, J=7.2 Hz, 3H), 0.71-0.64 (m, 1H), 0.43-0.32 (m, 2H), 0.03-0.02 (m, 1H)

Example 111

(2S,3R)-3-cyclopropyl-3-(1'-(1-(5-cyclopropyl-2-(trifluoromethoxy)phenyl)ethyl)spiro[chroman-2,4'-piperidin]-7-yl)-2-methylpropanoic Acid

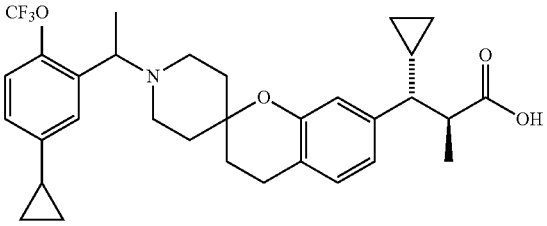

Step A:
1-(5-bromo-2-(trifluoromethoxy)phenyl)ethanol

A flask containing 5-bromo-2-(trifluoromethoxy)benzaldehyde (2.00 g, 7.43 mmol) was evacuated and backfilled with nitrogen three times. Then THF (30 mL) was added, and the resulting mixture was cooled to −15° C. Methylmagnesium bromide (2.73 mL, 8.18 mmol) was added via syringe over 2 min, and the reaction was stirred at −15° C. for 10 min and at 0° C. for 1 h. Then the reaction mixture was diluted with saturated aqueous NH$_4$Cl (20 mL) and extracted with EtOAc (50 mL×3). The combined organic layers were washed with saturated brine (50 mL), dried over Na$_2$SO$_4$ and filtered. The filtrate was concentrated by rotary evaporator to give a residue, which was purified by flash column chromatography (silica gel, PE:EtOAc=100:1-50:1, v/v) to give the title compound.

Step B:
1-(5-bromo-2-(trifluoromethoxy)phenyl)ethyl methanesulfonate

A solution of 1-(5-bromo-2-(trifluoromethoxy)phenyl)ethanol (7.58 g, 26.6 mmol) and Et$_3$N (11.1 mL, 80.0 mmol) in DCM (70 mL) was cooled to 0° C. Ms-Cl (3.11 mL, 39.9 mmol) was added dropwise over 10 min. The reaction was stirred at 20° C. for 2 h. Then saturated aqueous NaHCO$_3$ (50 mL) was added to the reaction mixture, and the mixture was extracted with DCM (100 mL×3). The combined organic layers were washed with brine (50 mL), dried over anhydrous Na$_2$SO$_4$ and filtered. The filtrate was concentrated by rotary evaporator to give the title compound, which was directly used in the next step. $^1$H NMR (400 MHz, CDCl$_3$): δ=7.74-7.67 (m, 1H), 7.56-7.49 (m, 1H), 7.22-7.14 (m, 1H), 6.05-5.94 (m, 1H), 2.95 (s, 3H), 1.70 (d, J=6.3 Hz, 3H)

Step C: (2S,3R)-methyl 3-(1'-(1-(5-bromo-2-(trifluoromethoxy)phenyl)-ethyl)-spiro[chroman-2,4'-piperidin]-7-yl)-3-cyclopropyl-2-methylpropanoate A suspension of 1-(5-bromo-2-(trifluoromethoxy)phenyl)ethyl methanesulfonate (9.66 g, 26.6 mmol), (2S,3R)-methyl 3-cyclopropyl-2-methyl-3-(spiro[chroman-2,4'-piperidin]-7-yl)propanoate (10.1 g, 29.3 mmol), K$_2$CO$_3$ (7.35 g, 53.2 mmol) and sodium iodide (3.99 g, 26.6 mmol) in MeCN (200 mL) was heated to 85° C. for 5 h. The reaction mixture was cooled to RT, diluted with water (100 mL), and extracted with EtOAc (200 mL×3). The combined organic layers were washed with brine (100 mL×2), dried over MgSO$_4$ and filtered. The filtrate was concentrated by rotary evaporator to give a residue, which was purified by flash column chromatography (silica gel, PE:EtOAc=200:1-50:1, v/v) to give the title compound. MS (ESI): m/z 610.2, 612.2 [M+H]$^+$ $^1$H NMR (400 MHz, CDCl$_3$): δ=7.79 (d, J=2.0 Hz, 1H), 7.38 (dd, J=2.3, 8.6 Hz, 1H), 7.10 (d, J=8.6 Hz, 1H), 6.97 (d, J=7.4 Hz, 1H), 6.67-6.58 (m, 2H), 3.86-3.77 (m, 1H), 3.73 (s, 3H), 2.91-2.69 (m, 4H), 2.52-2.36 (m, 3H), 1.96-1.54 (m, 7H), 1.30 (d, J=6.7 Hz, 3H), 1.12-1.00 (m, 1H), 0.95 (d, J=6.7 Hz, 3H), 0.61-0.48 (m, 1H), 0.40-0.29 (m, 1H), 0.29-0.16 (m, 1H), 0.10--0.04 (m, 1H)

Step D: (2S,3R)-methyl 3-cyclopropyl-3-(1'-(1-(5-cyclopropyl-2-(trifluoromethoxy)-phenyl)-ethyl) spiro[chroman-2,4'-piperidin]-7-yl)-2-methylpropanoate A flask containing (2S,3R)-methyl 3-(1'-(1-(5-bromo-2-(trifluoromethoxy)phenyl)ethyl)-spiro[chroman-2,4'-piperidin]-7-yl)-3-cyclopropyl-2-methylpropanoate (100 mg, 0.164 mmol), cyclopropylboronic acid (28.1 mg, 0.328 mmol), 2-dicyclohexyl-phosphino-2',6'-dimethoxy-biphenyl (6.72 mg, 0.016 mmol), tripotassium phosphate (139 mg, 0.655 mmol) and palladium(II) acetate (1.84 mg, 8.19 μmol) was evacuated and backfilled with nitrogen three times. To the flask was added dioxane (1.5 mL) and water (0.15 mL). The reaction mixture was heated to 85° C. for 6 h, then diluted with 5 mL of water and extracted with EtOAc (10 mL×3). The combined organic layers were washed with brine (10 mL), dried over Na$_2$SO$_4$ and filtered. The filtrate was concentrated by rotary evaporator to give a residue, which was purified by prep-TLC (silica gel, PE:EtOAc=10:1, v/v) to give the title compound. MS (ESI): m/z 572.3 [M+H]$^+$ Step E: (2S,3R)-3-cyclopropyl-3-(1'-(1-(5-cyclopropyl-2-(trifluoromethoxy)-phenyl)ethyl)-spiro[chroman-2,4'-piperidin]-7-yl)-2-methylpropanoic Acid To a solution of (2S,3R)-methyl 3-cyclopropyl-3-(1'-(1-(5-cyclopropyl-2-(trifluoro-methoxy)phenyl)ethyl)-spiro[chroman-2,4'-piperidin]-7-yl)-2-methylpropanoate (95.0 mg, 0.166 mmol) in MeOH (1 mL), THF (1 mL) and water (1 mL) was added lithium hydroxide hydrate (105 mg, 2.49 mmol). The reaction was heated to 55° C. for 12 hours, then cooled to room temperature and neutralized to pH 7 with concentrated HCl. The solvent was removed by rotary evaporator. The resulting residue was dissolved in MeCN and DMSO and filtered. The filtrate was purified by preparative HPLC to give the title compound. The title compound was treated with 1 equivalent of aqueous NaOH (10 wt %) and lyophilizated to give the sodium salt of the title compound. Preparative HPLC conditions: Column: Waters XSELECT C18 150*30 mm*5 um; Condition: water (0.1% TFA)-ACN; Begin B: 36; End B: 66; Gradient Time (min): 10; 100% B Hold Time (min): 2; FlowRate (mL/min): 25; Injections: 6. MS (ESI): m/z [M+H]$^+$ $^1$H NMR (400 MHz, CD$_3$OD): δ=7.42 (d, J=1.5 Hz, 1H), 7.21 (d, J=8.4 Hz, 1H), 7.10 (dd, J=1.9, 8.5 Hz, 1H), 6.95 (d, J=7.7 Hz, 1H), 6.65 (d, J=7.7 Hz, 1H), 6.56 (s, 1H), 4.23-4.14 (m, 1H), 3.20-3.10 (m, 1H), 2.80-2.59 (m, 6H), 2.02-1.64 (m, 8H), 1.49 (d, J=6.6 Hz, 3H), 1.12-0.98 (m, 3H), 0.88 (d, J=6.8 Hz, 3H), 0.79-0.67 (m, 2H), 0.62-0.51 (m, 1H), 0.40-0.20 (m, 2H), 0.01--0.12 (m, 1H)

TABLE 30

The compounds in Examples 112-122 were prepared in a similar manner to Example 111 using the appropriate starting materials and reagents.

| Example | Structure | M.W. | Compound Name | LC/MS (ESI) observed [M + H]$^+$ |
|---|---|---|---|---|
| 112 | 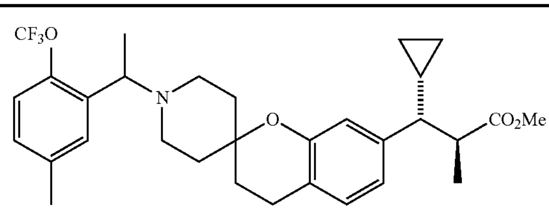 | 531.61 | (2S,3R)-3-cyclopropyl-2-methyl-3-(1'-(1-(5-methyl-2-(trifluoromethoxy)phenylethyl)spiro[chroman-2,4'-piperidin]-7-yl)propanoic acid | 532.2 |

TABLE 30-continued

The compounds in Examples 112-122 were prepared in a similar manner to Example 111 using the appropriate starting materials and reagents.

| Example | Structure | M.W. | Compound Name | LC/MS (ESI) observed [M + H]+ |
|---|---|---|---|---|
| 113 | 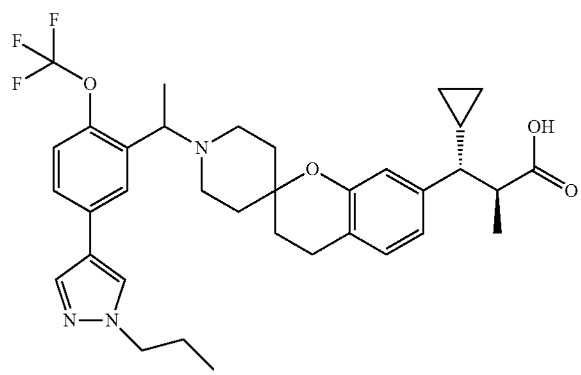 [SMILES: CCCn1cc(-c2ccc(OC(F)(F)F)c(C(C)N3CCC4(CCc5ccc([C@H](C6CC6)[C@H](C)C(=O)O)cc5O4)CC3)c2)cn1] | 625.72 | sodium (2S,3R)-3-cyclopropyl-2-methyl-3-(1'-S or R)-1-(5-(1-propyl-1H-pyrazol-4-yl)-2-(trifluoromethoxy)phenyl)ethyl)spiro[chroman-2,4'-piperidin]-7-yl)propanoate | 626.4 |
| 114 | 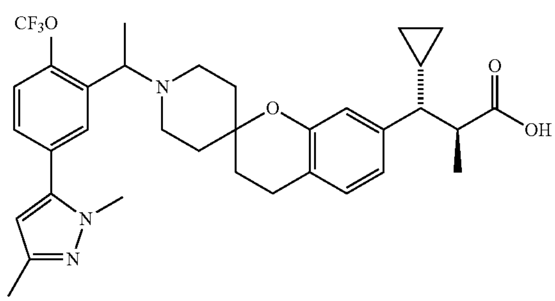 | 611.7 | (2S,3R)-3-cyclopropyl-3-(1'-((RS)-1-(5-(1,3-dimethyl-1H-pyrazol-5-yl)-2-(trifluoromethoxy)phenyl)ethyl)spiro[chroman-2,4'-piperidin]-7-yl)-2-methylpropanoic acid | 612.2 |
| 115 | 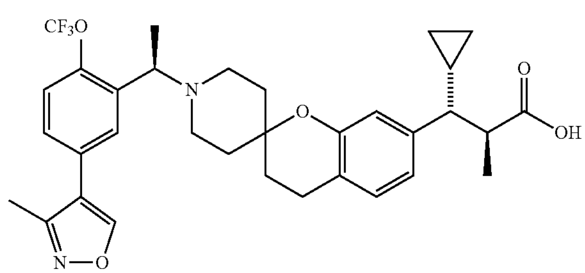 | 598.6 | (2S,3R)-3-cyclopropyl-2-methyl-3-(1'-((R or S)-1-(5-(3-methylisoxazol-4-yl)-2-(trifluoromethoxy)phenyl)ethyl)spiro[chroman-2,4'-piperidin]-7-yl)propanoic acid | 599.2 |
| 116 | 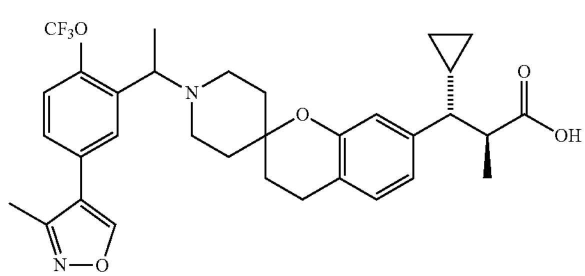 | 598.6 | (2S,3R)-3-cyclopropyl-2-methyl-3-(1'-((R or S)-1-(5-(3-methylisoxazol-4-yl)-2-(trifluoromethoxy)phenyl)ethyl)spiro[chroman-2,4'-piperidin]-7-yl)propanoic acid | 599.2 |

TABLE 30-continued

The compounds in Examples 112-122 were prepared in a similar manner to
Example 111 using the appropriate starting materials and reagents.

| Example | Structure | M.W. | Compound Name | LC/MS (ESI) observed [M + H]+ |
|---|---|---|---|---|
| 117 | 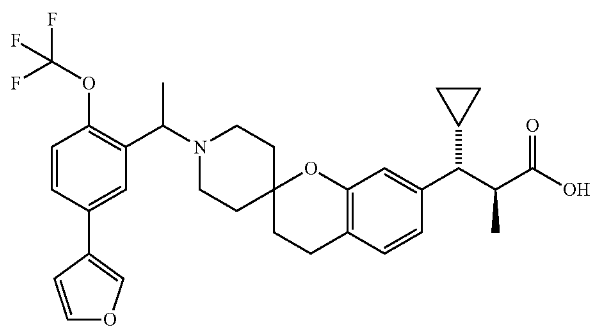 [SMILES: CC(c1cc(-c2ccoc2)ccc1OC(F)(F)F)N1CCC2(CCc3ccc([C@H](C4CC4)[C@H](C)C(=O)O)cc3O2)CC1] | 583.64 | (2S,3R)-3-cyclopropyl-3-(1'-((R or S)-1-(5-(furan-3-yl)-2-(trifluoro-methoxy)-phenyl)ethyl)spiro[chroman-2,4'-piperidin]-7-yl)-2-methylpropanoic acid | 584.4 |
| 118 | 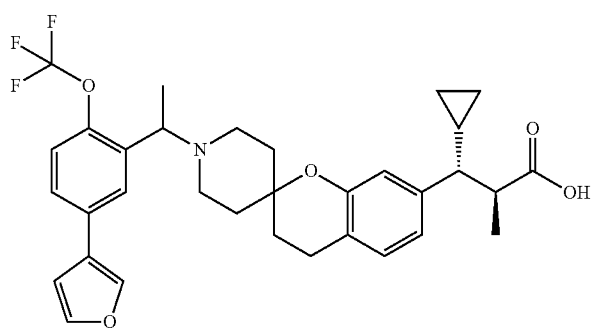 [SMILES: CC(c1cc(-c2ccoc2)ccc1OC(F)(F)F)N1CCC2(CCc3ccc([C@H](C4CC4)[C@H](C)C(=O)O)cc3O2)CC1] | 583.64 | (2S,3R)-3-cyclopropyl-3-(1'-((S or R)-1-(5-(furan-3-yl)-2-(trifluoromethoxy)phenyl)ethyl)spiro[chroman-2,4'-piperidin]-7-yl)-2-methylpropanoic acid | 584.4 |
| 119 | 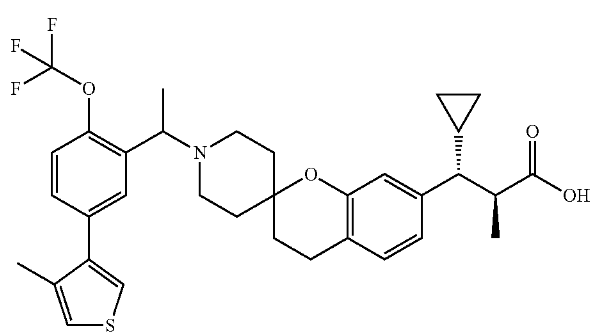 [SMILES: Cc1cscc1-c1ccc(OC(F)(F)F)c(C(C)N2CCC3(CCc4ccc([C@H](C5CC5)[C@H](C)C(=O)O)cc4O3)CC2)c1] | 613.7 | (2S,3R)-3-cyclopropyl-2-methyl-3-(1'-(1-(5-4-methylthiophen-3-yl)-2-(trifluoromethoxy)phenyl)ethyl)spiro[chroman-2,4'-piperidin]-7-yl)-propanoic acid | 614.3 |
| 120 | 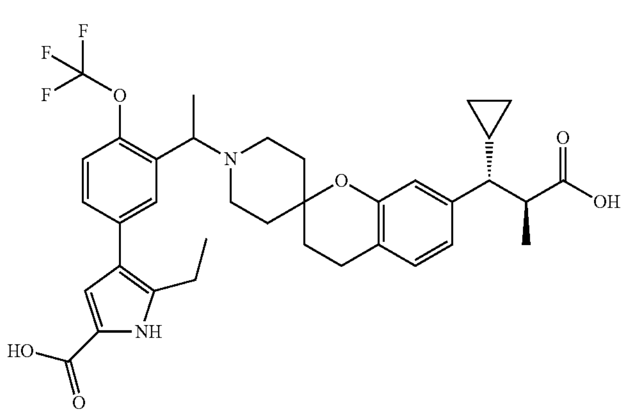 [SMILES: CCc1[nH]c(C(=O)O)cc1-c1ccc(OC(F)(F)F)c(C(C)N2CCC3(CCc4ccc([C@H](C5CC5)[C@H](C)C(=O)O)cc4O3)CC2)c1] | 654.72 | 4-(3-((S or R)-1-(7-((1R,2S)-2-carboxy-1-cyclopropylpropyl)spiro[chroman-2,4'-piperidin]-1'-yl)ethyl)-4-(trifluoro-methoxy)phenyl)-5-ethyl-1H-pyrrole-2-carboxylic acid | 655.3 |

TABLE 30-continued

The compounds in Examples 112-122 were prepared in a similar manner to Example 111 using the appropriate starting materials and reagents.

| Example | Structure | M.W. | Compound Name | LC/MS (ESI) observed [M + H]+ |
|---|---|---|---|---|
| 121 | 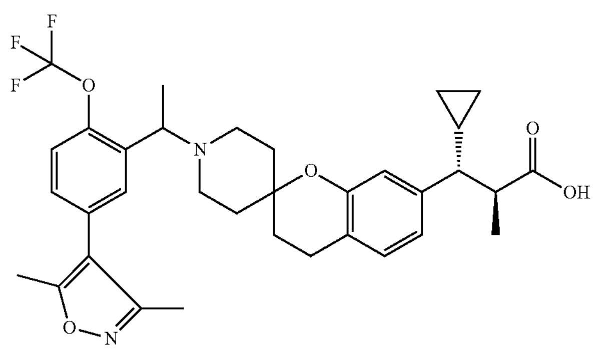 [SMILES: Cc1noc(C)c1-c1ccc(OC(F)(F)F)c(C(C)N2CCC3(CCc4ccc([C@H](C5CC5)[C@H](C)C(=O)O)cc4O3)CC2)c1] | 612.68 | (2S,3R)-3-cyclopropyl-3-(1'-(1-(5-(3,5-dimethylisoxazol-4-yl)-2-(trifluoromethoxy)phenyl)ethyl)spiro[chroman-2,4'-piperidin]-7-yl)-2-methyl-propanoic acid | 613.2 |
| 122 | 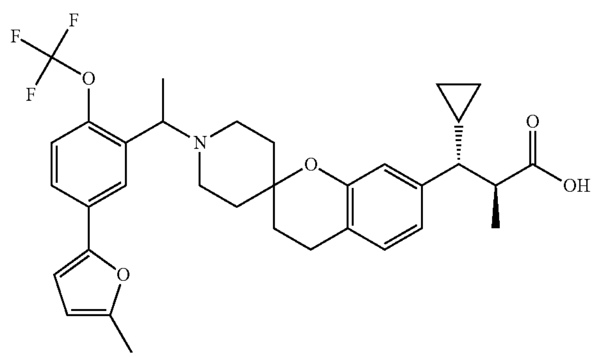 [SMILES: Cc1ccc(-c2ccc(OC(F)(F)F)c(C(C)N3CCC4(CCc5ccc([C@H](C6CC6)[C@H](C)C(=O)O)cc5O4)CC3)c2)o1] | 597.7 | (2S,3R)-3-cyclopropyl-2-methyl-3-(1'-((RS)-1-(5-(5-methylfuran-2-yl)-2-(trifluoromethoxy)phenyl)ethyl)spiro[chroman-2,4'-piperidin]-7-yl)propanoic acid | 598.2 |

Example 112

$^1$H NMR (400 MHz, CD$_3$OD): δ=7.66 (s, 1H), 7.45 (d, J=7.9 Hz, 1H), 7.38 (d, J=8.4 Hz, 1H), 7.02 (d, J=7.7 Hz, 1H), 6.70 (d, J=7.5 Hz, 1H), 6.61 (s, 1H), 3.82-3.71 (m, 1H), 3.50-3.34 (m, 1H), 3.22-3.12 (m, 2H), 2.85-2.76 (m, 2H), 2.76-2.67 (m, 1H), 2.45 (s, 3H), 2.21-1.97 (m, 3H), 1.95-1.82 (m, 4H), 1.79 (d, J=6.8 Hz, 3H), 1.13-0.99 (m, 1H), 0.88 (d, J=6.8 Hz, 3H), 0.65-0.52 (m, 1H), 0.38-0.23 (m, 2H), 0.01--0.12 (m, 1H)

Example 113

$^1$H NMR (400 MHz, CD$_3$OD): δ=8.06 (s, 1H), 7.91-7.82 (m, 2H), 7.59 (dd, J=2.0, 8.6 Hz, 1H), 7.31 (d, J=7.4 Hz, 1H), 6.94 (d, J=7.8 Hz, 1H), 6.63 (d, J=7.4 Hz, 1H), 6.55 (s, 1H), 4.18-4.06 (m, 3H), 3.10 (d, J=11.0 Hz, 1H), 2.77-2.55 (m, 6H), 1.95-1.75 (m, 8H), 1.71-1.61 (m, 1H), 1.50 (d, J=6.7 Hz, 3H), 1.09-0.98 (m, 1H), 0.93 (t, J=7.4 Hz, 3H), 0.87 (d, J=6.7 Hz, 3H), 0.55 (d, J=3.9 Hz, 1H), 0.36-0.19 (m, 2H), −0.07 (dd, J=4.3, 9.0 Hz, 1H)

Example 114

$^1$H NMR (400 MHz, CD$_3$OD): δ=7.90-7.50 (m, 3H), 7.01 (d, J=7.7 Hz, 1H), 6.70 (d, J=7.9 Hz, 1H), 6.63-6.57 (m, 1H), 6.30 (s, 1H), 5.10-4.91 (m, 2H), 3.90-3.69 (m, 3H), 3.50-3.32 (m, 2H), 3.29-3.15 (m, 2H), 2.85-2.66 (m, 3H), 2.26 (d, J=1.8 Hz, 2H), 2.22-1.94 (m, 3H), 1.93-1.75 (m, 7H), 1.11-0.98 (m, 1H), 0.93-0.84 (m, 3H), 0.63-0.53 (m, 1H), 0.36-0.22 (m, 2H), 0.03-0.10 (m, 1H)

Example 115

$^1$H NMR (400 MHz, CD$_3$OD): δ=8.84 (s, 1H), 7.78 (d, J=2.0 Hz, 1H), 7.57-7.48 (m, 1H), 7.41 (d, J=7.4 Hz, 1H), 6.96 (d, J=7.8 Hz, 1H), 6.63 (d, J=7.8 Hz, 1H), 6.56 (s, 1H), 4.07 (q, J=6.3 Hz, 1H), 3.08-2.98 (m, 1H), 2.79-2.51 (m, 6H), 2.44 (s, 3H), 1.96-1.71 (m, 6H), 1.69-1.58 (m, 1H), 1.48 (d, J=1.0 Hz, 3H), 1.03 (dd, J=4.3, 8.6 Hz, 1H), 0.88 (d, J=6.7 Hz, 3H), 0.61-0.52 (m, 1H), 0.37-0.22 (m, 2H), 0.01-0.10 (m, 1H)

Example 116

$^1$H NMR (400 MHz, CD$_3$OD): δ=8.92 (s, 1H), 7.88 (br. s., 1H), 7.80-7.74 (m, 1H), 7.61 (d, J=7.8 Hz, 1H), 7.02 (d, J=7.4 Hz, 1H), 6.70 (d, J=7.8 Hz, 1H), 6.60 (s, 1H), 5.00 (q, J=6.7 Hz, 1H), 3.83-3.64 (m, 1H), 3.50-3.36 (m, 1H), 3.30-3.15 (m, 2H), 2.80 (t, J=6.5 Hz, 2H), 2.76-2.65 (m, 1H), 2.46 (s, 3H), 2.21-1.78 (m, 10H), 1.11-0.98 (m, 1H), 0.88 (d, J=7.0 Hz, 3H), 0.63-0.54 (m, 1H), 0.37-0.23 (m, 2H), 0.00--0.12 (m, 1H)

Example 117

$^1$H NMR (400 MHz, CD$_3$OD): δ=7.96 (s, 1H), 7.86-7.81 (m, 1H), 7.65-7.54 (m, 2H), 7.33 (d, J=7.4 Hz, 1H), 6.96 (d,

J=7.4 Hz, 1H), 6.84 (s, 1H), 6.63 (d, J=7.8 Hz, 1H), 6.56 (s, 1H), 4.14-4.06 (m, 1H), 2.80-2.50 (m, 6H), 2.02-1.74 (m, 6H), 1.68-1.60 (m, 1H), 1.50 (d, J=6.7 Hz, 3H), 1.33-1.27 (m, 1H), 1.06-0.99 (m, 1H), 0.87 (d, J=7.0 Hz, 3H), 0.59-0.51 (m, 1H), 0.35-0.22 (m, 2H), −0.03-−0.10 (m, 1H)

Example 118

$^1$H NMR (400 MHz, CD$_3$OD): δ=7.97 (s, 1H), 7.87-7.82 (m, 1H), 7.65-7.55 (m, 2H), 7.34 (d, J=7.4 Hz, 1H), 6.96 (d, J=7.8 Hz, 1H), 6.85 (s, 1H), 6.64 (d, J=7.8 Hz, 1H), 6.56 (s, 1H), 4.20-4.12 (m, 1H), 2.80-2.56 (m, 6H), 1.98-1.75 (m, 6H), 1.69-1.62 (m, 1H), 1.57-1.46 (m, 3H), 1.33-1.26 (m, 1H), 1.08-1.02 (m, 1H), 0.87 (d, J=7.0 Hz, 3H), 0.60-0.53 (m, 1H), 0.35-0.24 (m, 2H), −0.03-−0.10 (m, 1H)

Example 119

$^1$H NMR (400 MHz, CD$_3$OD): δ=7.66 (d, J=1.5 Hz, 1H), 7.44-7.38 (m, 1H), 7.38-7.27 (m, 2H), 7.11 (br. s., 1H), 6.92 (d, J=7.7 Hz, 1H), 6.60 (d, J=7.7 Hz, 1H), 6.51 (s, 1H), 4.18-4.04 (m, 1H), 3.04 (d, J=10.6 Hz, 1H), 2.76-2.48 (m, 6H), 2.37-2.14 (m, 3H), 1.97-1.67 (m, 6H), 1.66-1.54 (m, 1H), 1.45 (d, J=6.8 Hz, 3H), 1.07-0.96 (m, 1H), 0.83 (d, J=6.8 Hz, 3H), 0.52 (br. s., 1H), 0.33-0.18 (m, 2H), −0.09 (br. s., 1H)

Example 120

$^1$H NMR (400 MHz, CDCl$_3$): δ=9.38 (br. s., 1H), 7.74 (s, 1H), 7.53 (d, J=8.6 Hz, 1H), 7.39 (d, J=7.7 Hz, 1H), 7.15 (s, 1H), 6.98 (d, J=7.7 Hz, 1H), 6.68 (d, J=7.7 Hz, 1H), 6.42 (s, 1H), 4.83 (br. s., 1H), 3.80-3.71 (m, 1H), 3.41-3.32 (m, 2H), 3.11-2.98 (m, 2H), 2.87 (q, J=7.4 Hz, 2H), 2.78-2.65 (m, 3H), 2.30-2.14 (m, 2H), 2.06-1.94 (m, 2H), 1.86 (d, J=6.2 Hz, 7H), 1.34-1.29 (m, 3H), 1.04-0.98 (m, 1H), 0.93 (d, J=6.8 Hz, 3H), 0.67-0.57 (m, 1H), 0.37-0.27 (m, 2H), 0.02-−0.08 (m, 1H)

Example 121

$^1$H NMR (400 MHz, CDCl$_3$): δ=7.86 (s, 1H), 7.48-7.35 (m, 2H), 7.01 (d, J=7.8 Hz, 1H), 6.75-6.67 (m, 1H), 6.61 (br. s., 1H), 4.71-4.58 (m, 1H), 3.97 (d, J=9.8 Hz, 1H), 3.14 (d, J=11.0 Hz, 2H), 3.02 (br. s., 1H), 2.87-2.72 (m, 3H), 2.46 (s, 3H), 2.32 (s, 3H), 2.31-2.24 (m, 1H), 2.22-2.05 (m, 2H), 1.98-1.84 (m, 7H), 1.16-1.05 (m, 1H), 1.00 (d, J=7.0 Hz, 3H), 0.70-0.59 (m, 1H), 0.44-0.33 (m, 2H), 0.11-−0.01 (m, 1H)

Example 122

$^1$H NMR (400 MHz, CD$_3$OD): δ=8.17 (br. s., 1H), 7.70 (d, J=7.2 Hz, 1H), 7.31 (d, J=8.8 Hz, 1H), 7.00 (d, J=7.6 Hz, 1H), 6.71 (t, J=7.6 Hz, 2H), 6.58 (s., 1H), 6.09 (s., 1H), 4.57 (br. s., 1H), 3.93 (d, J=10 Hz, 1H), 3.13 (s, 2H), 2.96 (m, 1H), 2.82 (t, J=6.8 Hz, 1H), 2.74 (d, J=3.2 Hz, 2H), 2.38 (s, 3H), 2.21 (s, 1H), 2.07 (d, J=12 Hz, 1H), 1.93-1.87 (m, 8H), 1.08 (br. s., 1H), 0.98 (d, J=6.8 Hz, 3H), 0.64 (br. s., 1H), 0.36 (d, J=4.8 Hz, 2H), 0.03 (br. s., 1H).

Example 123

(2S,3R)-3-(1'-(1-(5-cyano-2-(trifluoromethoxy)phenyl)ethyl)spiro[chroman-2,4'-piperidin]-7-yl)-3-cyclopropyl-2-methylpropanoic Acid

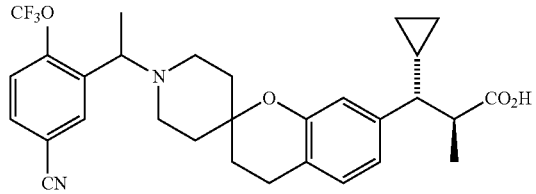

Step A: (2S,3R)-3-(1'-(1-(5-bromo-2-(trifluoromethoxy)phenyl)ethyl)spiro-[chroman-2,4'-piperidin]-7-yl)-3-cyclopropyl-2-methylpropanoic Acid To a solution of (2S,3R)-methyl 3-(1'-(1-(5-bromo-2-(trifluoromethoxy)phenyl)ethyl)spiro[chroman-2,4'-piperidin]-7-yl)-3-cyclopropyl-2-methylpropanoate (150 mg, 0.246 mmol) in MeOH (1 mL), THF (1 mL) and water (1 mL) was added lithium hydroxide hydrate (155 mg, 3.69 mmol). The reaction was heated to 55° C. for 12 hours, then cooled to room temperature and neutralized to pH 7 with concentrated HCl. The solvent was removed by rotary evaporator. The resulting residue was diluted with saturated brine (5 mL) and extracted with EtOAc (5 mL×3). The combined organic layers were washed with saturated brine (5 mL), dried over MgSO$_4$ and filtered. The filtrate was concentrated by rotary evaporator to give the title compound, which was used directly in the next step. MS (ESI): m/z 596.1, 598.1 [M+H]$^+$ Step B: (2S,3R)-3-(1'-(1-(5-cyano-2-(trifluoromethoxy)phenyl)ethyl)spiro-[chroman-2,4'-piperidin]-7-yl)-3-cyclopropyl-2-methylpropanoic Acid To a solution of (2S,3R)-3-(1'-(1-(5-bromo-2-(trifluoromethoxy)phenyl)ethyl)spiro[chroman-2,4'-piperidin]-7-yl)-3-cyclopropyl-2-methylpropanoic acid (100 mg, 0.168 mmol) in 1,4-dioxane (1.6 mL) and water (0.4 mL) were added potassium ferrocyanide trihydrate (212 mg, 0.503 mmol), K$_2$CO$_3$ (69.5 mg, 0.503 mmol), 2-(dicyclohexylphosphino)-2',4',6'-triisopropylbiphenyl (16.0 mg, 0.0340 mmol) and Pd(OAc)$_2$ (3.76 mg, 0.0170 mmol). The reaction was stirred at 100° C. for 3 h under a nitrogen atmosphere, then cooled to room temperature, diluted with brine (5 mL) and extracted with EtOAc (5 mL×3). The combined organic layers were washed with brine (5 mL), dried over Na$_2$SO$_4$ and filtered. The filtrate was concentrated by rotary evaporator to give a residue, which was purified by preparative HPLC to give the title compound. The title compound was treated with 1 equivalent of aqueous NaOH (10 wt %) and lyophilized to give the sodium salt of the title compound. Preparative HPLC conditions: Column: Waters XSELECT C18 150*30 mm*5 um; Condition water (0.1% TFA)-ACN; Begin B: 22; End B: 42; Gradient Time (min): 10; 100% B Hold Time (min): 2; FlowRate (mL/min): 25; Injections: 7. MS (ESI): m/z 543.2 [M+H]$^+$ $^1$H NMR (400 MHz, CD$_3$OD): δ=8.26 (s, 1H), 8.03 (d, J=8.6 Hz, 1H), 7.70 (d, J=7.9 Hz, 1H), 7.02 (d, J=7.7 Hz, 1H), 6.77-6.67 (m, 1H), 6.65 (s, 1H), 5.08-5.00 (m, 1H), 3.86-3.37 (m, 2H), 3.28-3.15 (m, 2H), 2.86-2.65 (m, 3H), 2.22-1.76 (m, 10H), 1.15-0.99 (m, 1H), 0.89 (d, J=6.8 Hz, 3H), 0.66-0.52 (m, 1H), 0.40-0.22 (m, 2H), 0.04--0.13 (m, 1H)

0-10:1, v/v) to give the title compound. MS (ESI) m/z: 264.7 [M+H]$^+$ $^1$H NMR (400 MHz, DMSO-d6) δ=8.71 (d, J=2.2 Hz, 1H), 8.63 (d, J=2.0 Hz, 1H), 3.93 (s, 3H)

TABLE 31

The compound of Example 124 was prepared in a similar manner to Example 123 using the appropriate starting material and reagents.

| Example | Structure | M.W. | Compound Name | LC/MS (ESI) observed [M + H]$^+$ |
|---|---|---|---|---|
| 124 | 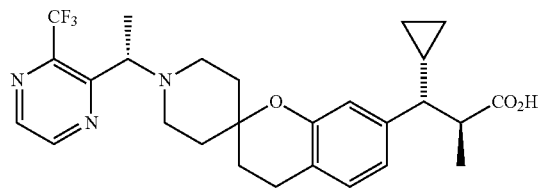 [SMILES: C[C@H](C(=O)O)[C@H](c1ccc2c(c1)OC1(CC2)CCN([C@@H](C)c2nccnc2C(F)(F)F)CC1)C1CC1] | 528.56 | (2S,3R)-3-(1'-(5-cyano-2-(trifluoro-methoxy)-benzyl)spiro[chroman-2,4'-piperidin]-7-yl)-3-cyclopropyl-2-methylpropanoic acid | 529.1 |

Example 124

$^1$H NMR (400 MHz, CD$_3$OD): δ=8.16 (d, J=1.8 Hz, 1H), 8.05 (dd, J=1.9, 8.7 Hz, 1H), 7.74-7.67 (m, J=1.5, 8.8 Hz, 1H), 7.04 (d, J=7.7 Hz, 1H), 6.79-6.69 (m, 2H), 4.58 (s, 2H), 3.61-3.38 (m, 4H), 2.88-2.67 (m, 3H), 2.18-2.07 (m, 2H), 2.02-1.83 (m, 4H), 1.15-1.02 (m, 1H), 0.91 (d, J=6.8 Hz, 3H), 0.65-0.55 (m, 1H), 0.39-0.24 (m, 2H), 0.04--0.09 (m, 1H)

Example 125

(2S,3R)-3-cyclopropyl-2-methyl-3-(1'-((RS)-1-(3-(trifluoromethyl)pyrazin-2-yl)ethyl)spiro[chroman-2,4'-piperidin]-7-yl)propanoic Acid Step A: methyl 3-iodopyrazine-2-carboxylate To a solution of methyl 3-amino-pyrazine-2-carboxylate (5.00 g, 32.7 mmol) in 1,2-dimethoxyethane (80 mL) were added I$_2$ (4.14 g, 16.3 mmol), copper(I) iodide (1.87 g, 9.80 mmol) and cesium iodide (8.48 g, 32.7 mmol) under nitrogen. Then isoamyl nitrite (13.2 mL, 98.0 mmol) was added dropwise at 20° C. The reaction was stirred at 75° C. for 2 h, then quenched with water (100 mL). The aqueous layer was extracted with EtOAc (100 mL×3). The combined organic layers were washed with brine (30 mL), dried over anhydrous MgSO$_4$ and filtered. The filtrate was concentrated in vacuo to give a residue, which was purified by silica gel chromagraphy eluting with PE/EtOAc (SiO$_2$, PE:EtOAc=1:0-10:1, v/v) to give the title compound. MS (ESI) m/z: 264.7 [M+H]$^+$ $^1$H NMR (400 MHz, DMSO-d6) δ=8.71 (d, J=2.2 Hz, 1H), 8.63 (d, J=2.0 Hz, 1H), 3.93 (s, 3H)

Step B: methyl 3-(trifluoromethyl)pyrazine-2-carboxylate

To a solution of methyl 3-iodopyrazine-2-carboxylate (2.50 g, 9.47 mmol) in dry DMF (38 mL) was added copper(I) iodide (4.51 g, 23.7 mmol) at 15° C. Then methyl 2,2-difluoro-2-(fluoro-sulfonyl)acetate (14.6 g, 76.0 mmol) was added dropwise over 5 min under nitrogen. The reaction was stirred at 75° C. for 3 hours, then cooled to room temperature. Water (50 mL) was added to the reaction, and the mixture was extracted with EtOAc (50 mL×3). The combined organic layers were washed with brine (80 mL×2), dried over anhydrous MgSO$_4$ and filtered. The filtrate was concentrated in vacuo to give a residue, which was purified by silica gel chromagraphy eluting with PE/EtOAc (SiO$_2$, PE:EtOAc=50:1-10:1, v/v) to give the title compound. MS (ESI) m/z: 206.7 [M+H]$^+$ $^1$H NMR (400 MHz, CDCl$_3$) δ=8.83 (d, J=8.8 Hz, 2H), 4.06 (s, 3H) $^{19}$F NMR (376 MHz, CDCl$_3$) δ=-65.28 (s, 1F)

Step C: 3-(trifluoromethyl)pyrazine-2-carbaldehyde

To a solution of methyl 3-(trifluoromethyl)pyrazine-2-carboxylate (700 mg, 3.40 mmol) in THF (10 mL) was added diisobutylaluminum hydride (5.09 mL, 5.09 mmol) dropwise over 1 min at −78° C. under nitrogen. The reaction was stirred at −78° C. for 1 h, then quenched with saturated NH$_4$Cl solution (20 mL) at −78° C. and extracted with EtOAc (20 mL×3). The combined organic layers were washed with brine (30 mL), dried over anhydrous MgSO$_4$ and filtered. The filtrate was concentrated in vacuo to give a residue, which was purified by prep-TLC (SiO$_2$, PE/EtOAc=2:1, v/v) to give the title compound. MS (ESI) m/z: 176.8 [M+H]$^+$ 1H NMR (400 MHz, CDCl$_3$) δ=10.33 (s, 1H), 9.02 (s, 1H), 8.88 (d, J=1.6 Hz, 1H)

Step D: 1-(3-(trifluoromethyl)pyrazin-2-yl)ethanol

To a solution of 3-(trifluoro-methyl)pyrazine-2-carbaldehyde (400 mg, 2.27 mmol) in THF (3.0 mL) was added methylmagnesium bromide (1.89 mL, 5.68 mmol) dropwise over 1 min at 0° C. under nitrogen. The reaction was stirred at 0° C. for 0.5 h and at 20° C. for 1 h, then poured slowly into saturated NH$_4$Cl solution (5 mL) at 0° C. Water (5 mL) was added to the mixture, and the mixture was extracted with EtOAc (10 mL×2). The combined organic layers were washed with brine (10 mL), dried over Na$_2$SO$_4$ and filtered. The filtrate was concentrated under reduced pressure to give a residue, which was purified by prep-TLC (SiO$_2$, PE:EtOAc=2:1, v/v) to give the title compound. MS (ESI) m/z: 174.8 [M–OH]$^+$ Step F: 1-(3-(trifluoromethyl)pyrazin-2-yl)ethyl methanesulfonate To a solution of 1-(3-(trifluoromethyl)pyrazin-2-yl)ethanol (68.0 mg, 0.354 mmol) in DCM (2 mL) was added TEA (0.148 mL, 1.06 mmol) under nitrogen. Then Ms-Cl (0.041 mL, 0.531 mmol) was added dropwise over 1 min to the mixture at 0° C. under nitrogen. The reaction was stirred at 0° C. for 1 h, then quenched with water (5 mL) and extracted with DCM (5 mL×3). The combined organic layers were washed with brine (10 mL), dried over anhydrous MgSO$_4$ and filtered. The filtrate was concentrated under reduced pressure to give the title compound, which was used directly in the next step without further purification. MS (ESI) m/z: 270.8 [M+H]$^+$ Step G: (2S,3R)-methyl 3-cyclopropyl-2-methyl-3-(1'-((RS)-1-(3-(trifluoromethyl)-pyrazin-2-yl)ethyl) spiro[chroman-2,4'-piperidin]-7-yl)propanoate To a solution of (2S,3R)-methyl 3-cyclopropyl-2-methyl-3-(spiro[chroman-2,4'-piperidin]-7-yl)-propanoate (60.000 mg, 0.175 mmol) in MeCN (2 mL) were added sodium iodide (79.0 mg, 0.524 mmol), 1-(3-(trifluoromethyl) pyrazin-2-yl)ethyl methanesulfonate (47.2 mg, 0.175 mmol) and K$_2$CO$_3$ (121 mg, 0.873 mmol) under nitrogen. The reaction was stirred at 80° C. for 2 h. Then water (10 mL) was added to the mixture and the mixture was extracted with EtOAc (10 mL×3). The combined organic layers were washed with brine (20 mL), dried over anhydrous MgSO$_4$ and filtered. The filtrate was concentrated in vacuo to give a residue, which was purified by prep-TLC (SiO$_2$, PE/EtOAc=2:1, v/v) to give the title compound. MS (ESI) m/z: 518.1 [M+H]$^+$ Step H: (2S,3R)-3-cyclopropyl-2-methyl-3-(1'-((RS)-1-(3-(trifluoromethyl)pyrazin-2-yl)ethyl)spiro [chroman-2,4'-piperidin]-7-yl)propanoic Acid To a solution of (2S,3R)-methyl 3-cyclopropyl-2-methyl-3-(1'-((RS)-1-(3-(trifluoromethyl)-pyrazin-2-yl)ethyl)spiro-[chroman-2,4'-piperidin]-7-yl)propanoate (56.0 mg, 0.108 mmol) in MeOH (1.5 mL), THF (1.5 mL) and water (1.5 mL) was added LiOH (78.0 mg, 3.25 mmol) under nitrogen. The reaction mixture was stirred at 55° C. for 14 h, then concentrated in vacuo to remove the solvent. Water (15 mL) was added to the resulting residue, followed by the addition of citric acid to adjust the mixture pH to pH-5. Then the mixture was extracted with EtOAc (10 mL×3). The combined organic layers were washed with brine (15 mL), dried over anhydrous MgSO$_4$ and filtered. The filtrate was concentrated under reduced pressure to give a residue, which was purified by prep HPLC (TFA) to give the title compound, which was used directly in the next step without further purification. Preparative HPLC conditions: a MS trigger instrument fitted with a YMC-Actus Pro C18 150*30 5 um using water and acetonitrile as the eluents, mobile phase A: water (0.1% TFA)-ACN, mobile phase B: acetonitrile, gradient: 22-52% B, 0-11.0 min; 100% B, 11.1-13.0 min; 10% B, 13.1-16 min, FlowRate: 25 mL/min. MS (ESI) m/z: 504.2 [M+H]$^+$ $^1$H NMR (400 MHz, CD$_3$OD) δ=9.00 (br. s., 1H), 8.81 (br. s., 1H), 7.01 (d, J=7.4 Hz, 1H), 6.77-6.64 (m, 2H), 3.64-3.35 (m, 2H), 3.29-3.10 (m, 2H), 2.94 (br. s., 1H), 2.86-2.67 (m, 3H), 2.17-1.75 (m, 7H), 1.66 (d, J=6.3 Hz, 3H), 1.16-1.01 (m, 1H), 0.90 (d, J=6.7 Hz, 3H), 0.66-0.53 (m, 1H), 0.39-0.22 (m, 2H), 0.03--0.09 (m, 1H)

Example 126

(2S,3R)-3-cyclopropyl-3-(2,2-(R)-2-(1-(2,5-bis(trifluoromethyl)phenyl)ethyl)-2-azaspiro[3.3]heptane-chroman-7-yl)-2-methylpropanoic Acid

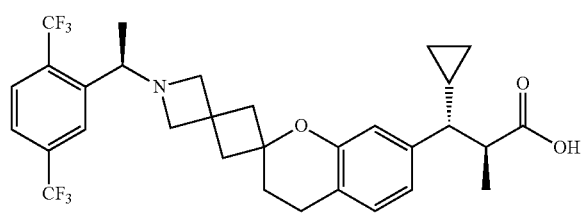 [SMILES: C[C@H](C(=O)O)[C@H](c1ccc2c(c1)OC1(CC2)CC2(CN([C@H](C)c3cc(C(F)(F)F)ccc3C(F)(F)F)C2)C1)C1CC1]

Step A: (2S,3R)-methyl 3-cyclopropyl-3-(3',3'-(2-azaspiro[3.3]heptane-2-carboxylate)-4-oxospiro [chroman-2,1'-cyclobutan]-7-yl)-2-methylpropanoate To a solution of (2S,3R)-methyl 3-(4-acetyl-3-hydroxyphenyl)-3-cyclopropyl-2-methylpropanoate (400 mg, 1.45 mmol) in MeOH (10 mL) were added tert-butyl 6-oxo-2-azaspiro[3.3]heptane-2-carboxylate (398 mg, 1.88 mmol) and pyrrolidine (309 mg, 4.34 mmol) at 18° C. under nitrogen. The reaction was stirred at 80° C. for 2 h, then concentrated under reduced pressure. The resulting residue was diluted with water (20 mL) and extracted with EtOAc (20 mL×2). The combined organic layers were washed with brine (10 mL×2), dried over MgSO$_4$ and filtered. The filtrate was concentrated under reduced pressure to give a residue, which was purified by prep-TLC (SiO$_2$, PE/EtOAc=5:1, v/v)) to give the title compound. MS (ESI) m/z: 470.2 [M+H]$^+$ $^1$H NMR (400 MHz, CDCl$_3$δ=7.79 (d, J=8.2 Hz, 1H), 6.83 (d, J=7.8 Hz, 1H), 6.75 (s, 1H), 3.97 (d, J=10.2 Hz, 4H), 3.73 (s, 3H), 2.87-2.72 (m, 3H), 2.56-2.47 (m, 2H), 2.46-2.38 (m, 2H), 1.94 (t, J=10.0 Hz, 1H), 1.44 (s, 9H), 1.10-0.99 (m, 1H), 0.95 (d, J=7.0 Hz, 3H), 0.65-0.53 (m, 1H), 0.42-0.22 (m, 2H), 0.04--0.06 (m, 1H)

Step B: (2S,3R)-methyl 3-cyclopropyl-3-(3',3'-(2-azaspiro[3.3]heptane-2-carboxylate)-4-oxospiro [chroman-2,1'-cyclobutan]-7-yl)-2-methylpropanoate To a solution of (2S,3R)-methyl 3-cyclopropyl-3-(3',3'-(2-azaspiro[3.3]heptane-2-carboxylate)-4-oxospiro[chroman-2,1'-cyclobutan]-7-yl)-2-methylpropanoate (630 mg, 1.342 mmol) in EtOH (10 mL) was added NaBH$_4$ (102 mg, 2.68 mmol) under nitrogen. The reaction was stirred at 0° C. for 2 h, then quenched with saturated NH$_4$Cl solution (30 mL) at 25° C. and extracted with EtOAc (20 mL×3). The combined organic layers were washed with brine (30 mL), dried over anhydrous MgSO$_4$ and filtered. The filtrate was concentrated in vacuo to give a residue, which was purified by prep-TLC (SiO$_2$, PE/EtOAc=2:1, v/v)) to give the title compound. MS (ESI) m/z: 494.3 [M+Na]$^+$ $^1$H NMR (400 MHz, CDCl$_3$) δ=7.31 (d, J=7.8 Hz, 1H), 6.75 (d, J=7.8 Hz, 1H), 6.62 (s, 1H), 4.83 (d, J=4.3 Hz, 1H), 4.05-3.92 (m, 4H), 3.73 (s, 3H), 2.87-2.72 (m, 1H), 2.64 (d, J=11.3 Hz, 1H), 2.48 (t, J=9.8 Hz, 2H), 2.41-2.31 (m, 1H), 2.19-2.10 (m, 1H), 2.05-1.99 (m, 1H), 1.86 (t, J=10.2 Hz, 1H), 1.79 (br. s., 1H), 1.44 (s, 9H), 1.10-0.98 (m, 1H), 0.94 (d, J=7.0 Hz, 3H), 0.61-0.49 (m, 1H), 0.39-0.28 (m, 1H), 0.27-0.17 (m, 1H), 0.05--0.06 (m, 1H)

Step C: (2S,3R)-methyl 3-cyclopropyl-3-(3',3'-azaspiro[3.3]heptane-[chroman-2,1'-cyclobutan]-7-yl)-2-methylpropanoate To a solution of (2S,3R)-methyl 3-cyclopropyl-3-(3',3'-(2-azaspiro[3.3]heptane-2-carboxylate)-4-oxospiro[chroman-2,1'-cyclobutan]-7-yl)-2-methylpropanoate (650 mg, 1.38 mmol) in DCM (10 mL) were added triethylsilane (4 mL, 25.0 mmol) and TFA (4 mL, 51.9 mmol). The reaction mixture was stirred at 25° C. for 30 min. Then the solvent was removed under reduced pressure to give a residue. Saturated aqueous NaHCO₃ solution was added to the residue to adjust the pH to pH ~9, and the mixture was extracted with EtOAc (10 mL×3). The combined organic layers were washed with brine (10 mL), dried over MgSO₄ and filtered. The filtrate was concentrated in vacuo to give the title compound, which was used in the next step directly without further purification. MS (ESI) m/z: 356.2 [M+H]$^+$ Step D: (2S,3R)-methyl 3-cyclopropyl-3-(2,2-(R)-2-(1-(2,5-bis(trifluoromethyl)-phenyl)ethyl)-2-azaspiro[3.3]heptane-chroman-7-yl)-2-methylpropanoate To a solution of (2S,3R)-methyl 3-cyclopropyl-3-(3',3'-azaspiro[3.3]heptane[chroman-2,1'-cyclobutan]-7-yl)-2-methylpropanoate (100 mg, 0.281 mmol) in MeCN (3 mL) were added (S)-1-(2,5-bis(trifluoromethyl)phenyl)ethyl methanesulfonate (142 mg, 0.422 mmol) and K₂CO₃ (194 mg, 1.41 mmol) under nitrogen. The reaction was stirred at 80° C. for 18 h. Then water (15 mL) was added and the mixture was extracted with EtOAc (10 mL×3). The combined organic layers were washed with brine (20 mL), dried over anhydrous MgSO₄ and filtered. The filtrate was concentrated in vacuo to give a residue, which was purified by prep-TLC (SiO₂, PE/EtOAc=10:1, v/v) to give the title compound. MS (ESI) m/z: 596.3 [M+H]$^+$ Step E: (2S,3R)-3-cyclopropyl-3-(2,2-(R)-2-(1-(2,5-bis(trifluoromethyl)phenyl)ethyl)-2-azaspiro[3.3]heptane-chroman-7-yl)-2-methylpropanoic Acid To a solution of (2S,3R)-methyl 3-cyclopropyl-3-(2,2-(R)-2-(1-(2,5-bis(trifluoromethyl)-phenyl)ethyl)-2-azaspiro[3.3]heptane-chroman-7-yl)-2-methyl-propanoate (85.0 mg, 0.143 mmol) in MeOH (1.5 mL), THF (1.5 mL) and water (1.5 mL) was added LiOH (103 mg, 4.28 mmol) under nitrogen. The reaction was stirred at 55° C. for 14 h, then concentrated in vacuo to remove the solvent. Water (15 mL) was added to the resulting residue, followed by the addition of citric acid to adjust the mixture pH to pH-5. Then the mixture was extracted with EtOAc (10 mL×3). The combined organic layers were washed with brine (15 mL), dried over anhydrous MgSO₄ and filtered. The filtrate was concentrated under reduced pressure to give a residue, which was purified by Prep HPLC (neutral) to give the title compound. MS (ESI) m/z: 582.3 [M+H]$^+$ Preparative HPLC conditions: MS trigger instrument fitted with a Phenomenex Gemini C18 250*21.2 mm*5 um using water and acetonitrile as the eluents, Mobile phase A: water (10 mM NH4HCO3)-ACN, mobile phase B: acetonitrile, Gradient: 45-75% B, 0-11.0 min, 100% B, 11.1-13.0 min, 10% B, 13.1-16 min, FlowRate: 25 mL/min. MS (ESI) m/z: 582.3 [M+H]$^+$ $^1$H NMR (400 MHz, CDCl₃) δ=8.15 (br. s., 1H), 7.74 (d, J=8.2 Hz, 1H), 7.59 (d, J=7.8 Hz, 1H), 6.95 (d, J=7.8 Hz, 1H), 6.65 (d, J=7.8 Hz, 1H), 6.59 (s, 1H), 3.78 (br. s., 1H), 3.33 (br. s., 1H), 3.19 (d, J=8.6 Hz, 3H), 2.80 (d, J=7.0 Hz, 1H), 2.72 (t, J=6.1 Hz, 2H), 2.51-2.37 (m, 2H), 2.35-2.22 (m, 2H), 1.91 (t, J=9.8 Hz, 1H), 1.82 (t, J=6.1 Hz, 2H), 1.21 (d, J=5.9 Hz, 3H), 1.15-1.03 (m, 1H), 0.98 (d, J=6.7 Hz, 3H), 0.65-0.54 (m, 1H), 0.41-0.29 (m, 2H), 0.09--0.02 (m, 1H)

TABLE 32

The compound of Example 127 was prepared in a similar manner to Example 126 using the appropriate starting material and reagents.

| Example | Structure | M.W. | Compound Name | LC/MS (ESI) observed [M + H]$^+$ |
|---|---|---|---|---|
| 127 | 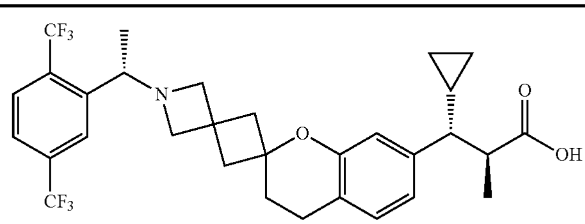 | 581.2 | (2S,3R)-3-cyclopropyl-3-(2,2-(S)-2-(1-(2,5-bis(trifluoromethyl)phenyl)ethyl)-2-azaspiro[3.3]-heptane-chroman-7-yl)-2-methylpropanoic acid | 582.3 |

Example 127

MS (ESI) m/z: 582.3 [M+H]$^+$ $^1$H NMR (400 MHz, CDCl₃) δ=8.16 (br. s., 1H), 7.74 (d, J=8.2 Hz, 1H), 7.60 (d, J=8.2 Hz, 1H), 6.95 (d, J=7.8 Hz, 1H), 6.65 (d, J=7.8 Hz, 1H), 6.59 (s, 1H), 3.85-3.73 (m, 1H), 3.40-3.14 (m, 4H), 2.86-2.76 (m, 1H), 2.72 (t, J=6.3 Hz, 2H), 2.49-2.38 (m, 2H), 2.36-2.23 (m, 2H), 1.92 (t, J=9.6 Hz, 1H), 1.82 (t, J=6.3 Hz, 2H), 1.21 (d, J=5.9 Hz, 3H), 1.16-1.04 (m, 1H), 0.98 (d, J=6.7 Hz, 3H), 0.66-0.57 (m, 1H), 0.42-0.30 (m, 2H), 0.09--0.02 (m, 1H)

Example 128

Methyl (2S,3R)-3-(1''-((S)-1-(2,5-bis(trifluoromethyl)phenyl)ethyl)dispiro-[chromane-2,1'-cyclobutane-3',3''-pyrrolidin]-7-yl)-3-cyclopropyl-2-methylpropanoate

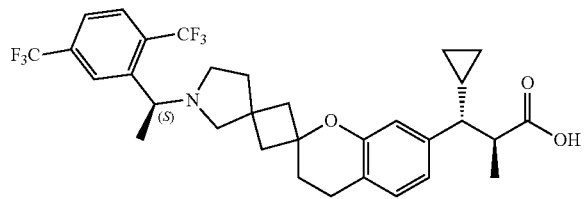

Step A: tert-Butyl 7-((1R,2S)-1-cyclopropyl-3-methoxy-2-methyl-3-oxopropyl)-4-oxodispiro[chromane-2,1'-cyclobutane-3',3''-pyrrolidine]-1''-carboxylate (2S,3R)-methyl 3-(4-acetyl-3-hydroxyphenyl)-3-cyclopropyl-2-methylpropanoate (4.9 g, 17.73 mmol) and 6-Boc-2-oxo-6-aza-spiro[3.4]octane (4.99 g, 22.17 mmol) were combined in dry MeOH (44.3 ml) and pyrrolidine (1.466 ml, 17.73 mmol) was added. The reaction was stirred at 65° C. overnight. Then additional 6-Boc-2-oxo-6-aza-spiro[3.4]octane (2.0 g, 8.89 mmol) was added and the reaction was stirred at 65° C. for 12 h. Then the reaction was concentrated and purified by ISCO (120 g, 0-30% EtOAc/hexane) to give the title compound.

Step B: tert-butyl 7-((1R,2S)-1-cyclopropyl-3-methoxy-2-methyl-3-oxopropyl)-4-hydroxydispiro[chromane-2,1'-cyclobutane-3',3''-pyrrolidine]-1''-carboxylate To a suspension of tert-butyl 7-((1R,2S)-1-cyclopropyl-3-methoxy-2-methyl-3-oxopropyl)-4-oxodispiro-[chromane-2,1'-cyclobutane-3',3''-pyrrolidine]-1''-carboxylate (racemic, 626 mg, 1.294 mmol) in MeOH (6 ml) was added NaBH4 (50.0 mg, 1.294 mmol). The reaction was stirred at rt under nitrogen overnight, and then concentrated to give a residue. The residue was partitioned between EtOAc and water. The organic layer was separated, washed with brine, dried over MgSO4, and filtered. The filtrate was concentrated to afford the title compound, which was used in the next step without further purification.

Step C: Methyl (2S,3R)-3-cyclopropyl-3-(dispiro[chromane-2,1'-cyclobutane-3',3''-pyrrolidin]-7-yl)-2-methylpropanoate To a solution of tert-butyl 7-((1R,2S)-1-cyclo-propyl-3-methoxy-2-methyl-3-oxopropyl)-4-hydroxydispiro[chromane-2,1'-cyclobutane-3',3''-pyrrolidine]-1''-carboxylate (680 mg, 1.400 mmol) and triethylsilane (335 μl, 2.10 mmol) in DCM (7 ml) was added TFA (755 μl, 9.80 mmol). The reaction was stirred at room temperature under nitrogen overnight. Then the reaction was partitioned between 50 ml of 1N HCl and hexanes. The organic layer was discarded and the aqueous layer was basified with 1N NaOH and extracted with DCM. The organic layer was dried over MgSO4, filtered and concentrated to afford the title compound, which was used in the next step without further purification.

Step D: methyl (2S,3R)-3-(1''-((S)-1-(2,5-bis(trifluoromethyl)phenyl)ethyl)-dispiro-[chromane-2,1'-cyclobutane-3',3''-pyrrolidin]-7-yl)-3-cyclopropyl-2-methylpropanoate A solution of methyl (2S,3R)-3-cyclopropyl-3-(dispiro-[chromane-2,1'-cyclobutane-3',3''-pyrrolidin]-7-yl)-2-methylpropanoate (360 mg, 0.974 mmol), (R)-1-(2,5-bis(trifluoro-methyl)phenyl)ethyl methanesulfonate (491 mg, 1.461 mmol) and DIPEA (340 μl, 1.949 mmol) in acetonitrile (5 mL) was heated at 75° C. for 19 h. Then the reaction was concentrated and the resulting residue was purified using preparative TLC plates eluting with 20% EtOAc/hexane to afford the title compound.

Step E: (2S,3R)-3-(1''-((S)-1-(2,5-bis(trifluoromethyl)phenyl)ethyl)-dispiro-[chromane-2,1'-cyclobutane-3',3''-pyrrolidin]-7-yl)-3-cyclopropyl-2-methylpropanoic Acid To the methyl (2S,3R)-3-(1''-((S)-1-(2,5-bis(trifluoromethyl)-phenyl)-ethyl)dispiro[chromane-2,1'-cyclobutane-3',3''-pyrrolidin]-7-yl)-3-cyclo-propyl-2-methylpropanoate (274 mg, 0.449 mmol) was added THF (6 ml), followed by MeOH (3 ml) and LiOH (1M, 3.60 ml, 3.60 mmol). The reaction mixture was capped in a reaction vial and heated at 55° C. for 50 hrs. Then the reaction was neutralized with 1N HCl (~2-3 mL) to pH=~7 and partitioned between pH 7 buffer and DCM. The organic layer was separated, washed with brine, dried over MgSO4, filtered and concentrated to give a residue, which was purified by preparative TLC eluting with 5% MeOH/DCM to afford the title compound. 1H NMR (CH3OH-d4, 500 MHz): dH −0.15 (1H, s), 0.19 (2H, br s), 0.46 (1H, s), 0.79 (3H, s), 0.95 (1H, br s), 1.29 (3H, d, J=6.4 Hz), 1.76-1.70 (2H, m), 2.00-1.83 (3H, m), 2.18-2.04 (4H, m), 2.75-2.36 (7H, m), 3.71 (1H, t, J=7.5 Hz), 6.43 (1H, d, J=32.5 Hz), 6.52 (1H, d, J=7.5 Hz), 6.82 (1H, dd, J=7.6, 4.3 Hz), 7.65 (1H, d, J=8.3 Hz), 7.78 (1H, d, J=8.3 Hz), 8.16 (1H, d, J=6.4 Hz).

Example 129

Sodium (2S,3R)-3-(1'-(2,5-bis(trifluoromethyl)benzyl)spiro[chromane-2,4'-piperidin]-7-yl)-3-cyclopropyl-2-methylpropanoate

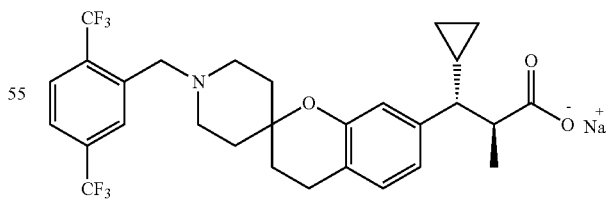

Step A: 1-(2,5-Bis(trifluoromethyl)benzyl)piperidin-4-one

To a solution of piperidin-4-one (1 g, 10.1 mmol) in DMF (20 mL) at rt was added 2,5-bis(trifluoromethyl)benzyl bromide (3.10 g, 10.1 mmol) and K2CO3 (2.8 g, 20.2 mmol).

The reaction was stirred at rt for 12h. Then the reaction mixture was diluted with H₂O (25 mL), extracted with EtOAc (3×25 mL), washed with brine, dried over MgSO₄, and filtered. The filtrate was concentrated and purified by column chromatography on silica gel to give the title compound. LC/MS: m/e 344.34 (M+H+H₂O)⁺.

Step B: Methyl (2S,3R)-3-(1'-(2,5-bis(trifluoromethyl)benzyl)-4-oxospiro[chromane-2,4'-piperidin]-7-yl)-3-cyclopropyl-2-methylpropanoate (2S,3R)-methyl 3-(4-acetyl-3-hydroxyphenyl)-3-cyclopropyl-2-methylpropanoate (629 mg, 2.3 mmol) and 1-(2,5-bis(trifluoromethyl)benzyl)piperidin-4-one (740 mg, 2.3 mmol) were combined in dry MeOH (8 mL), and pyrrolidine (0.2 ml, 2.7 mmol) was added. The reaction was heated to 60° C. for 12 h. Then the MeOH was removed, and the resulting residue was diluted with H₂O, extracted with EtOAc (3×), washed with brine, dried over MgSO₄, and filtered. The filtrate was concentrated and purified by column chromatography on silica gel to give the title compound. LC/MS: m/e 584.70 (M+H)⁺.

Step C: Methyl (2S,3R)-3-(1'-(2,5-bis(trifluoromethyl)benzyl)spiro[chromane-2,4'-piperidin]-7-yl)-3-cyclopropyl-2-methylpropanoate To a solution of (2S,3R)-methyl 3-(1'-(2,5-bis(trifluoromethyl)benzyl)-4-oxospiro[chroman-2,4'-piperidin]-7-yl)-3-cyclopropyl-2-methylpropanoate (629 mg, 1.1 mmol) in AcOH (8 mL) was added zinc (1.7 g, 26 mmol) at rt under N₂. The reaction was heated to 70° C. for 2 h, and then cooled to rt. The AcOH was removed under reduced pressure. The resulting residue was taken up in EtOAc and poured into saturated NaHCO₃ solution. The combined organic layers were washed with brine and dried over MgSO₄ and concentrated. The resulting residue was purified by column chromatography on silica gel to give the title compound. LC/MS: m/e 570.70 (M+H)⁺.

Step D: Sodium (2S,3R)-3-(1'-(2,5-bis(trifluoromethyl)benzyl)spiro[chromane-2,4'-piperidin]-7-yl)-3-cyclopropyl-2-methylpropanoate To (2S,3R)-Methyl 3-(1'-(2,5-bis(trifluoromethyl)benzyl) spiro[chroman-2,4'-piperidin]-7-yl)-3-cyclopropyl-2-methylpropanoate (538 mg, 0.945 mmol) in THF (3 ml)/MeOH (3 mL)/H₂O (2 mL) at rt was added LiOH (159 mg, 3.8 mmol), the resulting mixture was stirred at rt for 12 h. Then the reaction mixture was diluted with H₂O, acidified with 1N HCl to pH 4-5, extracted with EtOAc (3×), washed with brine, dried over MgSO₄, and filtered. The filtrate was concentrated and purified by column chromatography on silica gel to give the title compound. LC/MS: m/e 556.69 (M+H)⁺ ¹H NMR (CH₃OH-d₄, 500 MHz): 0.03 (m, 1H) 0.32 (1H, t, J=6.9 Hz), 0.52 (1H, dd, J=9.4, 5.0 Hz), 0.64 (1H, d, J=7.4 Hz), 0.93 (3H, d, J=6.8 Hz), 1.17-1.14 (1H, m), 1.40 (1H, m), 1.86-1.80 (2H, m), 2.03-1.91 (4H, m), 2.76-2.68 (5H, m), 2.87 (2H, t, J=6.8 Hz), 3.90 (2H, s), 6.75-6.74 (2H, m), 7.04 (1H, d, J=8.0 Hz), 7.84 (1H, d, J=8.3 Hz), 7.99 (1H, d, J=8.2 Hz), 8.33 (1H, s).

Example 130

Sodium (2S,3R)-3-(1'-((R)-1-(2,5-Bis(trifluoromethyl)phenyl)ethyl)spiro[chromane-2,4'-piperidin]-7-yl)-3-cyclopropyl-2-methylpropanoate

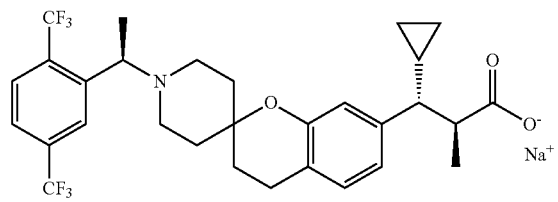 [SMILES: C[C@H](C(=O)[O-])[C@H](c1ccc2c(c1)OC1(CC2)CCN([C@H](C)c2cc(C(F)(F)F)ccc2C(F)(F)F)CC1)C1CC1 ; [Na+]]

Step A: tert-Butyl 7-((1R,2S)-1-cyclopropyl-3-methoxy-2-methyl-3-oxopropyl)-4-oxospiro[chromane-2,4'-piperidine]-1'-carboxylate (2S,3R)-Methyl-3-(4-acetyl-3-hydroxyphenyl)-3-cyclopropyl-2-methylpropanoate (2.7 g, 9.8 mmol) and tert-butyl 4-oxopiperidine-1-carboxylate (1.9 g, 9.8 mmol) were combined in dry MeOH (49 mL), and pyrrolidine (0.9 mL, 11.7 mmol) was added. The reaction was heated to 60° C. for 12 h, then the MeOH was removed. The resulting residue was purified by column chromatography (40 g, 0-20% EtOAc/hexane) to give the title compound. LC/MS: m/e 458.57 (M+H)⁺.

Step B: tert-Butyl 7-((1R,2S)-1-cyclopropyl-3-methoxy-2-methyl-3-oxopropyl)-4-hydroxyspiro[chromane-2,4'-piperidine]-1'-carboxylate tert-Butyl 7-((1R,2S)-1-cyclopropyl-3-methoxy-2-methyl-3-oxopropyl)-4-oxospiro[chroman-2,4'-piperidine]-1'-carboxylate (400 mg, 0.87 mmol) in MeOH (8.7 mL) was treated with NaBH₄ (33.1 mg, 0.87 mmol) at rt for 2 h. Then the reaction was concentrated and partitioned between EtOAc and water. The organic layer was—washed with brine, dried over sodium sulfate, and filtered. The filtrate was concentrated to give the title compound, which was used without further purification. LC/MS: m/e 460.55 (M+H)⁺.

Step C: Methyl (2S,3R)-3-cyclopropyl-2-methyl-3-(spiro[chromane-2,4'-piperidin]-7-yl)propanoate tert-Butyl 7-((1R,2S)-1-cyclopropyl-3-methoxy-2-methyl-3-oxopropyl)-4-hydroxyspiro[chroman-2,4'-piperidine]-1'-carboxylate (410 mg, 0.89 mmol) in DCM (8.9 mL) was treated with triethylsilane (570 µl, 3.6 mmol), followed by the slow addition of TFA (206 µl, 2.68 mmol) over 10 minutes. The reaction was stirred for 72 h, then concentrated and partitioned between DCM (65 mL) and 1N NaOH (30 mL). The organic layer was washed with water (20 mL), brine (30 mL), dried over sodium sulfate, and filtered. The filtrate was concentrated to give the title compound, which was used without further purification. LC/MS: m/e 344.43 (M+H)⁺.

Step D: (2S,3R)-3-(1'-((R)-1-(2,5-Bis(trifluoromethyl)phenyl)ethyl)spiro[chromane-2,4'-piperidin]-7-yl)-3-cyclopropyl-2-methylpropanoic Acid (2S,3R)-methyl 3-cyclopropyl-2-methyl-3-(spiro[chroman-2,4'-piperidin]-7-yl)propanoate (200 mg, 0.6 mmol), (S)-1-(2,5-bis(trifluoromethyl)phenyl)ethyl methanesulfonate (294 mg, 0.873 mmol) and TEA (0.162 mL, 1.16 mmol) in ACN (2 mL) were stirred at 62° C. for 16 h. Then the reaction mixture was partitioned between 15% EtOAc/hexanes and water. The organic layer was separated, washed with brine, dried over sodium sulfate, filtered and concentrated to give the crude product. The crude product was re-dissolved in 1:2:1 MeOH/THF/H₂O (5 mL total volume) and LiOH (55.8 mg, 2.329 mmol), and the reaction was heated to 55° C. for 24 h. After neutralization, the mixture was extracted with EtOAc and purified via column chromatography to give the title compound. LC/MS: m/e 570.65 (M+H)⁺.

Step E: Sodium (2S,3R)-3-(1'-((R)-1-(2,5-bis(trifluoromethyl)phenyl)ethyl)spiro[chromane-2,4'-piperidin]-7-yl)-3-cyclopropyl-2-methylpropanoate A solution of (2S,3R)-3-(1'-((R)-1-(2,5-bis(trifluoromethyl)phenyl)ethyl)spiro[chromane-2,4'-piperidin]-7-yl)-3-cyclopropyl-2-methylpropanoic acid (165 mg) in ACN (931 µL) was treated with NaOH (279 µL, 0.28 mmol). Water was added to make the solution homogenous and then the solution was freeze dried to obtain the title compound. ¹H NMR (500 MHz, CD₃OD) δ 8.27 (s, 1H), 7.87 (d, J=8.2 Hz, 1H), 7.76-7.70 (m, 1H), 6.92 (d, J=8.1 Hz, 1H), 6.66-6.61 (m, 2H), 3.80 (m, 1H), 3.07 (m, 1H), 2.74 (td, J=6.8, 2.8 Hz, 2H), 2.61 (dq, J=10.4, 6.9 Hz, 1H), 2.52-2.43 (m, 2H), 2.32-2.26 (m, 1H), 1.95-1.86 (m, 2H), 1.85-1.68 (m, 4H), 1.60-1.50 (m, 1H) 1.35 (d, J=6.4 Hz, 3H), 1.05 (ddq, J=13.5, 9.1, 4.9 Hz, 1H), 0.83 (d, J=6.9 Hz, 3H), 0.59-0.49 (m, 1H), 0.46-0.37 (m, 1H), 0.21 (tt, J=8.9, 4.7 Hz, 1H), −0.08 (dq, J=9.9, 5.1 Hz, 1H). LC/MS: m/e 570.63 (M+H)⁺.

Example 131

Sodium (2S,3R)-3-(1'-((S)-1-(2,5-bis(trifluoromethyl)phenyl)ethyl)spiro[chromane-2,4'-piperidin]-7-yl)-3-cyclopropyl-2-methylpropanoate

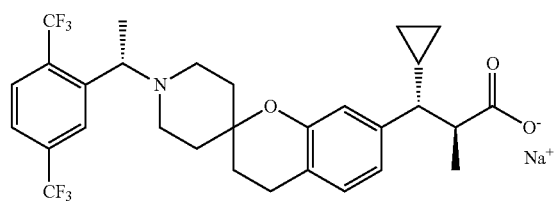 [SMILES: C[C@H](C(=O)[O-])[C@H](c1ccc2c(c1)OC1(CC2)CCN([C@@H](C)c2cc(C(F)(F)F)ccc2C(F)(F)F)CC1)C1CC1 ; [Na+]]

The title compound was prepared following the same procedure described for Example 130 using (R)-1-(2,5-bis(trifluoromethyl)phenyl)ethyl methanesulfonate instead of (S)-1-(2,5-bis(trifluoro-methyl)phenyl)ethyl methanesulfonate as the starting material. LC/MS: m/e 570.63 (M+H)⁺.

Example 132

Sodium (2S,3R)-3-cyclopropyl-3-(1'-((S)-1-(5-fluoro-2-(trifluoromethoxy)phenyl)ethyl)spiro[chromane-2,4'-piperidin]-7-yl)-2-methylpropanoate

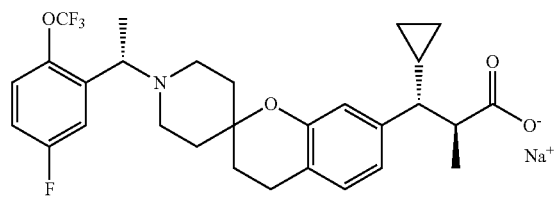 [SMILES: C[C@H](C(=O)[O-])[C@H](c1ccc2c(c1)OC1(CC2)CCN([C@@H](C)c2cc(F)ccc2OC(F)(F)F)CC1)C1CC1 ; [Na+]]

The title compound was prepared following the same procedure described for Example 130 using (R)-1-(5-fluoro-2-(trifluoromethoxy)phenyl)ethyl methanesulfonate as the starting material instead of (S)-1-(2,5-bis(trifluoromethyl)phenyl)ethyl methanesulfonate. LC/MS: m/e 536.55 (M+H)⁺.

Example 133

Sodium (2S,3R)-3-(1'-(1-(5-chloro-2-(trifluoromethoxy)phenyl)ethyl)spiro[chromane-2,4'-piperidin]-7-yl)-3-cyclopropyl-2-methylpropanoate

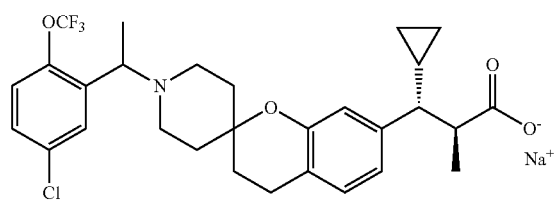 [SMILES: CC(c1cc(Cl)ccc1OC(F)(F)F)N1CCC2(CCc3ccc([C@H](C4CC4)[C@H](C)C(=O)[O-])cc3O2)CC1 ; [Na+]]

The title compound was prepared following the same procedure described for Example 130 using 1-(5-chloro-2-(trifluoromethoxy)phenyl)ethyl methanesulfonate as the starting material instead of (S)-1-(2,5-bis(trifluoromethyl)phenyl)ethyl methanesulfonate. LC/MS: m/e 552.47 (M+H)⁺.

Example 134

Sodium (2S,3R)-3-(1'-(1-(5-chloro-2-(trifluoromethoxy)phenyl)ethyl)spiro[chromane-2,4'-piperidin]-7-yl)-3-cyclopropyl-2-methylpropanoate

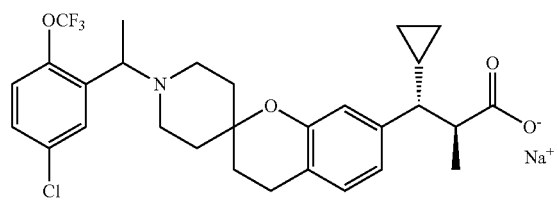 [SMILES: CC(c1cc(Cl)ccc1OC(F)(F)F)N1CCC2(CCc3ccc([C@H](C4CC4)[C@H](C)C(=O)[O-])cc3O2)CC1 ; [Na+]]

The title compound was prepared following the same procedure described for Example 130 using 1-(5-chloro-2-(trifluoromethoxy)phenyl)ethyl methanesulfonate (slower isomer) as the starting material instead of (S)-1-(2,5-bis(trifluoromethyl)phenyl)ethyl methanesulfonate. LC/MS: m/e 552.46 (M+H)$^+$.

Biological Assays

Generation of GPR40-Expressing Cells:

Human GPR40 stable cell-lines were generated in HEK cells. The expression plasmids were transfected using lipofectamine (Life Technologies) following manufacturer's instructions. Stable cell-lines were generated following drug selection and single cell cloning.

Inositol Phosphate Turnover (IP1) Assay:

The assay was performed in 384-well format. HEK cells stably expressing human GPR40 were plated at 7500 cells per well in growth medium (DMEM/10% fetal calf serum). Cell plates were then incubated 16 hours at 37 degrees in a 5% $CO_2$ incubator. Measurement of Inositol Phosphate Turnover (IP1) was performed using the CisBio IP-One kit (Part number 62IPAPEB). After the 16 hour incubation, the growth media was removed by centrifugation using the BlueWasher (AusWasher GUI Ver. v1.0.1.8) Protocol #21-"Light Dry" and 10 ul of stimulation buffer (prepared as described in the kit) was added to each well. In a separate plate, compounds were diluted in DMSO (200-fold over the final concentration in the assay well) and 50 nl was acoustically transferred to the appropriate well in the assay cell plate. The plates were then incubated for 60 minutes at 37 degrees in a 5% $CO_2$ incubator. 10 ul of detection buffer (also prepared as described in the IP-One kit) was added to each well and the plates were incubated at room temperature for 60 minutes in the dark. The plates were then read in a Perkin Elmer EnVision or equivalent reader able to measure FRET. Fluorescent ratio of emission at 665 and 620 nm was then converted to IP1 concentration by back calculating from an IP 1 standard curve prepared at the time of the assay. Data was normalized to % activity using a reference compound and EC50s determined using a standard 4-parameter fit.

The compounds of the present invention, including the compounds in Examples 1-134, have $EC_{50}$ values less than 2000 nanomolar (nM) in the Inositol Phosphate Turnover Assay 1 described above. Inositol Phosphate Turnover (IP1) Assay $EC_{50}$ values for specific compounds are shown in Table I.

TABLE I

Inositol Phophate Turnover (IP1) Assay $EC_{50}$ values

| Example | Human IP1 $EC_{50}$ (nM) |
|---|---|
| 2 | 3.29 |
| 3 | 11.69 |
| 4 | 8.063 |
| 5 | 2.712 |
| 6 | 12.14 |
| 7 | 2.141 |
| 8 | 20.57 |
| 9 | 0.7302 |
| 11 | 0.4342 |
| 12 | 995 |
| 13 | 3.6 |
| 14 | 36.32 |
| 15 | 5.898 |
| 16 | 112.9 |
| 17 | 37.25 |
| 18 | 46.11 |
| 19 | 37.55 |
| 20 | 13.51 |
| 21 | 3.655 |
| 22 | 38.3 |
| 23 | 14.27 |
| 24 | 11.21 |
| 25 | 18.33 |
| 26 | 97.85 |
| 27 | 49.54 |
| 28 | 10.96 |
| 29 | 114.9 |
| 30 | 50.4 |
| 31 | 49.87 |
| 32 | 176.8 |
| 33 | 50 |
| 34 | 8.902 |
| 35 | 5.787 |
| 36 | 4.78 |
| 37 | 683.5 |
| 38 | 506.5 |
| 39 | 565.7 |
| 40 | 166.9 |
| 41 | 12.92 |
| 42 | 46.56 |
| 43 | 60.19 |
| 44 | 311.3 |
| 45 | 148.5 |
| 46 | 22.65 |
| 47 | 2.644 |
| 48 | 1.065 |
| 49 | 0.5273 |
| 50 | 1.39 |
| 51 | 14.06 |
| 52 | 2.662 |
| 53 | 106.6 |
| 54 | 6.475 |
| 55 | 7.588 |
| 56 | 856.4 |
| 57 | 1.399 |
| 58 | 4.431 |
| 59 | 3.301 |
| 60 | 17.32 |
| 61 | 117.6 |
| 62 | 385.9 |
| 63 | 2.978 |
| 64 | 27.87 |
| 65 | 27.96 |
| 66 | 4.267 |
| 67 | 1.12 |
| 68 | 0.4102 |
| 69 | 0.4156 |
| 70 | 1.741 |
| 71 | 545.2 |
| 72 | 995 |
| 73 | 186 |
| 74 | 18.29 |
| 75 | 0.3736 |
| 76 | 11.69 |
| 77 | 23.39 |
| 78 | 14.27 |
| 79 | 2.445 |
| 80 | 3.218 |
| 81 | 102.4 |
| 82 | 248.8 |
| 83 | 798 |
| 84 | 28.51 |
| 85 | 36.15 |
| 86 | 46.47 |
| 87 | 15.31 |
| 88 | 57.04 |
| 89 | 13.07 |
| 90 | 7.237 |
| 91 | 8.622 |
| 92 | 24.64 |
| 93 | 5.705 |
| 94 | 2.615 |
| 95 | 48.61 |
| 96 | 12.28 |

TABLE I-continued

Inositol Phophate Turnover (IP1) Assay EC$_{50}$ values

| Example | Human IP1 EC$_{50}$ (nM) |
|---|---|
| 97 | 16.23 |
| 98 | 1.617 |
| 99 | 1.621 |
| 100 | 4.186 |
| 101 | 16.99 |
| 102 | 995 |
| 103 | 140.5 |
| 104 | 59.82 |
| 105 | 126.1 |
| 106 | 15.57 |
| 107 | 2.118 |
| 108 | 15.75 |
| 109 | 2.509 |
| 110 | 0.8122 |
| 111 | 20.17 |
| 112 | 21.53 |
| 113 | 579.2 |
| 114 | 91.59 |
| 115 | 41.73 |
| 116 | 323.1 |
| 117 | 36.86 |
| 118 | 2.289 |
| 119 | 15 |
| 120 | 500.6 |
| 121 | 110 |
| 122 | 42.45 |
| 123 | 30.4 |
| 124 | 64.06 |
| 125 | 415.1 |
| 126 | 8.523 |
| 127 | 0.4596 |
| 128 | 12.2 |
| 129 | 3.8 |
| 130 | 3.1 |
| 131 | >1000 |
| 132 | 11.2 |
| 133 | 3.3 |
| 134 | 1.4 |

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural formula I:

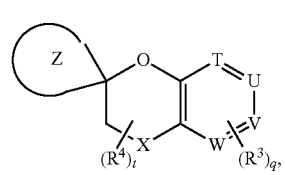

or a pharmaceutically acceptable salt thereof;
wherein
T is CH;
U is CR$^1$;
V is CR$^2$;
W is CH;
X is selected from the group consisting of:
 (1) oxygen,
 (2) —CR$^b$R$^b$,
 (3) —C=O, and
 (4) —C(R$^b$)OR$^b$, and
 (5) N(R$^b$);
Z is selected from:

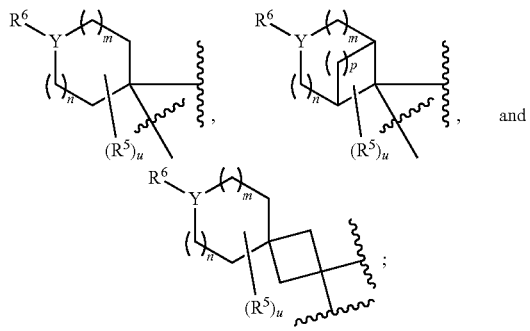

Y is selected from the group consisting of:
 (1) —C(R$^g$)—,
 (2) —C(F)—, and
 (3) —N—;
R$^1$ and R$^2$ are each independently selected from:
 (1) hydrogen, and
 (2) —C$_{1-6}$alkyl,
wherein each alkyl is unsubstituted or substituted with one to three substituents selected from R$^L$, and wherein one of R$^1$ and R$^2$ is C$_{1-6}$ alkyl, wherein —C$_{1-6}$ alkyl is substituted with R$^7$;
each R$^3$ is independently selected from the group consisting of:
 (1) hydrogen,
 (2) halogen, —CN,
 (3) —CF$_3$, and
 (4) —C$_{1-6}$alkyl;

$R^4$ is independently selected from the group consisting of:
(1) hydrogen,
(2) halogen,
(3) —$CF_3$, and
(4) —$C_{1-6}$alkyl;

$R^5$ is independently selected from the group consisting of:
(1) hydrogen,
(2) halogen,
(3) —CN,
(4) —$CF_3$,
(5) —$C_{1-6}$alkyl, and
(6) —$C_{1-5}$spirocycloalkyl,
or two $R^5$ groups, and the carbons they are attached to, form a —$C_{3-6}$cycloalkyl ring or a —$C_{2-5}$cycloheteroalkyl ring;

$R^6$ is selected from the group consisting of:
(1) aryl,
(2) aryl-$SO_2$,
(3) aryl-$C_{1-10}$ alkyl-,
(4) aryl-N($R^i$)—,
(5) aryl-$C_{1-10}$ alkyl-N($R^i$)—,
(6) heteroaryl,
(7) heteroaryl-$C_{1-10}$ alkyl-, and
(8) heteroaryl-N($R^i$)—,
wherein each $CH_2$ is unsubstituted or substituted with 1-2 substituents selected from $R^a$, and wherein each aryl, and heteroaryl is unsubstituted or substituted with 1-5 substituents selected from $R^a$:

$R^7$ is selected from the group consisting of:
(1) —$CO_2R^8$,
(2) —$C_{1-6}$alkyl-$CO_2R^8$,
(3) —$C_{1-6}$alkyl-$CONHSO_2R^m$,
(4) —$C_{1-6}$alkyl-$SO_2NHCOR^m$,
(5) —$C_{1-6}$alkyl-tetrazolyl, and
(6) a cycloheteroalkyl selected from the group consisting of:

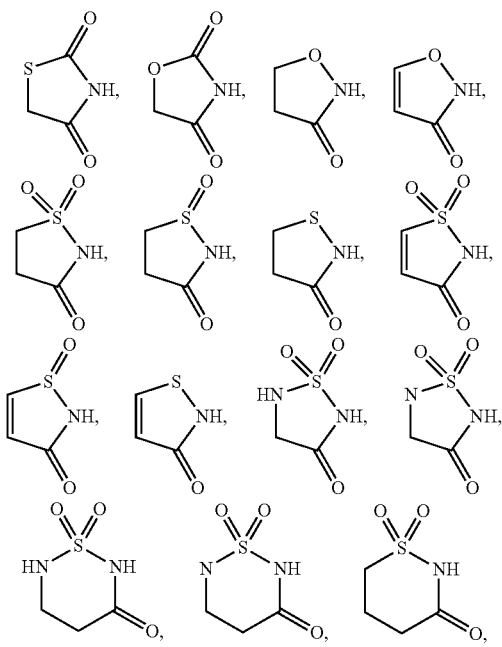

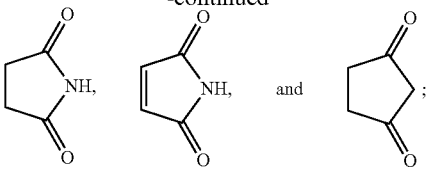

$R^8$ is selected from the group consisting of:
(1) hydrogen,
(2) —$C_{1-6}$alkyl,
(3) —$C_{3-6}$ cycloalkyl, and
(4) aryl-$C_{1-6}$alkyl,
wherein each alkyl, cycloalkyl and aryl is unsubstituted or substituted with one to three substituents selected from $R^j$;

$R^a$ is selected from the group consisting of:
(1) —$C_{1-6}$alkyl,
(2) —$OC_{1-6}$alkyl,
(3) halogen,
(4) —$S(O)_nR^e$,
(5) —$S(O)_nNR^cR^d$,
(6) —$NR^cR^d$,
(7) —$C(O)R^e$,
(8) —$OC(O)R^e$,
(9) —$CO_2R^e$,
(10) —CN,
(11) —$C(O)NR^cR^d$,
(12) —$CF_3$,
(13) —$OCF_3$,
(14) —$OCHF_2$,
(15) —$OCH_2CF_3$,
(16) aryl,
(17) heteroaryl,
(18) $C_{3-6}$cycloalkyl, and
(19) $C_{2-5}$cycloheteroalkyl,
wherein each alkyl, cycloalkyl, cycloheteroalkyl, aryl and heteroaryl is unsubstituted or substituted with 1-3 substituents selected from: halogen, —$C_{1-6}$alkyl, —O—$C_{1-6}$alkyl, —$CF_3$, $CO_2H$, and —$CO_2C_{1-6}$ alkyl;

each $R^b$ is independently selected from the group consisting of:
(1) hydrogen,
(2) —$C(O)R^d$, and
(3) —$C_{1-10}$alkyl,
wherein each alkyl is unsubstituted or substituted with one to five halogens;

$R^c$ and $R^d$ are each independently selected from the group consisting of:
(1) hydrogen,
(2) $C_{1-10}$alkyl,
(3) $C_{2-10}$alkenyl,
(4) $C_{3-6}$cycloalkyl,
(5) $C_{3-6}$ cycloalkyl-$C_{1-10}$alkyl-,
(6) $C_{2-5}$cycloheteroalkyl,
(7) $C_{2-5}$cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-,
wherein each alkyl, alkenyl, cycloalkyl, cycloheteroalkyl, aryl and heteroaryl is unsubstituted or substituted with one to three $R^f$ substituents;

each $R^e$ is independently selected from the group consisting of:
(1) hydrogen,
(2) —$C_{1-10}$alkyl,
(3) —$C_{2-10}$ alkenyl,
(4) —$C_{3-6}$ cycloalkyl,
(5) —$C_{3-6}$ cycloalkyl-$C_{1-10}$alkyl-,
(6) —$C_{2-5}$cycloheteroalkyl,
(7) —$C_{2-5}$cycloheteroalkyl-$C_{1-10}$alkyl,
(8) aryl,
(9) aryl-$C_{1-10}$alkyl-,
(10) heteroaryl, and
(11) heteroaryl-$C_{1-10}$alkyl-,
wherein each alkyl, alkenyl, cycloalkyl, cycloheteroalkyl, aryl and heteroaryl is unsubstituted or substituted with one to three substituents selected from $R^h$;
each $R^f$ is selected from the group consisting of:
(1) halogen,
(2) $C_{1-10}$alkyl,
(3) —OH,
(4) —O—$C_{1-4}$alkyl,
(5) —$S(O)_m$—$C_{1-4}$alkyl,
(6) —CN,
(7) —$CF_3$,
(8) —$OCHF_2$, and
(9) —$OCF_3$,
wherein each alkyl is unsubstituted or substituted with one to three substituents independently selected from: —OH, halogen, $C_{1-6}$alkyl, cyano and $S(O)_2C_{1-6}$alkyl;
$R^g$ is selected from the group consisting of:
(1) hydrogen, and
(2) —$C_{1-10}$alkyl,
wherein each alkyl is unsubstituted or substituted with one to five halogens;
each $R^h$ is selected from the group consisting of:
(1) halogen,
(2) $C_{1-10}$alkyl,
(3) —OH,
(4) —O—$C_{1-4}$alkyl,
(5) —$S(O)_m$—$C_{1-4}$alkyl,
(6) —CN,
(7) —$CF_3$,
(8) —$OCHF_2$, and
(9) —$OCF_3$,
wherein each alkyl is unsubstituted or substituted with one to three substituents independently selected from: —OH, halogen, $C_{1-6}$alkyl, cyano and $S(O)_2C_{1-6}$alkyl;
$R^i$ is independently selected from the group consisting of:
(1) hydrogen, and
(2) —$C_{1-6}$ alkyl;
$R^j$ is independently selected from the group consisting of:
(1) —$C_{1-6}$alkyl,
(2) —$OR^e$,
(3) —$NR^cS(O)_mR^e$,
(4) halogen,
(5) —$S(O)_mR^e$,
(6) —$S(O)_mNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;
each $R^k$ is independently selected from the group consisting of:
(1) —$C_{1-10}$alkyl,
(2) —$C_{2-10}$ alkenyl,
(3) —$C_{3-6}$ cycloalkyl,
(4) —$C_{3-6}$ cycloalkyl-$C_{1-10}$alkyl-,
(5) —$C_{2-5}$cycloheteroalkyl,
(6) —$C_{2-5}$cycloheteroalkyl-$C_{1-10}$alkyl-,
(7) aryl,
(8) heteroaryl,
(9) aryl-$C_{1-10}$alkyl-, and
(10) heteroaryl-$C_{1-10}$ alkyl-,
each $R^L$ is independently selected from the group consisting of:
(1) —$CO_2C_{1-6}$alkyl,
(2) —$C_{1-10}$alkyl,
(3) —$C_{2-10}$alkenyl,
(4) —$C_{2-10}$alkynyl,
(5) —$C_{3-6}$cycloalkyl,
(6) —$C_{2-6}$cycloheteroalkyl,
(7) aryl, and
(8) heteroaryl,
wherein each alkyl, alkenyl, alkynyl, cycloalkyl, cycloheteroalkyl, aryl and heteroaryl is unsubstituted or substituted with 1-4 substituents selected from $C_{1-6}$alkyl, halogen, and —$OC_{1-6}$alkyl;
each n is independently selected from: 0, 1 or 2;
each m is independently selected from: 0, 1 or 2;
each p is independently selected from: 0, 1, or 2;
each q is independently selected from: 0, 1 or 2;
each t is independently selected from: 0, 1 or 2; and
each u is independently selected from: 0, 1, 2, or 3.

2. The compound according to claim 1 wherein T is CH, U is $CR^1$, V is CH, and W is CH; or a pharmaceutically acceptable salt thereof.

3. The compound according to claim 1 wherein X is selected from the group consisting of:
(1) —$C(R^b)(R^b)$,
(2) —C=O, and
(3) —$C(R^b)OR^b$;
or a pharmaceutically acceptable salt thereof.

4. The compound according to claim 1 wherein X is —$C(R^b)(R^b)$; or a pharmaceutically acceptable salt thereof.

5. The compound according to claim 1 wherein Y is selected from the group consisting of:
(1) —$C(R^g)$—, and
(2) —N—;
or a pharmaceutically acceptable salt thereof.

6. The compound according to claim 1 wherein Y is —N—; or a pharmaceutically acceptable salt thereof.

7. The compound according to claim 1 wherein $R^6$ is phenyl-$CH_2$—, wherein $CH_2$ is unsubstituted or substituted with 1-2 substituents selected from $R^a$, and wherein phenyl is unsubstituted or substituted with 1-3 substituents selected from $R^a$; or a pharmaceutically acceptable salt thereof.

8. The compound according to claim 1 wherein $R^1$ is selected from —$C_{1-6}$alkyl, wherein each alkyl is unsubstituted or substituted with one to three substituents selected from $R^L$, and wherein $R^1$ is substituted with $R^7$; and $R^2$ is hydrogen; or a pharmaceutically acceptable salt thereof.

9. The compound according to claim 1 wherein $R^3$ is hydrogen or halogen; $R^4$ is hydrogen; and $R^5$ is hydrogen; or a pharmaceutically acceptable salt thereof.

10. The compound according to claim 1 wherein $R^3$ is hydrogen; $R^4$ is hydrogen; and $R^5$ is hydrogen; or a pharmaceutically acceptable salt thereof.

11. The compound according to claim 1 wherein $R^7$ is —CO$_2$R$^8$; or a pharmaceutically acceptable salt thereof.

12. The compound according to claim 1 wherein $R^8$ is hydrogen; or a pharmaceutically acceptable salt thereof.

13. The compound according to claim 1 of structural Formula Ib:

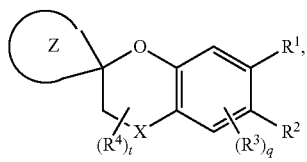

Ib wherein
X is selected from the group consisting of:
(1) —C($R^b$)($R^b$),
(2) C=O, and
(3) —C($R^b$)O$R^b$;
Z is selected from:

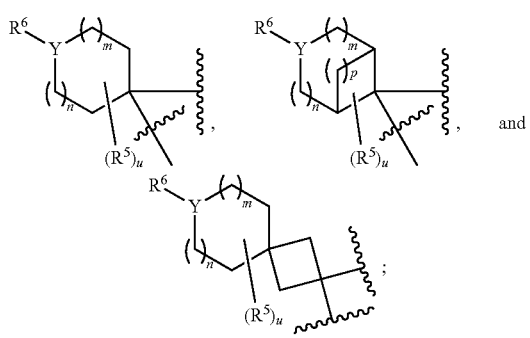

and

Y is selected from the group consisting of:
(1) —C($R^g$)—, and
(2) —N—;
$R^1$ and $R^2$ are each independently selected from:
(1) hydrogen, and
(2) —C$_{1-6}$alkyl,
wherein each alkyl is unsubstituted or substituted with one to three substituents selected from $R^L$, and wherein one of $R^1$ and $R^2$ is C$_{1-6}$ alkyl substituted with $R^7$;
each $R^3$ is independently selected from the group consisting of:
(1) hydrogen, and
(2) halogen;
$R^4$ is hydrogen;
$R^5$ is hydrogen;
$R^6$ is selected from the group consisting of:
(1) aryl,
(2) aryl-SO$_2$—,
(3) aryl-C$_{1-10}$ alkyl-,
(4) aryl-N(R$^i$)—,
(5) aryl-C$_{1-10}$ alkyl-N(R$^i$)—,
(6) heteroaryl,
(7) heteroaryl-C$_{1-10}$ alkyl-, and
(8) heteroaryl-N(R$^i$)—,
wherein each CH$_2$ is unsubstituted or substituted with 1-2 substituents selected from R$^a$, and wherein each aryl, and heteroaryl is unsubstituted or substituted with 1-5 substituents selected from R$^a$;
$R^7$ is —CO$_2$R$^8$;
$R^8$ is hydrogen;
each $R^L$ is independently selected from the group consisting of: —C$_{1-10}$alkyl, —C$_{2-10}$ alkenyl, —C$_{2-10}$ alkynyl, and —C$_{3-6}$cycloalkyl, wherein alkyl, alkenyl, alkynyl, and cycloalkyl are unsubstituted or substituted with 1-4 substituents selected from C$_{1-6}$alkyl, halogen, and —OC$_{1-6}$ alkyl;
n is 0 or 1;
m is 0, 1 or 2;
p is 0 or 2;
q is 0 or 1;
t is 0 or 1; and
u is 0 or 1;
or a pharmaceutically acceptable salt thereof.

14. The compound according to claim 1 of structural formula Iy:

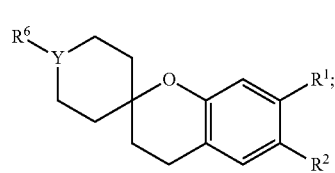

Iy wherein
Y is —N—;
$R^1$ is —C$_{1-6}$ alkyl, wherein each alkyl is unsubstituted or substituted with one to three substituents selected from $R^L$, and wherein $R^1$ is substituted with $R^7$;
$R^2$ is hydrogen;
$R^6$ is phenyl-CH$_2$—, wherein each CH$_2$ is unsubstituted or substituted with 1-2 substituents selected from R$^a$, and wherein each phenyl is unsubstituted or substituted with 1-3 substituents selected from R$^a$;
$R^7$ is —CO$_2$R$^8$;
$R^8$ is hydrogen; and
each $R^L$ is independently selected from the group consisting of: —CH$_3$, and cyclopropyl;
or a pharmaceutically acceptable salt thereof.

15. The compound according to claim 13 selected from:

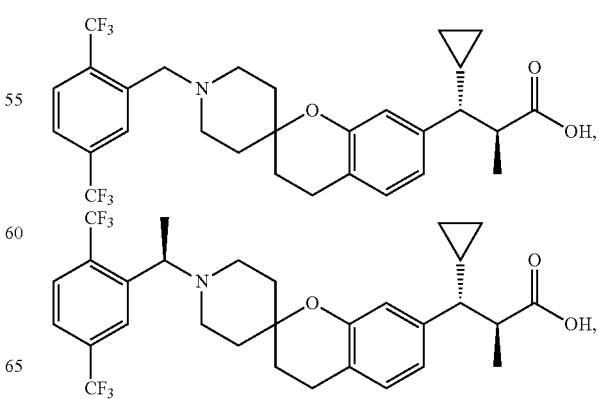

-continued

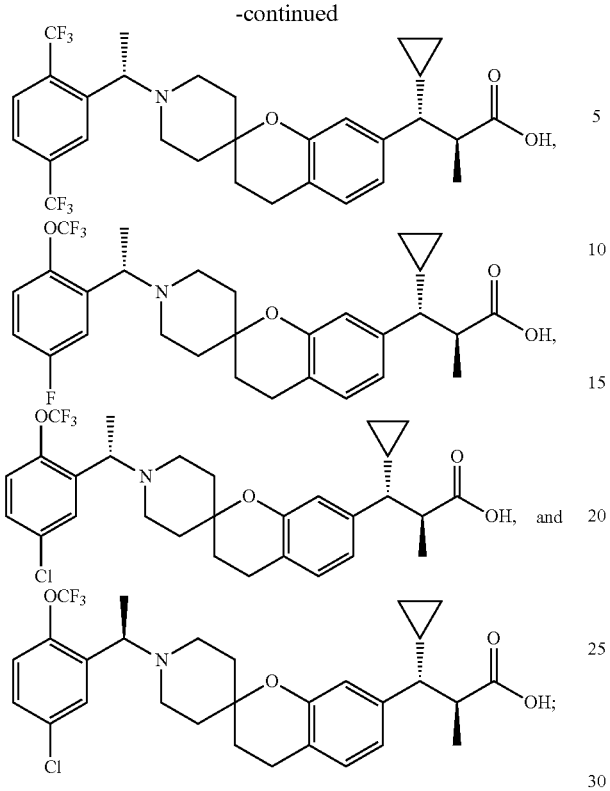

or a pharmaceutically acceptable salt thereof.

16. A pharmaceutical composition comprising a compound of claim 1, or a pharmaceutically acceptable salt thereof, and a pharmaceutically acceptable carrier.

17. A method of treating type 2 diabetes mellitus in a patient in need of treatment comprising the administration to the patient of a therapeutically effective amount of a compound of claim 1, or a pharmaceutically acceptable salt thereof.

18. A pharmaceutical composition comprising
(1) a compound of claim 1, or a pharmaceutically acceptable salt thereof;
(2) one or more compounds selected from the group consisting of:
  (a) PPAR gamma agonists and partial agonists;
  (b) biguanides;
  (c) protein tyrosine phosphatase-1B (PTP-1B) inhibitors;
  (d) dipeptidyl peptidase IV (DP-IV) inhibitors;
  (e) insulin or an insulin mimetic;
  (f) sulfonylureas;
  (g) α-glucosidase inhibitors;
  (h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA: cholesterol acyltransferase (ACAT) inhibitors, (vii) CETP inhibitors, and (viii) phenolic anti-oxidants;
  (i) PPARα/γ dual agonists,
  (j) PPARδ agonists,
  (k) antiobesity compounds,
  (l) ileal bile acid transporter inhibitors;
  (m) anti-inflammatory agents;
  (n) glucagon receptor antagonists;
  (o) GLP-1;
  (p) GIP-1;
  (q) GLP-1 analogs;
  (r) HSD-1 inhibitors;
  (s) SGLT-2 inhibitors; and
  (t) SGLT-1/SGLT-2 inhibitors; and
(3) a pharmaceutically acceptable carrier.

19. A pharmaceutical composition comprising a compound according to claim 1, or a pharmaceutically acceptable salt thereof, and a compound selected from simvastatin, ezetimibe and sitagliptin; and a pharmaceutically acceptable carrier.

* * * * *